(12) United States Patent
Duan et al.

(10) Patent No.: US 12,312,619 B2
(45) Date of Patent: May 27, 2025

(54) DEAMINASES AND VARIANTS THEREOF FOR USE IN BASE EDITING

(71) Applicant: ACCUREDIT THERAPEUTICS (SUZHOU) CO., LTD., Jiangsu (CN)

(72) Inventors: Feifei Duan, Jiangsu (CN); Songyuan Li, Jiangsu (CN); Huanle Liu, Jiangsu (CN); Fuxin Shi, Winchester, MA (US); Ke Qin, Jiangsu (CN); Jialin Tao, Jiangsu (CN); Pengfei Hu, Jiangsu (CN); Han Qiu, Jiangsu (CN)

(73) Assignee: Accuredit Therapeutics (Suzhou) Co., Ltd.

( * ) Notice: Subject to any disclaimer, the term of this patent is extended or adjusted under 35 U.S.C. 154(b) by 0 days.

(21) Appl. No.: 18/814,865

(22) Filed: Aug. 26, 2024

(65) Prior Publication Data

US 2024/0409915 A1    Dec. 12, 2024

(30) Foreign Application Priority Data

Jul. 18, 2023    (WO) ................ PCT/CN2023/107820

(51) Int. Cl.
  *C12N 9/00*    (2006.01)
  *C12N 9/78*    (2006.01)
  *A61K 38/00*   (2006.01)

(52) U.S. Cl.
  CPC ........ *C12N 9/78* (2013.01); *C12Y 305/04004* (2013.01); *A61K 38/00* (2013.01)

(58) Field of Classification Search
  CPC .... C12Y 305/04004; C12Y 305/04005; C12N 9/78; C12N 9/52; C12N 9/80; C12N 15/1058; C07K 2319/81
  USPC ...................................................... 424/94.6
  See application file for complete search history.

(56) References Cited

U.S. PATENT DOCUMENTS

| | | |
|---|---|---|
| 10,947,530 B2 | 3/2021 | Liu et al. |
| 11,155,803 B2 | 10/2021 | Gaudelli et al. |
| 2020/0308571 A1 | 10/2020 | Joung et al. |
| 2020/0399626 A1 | 12/2020 | Liu et al. |
| 2021/0130805 A1 | 5/2021 | Gaudelli et al. |
| 2021/0147861 A1 | 5/2021 | Graham et al. |
| 2021/0261955 A1 | 8/2021 | Slaymaker et al. |

FOREIGN PATENT DOCUMENTS

| | | |
|---|---|---|
| WO | WO 2018027078 | 2/2018 |
| WO | WO 2020028823 | 2/2020 |
| WO | WO 2020160517 | 8/2020 |
| WO | WO 2022240858 | 11/2022 |
| WO | WO 2023185697 | 10/2023 |

OTHER PUBLICATIONS

Chylinski et al., "The tracrRNA and Cas9 families of type II CRISPR-Cas immunity systems," RNA Biology, May 2013, 10(5):726-737.
Deltcheva et al., "CRISPR RNA maturation by trans-encoded small RNA and host factor RNase III," Nature, Mar. 31, 2011, 471(7340):602-607.
Ferretti et al., "Complete genome sequence of an M1 strain of *Streptococcus pyogenes*," Proc. Natl. Acad. Sci. USA, Apr. 10, 2001, 98(8):4658-4663.
Finn et al., "A Single Administration of CRISPR/Cas9 Lipid Nanoparticles Achieves Robust and Persistent In Vivo Genome Editing," Cell Rep., Feb. 27, 2018, 22(9):2227-2235.
Gaudelli et al., "Directed evolution of ednine base editors with increased activity and therapeutic application," Nat. Biotech., Apr. 13, 2020, 38(7):892-900.
GenBank Accession No. ADD78052.1, "TadA [Pantoea ananatis LMG 20103]," dated Jan. 30, 2014, 2 pages.
GenBank Accession No. AFJ46116.1, "tRNA-specific adenosine deaminase [Shimwellia blattae DSM 4481 = NBRC 105725]," dated Mar. 16, 2017, 2 pages.
GenBank Accession No. MRS14637.1, "tRNA adenosine(34) deaminase TadA [Enterobacteriaceae bacterium RIT691]," dated Nov. 18, 2019, 2 pages.
GenBank Accession No. NDJ56784.1, "tRNA adenosine(34) deaminase TadA [Enterobacteriaceae bacterium 4M9]," dated Feb. 2, 2020, 2 pages.
GenBank Accession No. WP_002438082.1, "tRNA adenosine(34) deaminase TadA [Atlantibacter hermannii]," dated Jul. 5, 2022, 2 pages.
GenBank Accession No. WP_023266468.1, "tRNA adenosine(34) deaminase TadA [Shewanella decolorationis]," dated Jul. 5, 2022, 2 pages.
GenBank Accession No. WP_031376271.1, "tRNA adenosine(34) deaminase TadA [Pantoea]," dated Jul. 5, 2022, 2 pages.
GenBank Accession No. WP_056238852.1, "tRNA adenosine(34) deaminase TadA [*Erwinia* sp. Leaf53]," dated Jul. 5, 2022, 2 pages.
GenBank Accession No. WP_094119762.1, "tRNA adenosine(34) deaminase TadA [Pantoea conspicua]," dated Jul. 5, 2022, 2 pages.
GenBank Accession No. WP_123336846.1, "tRNA adenosine(34) deaminase TadA [*Erwinia* sp. JUb26]," dated Jul. 5, 2022, 2 pages.
GenBank Accession No. WP_128175936.1, "tRNA adenosine(34) deaminase TadA [Pantoea] beijingensis]," dated Jul. 5, 2022, 2 pages.
GenBank Accession No. WP_137386298.1, "tRNA adenosine(34) deaminase TadA [unclassified Pantoea]," dated Feb. 5, 2023, 2 pages.
GenBank Accession No. WP_155107477.1, "tRNA adenosine(34) deaminase TadA [Intestinirhabdus alba]," dated Jul. 5, 2022, 2 pages.

(Continued)

*Primary Examiner* — Robert B Mondesi
*Assistant Examiner* — Mohammad Y Meah
(74) *Attorney, Agent, or Firm* — Fish & Richardson P.C.

(57) ABSTRACT

Provided herein are adenosine deaminases and variants thereof, nucleobase editors comprising deaminases, compositions comprising such editors, and methods of using such editors to generate modifications in target nucleobase sequences.

16 Claims, 22 Drawing Sheets

Specification includes a Sequence Listing.

(56) References Cited

OTHER PUBLICATIONS

GenBank Accession No. WP_161662209.1, "tRNA adenosine(34) deaminase TadA [Atlantibacter hermannii]," dated Jul. 5, 2022, 2 pages.
GenBank Accession No. WP_263457953.1, "Multispecies: tRNA adenosine(34) deaminase TadA [Tenebrionibacter/Tenebrionicola group]," dated Oct. 17, 2022, 2 pages.
International Search Report and Written Opinion in International Appln. No. PCT/CN2024/094938, mailed on Aug. 16, 2024, 17 pages.
Jiang et al., "BE-PLUS: a new base editing tool with broadened editing window and enhanced fidelity," Cell Res., Jun. 6, 2018, 28(8):855-861.
Jiang et al., "Structures of a CRISPR-Cas9 R-loop complex primed for DNA cleavage," Science, Feb. 19, 2016, 351(6275):867-871.
Jinek et al., "Programmable dual-RNA-guided DNA endonuclease in adaptive bacterial immunity," Science, Aug. 17, 2012, 337(6096):816-821.
Koonin et al., "Diversity, classification and evolution of CRISPR-Cas systems," Curr. Opin. Microbiol., Jun. 2017, 37:67-78.
Kropocheva et al., "Prokaryotic Argonaute Proteins as a Tool for Biotechnology," Mol. Biol., Aug. 30, 2022, 56(6):854-873.
Li et al., "Cytosine base editing systems with minimized off-target effect and molecular size," Nat. Comm., Aug. 8, 2022, 13(1):4531, 8 pages.
Makarova et al. "Classification and Nomenclature of CRISPR-Cas Systems: Where from Here?" CRISPR J., Oct. 2018, 1(5):325-336.
Nishimasu et al., "Crystal structure of Cas9 in complex with guide RNA and target DNA," Cell, Feb. 27, 2014, 156(5):935-949.
Ranzau et al., "The Wild-Type tRNA Adenosine Deaminase Enzyme TadA is Capable of Sequence-Specific DNA Base Editing," ChemBioChem, May 24, 2023, 24(16):e202200788, 18 pages.
Shmakov et al., "Diversity and evolution of class 2 CRISPR-Cas systems," Nat. Rev. Microbiol., Mar. 2017, 15(3):169-182.
Yan et al., "Functionally diverse type V CRISPR-Cas systems," Science, Jan. 4, 2019, 363(6422):88-91.
Yang et al., "Engineering and optimizing deaminase fusions for genome editing," Nat. Comm., Nov. 2, 2016, 7(1):13330.
Yu et al., "Cytosine base editors with minimized unguided DNA and RNA off-target events and high on-target activity," Nat. Comm., Apr. 28, 2020, 11(1):2052, 10 pages.
Zhang et al., "TadA orthologs enable both cytosine and adenine editing of base editors," Nat. Comm., Jan. 26, 2023, 14(1):414, 10 pages.
UniProt Accession No. A0A6I2HYH0, "tRNA-specific adenosine deaminase," dated May 29, 2024, 2 pages.

SEQUENCE LISTING

```
Sequence total quantity: 273
SEQ ID NO: 1            moltype = AA  length = 201
FEATURE                 Location/Qualifiers
source                  1..201
                        mol_type = protein
                        organism = synthetic construct
SEQUENCE: 1
MPVQLAPGRV YNAPAFITGV TPLSDIQLSH EYWMRHALTL AKRAWDAREV PVGAVLVHNN   60
RAIGEGWNRP IGHHDPTAHA EIMALRQGGL VLENYRLLDA TLYVTLEPCV MCAGAMVHSR  120
IARVVFGARD AKTGAAGSLM DVLHHPGMNH RVEVTEGVLG EECAALLSEF FRMRRREIKA  180
LKRASAQTDE GQSAAAGPGE R                                           201

SEQ ID NO: 2            moltype =     length =
SEQUENCE: 2
```

```
000

SEQ ID NO: 3              moltype =     length =
SEQUENCE: 3
000

SEQ ID NO: 4              moltype = AA   length = 184
FEATURE                   Location/Qualifiers
source                    1..184
                          mol_type = protein
                          organism = synthetic construct
SEQUENCE: 4
MYNAPRFSTG VDALSETELN HEYWMRHALN LAQRAWEEGE VPVGAVLVYQ DKVIGEGWNR    60
PIGRHDPTAH AEIMALRQGG MVLQNYRLID ATLYVTLEPC VMCAGAMIHS RIGRVVFGAR   120
DAKTGAAGSL IDVLHHPGMN HRVEVTEGVL AESCSSLLSD FFRERREQKK ALKRASQDPR   180
SSDA                                                               184

SEQ ID NO: 5              moltype = AA   length = 166
FEATURE                   Location/Qualifiers
source                    1..166
                          mol_type = protein
                          organism = synthetic construct
SEQUENCE: 5
MSDTEFTHEY WMQHALTLAQ RAWDEGEVPV GAVLVQDNRV IGEGWNRPIG RHDPTAHAEI    60
MALRQGGMVL QNYRLLNTTL YVTLEPCIMC AGAMVHSRIG TLVFGARDAK TGAVGSLMNV   120
PAHPGMNHHM QVIEGVLAPS CSALLSDFFR VRRLEKKAQK EASRKD                 166

SEQ ID NO: 6              moltype = AA   length = 166
FEATURE                   Location/Qualifiers
source                    1..166
                          mol_type = protein
                          organism = synthetic construct
SEQUENCE: 6
MSETEFSHEY WMRHALTLAQ RAWDEGEVPV GAVLVQDNRV IGEGWNRPIG RHDPTAHAEI    60
MALRQGGMVL QNYRLLNTTL YVTLEPCIMC AGAMVHSRIG TLVFGARDAK TGAVGSLMNI   120
PAHPQMNHHM QIIEGVLAPT CSALLSEFFR VRRLEKKAQK EALRKD                 166

SEQ ID NO: 7              moltype = AA   length = 166
FEATURE                   Location/Qualifiers
source                    1..166
                          mol_type = protein
                          organism = synthetic construct
SEQUENCE: 7
MSDNHDHEYW MQHALTLARR AWDEGEVPVG AVLVRNGEII GEGWNRPIGR HDPTAHAEIM    60
ALRQGGVVLQ NYRLLDATLY VTLEPCVMCA GAMVHSRIGR LVFGARDAKT GAAGSLMDVL   120
AHPGMNHRVE VTEGVLAPAC STLLSDFFRE RRLQQKALKE ASRKPE                 166

SEQ ID NO: 8              moltype = AA   length = 173
FEATURE                   Location/Qualifiers
source                    1..173
                          mol_type = protein
                          organism = synthetic construct
SEQUENCE: 8
MTTPALTHEY WMNYALTLAR RAWDEGEVPV GAVLVYDNRV IGEGWNRSIG KHDPTAHAEI    60
MALRQGGMVQ QNYRLLDTTL YVTLEPCVMC AGAMIHSRIG TLVFGARDAK TGAVGSQMDI   120
LNHPGMNHQV QIIEGVLAPQ CSALLSDFFR MRRKEKKALK IASRDPHPAA PQR          173

SEQ ID NO: 9              moltype = AA   length = 165
FEATURE                   Location/Qualifiers
source                    1..165
                          mol_type = protein
                          organism = synthetic construct
SEQUENCE: 9
MDNHDHEYWM QHALTLAQRA WEEGEVPVGA VLVLNGQAIG EGWNRPIGRH DPTAHAEMMA    60
LRQGGAVLQN YRLLNATLYV TLEPCVMCAG AMVHSRIARL VFGARDAKTG AAGSLLDVLA   120
HPGMNHRVAV TEGVLAPACS ALLSDFFRQR RQQQKALKDA NRKRD                  165

SEQ ID NO: 10             moltype = AA   length = 169
FEATURE                   Location/Qualifiers
source                    1..169
                          mol_type = protein
                          organism = synthetic construct
SEQUENCE: 10
MSDNNDEFWM RHALTLARRA WQEGEVPVGA VLVHEGRVIG EGWNRPIGHH DPTAHAEIMA    60
LRQGGKVIEN YRLLDTTLYV TLEPCVMCAG AMVHGRVGRL VFGARDAKTG AAGSLIDVLS   120
HPGMNHQVQV DEGVLAEECA AMLSDFFRQR RAEKKALRQQ QQQGTSSAE               169

SEQ ID NO: 11             moltype = AA   length = 166
FEATURE                   Location/Qualifiers
```

```
                        source            1..166
                                          mol_type = protein
                                          organism = synthetic construct
SEQUENCE: 11
MTDYNDELWM RHALTLARRA WDEGEVPVGA VLVQDNRVIG EGWNRPIGHH DPTAHAEMMA    60
LRQGGKVLEN YRLLDTTLYV TLEPCVMCAG AIVHSRIGRL VFGARDGKTG AAGSLIDILG   120
HPGMNHQVIV SEGILAETCA GMLSDFFRQR REEKKALRKT RETPDR                  166

SEQ ID NO: 12           moltype = AA    length = 164
FEATURE                 Location/Qualifiers
source                  1..164
                        mol_type = protein
                        organism = synthetic construct
SEQUENCE: 12
MSDNNDEYWM RHALMLARRA WDEGEVPVGA VLVHEGRVIG EGWNRPIGHH DPTAHAEIMA    60
LRQGGKVIEN YRLLDTTLYV TLEPCVMCAG AMVHSRIGRL VFGARDEKTG AAGSLLDVLG   120
HPGMNHQVQI EEGILAAECA AMLSDFFRHR RAEKKALRQA GKLL                    164

SEQ ID NO: 13           moltype =   length =
SEQUENCE: 13
000

SEQ ID NO: 14           moltype = AA    length = 171
FEATURE                 Location/Qualifiers
source                  1..171
                        mol_type = protein
                        organism = synthetic construct
SEQUENCE: 14
MLPGVVCVTQ EQDEYWMRRA LTLAQRAWEQ GEVPVGAVLV QGDRVIGEGW NRPIGQHDPT    60
AHAEIMALRQ GGKVLENYRL LNTTLYVTLE PCIMCAGAMV HSRIGRLVYG AHDVKTGAAG   120
SLIDILGHPG MNHQVALHQG VLEEECAAML SDFFRMRRQQ QKALRQAQRE S            171

SEQ ID NO: 15           moltype = AA    length = 164
FEATURE                 Location/Qualifiers
source                  1..164
                        mol_type = protein
                        organism = synthetic construct
SEQUENCE: 15
MNPQTDEYWM RYALELAKRA WEQGEVPVGA VLVQGDKVIG EGWNRPIGQH DPTAHAEIMA    60
LRQGGKVLEN YRLLDTTLYV TLEPCVMCAG AMVHGRITRL VYGAKDDKTG AAGSLLDVIG   120
HPGMNHQIQI DCGVLAEECA GMLSDFFRMR REQKKALRQA QRTG                    164

SEQ ID NO: 16           moltype = AA    length = 164
FEATURE                 Location/Qualifiers
source                  1..164
                        mol_type = protein
                        organism = synthetic construct
SEQUENCE: 16
MNQQRDEYWM RHALGLARLA WEQGEVPVGA VLVQDERVIG EGWNRPIGQH DPTAHAEMMA    60
LRQGGKVLEN YRLNTTLYV TLEPCVMCAG AMVHSRITRL VYGAHDVKTG AAGSLLDVLG    120
HPGMNHQIEL HSGVLAEECA AMLSDFFRMR REQKKALRQA QRQS                    164

SEQ ID NO: 17           moltype = AA    length = 164
FEATURE                 Location/Qualifiers
source                  1..164
                        mol_type = protein
                        organism = synthetic construct
SEQUENCE: 17
MNQQHDEYWM RHALGLARLA WEQGEVPVGA VLVQADRVIG EGWNRPIGQH DPTAHAEMMA    60
LRQGGKVLEN YRLLNTTLYV TLEPCVMCAG AMVHSRITRL VYGAHDVKTG AAGSLLDVLG   120
HPGMNHQVEL HSGVLADECA AMLSDFFQMR REQKKALRQA QRQG                    164

SEQ ID NO: 18           moltype =   length =
SEQUENCE: 18
000

SEQ ID NO: 19           moltype =   length =
SEQUENCE: 19
000

SEQ ID NO: 20           moltype =   length =
SEQUENCE: 20
000

SEQ ID NO: 21           moltype =   length =
SEQUENCE: 21
000

SEQ ID NO: 22           moltype =   length =
```

```
SEQUENCE: 22
000

SEQ ID NO: 23              moltype =    length =
SEQUENCE: 23
000

SEQ ID NO: 24              moltype = AA   length = 212
FEATURE                    Location/Qualifiers
source                     1..212
                           mol_type = protein
                           organism = synthetic construct
SEQUENCE: 24
MEQIKLDPKT LHAKTNSSDE LGCDEVSADV LAGEQPCLEQ ASLEQARVDE HWMRVAMTMA    60
EKAEAAGEVP VGAVLVKDGQ QIAAGYNLSI SEHDPCAHAE IQCLRAAGQT IENYRLLDTT   120
LYVTLEPCAM CAGAMVHSRI ARVVFGAKDE KTGAAGTVLN LLQHPAFNHQ VEVTSGVLAQ   180
ECADQLSRFF KRRREEKKAL KQAQKAQQGT LS                                 212

SEQ ID NO: 25              moltype = AA   length = 170
FEATURE                    Location/Qualifiers
source                     1..170
                           mol_type = protein
                           organism = synthetic construct
SEQUENCE: 25
MTESETDHIR WMRHALSLAQ RAWDEGEVPV GAVLVYQGQV IGEGWNRPIG HHDPTAHAEM    60
MALRQGGIVL QNYRLLDTTL YVTLEPCVMC AGAMVHSRIG QLIYGASDVK TGAAGSLMDV   120
LGHPGMNHKV SVAGGVLAQE CAGLLSDFFR MRRQVHKANK QAARQPSEDQ              170

SEQ ID NO: 26              moltype = AA   length = 170
FEATURE                    Location/Qualifiers
source                     1..170
                           mol_type = protein
                           organism = synthetic construct
SEQUENCE: 26
MTGSETDHIR WMRHALTLAQ RAWDEGEVPV GAVLVYQGQV IGEGWNRPIG HHDPTAHAEM    60
MALRQGGIVL QNYRLLDTTL YVTLEPCVMC AGAMVHSRIG QLIYGASDVK TGAAGSLMDV   120
LGHPGMNHKV SVAGGVLAQE CAGLLSDFFR MRRQVHKANK QAARQQSEDQ              170

SEQ ID NO: 27              moltype = AA   length = 170
FEATURE                    Location/Qualifiers
source                     1..170
                           mol_type = protein
                           organism = synthetic construct
SEQUENCE: 27
MSDTLIDEKW MRHALTLARR AWEEGEVPVG AVLVQGDTVI GEGWNRPIGH HDPTAHAEIM    60
ALRQGGKVLE NYRLLDTTLY VTLEPCVMCA GAMVHGRVGR LVFGARDEKT GAAGSLLDIL   120
GHAGMNHQVR VDQGVLAAEC AAMLSDFFRH RRAEKKALRD RLRAERLKGE              170

SEQ ID NO: 28              moltype = AA   length = 163
FEATURE                    Location/Qualifiers
source                     1..163
                           mol_type = protein
                           organism = synthetic construct
SEQUENCE: 28
MTDYNDEFWM RHALTLAQRA WDEGEVPVGA VLVQGNRVIG EGWNRPIGHH DPTAHAEIMA    60
LRQGGKVLEN YRLIDTTLYV TLEPCVMCAG AIVHSRIGRL VFGARDEKTG AAGSLLDVLG   120
HPGMNHQVKM TEGILAQQCA GMLSDFFRMR REQKKALRKS VKQ                     163

SEQ ID NO: 29              moltype = AA   length = 166
FEATURE                    Location/Qualifiers
source                     1..166
                           mol_type = protein
                           organism = synthetic construct
SEQUENCE: 29
MTDHNDEYWM RHALRLARRA WDEGEVPVGA VLVLDNQVIG EGWNRPIGHH DPTAHAEMMA    60
LRQGGKMIEN YRLLDTTLYV TLEPCVMCAG AMIHSRIGRL VYGARDAKTG AAGSLLDVLG   120
HPGMNHQVPA ECGLLNDECA AMLSDFFRQR RAEKKMLRQQ QNPGRV                  166

SEQ ID NO: 30              moltype = AA   length = 164
FEATURE                    Location/Qualifiers
source                     1..164
                           mol_type = protein
                           organism = synthetic construct
SEQUENCE: 30
MSDNNDEYWM RHALMLARRA WDEGEVPVGA VLVHEGRAIG EGWNRPIGHH DPTAHAEIMA    60
LRQGGKVIEN YRLNTTLYV TLEPCVMCAG AMVHSRIGRL VFGARDGKTG AAGSLLDVLG   120
HPGMNHQVQI EEGILATECA AMLSDFFRHR RAEKKAQRQA GKLL                    164

SEQ ID NO: 31              moltype = AA   length = 164
```

```
FEATURE                 Location/Qualifiers
source                  1..164
                        mol_type = protein
                        organism = synthetic construct
SEQUENCE: 31
MTQEQDEYWM RRALTLAQRA WEQGEVPVGA VLVQGDRVIG EGWNRPIGQH DPTAHAEIMA    60
LRQGGKVLEN YRLLNTTLYV TLEPCIMCAG AMVHSRIGRL VYGAHDAKTG AAGSLIDILG   120
HPGMNHQVAL HQGVLEEECA AMLSDFFRMR RQQQKALRQA QRES                    164

SEQ ID NO: 32           moltype =    length =
SEQUENCE: 32
000

SEQ ID NO: 33           moltype =    length =
SEQUENCE: 33
000

SEQ ID NO: 34           moltype =    length =
SEQUENCE: 34
000

SEQ ID NO: 35           moltype =    length =
SEQUENCE: 35
000

SEQ ID NO: 36           moltype = AA   length = 201
FEATURE                 Location/Qualifiers
source                  1..201
                        mol_type = protein
                        organism = synthetic construct
SEQUENCE: 36
MPVQLAPGRV YNAPAFITGV TPLSDIQLSH EYWMRHALTL AKRARDAREV PVGAVLVLNN    60
RAIGEGWNRA IGHHDPTAHA EIMALRQGGL VLENYRLLDA TLYVTFEPCV MCAGAMVHSR   120
IARVVFGVRN AKTGAAGSLM DVLHYPGMNH RVEVTEGVLG EECAALLCEF FRMPRRVFNA   180
LKRASAQTDE GQSAAAGPGE R                                             201

SEQ ID NO: 37           moltype =    length =
SEQUENCE: 37
000

SEQ ID NO: 38           moltype =    length =
SEQUENCE: 38
000

SEQ ID NO: 39           moltype = AA   length = 184
FEATURE                 Location/Qualifiers
source                  1..184
                        mol_type = protein
                        organism = synthetic construct
SEQUENCE: 39
MYNAPRFSTG VDALSETELN HEYWMRHALN LAQRAREEGE VPVGAVLVYQ DKVIGEGWNR    60
AIGLHDPTAH AEIMALRQGG MVLQNYRLID ATLYVTFEPC VMCAGAMIHS RIGRVVFGVR   120
NAKTGAAGSL IDVLHYPGMN HRVEVTEGVL AESCSSLLCY FFREPREQKN ALKRASQDPR   180
SSDA                                                                184

SEQ ID NO: 40           moltype = AA   length = 166
FEATURE                 Location/Qualifiers
source                  1..166
                        mol_type = protein
                        organism = synthetic construct
SEQUENCE: 40
MSDTEFTHEY WMQHALTLAQ RARDEGEVPV GAVLVQDNRV IGEGWNRAIG LHDPTAHAEI    60
MALRQGGMVL QNYRLLNTTL YVTFEPCIMC AGAMVHSRIG TLVFGVRNAK TGAVGSLMNV   120
PAYPGMNHHM QVIEGVLAPS CSALLCYFFR VPRLVKNAQK EASRKD                  166

SEQ ID NO: 41           moltype = AA   length = 166
FEATURE                 Location/Qualifiers
source                  1..166
                        mol_type = protein
                        organism = synthetic construct
SEQUENCE: 41
MSETEFSHEY WMRHALTLAQ RARDEGEVPV GAVLVQDNRV IGEGWNRAIG LHDPTAHAEI    60
MALRQGGMVL QNYRLLNTTL YVTFEPCIMC AGAMVHSRIG TLVFGVRNAK TGAVGSLMNI   120
PAYPGMNHHM QIIEGVLAPT CSALLCEFFR VPRLVKNAQK EALRKD                  166

SEQ ID NO: 42           moltype = AA   length = 166
FEATURE                 Location/Qualifiers
source                  1..166
                        mol_type = protein
```

```
                    organism = synthetic construct
SEQUENCE: 42
MSDNHDHEYW MQHALTLARR ARDEGEVPVG AVLVRNGEII GEGWNRAIGL HDPTAHAEIM    60
ALRQGGVVLQ NYRLLDATLY VTFEPCVMCA GAMVHSRIGR LVFGVRNAKT GAAGSLMDVL   120
AYPGMNHRVE VTEGVLAPAC STLLCYFFRE PRLQQNALKE ASRKPE                  166

SEQ ID NO: 43           moltype = AA   length = 173
FEATURE                 Location/Qualifiers
source                  1..173
                        mol_type = protein
                        organism = synthetic construct
SEQUENCE: 43
MTTPALTHEY WMNYALTLAR RARDEGEVPV GAVLVYDNRV IGEGWNRSIG KHDPTAHAEI    60
MALRQGGMVQ QNYRLLDTTL YVTFEPCVMC AGAMIHSRIG TLVFGVRNAK TGAVGSQMDI   120
LNYPGMNHQV QIIEGVLAPQ CSALLCYFFR MPRKVKNALK IASRDPHPAA PQR          173

SEQ ID NO: 44           moltype = AA   length = 165
FEATURE                 Location/Qualifiers
source                  1..165
                        mol_type = protein
                        organism = synthetic construct
SEQUENCE: 44
MDNHDHEYWM QHALTLAQRA REEGEVPVGA VLVLNGQAIG EGWNRAIGLH DPTAHAEMMA    60
LRQGGAVLQN YRLLNATLYV TFEPCVMCAG AMVHSRIARL VFGVRNAKTG AAGSLLDVLA   120
YPGMNHRVAV TEGVLAPACS ALLCYFFRQP RQQQNALKDA NRKRD                   165

SEQ ID NO: 45           moltype = AA   length = 169
FEATURE                 Location/Qualifiers
source                  1..169
                        mol_type = protein
                        organism = synthetic construct
SEQUENCE: 45
MSDNNDEFWM RHALTLARRA RQEGEVPVGA VLVLEGRVIG EGWNRAIGHH DPTAHAEIMA    60
LRQGGKVIEN YRLLDTTLYV TFEPCVMCAG AMVHGRVGRL VFGVRNAKTG AAGSLIDVLS   120
YPGMNHQVQV DEGVLAEECA AMLCYFFRQP RAVKNALRQQ QQQGTSSAE               169

SEQ ID NO: 46           moltype = AA   length = 166
FEATURE                 Location/Qualifiers
source                  1..166
                        mol_type = protein
                        organism = synthetic construct
SEQUENCE: 46
MTDYNDELWM RHALTLARRA RDEGEVPVGA VLVQDNRVIG EGWNRAIGHH DPTAHAEMMA    60
LRQGGKVLEN YRLLDTTLYV TFEPCVMCAG AIVHSRIGRL VFGVRNGKTG AAGSLIDILG   120
YPGMNHQVIV SEGILAETCA GMLCYFFRQP REVKNALRKT RETPDR                  166

SEQ ID NO: 47           moltype = AA   length = 164
FEATURE                 Location/Qualifiers
source                  1..164
                        mol_type = protein
                        organism = synthetic construct
SEQUENCE: 47
MSDNNDEYWM RHALMLARRA RDEGEVPVGA VLVLEGRVIG EGWNRAIGHH DPTAHAEIMA    60
LRQGGKVIEN YRLLDTTLYV TFEPCVMCAG AMVHSRIGRL VFGVRNEKTG AAGSLLDVLG   120
YPGMNHQVQI EEGILAAECA AMLCYFFRHP RAVKNALRQA GKLL                    164

SEQ ID NO: 48           moltype =      length =
SEQUENCE: 48
000

SEQ ID NO: 49           moltype = AA   length = 171
FEATURE                 Location/Qualifiers
source                  1..171
                        mol_type = protein
                        organism = synthetic construct
SEQUENCE: 49
MLPGVVCVTQ EQDEYWMRRA LTLAQRAREQ GEVPVGAVLV QGDRVIGEGW NRAIGQHDPT    60
AHAEIMALRQ GGKVLENYRL LNTTLYVTFE PCIMCAGAMV HSRIGRLVYG VHNVKTGAAG   120
SLIDILGYPG MNHQVALHQG VLEEECAAML CYFFRMPRQQ QNALRQAQRE S            171

SEQ ID NO: 50           moltype = AA   length = 164
FEATURE                 Location/Qualifiers
source                  1..164
                        mol_type = protein
                        organism = synthetic construct
SEQUENCE: 50
MNPQTDEYWM RYALELAKRA REQGEVPVGA VLVQGDKVIG EGWNRAIGQH DPTAHAEIMA    60
LRQGGKVLEN YRLLDTTLYV TFEPCVMCAG AMVHGRITRL VYGVKNDKTG AAGSLLDVIG   120
YPGMNHQIQI DCGVLAEECA GMLCYFFRMP REQKNALRQA QRTG                    164
```

```
SEQ ID NO: 51            moltype = AA   length = 164
FEATURE                  Location/Qualifiers
source                   1..164
                         mol_type = protein
                         organism = synthetic construct
SEQUENCE: 51
MNQQRDEYWM RHALGLARLA REQGEVPVGA VLVQDERVIG EGWNRAIGQH DPTAHAEMMA    60
LRQGGKVLEN YRLLNTTLYV TFEPCVMCAG AMVHSRITRL VYGVHNVKTG AAGSLLDVLG   120
YPGMNHQIEL HSGVLAEECA AMLCYFFRMP REQKNALRQA QRQS                    164

SEQ ID NO: 52            moltype = AA   length = 164
FEATURE                  Location/Qualifiers
source                   1..164
                         mol_type = protein
                         organism = synthetic construct
SEQUENCE: 52
MNQQHDEYWM RHALGLARLA REQGEVPVGA VLVQADRVIG EGWNRAIGQH DPTAHAEMMA    60
LRQGGKVLEN YRLLNTTLYV TFEPCVMCAG AMVHSRITRL VYGVHNVKTG AAGSLLDVLG   120
YPGMNHQVEL HSGVLADECA AMLCYFFQMP REQKNALRQA QRQG                    164

SEQ ID NO: 53            moltype =      length =
SEQUENCE: 53
000

SEQ ID NO: 54            moltype =      length =
SEQUENCE: 54
000

SEQ ID NO: 55            moltype =      length =
SEQUENCE: 55
000

SEQ ID NO: 56            moltype =      length =
SEQUENCE: 56
000

SEQ ID NO: 57            moltype =      length =
SEQUENCE: 57
000

SEQ ID NO: 58            moltype =      length =
SEQUENCE: 58
000

SEQ ID NO: 59            moltype = AA   length = 212
FEATURE                  Location/Qualifiers
source                   1..212
                         mol_type = protein
                         organism = synthetic construct
SEQUENCE: 59
MEQIKLDPKT LHAKTNSSDE LGCDEVSADV LAGEQPCLEQ ASLEQARVDE HWMRVAMTMA    60
EKAEAAGEVP VGAVLVKDGQ QIAAGYNLSI SEHDPCAHAE IQCLRAAGQT IENYRLLDTT   120
LYVTFEPCAM CAGAMVHSRI ARVVFGVKNE KTGAAGTVLN LLQYPAFNHQ VEVTSGVLAQ   180
ECADQLCRFF KRPREVKNAL KQAQKAQQGT LS                                 212

SEQ ID NO: 60            moltype =      length =
SEQUENCE: 60
000

SEQ ID NO: 61            moltype =      length =
SEQUENCE: 61
000

SEQ ID NO: 62            moltype =      length =
SEQUENCE: 62
000

SEQ ID NO: 63            moltype =      length =
SEQUENCE: 63
000

SEQ ID NO: 64            moltype =      length =
SEQUENCE: 64
000

SEQ ID NO: 65            moltype =      length =
SEQUENCE: 65
000
```

```
SEQ ID NO: 66          moltype =      length =
SEQUENCE: 66
000

SEQ ID NO: 67          moltype =      length =
SEQUENCE: 67
000

SEQ ID NO: 68          moltype =      length =
SEQUENCE: 68
000

SEQ ID NO: 69          moltype =      length =
SEQUENCE: 69
000

SEQ ID NO: 70          moltype =      length =
SEQUENCE: 70
000

SEQ ID NO: 71          moltype = AA   length = 201
FEATURE                Location/Qualifiers
source                 1..201
                       mol_type = protein
                       organism = synthetic construct
SEQUENCE: 71
MPVQLAPGRV YNAPAFITGV TPLSDIQLSH EYWMRHALTL AKRARDAREV PVGAVLVLNN   60
RAIGEGWNRA IGHHDPTAHA EIMALRQGGL VLENYRLLDA TLYVTFEPCV MCAGAMVHSR  120
IARVVFGVRN SKRGAAGSLM NVLNYPGMNH RVEVTEGVLG EECAALLCEF YRMPRRVFNA  180
LKRASAQINE GQSAAAGPGE R                                            201

SEQ ID NO: 72          moltype =      length =
SEQUENCE: 72
000

SEQ ID NO: 73          moltype =      length =
SEQUENCE: 73
000

SEQ ID NO: 74          moltype = AA   length = 184
FEATURE                Location/Qualifiers
source                 1..184
                       mol_type = protein
                       organism = synthetic construct
SEQUENCE: 74
MYNAPRFSTG VDALSETELN HEYWMRHALN LAQRAREEGE VPVGAVLVYQ DKVIGEGWNR   60
AIGLHDPTAH AEIMALRQGG MVLQNYRLID ATLYVTFEPC VMCAGAMIHS RIGRVVFGVR  120
NSKRGAAGSL INVLNYPGMN HRVEVTEGVL AESCSSLLCD FYREPREQKN ALKRASQDPR  180
SSNA                                                               184

SEQ ID NO: 75          moltype = AA   length = 166
FEATURE                Location/Qualifiers
source                 1..166
                       mol_type = protein
                       organism = synthetic construct
SEQUENCE: 75
MSDTEFTHEY WMQHALTLAQ RARDEGEVPV GAVLVQDNRV IGEGWNRAIG LHDPTAHAEI   60
MALRQGGMVL QNYRLLNTTL YVTFEPCIMC AGAMVHSRIG TLVFGVRNSK RGAVGSLMNV  120
PAYPGMNHHM QVIEGVLAPS CSALLCDFYR VPRLVKNAQK EASRKN                 166

SEQ ID NO: 76          moltype = AA   length = 166
FEATURE                Location/Qualifiers
source                 1..166
                       mol_type = protein
                       organism = synthetic construct
SEQUENCE: 76
MSETEFSHEY WMRHALTLAQ RARDEGEVPV GAVLVQDNRV IGEGWNRAIG LHDPTAHAEI   60
MALRQGGMVL QNYRLLNTTL YVTFEPCIMC AGAMVHSRIG TLVFGVRNSK RGAVGSLMNI  120
PAYPQMNHHM QIIEGVLAPT CSALLCEFYR VPRLVKNAQK EALRKN                 166

SEQ ID NO: 77          moltype = AA   length = 166
FEATURE                Location/Qualifiers
source                 1..166
                       mol_type = protein
                       organism = synthetic construct
SEQUENCE: 77
MSDNHDHEYW MQHALTLARR ARDEGEVPVG AVLVRNGEII GEGWNRAIGL HDPTAHAEIM   60
ALRQGGVVLQ NYRLLDATLY VTFEPCVMCA GAMVHSRIGR LVFGVRNSKR GAAGSLMNVL  120
```

```
AYPGMNHRVE VTEGVLAPAC STLLCDFYRE PRLQQNALKE ASRKPE             166

SEQ ID NO: 78           moltype = AA   length = 173
FEATURE                 Location/Qualifiers
source                  1..173
                        mol_type = protein
                        organism = synthetic construct
SEQUENCE: 78
MTTPALTHEY WMNYALTLAR RARDEGEVPV GAVLVYDNRV IGEGWNRSIG KHDPTAHAEI  60
MALRQGGMVQ QNYRLLDTTL YVTFEPCVMC AGAMIHSRIG TLVFGVRNSK RGAVGSQMNI 120
LNYPGMNHQV QIIEGVLAPQ CSALLCDFYR MPRKVKNALK IASRDPHPAA PQR        173

SEQ ID NO: 79           moltype = AA   length = 165
FEATURE                 Location/Qualifiers
source                  1..165
                        mol_type = protein
                        organism = synthetic construct
SEQUENCE: 79
MDNHDHEYWM QHALTLAQRA REEGEVPVGA VLVLNGQAIG EGWNRAIGLH DPTAHAEMMA  60
LRQGGAVLQN YRLLNATLYV TFEPCVMCAG AMVHSRIARL VFGVRNSKRG AAGSLLNVLA 120
YPGMNHRVAV TEGVLAPACS ALLCDFYRQP RQQQNALKDA NRKRN                 165

SEQ ID NO: 80           moltype = AA   length = 169
FEATURE                 Location/Qualifiers
source                  1..169
                        mol_type = protein
                        organism = synthetic construct
SEQUENCE: 80
MSDNNDEFWM RHALTLARRA RQEGEVPVGA VLVLEGRVIG EGWNRAIGHH DPTAHAEIMA  60
LRQGGKVIEN YRLLDTTLYV TFEPCVMCAG AMVHGRVGRL VFGVRNSKRG AAGSLINVLS 120
YPGMNHQVQV DEGVLAEECA AMLCDFYRQP RAVKNALRQQ QQQGTSSAE             169

SEQ ID NO: 81           moltype = AA   length = 166
FEATURE                 Location/Qualifiers
source                  1..166
                        mol_type = protein
                        organism = synthetic construct
SEQUENCE: 81
MTDYNDELWM RHALTLARRA RDEGEVPVGA VLVQDNRVIG EGWNRAIGHH DPTAHAEMMA  60
LRQGGKVLEN YRLLDTTLYV TFEPCVMCAG AIVHSRIGRL VFGVRNGKRG AAGSLINILG 120
YPGMNHQVIV SEGILAETCA GMLCDFYRQP REVKNALRKT RETPNR                166

SEQ ID NO: 82           moltype = AA   length = 164
FEATURE                 Location/Qualifiers
source                  1..164
                        mol_type = protein
                        organism = synthetic construct
SEQUENCE: 82
MSDNNDEYWM RHALMLARRA RDEGEVPVGA VLVLEGRVIG EGWNRAIGHH DPTAHAEIMA  60
LRQGGKVIEN YRLLDTTLYV TFEPCVMCAG AMVHSRIGRL VFGVRNEKRG AAGSLLNVLG 120
YPGMNHQVQI EEGILAAECA AMLCDFYRHP RAVKNALRQA GKLL                  164

SEQ ID NO: 83           moltype =      length =
SEQUENCE: 83
000

SEQ ID NO: 84           moltype = AA   length = 171
FEATURE                 Location/Qualifiers
source                  1..171
                        mol_type = protein
                        organism = synthetic construct
SEQUENCE: 84
MLPGVVCVTQ EQDEYWMRRA LTLAQRAREQ GEVPVGAVLV QGDRVIGEGW NRAIGQHDPT  60
AHAEIMALRQ GGKVLENYRL LNTTLYVTFE PCIMCAGAMV HSRIGRLVYG VHNVKRGAAG 120
SLINILGYPG MNHQVALHQG VLEEECAAML CDFYRMPRQQ QNALRQAQRE S          171

SEQ ID NO: 85           moltype = AA   length = 164
FEATURE                 Location/Qualifiers
source                  1..164
                        mol_type = protein
                        organism = synthetic construct
SEQUENCE: 85
MNPQTDEYWM RYALELAKRA REQGEVPVGA VLVQGDKVIG EGWNRAIGQH DPTAHAEIMA  60
LRQGGKVLEN YRLLDTTLYV TFEPCVMCAG AMVHGRITRL VYGVKNDKRG AAGSLLNVIG 120
YPGMNHQIQI DCGVLAEECA GMLCDFYRMP REQKNALRQA QRIG                  164

SEQ ID NO: 86           moltype = AA   length = 164
FEATURE                 Location/Qualifiers
source                  1..164
```

```
                    mol_type = protein
                    organism = synthetic construct
SEQUENCE: 86
MNQQRDEYWM RHALGLARLA REQGEVPVGA VLVQDERVIG EGWNRAIGQH DPTAHAEMMA    60
LRQGGKVLEN YRLLNTTLYV TFEPCVMCAG AMVHSRITRL VYGVHNVKRG AAGSLLNVLG   120
YPGMNHQIEL HSGVLAEECA AMLCDFYRMP REQKNALRQA QRQS                   164

SEQ ID NO: 87           moltype = AA   length = 164
FEATURE                 Location/Qualifiers
source                  1..164
                        mol_type = protein
                        organism = synthetic construct
SEQUENCE: 87
MNQQHDEYWM RHALGLARLA REQGEVPVGA VLVQADRVIG EGWNRAIGQH DPTAHAEMMA    60
LRQGGKVLEN YRLLNTTLYV TFEPCVMCAG AMVHSRITRL VYGVHNVKRG AAGSLLNVLG   120
YPGMNHQVEL HSGVLADECA AMLCDFYQMP REQKNALRQA QRQG                   164

SEQ ID NO: 88           moltype =      length =
SEQUENCE: 88
000

SEQ ID NO: 89           moltype =      length =
SEQUENCE: 89
000

SEQ ID NO: 90           moltype =      length =
SEQUENCE: 90
000

SEQ ID NO: 91           moltype =      length =
SEQUENCE: 91
000

SEQ ID NO: 92           moltype =      length =
SEQUENCE: 92
000

SEQ ID NO: 93           moltype =      length =
SEQUENCE: 93
000

SEQ ID NO: 94           moltype = AA   length = 212
FEATURE                 Location/Qualifiers
source                  1..212
                        mol_type = protein
                        organism = synthetic construct
SEQUENCE: 94
MEQIKLDPKT LHAKTNSSDE LGCDEVSADV LAGEQPCLEQ ASLEQARVDE HWMRVAMTMA    60
EKAEAAGEVP VGAVLVKDGQ QIAAGYNLSI SEHDPCAHAE IQCLRAAGQT IENYRLLDTT   120
LYVTFEPCAM CAGAMVHSRI ARVVFGVKNE KRGAAGTVLN LLQYPAFNHQ VEVTSGVLAQ   180
ECADQLCRFY KRPREVKNAL KQAQKAQQGI LS                                212

SEQ ID NO: 95           moltype =      length =
SEQUENCE: 95
000

SEQ ID NO: 96           moltype =      length =
SEQUENCE: 96
000

SEQ ID NO: 97           moltype =      length =
SEQUENCE: 97
000

SEQ ID NO: 98           moltype =      length =
SEQUENCE: 98
000

SEQ ID NO: 99           moltype =      length =
SEQUENCE: 99
000

SEQ ID NO: 100          moltype =      length =
SEQUENCE: 100
000

SEQ ID NO: 101          moltype =      length =
SEQUENCE: 101
000
```

| SEQ ID NO: 102 | moltype = length = |
| --- | --- |
| SEQUENCE: 102 | |
| 000 | |

| SEQ ID NO: 103 | moltype = length = |
| --- | --- |
| SEQUENCE: 103 | |
| 000 | |

| SEQ ID NO: 104 | moltype = length = |
| --- | --- |
| SEQUENCE: 104 | |
| 000 | |

| SEQ ID NO: 105 | moltype = length = |
| --- | --- |
| SEQUENCE: 105 | |
| 000 | |

| SEQ ID NO: 106 | moltype = DNA length = 9062 |
| --- | --- |
| FEATURE | Location/Qualifiers |
| source | 1..9062 |
| | mol_type = other DNA |
| | organism = synthetic construct |

SEQUENCE: 106
```
tctagagggc cgtttaaaac ccgctgatca gcctcgactg tgccttctag ttgccagcca    60
tctgttgttt gcccctcccc cgtgccttcc ttgaccctgg aaggtgccac tcccactgtc   120
ctttcctaat aaaatgagga aattgcatcg cattgtctga gtaggtgtca ttctattctg   180
gggggtgggg tggggcagga cagcaagggg gaggattggg aagacaatag caggcatgct   240
ggggatgcgg tgggctctat ggtttgttac tttatagaag aaattttgag ttttgttt    300
tttttaataa ataaataaac ataaataaat tgtttgttga atttattatt agtatgtaag   360
tgtaaatata ataaaactta atatctattc aaattaataa ataaacctcg atatacagac   420
cgataaaaca catgcgtcaa ttttacgcat gattatcttt aacgtacgtc acaatatgat   480
tatctttcta gggttaactt ctactgggcg gttttatgga cagcaagcga accggaattg   540
ccagctgggg cgccctctgg taaggttggg aagccctgca aagtaaactg gatggctttc   600
tcgccgccaa ggatctgatg gcgcagggga tcaagctctg atcaagagac aggatgagga   660
tcgtttcgca tgattgaaca agatggattg cacgcaggtt ctccggccgc ttgggtgga   720
aggctattcg gctatgactg gcacaacaga caatcggct gctctgatgc cgccgtgttc   780
cggctgtcag cgcaggggcg cccggttctt tttgtcaaga ccgacctgtc cggtgccctg   840
aatgaactgc aagacgaggc agcgcggcta tcgtggctgg ccacgacggg cgttccttgc   900
gcagctgtgc tcgacgttgt cactgaagcg ggaaggggact ggctgctatt gggcgaagtg   960
ccggggcagg atctcctgtc atctcacctt gctcctgccg agaaagtatc catcatggct  1020
gatgcaatgc ggcggctgca tacgcttgat ccggctacct gcccattcga ccaccaagcg  1080
aaacatcgca tcgagcgagc acgtactcgg atggaagccg gtcttgtcga tcaggatgat  1140
ctggacgaag agcatcaggg gctcgcgcca gccgaactgt tcgccaggct caaggcgagc  1200
atgcccgacg gcgaggatct cgtcgtgacc catggcgatg cctgcttgcc gaatatcatg  1260
gtggaaaatg gccgcttttc tggattcatc gactgtggcc ggctgggtgt ggcggaccgc  1320
tatcaggaca tagcgttggc tacccgtgat attgctgaag agcttggcgg cgaatgggct  1380
gaccgcttcc tcgtgcttta cggtatcgcc gctcccgatt cgcagcgcat cgccttctat  1440
cgccttcttg acgagttctt ctgaattatt aacgcttaca atttcctgat gcggtatttt  1500
ctccttacgc atctgtgcgg tatttcacac cgcatacagg tggcactttt cggggaaatg  1560
tgcgcggaac ccctatttgt ttatttttct aaatacattc aaatatgtat ccgctcatga  1620
gacaataacc ctgataaatg cttcaataat agcacgtgct aaaacttcat ttttaattta  1680
aaaggatcta ggtgaagatc cttttttgata atctcatgac caaaatccct taacgtgagt  1740
tttcgttcca ctgagcgtca gaccccgtag aaaagatcaa aggatcttct tgagatcctt  1800
tttttctgcg cgtaatctgc tgcttgcaaa caaaaaaacc accgctacca gcggtggttt  1860
gtttgccgga tcaagagcta ccaactcttt ttccgaaggt aactggcttc agcagagcgc  1920
agataccaaa tactgtcctt ctagtgtagc cgtagttagg ccaccacttc aagaactctg  1980
tagcaccgcc tacatacctc gctctgctaa tcctgttacc agtggctgct gccagtggcg  2040
ataagtcgtg tcttaccggg ttggactcaa gacgatagtt accggataag cgcagcggt  2100
cgggctgaac ggggggttcg tgcacacagc ccagcttgga gcgaacgacc tacaccgaac  2160
tgagatacct acagcgtgag ctatgagaaa gcgccacgct tcccgaaggg agaaaggcgg  2220
acaggtatcc ggtaagcggc agggtcgaa caggagagcg cacgagggag cttccagggg  2280
gaaacgcctg gtatctttat agtcctgtcg ggtttcgcca cctctgactt gagcgtcgat  2340
ttttgtgatg ctcgtcaggg gggcggagcc tatggaaaaa cgccagcaac gcggcctttt  2400
tacggttcct gggcttttgc tggccttttg ctcacatgtt ctttcctgcg ttatcccctg  2460
attctgtgga taactgtgag tatcaccgta tattccgctt cgcaccgcag gacgcttgtc  2520
aatattgctc tctctttcta aatagcgcga atccgtcgct gtgcattag acatctcag  2580
tcgccgcttg gagctcccgt gaggcgtgct tgtcaatgcg gtaagtgtca ctgatttga  2640
actataacga ccgcgtgagt caaaatgacg catgttctac ttacgtgaa cttttaagat  2700
ttaactcata cgataattat attgttattt catgttctac ttacgtgata acttattata  2760
tatattttt cttgttatat gcagatatac gcgttgacat tgattattga ctagttatta  2820
atagtaatca attacgggt cattagttca tagcccatat atggagttcc gcgttacata  2880
acttacggta aatggcccgc ctggctgacc gcccaacgac ccccgcccat tgacgtcaat  2940
aatgacgtat gttcccatag taacgccaat agggactttc cattgacgtc aatgggtgga  3000
gtatttacgg taaactgccc acttggcagt acatcaagtg tatcatatgc caagtacgcc  3060
ccctattgac gtcaatgacg gtaaatggcc cgcctggcat tatgcccagt acatgacctt  3120
atgggacttt cctacttggc agtacatcta cgtattagtc atcgctatta ccatggtgat  3180
gcggttttgg cagtacatca atgggcgtgg atagcggttt gactcacggg gatttccaag  3240
tctccacccc attgacgtca atgggagttt gttttggcac caaaatcaac gggactttcc  3300
aaaatgtcgt aacaactccg ccccattgac gcaaatgggc ggtaggcgtg tacggtggga  3360
```

```
ggtctatata agcagagctg gtttagtgaa ccgtcagatc cgctagagat ccgcggccgc   3420
taatacgact cactataggg agagccgcca ccatgaaacg gacagccgac ggaagcgagt   3480
tcgagtcacc aaagaagaag cggaaagtct ctgaggtgga gttttcccac gagtactgga   3540
tgagacatgc cctgaccctg gccaagaggg cacgggatga gagggaggtg cctgtgggag   3600
ccgtgctggt gctgaacaat agagtgatcg gcgagggctg gaacagagcc atcggcctgc   3660
acgacccaac agcccatgcc gaaattatgg ccctgagaca gggcggcctg gtcatgcaga   3720
actacagact gattgacgcc accctgtacg tgacattcga gccttgcgtg atgtgcgccg   3780
gcgccatgat ccactctagg atcggccgcg tggtgtttgg cgtgaggaac tcaaaaagag   3840
gcgccgcagg ctccctgatg aacgtgctga actaccccgg catgaatcac cgcgtcgaaa   3900
ttaccgaggg aatcctggca gatgaatgtg ccgccctgct gtgcgatttc tatcggatgc   3960
ctagacaggt gttcaatgct cagaagaagg cccagagctc catcaactcc ggaggatcta   4020
gcggaggctc ctctggctct gagacacctg gcacaagcga gagcgcaaca cctgaaagca   4080
gcgggggcag cagcggggg tcagacaaga agtacagcat cggcctggcc atcggcacca   4140
actctgtggg ctgggccgtg atcaccgacg agtacaaggt gcccagcaag aaattcaagg   4200
tgctgggcaa caccgaccgg cacagcatca agaagaacct gatcggagcc ctgctgttcg   4260
acagcggcga aacagccgag gccacccggc tgaagagaac cgccagaaga agatacacca   4320
gacggaagaa ccggatctgc tatctgcaag agatcttcag caacgagatg gccaaggtgg   4380
acgacagctt cttccacaga ctggaagagt ccttcctggt ggaagaggat aagaagcacg   4440
agcggcaccc catcttcggc aacatcgtgg acgaggtggc ctaccacgag aagtacccca   4500
ccatctacca cctgagaaag aaactggtgg acagcaccga caaggccgac ctgcggctga   4560
tctatctggc cctggcccac atgatcaagt tccggggcca cttcctgatc gagggcgacc   4620
tgaaccccga caacagcgac gtggacaagc tgttcatcca gctggtgcag acctacaacc   4680
agctgttcga ggaaaacccc atcaacgcca gcggcgtgga cgccaaggcc atcctgtctg   4740
ccagactgag caagagcaga cggctggaaa atctgatcgc ccagctgccc ggcgagaaga   4800
agaatggcct gttcggaaac ctgattgccc tgagcctggg cctgacccc aacttcaaga   4860
gcaacttcga cctggccgag gatgccaaac tgcagctgag caaggacacc tacgacgacg   4920
acctggacaa cctgctggcc cagatcggcg accagtacgc cgacctgttt ctggccgcca   4980
agaacctgtc cgacgccatc ctgctgagcg acatcctgag agtgaacacc gagatcacca   5040
aggccccct gagcgcctct atgatcaaga gatacgacga gcaccaccag gacctgaccc   5100
tgctgaaagc tctcgtgcgg cagcagctgc ctgagaagta caaagagatt ttcttcgacc   5160
agagcaagaa cggctacgcc ggctacattg acggcggagc cagccaggaa gagttctaca   5220
agttcatcaa gcccatcctg gaaaagatgg acggcaccga ggaactgctc gtgaagctga   5280
acagagagga cctgctgcgg aagcagcgga ccttcgacaa cggcagcatc ccccaccaga   5340
tccacctggg agagctgcac gccattctgc ggcggcagga agattttac ccattcctga   5400
aggacaaccg ggaaaagatc gagaagatcc tgaccttccg catccctac tacgtgggcc   5460
ctctggccag gggaaacagc agattcgcct ggatgaccag aaagagcgag gaaaccatca   5520
cccctggaa cttcgaggaa gtggtggaca agggcgcttc cgcccagagc ttcatcgagc   5580
ggatgaccaa cttcgataag aacctgccca acgagaaggt gctgcccaag cacagcctgc   5640
tgtacgagta cttcaccgtg tataacgagc tgaccaaagt gaaatacgtg accgagggaa   5700
tgagaaagcc cgccttcctg agcggcgagc agaaaaaggc catcgtggac ctgctgttca   5760
agaccaaccg gaaagtgacc gtgaagcagc tgaaagagga ctacttcaag aaaatcgagt   5820
gcttcgactc cgtggaaatc tccggcgtgg aagatcggtt caacgcctcc ctgggcacat   5880
accacgatct gctgaaaatt atcaaggaca aggacttcct ggacaatgag gaaaacgagg   5940
acattctgga agatatcgtg ctgaccctga cactgtttga ggacagagag atgatcgagg   6000
aacggctgaa aacctatgcc cacctgttcg acgacaaagt gatgaagcag ctgaagcggc   6060
ggagatacac cggctgggc aggctgagcc ggaagctgat caacggcatc cgggacaagc   6120
agtccggcaa gacaatcctg gatttcctga agtccgaccg cttcgccaac agaaacttca   6180
tgcagctgat ccacgacgac agcctgacct ttaaagagga catccagaaa gcccaggtgt   6240
ccggccaggg cgatagcctg cacgagcaca ttgccaatct ggccggcagc cccgccatta   6300
agaagggcat cctgcagaca gtgaaggtgg tggacgagct cgtgaaagtg atgggccggc   6360
acaagcccga gaacatcgtg atcgaaatgg ccagagaaaa ccagaccacc cagaagggac   6420
agaagaacag ccgcgagaga atgaagcgga tcgaagaggg catcaaagag ctgggcagcc   6480
agatcctgaa agaacacccc gtggaaaaca cccagctgca gaacgagaag ctgtacctgt   6540
actacctgca gaatgggcgg gatatgtacg tggaccagga actggacatc aaccggctgt   6600
ccgactacga tgtggaccat atcgtgcctc agagcttttt gaaggacgac tccatcgaca   6660
acaaggtgct gaccagagcc gacaagaacc ggggcaagag cgacaacgtg ccctccgaag   6720
aggtcgtgaa gaagatgaag aactactggc ggcagctgct gaacgccaag ctgattaccc   6780
agagaaagtt cgacaatctg accaaggccg agagaggcgg cctgagcgaa ctggataagg   6840
ccggcttcat caagagacag ctggtggaaa cccggcagat cacaaagcac gtggcacaga   6900
tcctggactc ccggatgaac actaagtacg acgagaatga caagctgatc cgggaagtga   6960
aagtgatcac cctgaagtcc aagctggtgt ccgatttccg gaaggatttc cagttttaca   7020
aagtgcgcga gatcaacaac taccaccacg cccacgacgc ctacctgaac gccgtcgtgg   7080
gaaccgccct gatcaaaaag taccctaagc tggaaagcga gttcgtgtac ggcgactaca   7140
aggtgtacga cgtgcggaag atgatcgcca agagcgagca ggaaatcggc aaggctaccg   7200
ccaagtactt cttctacagc aacatcatga actttttcaa gaccgagatt accctgccaa   7260
acggcgagat ccgaaagcgg cctctgatcg agacaaacgg cgaaccgggg gagatcgtgt   7320
gggataaggg ccgggatttt gccaccgtgc ggaaagtgct gagcatgccc caagtgaata   7380
tcgtgaaaaa gaccgaggtg cagacaggcg gcttcagcaa agagtctatc ctgcccaaga   7440
ggaacagcga taagctgatc gccagaaaga aggactggga ccctaagaag tacggcggct   7500
tcgacagccc caccgtggcc tattctgtgc tggtggtggc caaagtggaa aagggcaagt   7560
ccaagaaact gaagagtgtg aaagagctgc tggggatcac catcatggaa agaagcagct   7620
tcgagaagaa tcccatcgac tttctggaag ccaagggcta caaagaagtg aaaaaggacc   7680
tgatcatcaa gctgcctaag tactccctgt tcgagctgga aaacggccgg aagagaatgc   7740
tggcctctgc cggcgaactg cagaagggaa acgaactggc cctgccctcc aaatatgtga   7800
acttcctgta cctggccagc cactatgaga gctgaaggg ctcccccgag gataatgagc   7860
agaaacagct gtttgtggaa cagcacaagc actacctgga cgagatcatc gagcagatca   7920
gcgagttctc caagagagtg atcctggccg acgctaatct ggacaaagtg ctgtccgcct   7980
acaacaagca ccgggataag cccatcagag agcaggccga gatatcatc cacctgttta   8040
ccctgaccaa tctgggagcc cctgccgcct tcaagtactt tgacaccacc atcgaccgga   8100
```

```
agaggtacac cagcaccaaa gaggtgctgg acgccaccct gatccaccag agcatcaccg   8160
gcctgtacga gacacggatc gacctgtctc agctgggagg tgactctggc ggctcaaaaa   8220
gaaccgccga cggcagcgaa ttcgagccca agaagaagag gaaagtcgga agcggagcta   8280
ctaacttcag cctgctgaag caggctggag acgtggagga gaaccctgga cctatgagcg   8340
agctgatcaa ggagaacatg cacatgaagc tgtacatgga gggcacccgg aacaaccacc   8400
acttcaagtg cacatccgag ggcgaaggca agcccctacga gggcacccag accatgaaga   8460
tcaaggtggt cgagggcggc cctctcccct tcgcctttcga catcctggct accagcttca   8520
tgtacggcag caaagccttc atcaaccaca cccagggcat ccccgacttc tttaagcagt   8580
ccttccctga gggcttcaca tgggagagaa tcaccacata cgaagacggg ggcgtgctga   8640
ccgctaccca ggacaccagc ttccagaacg gctgcatcat ctacaacgtc aagatcaacg   8700
gggtgaacttt cccatccaac ggccctgtga tgcagaagaa aacacgcggc tgggaggcca   8760
acaccgagat gctgtacccc gctgacggcg cctgagagg ccacagccag atggccctga   8820
agctcgtggg cgggggctac ctgcactgct ccttcaagac cacatacaga tccaagaaac   8880
ccgctaagaa cctcaagatg cccggcttcc acttcgtgga ccacagactg gaaagaatca   8940
aggaggccga caaagagacc tacgtcgagc agcacgagat ggctgtggcc aagtactgcg   9000
acctccctag caaactgggg cacagatctg gtggttctcc caagaagaag aggaaagtct   9060
aa                                                                 9062

SEQ ID NO: 107        moltype = RNA  length = 20
FEATURE               Location/Qualifiers
source                1..20
                      mol_type = other RNA
                      organism = synthetic construct
SEQUENCE: 107
cacacacact tagaatctgt                                              20

SEQ ID NO: 108        moltype = RNA  length = 20
FEATURE               Location/Qualifiers
source                1..20
                      mol_type = other RNA
                      organism = synthetic construct
SEQUENCE: 108
gcagagagtc gccgtctcca                                              20

SEQ ID NO: 109        moltype = RNA  length = 20
FEATURE               Location/Qualifiers
source                1..20
                      mol_type = other RNA
                      organism = synthetic construct
SEQUENCE: 109
cccgcaccctt ggcgcagcgg                                             20

SEQ ID NO: 110        moltype = RNA  length = 20
FEATURE               Location/Qualifiers
source                1..20
                      mol_type = other RNA
                      organism = synthetic construct
SEQUENCE: 110
gtttagagtg agccatgtag                                              20

SEQ ID NO: 111        moltype =     length =
SEQUENCE: 111
000

SEQ ID NO: 112        moltype =     length =
SEQUENCE: 112
000

SEQ ID NO: 113        moltype = RNA  length = 22
FEATURE               Location/Qualifiers
source                1..22
                      mol_type = other RNA
                      organism = synthetic construct
SEQUENCE: 113
gtgtcaggta atgtgctaaa ca                                           22

SEQ ID NO: 114        moltype =     length =
SEQUENCE: 114
000

SEQ ID NO: 115        moltype = RNA  length = 20
FEATURE               Location/Qualifiers
source                1..20
                      mol_type = other RNA
                      organism = synthetic construct
SEQUENCE: 115
tctgcttctc cagccctggc                                              20

SEQ ID NO: 116        moltype = AA  length = 170
```

| FEATURE | Location/Qualifiers |
|---|---|
| source | 1..170<br>mol_type = protein<br>organism = synthetic construct |

SEQUENCE: 116
```
MTESETDHIR WMRHALSLAQ RARDEGEVPV GAVLVYQGQV IGEGWNRAIG HHDPTAHAEM   60
MALRQGGIVL QNYRLLDTTL YVTFEPCVMC AGAMVHSRIG QLIYGVSNVK RGAAGSLMNV  120
LGYPGMNHKV SVAGGVLAQE CAGLLCDFYR MPRQVHNANK QAARQPSENQ             170
```

| SEQ ID NO: 117 | moltype = AA  length = 170 |
|---|---|
| FEATURE | Location/Qualifiers |
| source | 1..170<br>mol_type = protein<br>organism = synthetic construct |

SEQUENCE: 117
```
MTGSETDHIR WMRHALTLAQ RARDEGEVPV GAVLVYQGQV IGEGWNRAIG HHDPTAHAEM   60
MALRQGGIVL QNYRLLDTTL YVTFEPCVMC AGAMVHSRIG QLIYGVSNVK RGAAGSLMNV  120
LGYPGMNHKV SVAGGVLAQE CAGLLCDFYR MPRQVHNANK QAARQQSENQ             170
```

| SEQ ID NO: 118 | moltype = AA  length = 170 |
|---|---|
| FEATURE | Location/Qualifiers |
| source | 1..170<br>mol_type = protein<br>organism = synthetic construct |

SEQUENCE: 118
```
MSDTLIDEKW MRHALTLARR AREEGEVPVG AVLVQGDTVI GEGWNRAIGH HDPTAHAEIM   60
ALRQGGKVLE NYRLLDTTLY VTFEPCVMCA GAMVHGRVGR LVFGVRNEKR GAAGSLLNIL  120
GYAGMNHQVR VDQGVLAAEC AAMLCDFYRH PRAVKNALRD RLRAERLKGE             170
```

| SEQ ID NO: 119 | moltype = AA  length = 163 |
|---|---|
| FEATURE | Location/Qualifiers |
| source | 1..163<br>mol_type = protein<br>organism = synthetic construct |

SEQUENCE: 119
```
MTDYNDEFWM RHALTLAQRA RDEGEVPVGA VLVQGNRVIG EGWNRAIGHH DPTAHAEIMA   60
LRQGGKVLEN YRLIDTTLYV TFEPCVMCAG AIVHSRIGRL VFGVRNEKRG AAGSLLNVLG  120
YPGMNHQVKM TEGILAQQCA GMLCDFYRMP REQKNALRKS VKQ                   163
```

| SEQ ID NO: 120 | moltype = AA  length = 166 |
|---|---|
| FEATURE | Location/Qualifiers |
| source | 1..166<br>mol_type = protein<br>organism = synthetic construct |

SEQUENCE: 120
```
MTDHNDEYWM RHALRLARRA RDEGEVPVGA VLVLDNQVIG EGWNRAIGHH DPTAHAEMMA   60
LRQGGKMIEN YRLLDTTLYV TFEPCVMCAG AMIHSRIGRL VYGVRNSKRG AAGSLLNVLG  120
YPGMNHQVPA ECGLLNDECA AMLCDFYRQP RAVKNMLRQQ QNPGRV                166
```

| SEQ ID NO: 121 | moltype = AA  length = 164 |
|---|---|
| FEATURE | Location/Qualifiers |
| source | 1..164<br>mol_type = protein<br>organism = synthetic construct |

SEQUENCE: 121
```
MSDNNDEYWM RHALMLARRA RDEGEVPVGA VLVLEGRAIG EGWNRAIGHH DPTAHAEIMA   60
LRQGGKVIEN YRLLNTTLYV TFEPCVMCAG AMVHSRIGRL VFGVRNGKRG AAGSLLNVLG  120
YPGMNHQVQI EEGILATECA AMLCDFYRHP RAVKNAQRQA GKLL                  164
```

| SEQ ID NO: 122 | moltype = AA  length = 164 |
|---|---|
| FEATURE | Location/Qualifiers |
| source | 1..164<br>mol_type = protein<br>organism = synthetic construct |

SEQUENCE: 122
```
MTQEQDEYWM RRALTLAQRA REQGEVPVGA VLVQGDRVIG EGWNRAIGQH DPTAHAEIMA   60
LRQGGKVLEN YRLLNTTLYV TFEPCIMCAG AMVHSRIGRL VYGVHNSKRG AAGSLINILG  120
YPGMNHQVAL HQGVLEEECA AMLCDFYRMP RQQQNALRQA QRES                  164
```

| SEQ ID NO: 123 | moltype = AA  length = 201 |
|---|---|
| FEATURE | Location/Qualifiers |
| source | 1..201<br>mol_type = protein<br>organism = synthetic construct |

SEQUENCE: 123
```
MPVQLAPGRV YNAPAFITGV TPLSDIQLSH EYWMRHALTL AKRARDAREV PVGAVLVLNN   60
RAIGEGWNRA IGHHDPTAHA EIMALRQGGL VLENYRLLDA TLYVTFEPCV MCAGAMVHSR  120
IARVVFGVRQ SKRGAAGSLM NVLNYPGMNH RVEVTEGVLG EECAALLCEF YRMPRRVFNA  180
LKRASAQINE GQSAAAGPGE R                                           201
```

```
SEQ ID NO: 124          moltype = AA  length = 184
FEATURE                 Location/Qualifiers
source                  1..184
                        mol_type = protein
                        organism = synthetic construct
SEQUENCE: 124
MYNAPRFSTG VDALSETELN HEYWMRHALN LAQRAREEGE VPVGAVLVYQ DKVIGEGWNR    60
AIGLHDPTAH AEIMALRQGG MVLQNYRLID ATLYVTFEPC VMCAGAMIHS RIGRVVFGVR   120
QSKRGAAGSL INVLNYPGMN HRVEVTEGVL AESCSSLLCD FYREPREQKN ALKRASQDPR   180
SSNA                                                                184

SEQ ID NO: 125          moltype = AA  length = 201
FEATURE                 Location/Qualifiers
source                  1..201
                        mol_type = protein
                        organism = synthetic construct
SEQUENCE: 125
MPVQLAPGRV YNAPAFITGV TPLSDIQLSH EYWMRHALTL AKRARDARAA PVGAVLVLNN    60
RAIGEGWNRA IGHHDPTAHA EIIALRQGGL VLENYRLLDA TLYVTFEPCV MCAGAMVNSR   120
IARVVFGVRN SKRGAAGSLM NVLNYPGMNH RVEVTEGVLG EECAALLCEF YRMPRRVFNA   180
LKRASAQINE GQSAAAGPGE R                                             201

SEQ ID NO: 126          moltype = AA  length = 201
FEATURE                 Location/Qualifiers
source                  1..201
                        mol_type = protein
                        organism = synthetic construct
SEQUENCE: 126
MPVQLAPGRV YNAPAFITGV TPLSDIQLSH EYWMRHALTL AKRARDAGAG PVGAVLVLNN    60
RAIGEGWNRA IGHHDPTAHA EIMALRQGGL VLENYRLFDA TLYVTFEPCV MCAGAMVNSR   120
IARVVFGVRN SKRGAAGSLM NVLNYPGMNH RVEVTEGVLG EECAALLCEF YRMPRRVFNS   180
LKRASAQINE GQSAAAGPGE R                                             201

SEQ ID NO: 127          moltype = AA  length = 184
FEATURE                 Location/Qualifiers
source                  1..184
                        mol_type = protein
                        organism = synthetic construct
SEQUENCE: 127
MYNAPRFSTG VDALSETELN HEYWMRHALN LAQRAREEGA APVGAVLVYQ DKVIGEGWNR    60
AIGLHDPTAH AEIIALRQGG MVLQNYRLID ATLYVTFEPC VMCAGAMINS RIGRVVFGVR   120
NSKRGAAGSL INVLNYPGMN HRVEVTEGVL AESCSSLLCD FYREPREQKN ALKRASQDPR   180
SSNA                                                                184

SEQ ID NO: 128          moltype = AA  length = 184
FEATURE                 Location/Qualifiers
source                  1..184
                        mol_type = protein
                        organism = synthetic construct
SEQUENCE: 128
MYNAPRFSTG VDALSETELN HEYWMRHALN LAQRAREEGA GPVGAVLVYQ DKVIGEGWNR    60
AIGLHDPTAH AEIMALRQGG MVLQNYRLFD ATLYVTFEPC VMCAGAMINS RIGRVVFGVR   120
NSKRGAAGSL INVLNYPGMN HRVEVTEGVL AESCSSLLCD FYREPREQKN SLKRASQDPR   180
SSNA                                                                184

SEQ ID NO: 129          moltype = AA  length = 166
FEATURE                 Location/Qualifiers
source                  1..166
                        mol_type = protein
                        organism = synthetic construct
SEQUENCE: 129
MSDTEFTHEY WMQHALTLAQ RARDEGAAPV GAVLVQDNRV IGEGWNRAIG LHDPTAHAEI    60
IALRQGGMVL QNYRLLNTTL YVTFEPCIMC AGAMVNSRIG TLVFGVRNSK RGAVGSLMNV   120
PAYPGMNHHM QVIEGVLAPS CSALLCDFYR VPRLVKNAQK EASRKN                  166

SEQ ID NO: 130          moltype = AA  length = 166
FEATURE                 Location/Qualifiers
source                  1..166
                        mol_type = protein
                        organism = synthetic construct
SEQUENCE: 130
MSDTEFTHEY WMQHALTLAQ RARDEGAGPV GAVLVQDNRV IGEGWNRAIG LHDPTAHAEI    60
MALRQGGMVL QNYRLFNTTL YVTFEPCIMC AGAMVNSRIG TLVFGVRNSK RGAVGSLMNV   120
PAYPGMNHHM QVIEGVLAPS CSALLCDFYR VPRLVKNSQK EASRKN                  166

SEQ ID NO: 131          moltype = AA  length = 173
FEATURE                 Location/Qualifiers
source                  1..173
```

```
                            mol_type = protein
                            organism = synthetic construct
SEQUENCE: 131
MTTPALTHEY WMNYALTLAR RARDEGAAPV GAVLVYDNRV IGEGWNRSIG KHDPTAHAEI    60
IALRQGGMVQ QNYRLLDTTL YVTFEPCVMC AGAMINSRIG TLVFGVRNSK RGAVGSQMNI   120
LNYPGMNHQV QIIEGVLAPQ CSALLCDFYR MPRKVKNALK IASRDPHPAA PQR          173

SEQ ID NO: 132              moltype = AA   length = 173
FEATURE                     Location/Qualifiers
source                      1..173
                            mol_type = protein
                            organism = synthetic construct
SEQUENCE: 132
MTTPALTHEY WMNYALTLAR RARDEGAGPV GAVLVYDNRV IGEGWNRSIG KHDPTAHAEI    60
MALRQGGMVQ QNYRLFDTTL YVTFEPCVMC AGAMINSRIG TLVFGVRNSK RGAVGSQMNI   120
LNYPGMNHQV QIIEGVLAPQ CSALLCDFYR MPRKVKNSLK IASRDPHPAA PQR          173

SEQ ID NO: 133              moltype = AA   length = 165
FEATURE                     Location/Qualifiers
source                      1..165
                            mol_type = protein
                            organism = synthetic construct
SEQUENCE: 133
MDNHDHEYWM QHALTLAQRA REEGAAPVGA VLVLNGQAIG EGWNRAIGLH DPTAHAEMIA    60
LRQGGAVLQN YRLLNATLYV TFEPCVMCAG AMVNSRIARL VFGVRNSKRG AAGSLLNVLA   120
YPGMNHRVAV TEGVLAPACS ALLCDFYRQP RQQQNALKDA NRKRN                   165

SEQ ID NO: 134              moltype = AA   length = 165
FEATURE                     Location/Qualifiers
source                      1..165
                            mol_type = protein
                            organism = synthetic construct
SEQUENCE: 134
MDNHDHEYWM QHALTLAQRA REEGAGPVGA VLVLNGQAIG EGWNRAIGLH DPTAHAEMMA    60
LRQGGAVLQN YRLFNATLYV TFEPCVMCAG AMVNSRIARL VFGVRNSKRG AAGSLLNVLA   120
YPGMNHRVAV TEGVLAPACS ALLCDFYRQP RQQQNSLKDA NRKRN                   165

SEQ ID NO: 135              moltype = AA   length = 169
FEATURE                     Location/Qualifiers
source                      1..169
                            mol_type = protein
                            organism = synthetic construct
SEQUENCE: 135
MSDNNDEFWM RHALTLARRA RQEGAAPVGA VLVLEGRVIG EGWNRAIGHH DPTAHAEIIA    60
LRQGGKVIEN YRLLDTTLYV TFEPCVMCAG AMVNGRVGRL VFGVRNSKRG AAGSLINVLS   120
YPGMNHQVQV DEGVLAEECA AMLCDFYRQP RAVKNALRQQ QQGTSSAE                169

SEQ ID NO: 136              moltype = AA   length = 169
FEATURE                     Location/Qualifiers
source                      1..169
                            mol_type = protein
                            organism = synthetic construct
SEQUENCE: 136
MSDNNDEFWM RHALTLARRA RQEGAGPVGA VLVLEGRVIG EGWNRAIGHH DPTAHAEIMA    60
LRQGGKVIEN YRLFDTTLYV TFEPCVMCAG AMVNGRVGRL VFGVRNSKRG AAGSLINVLS   120
YPGMNHQVQV DEGVLAEECA AMLCDFYRQP RAVKNSLRQQ QQGTSSAE                169

SEQ ID NO: 137              moltype = AA   length = 164
FEATURE                     Location/Qualifiers
source                      1..164
                            mol_type = protein
                            organism = synthetic construct
SEQUENCE: 137
MSDNNDEYWM RHALMLARRA RDEGAAPVGA VLVLEGRVIG EGWNRAIGHH DPTAHAEIIA    60
LRQGGKVIEN YRLLDTTLYV TFEPCVMCAG AMVNSRIGRL VFGVRNEKRG AAGSLLNVLG   120
YPGMNHQVQI EEGILAAECA AMLCDFYRHP RAVKNALRQA GKLL                    164

SEQ ID NO: 138              moltype = AA   length = 164
FEATURE                     Location/Qualifiers
source                      1..164
                            mol_type = protein
                            organism = synthetic construct
SEQUENCE: 138
MSDNNDEYWM RHALMLARRA RDEGAGPVGA VLVLEGRVIG EGWNRAIGHH DPTAHAEIMA    60
LRQGGKVIEN YRLFDTTLYV TFEPCVMCAG AMVNSRIGRL VFGVRNEKRG AAGSLLNVLG   120
YPGMNHQVQI EEGILAAECA AMLCDFYRHP RAVKNSLRQA GKLL                    164

SEQ ID NO: 139              moltype = AA   length = 212
FEATURE                     Location/Qualifiers
```

```
source                          1..212
                                mol_type = protein
                                organism = synthetic construct
SEQUENCE: 139
MEQIKLDPKT LHAKTNSSDE LGCDEVSADV LAGEQPCLEQ ASLEQARVDE HWMRVAMTMA    60
EKAEAAGAAP VGAVLVKDGQ QIAAGYNLSI SEHDPCAHAE IQCLRAAGQT IENYRLLDTT   120
LYVTFEPCAM CAGAMVNSRI ARVVFGVKNE KRGAAGTVLN LLQYPAFNHQ VEVTSGVLAQ   180
ECADQLCRFY KRPREVKNAL KQAQKAQQGI LS                                 212

SEQ ID NO: 140                  moltype = AA    length = 212
FEATURE                         Location/Qualifiers
source                          1..212
                                mol_type = protein
                                organism = synthetic construct
SEQUENCE: 140
MEQIKLDPKT LHAKTNSSDE LGCDEVSADV LAGEQPCLEQ ASLEQARVDE HWMRVAMTMA    60
EKAEAAGAGP VGAVLVKDGQ QIAAGYNLSI SEHDPCAHAE IQCLRAAGQT IENYRLFDTT   120
LYVTFEPCAM CAGAMVNSRI ARVVFGVKNE KRGAAGTVLN LLQYPAFNHQ VEVTSGVLAQ   180
ECADQLCRFY KRPREVKNSL KQAQKAQQGI LS                                 212

SEQ ID NO: 141                  moltype = RNA   length = 20
FEATURE                         Location/Qualifiers
source                          1..20
                                mol_type = other RNA
                                organism = synthetic construct
SEQUENCE: 141
gagtccgagc agaagaagaa                                                20

SEQ ID NO: 142                  moltype = DNA   length = 9806
FEATURE                         Location/Qualifiers
source                          1..9806
                                mol_type = other DNA
                                organism = synthetic construct
SEQUENCE: 142
tctagagggc cgtttaaac  ccgctgatca gcctcgactg tgccttctag ttgccagcca    60
tctgttgttt gccccctccc cgtgccttcc ttgaccctgg aaggtgccac tcccactgtc   120
ctttcctaat aaaatgagga aattgcatcg cattgtctga gtaggtgtca ttctattctg   180
gggggtgggg tggggcagga cagcaagggg gaggattggg aagacaatag caggcatgct   240
ggggatgcgg tgggctctat ggtttgttac tttatagaag aaattttgac ttttgattt    300
tttttaataa ataaataaac ataaataaat tgtttgttga atttattatt agtatgtaag   360
tgtaaatata ataaaactta atatctattc aaattaataa ataaacctcg atatacagac   420
cgataaaaca catgcgtcaa ttttacgcat gattatcttt aacgtacgtc acaatatgat   480
tatctttcta gggttaactt ctactgggcg gttttatgga cagcaagcga accggaattg   540
ccagctgggg cgccctctgg taaggttggg aagcccgtgca aagtaaactg gatggctttc   600
tcgccgccaa ggatcgatg  gcgcagggga tcaagctctg atcaagagac aggatgagga   660
tcgtttcgca tgattgaaca agatggattg cacgcaggtt ctccgccgc  ttgggtggag   720
aggctattcg gctatgactg ggcacaacag acaatcggct gctctgatgc cgccgtgttc   780
cggctgtcag cgcaggggcg cccgttctt  tttgtcaaga ccgacctgtc cggtgccctg   840
aatgaactgc aagacgaggc agcgcggcta tcgtggctgg ccacgacggg cgttccttgc   900
gcagctgtgc tcgacgttgt cactgaagcg ggaagggact ggctgctatt gggcgaagtg   960
ccggggcagg atctcctgtc atctcacctt gctcctgccg agaaagtatc catcatgcgt  1020
gatgcaatgc ggcggctgca tacgcttgat ccggctacct gcccattcga ccaccaagcg  1080
aaacatcgca tcgagcgagc acgtactcgg atggaagccg tcttgtcga  tcaggatgat  1140
ctggacgaag agcatcaggg gctcgcgcca gccgaactgt tcgccaggct caaggcgagc  1200
atgcccgacg gcgaggatct cgtcgtgacc catggcgatg cctgcttgcc gaatatcatg  1260
gtggaaaatg gccgcttttc tggattcatc gactgtggcc ggctgggtgt ggcggaccgc  1320
tatcaggaca tagcgttggc tacccgtgat attgctgaag agcttggcgg cgaatgggct  1380
gaccgcttcc tcgtgcttta cggtatcgcc gctcccgatt cgcagcgcat cgccttctat  1440
cgccttcttg acgagttctt ctgaattatt aacgcttaca atttcctgat gcggtatttt  1500
ctccttacgc atctgtgcgg tatttcacac cgcatacagg tggcactttt cggggaaatg  1560
tgcgcggaac ccctatttgt ttatttttct aaatacattc aaatatgtat ccgctcatga  1620
gacaataacc ctgataaatg cttcaataat agcacgtgct aaaacttcat ttttaattta  1680
aaaggatcta ggtgaagatc cttttttgata atctcatgac caaaatccct taacgtgagt  1740
tttcgttcca ctgagcgtca ccccgtag   aaaagatcaa aggatcttct tgagatcctt  1800
ttttctgcg  cgtaatctgc tgcttgcaaa caaaaaaacc accgctacca gcggtggttt  1860
gtttgccgga tcaagagcta ccaactcttt tccgaaggt  aactggcttc agcagagcgc  1920
agataccaaa tactgtcctt ctagtgtagc cgtagttagg ccaccacttc aagaactctg  1980
tagcaccgcc tacatacctc gctctgctaa tcctgttacc agtggctgct gccagtgcg   2040
ataagtcgtg tcttaccggg ttggactcaa gacgatagtt accggataag gcgcagcggt  2100
cgggctgaac ggggggttcg tgcacacagc ccagcttgga gcgaacgacc tacaccgaac  2160
tgagatacct acagcgtgag ctatgagaaa gcgccacgct tcccgaaggg agaaaggcgg  2220
acaggtatcc ggtaagcggc agggtcgaa  caggagagcg cacagggag  cttcagggg   2280
gaaacgcctg gtatctttat agtcctgtcg ggtttcgcca cctctgactt gagcgtcgat  2340
ttttgtgatg ctcgtcaggg gggcggagcc tatggaaaa  cgccagcaac gcggcctttt  2400
tacggttcct gggcttttgc tggccttttg ctcacatgtt cttgctgctt cgcgatgtac  2460
gggccagata tattaccct  agaaagatag tctgcgtaaa attgacgcat gcattcttga  2520
aatattgctc tctcttttcta aatagcgcga atcgtcgct  gtgcatttag acatctcag   2580
tcgccgcttg gagctccgt  gaggcgtgct tgtcaatgcg gtaagtgtca ctgatttga   2640
actataacga ccgcgtgagt caaaatgacg catgattatc ttttacgtga cttttaagat  2700
```

```
ttaactcata cgataattat attgttattt catgttctac ttacgtgata acttattata   2760
tatatatttt cttgttatat gcagatatac gcgttgacat tgattattga ctagttatta   2820
atagtaatca attacgggt cattagttca tagcccatat atggagttcc gcgttacata    2880
acttacggta aatggcccgc ctggctgacc gcccaacgac ccccgcccat tgacgtcaat   2940
aatgacgtat gttcccatag taacgccaat agggactttc cattgacgtc aatgggtgga   3000
gtatttacgg taaactgccc acttggcagt acatcaagtg tatcatatgc caagtacgcc   3060
ccctattgac gtcaatgacg gtaaatggcc cgcctggcat tatgcccagt acatgacctt   3120
atgggacttt cctacttggc agtacatcta cgtattagtc atcgctatta ccatggtgat   3180
gcggttttgg cagtacatca atgggcgtgg atagcggttt gactcacggg gatttccaag   3240
tctccacccc attgacgtca atgggagttt gttttggcac caaaatcaac gggactttcc   3300
aaaatgtcgt aacaactccg ccccattgac gcaaatgggc ggtaggcgtg tacggtggga   3360
ggtctatata agcagagctg gtttagtgaa ccgtcagatc cgctagagat ccgcggccgc   3420
taatacgact cactataggg agagccgcca ccatgaaacg gacagccgac ggaagcgagt   3480
tcgagtcacc aaagaagaag cggaaagtct cctcagagac tgggcctgtc gccgtcgatc   3540
caaccctgcg ccgccggatt gaacctcacg agtttgaagt gttctttgac ccccgggagc   3600
tgagaaagga gacatgcctg ctgtacgaga tcaactgggg aggcaggcac tccatctgga   3660
ggcacacctc tcagaacaca aataagcacg tggaggtgaa cttcatcgag aagtttacca   3720
cagagcggta cttctgcccc aataccagat gtagcatcac atggtttctg agctggtccc   3780
cttgcggaga gtgtagcagg gccatcaccg agttcctgtc cagatatcca cacgtgacac   3840
tgtttatcta catcgccagg ctgtatcacc acgcagaccc aaggaatagg cagggcctgc   3900
gcgatctgat cagctccggc gtgaccatcc agatcatgac agagcaggag tccggctact   3960
gctggcggaa cttcgtgaat tattctccta gcaacgaggc ccactggcct aggtacccac   4020
acctgtgggt gcgcctgtac gtgctgagc tgtattgcat catcctgggc ctgccccctt    4080
gtctgaatat cctgcggaga aagcagcccc agctgacctt ctttacaatc gccctgcagt   4140
cttgtcacta tcagaggctg ccaccccaca tcctgtgggc cacaggcctg aagtctggag   4200
gatctagcgg aggatcctct ggcagcgaga caccaggaac gcaacaccag   4260
agagcagtgg cggcagcagc ggcggcagcg acaagaagta cagcatcggc ctggccatcg   4320
gcaccaactc tgtgggctgg gccgtgatca ccgacgagta caaggtgccc agcaagaaat   4380
tcaaggtgct gggcaacacc gaccggcaca gcatcaagaa gaacctgatc ggagccctgc   4440
tgttcgacag cggcgaaaca gccgaggcca cccgcctgaa gagaaccgcc agaagaagat   4500
acaccagacg gaagaaccgg atctgctatc tgcaagagat cttcagcaac gagatggcca   4560
aggtggacga cagcttcttc cacagactgg aagagtcctt cctggtggaa gaggataaga   4620
agcacgagcg gcaccccatc ttcggcaaca tcgtggacga ggtggcctac cacgagaagt   4680
accccaccat ctaccacctg agaaagaaac tggtggacag caccgacaag gccgacctgc   4740
ggctgatcta tctggccctg gcccacatga tcaagttccg gggccacttc ctgatcgagg   4800
gcgacctgaa ccccgacaac agcgacgtgg acaagctgtt catccagctg gtgcagacct   4860
acaaccagct gttcgaggaa aacccccatca acgccagcgg cgtggacgcc aaggccatcc   4920
tgtctgccag actgagcaag agcagacggc tggaaaatct gatcgcccag ctgccgggcg   4980
agaagaagaa tggcctgttc ggaaacctga ttgccctgag cctgggcctg acccccaact   5040
tcaagagcaa cttcgacctg gccgaggatg ccaaactgca gctgagcaag gacacctacg   5100
acgacgacct ggacaacctg ctggcccaga tcggcgacca gtacgccgac ctgtttctgg   5160
ccgccaagaa cctgtccgac gccatcctgc tgagcgacat cctgagagtg aacaccgaga   5220
tcaccaaggc cccccctgagc gcctctatga tcaagagata cgacgagcac caccaggacc   5280
tgaccctgct gaaagctctc gtgcggcagc agctgcctga aagtacaaa gagattttct    5340
tcgaccagag caagaacggc tacgccggct acattgacgg cggagccagc caggaagagt   5400
tctacaagtt catcaagccc atcctggaaa agatggacgg caccgaggaa ctgctcgtga   5460
agctgaacag agaggacctg ctgcggaaga gccgtccct cgacaacgag agcatcccat   5520
accagatcca cctgggagag ctgcacgcca ttctgcggcg gcaggaagat ttttacccat   5580
tcctgaagga caaccgggaa aagatcgaga agatcctgac cttccgcatc ccctactacg   5640
tgggccctct ggcagggga aacagcagat tcgcctggat gaccagaaag agcgaggaaa   5700
ccatcacccc ctggaacttc gaggaagtgg tggacaaggg cgcttccgcc cagagcttca   5760
tcgagcggat gaccaacttc gataagaacc tgcccaacga gaaggtgctg cccaagcaca   5820
gcctgctgta cgagtacttc accgtgtata acgagctgac caaagtgaaa tacgtgaccg   5880
agggaatgag aaagcccgcc ttcctgagcg gcgagcagaa aaaggccatc gtggacctgc   5940
tgttcaagac caaccggaaa gtgaccgtga agcagctgaa agaggactac ttcaagaaaa   6000
tcgagtgctt cgactccgtg gaaatctccg gcgtggaaga tcggttcaac gcctccctga   6060
gcacatacca cgatctgctg aaaattatca ggacaagga cttcctggac aatgaggaaa    6120
acgaggacat tctggaagat atcgtgctga ccctgacact gtttgaggac agagagatga   6180
tcgaggaacg gctgaaaacc tatgcccacc tgttcgacga caaagtgatg aagcagctga   6240
agcggcggta taccggc tgggcaggc tgagccggaa gctgatcaac ggcatccgga    6300
acaagcagtc cggcaagaca atcctggatt tcctgaagtc cgacggcttc gccaacagaa   6360
acttcatgca gctgatccac gacgacagcc tgaccttaa agaggacatc cagaaagccc    6420
aggtgtccgg ccagggcgat agcctgcacg agcacattgc caatctggcc ggcagccccg   6480
ccattaagaa gggcatcctg cagacagtga aggtggtgga cgagctcgtg aaagtgatgg   6540
gccggcacaa gcccgagaac atcgtgatcg aaatggccag agagaaccag accacccaga   6600
agggacagaa gaacagccgc gagagaatga agcggatcga gagggcatc aaagagctgg    6660
gcagccagat cctgaaagaa cacccgtgg aaaacaccca gctgcagaac gagaagcgt     6720
acctgtacta cctgcagaat gggcgggata tgtacgtgga ccaggaactg gacatcaacc   6780
ggctgtccga ctacgatgtg gaccatatcg tgcctcagag ctttctgaag gacgactcca   6840
tcgacaacaa ggtgctgacc agaagcgaca agaaccgggg caagagcgac aacgtgccct   6900
ccgaagaggt cgtgaagaag atgaagaact actggcggca gctgctgaac gccaagctga   6960
ttacccagag aaagttcgac aatctgacca aggccgagag gaggcggctg agcgaactgg   7020
ataaggccgg cttcatcaag agacagctgg tggaaaccg gcagatcaca aagcacgtgg    7080
cacagatcct ggactcccgg atgaacacta agtacgacga gaatgacaag ctgatccgag   7140
aagtgaaagt gatcaccctg aagtccaagc tggtgtccga tttccggaag gatttccagt   7200
tttacaaagt gcgcgagatc aacaactacc accacgccca cgacgcctac ctgaacgccg   7260
tcgtgggaac cgcctgatc aaaaagtacc ctaagctgga aagcgagttc gtgtacggcg    7320
actacaaggt gtacgacgtg cggaagatga tcgccaagag cgagcaggaa tcggcaagg    7380
ctaccgccaa gtacttcttc tacagcaaca tcatgaactt tttcaagacc gagattaccc   7440
```

```
tggccaacgg cgagatccgg aagcggcctc tgatcgagac aaacggcgaa accggggaga  7500
tcgtgtggga taagggccgg gattttgcca ccgtgcggaa agtgctgagc atgcccaag   7560
tgaatatcgt gaaaaagacc gaggtgcaga caggcggctt cagcaaagag tctatcctgc  7620
ccaagaggaa cagcgataag ctgatcgcca gaaagaagga ctgggaccct aagaagtacg  7680
gcggcttcga cagccccacc gtggcctatt ctgtgctggt ggtggccaaa gtggaaaagg  7740
gcaagtccaa gaaactgaag agtgtgaaag agctgctggg gatcaccatc atggaagaa  7800
gcagcttcga gaagaatccc atcgactttc tggaagccaa gggctacaaa gaagtgaaaa  7860
aggacctgat catcaagctg cctaagtact ccctgttcga gctggaaaac ggccggaaga  7920
gaatgctggc ctctgccggc gaactgcaga agggaaacga actggccctg ccctccaaat  7980
atgtgaactt cctgtacctg gccagccact atgagaagct gaagggctcc cccgaggata  8040
atgagcagaa acagctgttt gtggaacagc acaagcacta cctggacgag atcatcgagc  8100
agatcagcga gttctccaag agagtgatcc tggccgacgc taatctggac aaagtgctgt  8160
ccgcctacaa caagcaccgg ataagcccca tcagagagca ggccgagaat atcatccacc  8220
tgtttacccc tgaccaatctg ggagcccctg ccgccttcaa gtactttgac accaccatcg  8280
accggaagag gtacaccagc accaaagagg tgctggacgc caccctgatc caccagagca  8340
tcaccggcct gtacgagaca cggatcgacc tgtctcagct gggaggtgac agcggcggga  8400
gcggcggag cggggggagc actaatctga gcgacatcat tgagaaggag actgggaaac  8460
agctggtcat tcaggagtcc atcctgatgc tgcctgagga ggtggaggaa gtgatcggca  8520
acaagccaga gtctgacatc ctggtgcaca ccgcctacga cgagtccaca gatgagaatg  8580
tgatgctgct gacctctgac gcccccgagt ataagccttg ggccctggtc atccaggatt  8640
ctaacggcga gaataagatc aagatgctga gcggaggatc cggaggatct ggaggcagca  8700
ccaacctgtc tgacatcatc gagaaggaga caggcaagca gctggtcatc caggagagca  8760
tcctgatgct gcccgaagaa gtcgaagaag tgatcggaaa caagcctgag agcgatatcc  8820
tggtccatac cgcctacgac gagagtaccg acgaaaatgt gatgctgctg acatccgacg  8880
ccccagagta taagccctgg gctctggtca tccaggattc caacggagag aacaaaatca  8940
aaatgctgtc tggcggctca aaaagaaccg ccgacgtgga cgaattcgag cccaagaaga  9000
agaggaaagt cggaagcgga gctactaact tcagcctgct gaagcaggct ggagacgtgg  9060
aggagaaccc tggacctatg agcgagctga tcaaggagaa catgcacatg aagctgtaca  9120
tggagggcac cgtgaacaac caccacttca gtgcacatc cgagggcgaa ggcaagcct   9180
acgagggcac ccagaccatg aagatcaagg tggtcgaggg cggccctctc cccttcgcct  9240
tcgacatcct ggctaccagc ttcatgtacg gcagcaaagc cttcatcaac cacacccagg  9300
gcatccccga cttctttaag cagtccttcc ctgagggctt cacatgggag agaatcacca  9360
catacgaaga cgggggcgtg ctgaccgcta cccaggacac cagcttccag aacggctgca  9420
tcatctacaa cgtcaagatc aacttccatc aacggggtga acttcccatc ggcaacgccct  9480
agaaaacacg cggctgggag gccaacaccg agatgctgta ccccgctgac ggcggcctga  9540
gaggccacag ccagatggcc ctgaagctcg tgggcgggg  ctacctgcac tgctccttca  9600
agaccacata cagatccaag aaacccgcta agaacctcaa gatgcccggc ttccacttcg  9660
tggaccacag actggaaaga atcaaggagg ccgacaaaga gacctacgtc gagcagcacg  9720
agatggctgt ggccaagtac tgcgacctcc ctagcaaact ggggcacaga tctggtggtt  9780
ctcccaagaa gaagaggaaa gtctaa                                      9806

SEQ ID NO: 143          moltype =    length =
SEQUENCE: 143
000

SEQ ID NO: 144          moltype =    length =
SEQUENCE: 144
000

SEQ ID NO: 145          moltype =    length =
SEQUENCE: 145
000

SEQ ID NO: 146          moltype =    length =
SEQUENCE: 146
000

SEQ ID NO: 147          moltype =    length =
SEQUENCE: 147
000

SEQ ID NO: 148          moltype =    length =
SEQUENCE: 148
000

SEQ ID NO: 149          moltype =    length =
SEQUENCE: 149
000

SEQ ID NO: 150          moltype =    length =
SEQUENCE: 150
000

SEQ ID NO: 151          moltype =    length =
SEQUENCE: 151
000

SEQ ID NO: 152          moltype =    length =
SEQUENCE: 152
```

```
000

SEQ ID NO: 153         moltype =    length =
SEQUENCE: 153
000

SEQ ID NO: 154         moltype =    length =
SEQUENCE: 154
000

SEQ ID NO: 155         moltype =    length =
SEQUENCE: 155
000

SEQ ID NO: 156         moltype =    length =
SEQUENCE: 156
000

SEQ ID NO: 157         moltype =    length =
SEQUENCE: 157
000

SEQ ID NO: 158         moltype =    length =
SEQUENCE: 158
000

SEQ ID NO: 159         moltype =    length =
SEQUENCE: 159
000

SEQ ID NO: 160         moltype =    length =
SEQUENCE: 160
000

SEQ ID NO: 161         moltype =    length =
SEQUENCE: 161
000

SEQ ID NO: 162         moltype =    length =
SEQUENCE: 162
000

SEQ ID NO: 163         moltype =    length =
SEQUENCE: 163
000

SEQ ID NO: 164         moltype =    length =
SEQUENCE: 164
000

SEQ ID NO: 165         moltype =    length =
SEQUENCE: 165
000

SEQ ID NO: 166         moltype =    length =
SEQUENCE: 166
000

SEQ ID NO: 167         moltype =    length =
SEQUENCE: 167
000

SEQ ID NO: 168         moltype =    length =
SEQUENCE: 168
000

SEQ ID NO: 169         moltype =    length =
SEQUENCE: 169
000

SEQ ID NO: 170         moltype =    length =
SEQUENCE: 170
000

SEQ ID NO: 171         moltype =    length =
SEQUENCE: 171
000

SEQ ID NO: 172         moltype =    length =
```

| | | |
|---|---|---|
| SEQUENCE: 172 000 | | |
| SEQ ID NO: 173 SEQUENCE: 173 000 | moltype = | length = |
| SEQ ID NO: 174 SEQUENCE: 174 000 | moltype = | length = |
| SEQ ID NO: 175 SEQUENCE: 175 000 | moltype = | length = |
| SEQ ID NO: 176 SEQUENCE: 176 000 | moltype = | length = |
| SEQ ID NO: 177 SEQUENCE: 177 000 | moltype = | length = |
| SEQ ID NO: 178 SEQUENCE: 178 000 | moltype = | length = |
| SEQ ID NO: 179 SEQUENCE: 179 000 | moltype = | length = |
| SEQ ID NO: 180 SEQUENCE: 180 000 | moltype = | length = |
| SEQ ID NO: 181 SEQUENCE: 181 000 | moltype = | length = |
| SEQ ID NO: 182 SEQUENCE: 182 000 | moltype = | length = |
| SEQ ID NO: 183 SEQUENCE: 183 000 | moltype = | length = |
| SEQ ID NO: 184 SEQUENCE: 184 000 | moltype = | length = |
| SEQ ID NO: 185 SEQUENCE: 185 000 | moltype = | length = |
| SEQ ID NO: 186 SEQUENCE: 186 000 | moltype = | length = |
| SEQ ID NO: 187 SEQUENCE: 187 000 | moltype = | length = |
| SEQ ID NO: 188 SEQUENCE: 188 000 | moltype = | length = |
| SEQ ID NO: 189 SEQUENCE: 189 000 | moltype = | length = |
| SEQ ID NO: 190 SEQUENCE: 190 000 | moltype = | length = |
| SEQ ID NO: 191 SEQUENCE: 191 000 | moltype = | length = |

```
SEQ ID NO: 192           moltype =    length =
SEQUENCE: 192
000

SEQ ID NO: 193           moltype =    length =
SEQUENCE: 193
000

SEQ ID NO: 194           moltype =    length =
SEQUENCE: 194
000

SEQ ID NO: 195           moltype =    length =
SEQUENCE: 195
000

SEQ ID NO: 196           moltype =    length =
SEQUENCE: 196
000

SEQ ID NO: 197           moltype =    length =
SEQUENCE: 197
000

SEQ ID NO: 198           moltype =    length =
SEQUENCE: 198
000

SEQ ID NO: 199           moltype =    length =
SEQUENCE: 199
000

SEQ ID NO: 200           moltype = AA   length = 163
FEATURE                  Location/Qualifiers
source                   1..163
                         mol_type = protein
                         organism = synthetic construct
SEQUENCE: 200
MKQQDEYWMR HALSLARRAW EQGEVPVGAV LVQNDRVIGE GWNRPIGQHD PTAHAEIMAL  60
RQGGKILENY RLLDTTLYVT LEPCVMCAGA MVHSRIARLV YGAHDSKSGA AGSLLDVLGH 120
PGMNHQVELH SGVLAEACAA MLSDFFRMRR EQKKALRQAQ RQG                   163

SEQ ID NO: 201           moltype = AA   length = 207
FEATURE                  Location/Qualifiers
source                   1..207
                         mol_type = protein
                         organism = synthetic construct
SEQUENCE: 201
MSDQNSNRPT PNFDLANKQT QEKEAVQEPL TEIAMEDIAT EEDIMWMRHA LTLADKAESI  60
GEVPVGACVV LNGELIGEGF NTPITDNDPS AHAELRAVKE AAAAVQNYRL IDATLYVTLE 120
PCSMCAGMLV HARVKRVVFG AKDAKTGAAG SVMNLLQHPA LNHQLEVVSG VLADECANKL 180
SDFFRKRRKE IKAAKKAKRL LEGDASN                                     207

SEQ ID NO: 202           moltype = AA   length = 207
FEATURE                  Location/Qualifiers
source                   1..207
                         mol_type = protein
                         organism = synthetic construct
SEQUENCE: 202
MKFKQAESEQ VQSKQAEIDV VSLSSVEKAP VSLDSPHFDQ SKVDKHWMRV AMAMAEKAEA  60
EGEVPVGAVL VKDGQQIAAG YNLSISQHDP CAHAEILCLR AAGQTVENYR LLDATLYVTL 120
EPCAMCAGAM VHSRIARVVF GARDEKTGAA GTVLNLLQHP AFNHQVEVTS GVLAQDCADQ 180
LSRFFKRRRE EKKALKQAQK AQQERIS                                     207

SEQ ID NO: 203           moltype = AA   length = 208
FEATURE                  Location/Qualifiers
source                   1..208
                         mol_type = protein
                         organism = synthetic construct
SEQUENCE: 203
MEQTKLDPKT LHAKTHSSDE LGCDEVSGGE QTCPKQAALE QAQVDEHWMR VAMAMAEKAE  60
AEGEVPVGAV LVKDGQQIAT GYNLSISQHD PCAHAEILCL RAAGQTVENY RLLDATLYVT 120
LEPCAMCAGA MVHSRIARVV FGARDEKTGA AGTVLNLLQH PVFNHQVEVT SGVLAQDCAD 180
QLSRFFKRRR EEKKALKQAQ KAQQERIS                                    208

SEQ ID NO: 204           moltype = AA   length = 208
FEATURE                  Location/Qualifiers
source                   1..208
                         mol_type = protein
```

```
                    organism = synthetic construct
SEQUENCE: 204
MEQIKLDPKT LHAKTHSSDE LGCDDVSGGE QTCPKQADLE QAQVDEHWMR VAMAMAEKAE     60
AEGEVPVGAV LVKDGQQIAA GYNLSISQHD PCAHAEILCL RAAGQTVENY RLLDATLYVT    120
LEPCAMCAGA MVHSRIARVV FGARDEKTGA AGTVLNLLQH PVFNHQVEVT SGVLAQDCAD    180
QLSRFFKRRR EEKKALKQAQ KAQQERIS                                      208

SEQ ID NO: 205          moltype = AA   length = 165
FEATURE                 Location/Qualifiers
source                  1..165
                        mol_type = protein
                        organism = synthetic construct
SEQUENCE: 205
MNPQTDEYWM RHALRLARLA WEQGEVPVGA VLVQGDTVIG EGWNRPIGQH DPTAHAEIMA     60
LRQGGKVLEN YRLLDTTLYV TLEPCVMCAG AMVHSRITRL VYGAKDEKTG AAGSLLDVIG    120
HPGMNHQIQI DSGVLAEECA AMLSDFFRMR REQKKALRQA QRDAG                   165

SEQ ID NO: 206          moltype = AA   length = 162
FEATURE                 Location/Qualifiers
source                  1..162
                        mol_type = protein
                        organism = synthetic construct
SEQUENCE: 206
MTDEDWMQYA IKLAAKAEEQ GEVPVGAVLV KDGVMLSEGW NQMISLNDPS AHAEMQAIRA     60
ASALVGNYRL PDCTLYVTLE PCSMCAGVMV HSRIKKVVFG ASDLKTGAAG SVLNLLQHHC    120
FNHQVEIVPG VLAQQCAAQL SGFFQRRRAE HKALKRIQPQ AD                      162

SEQ ID NO: 207          moltype = AA   length = 170
FEATURE                 Location/Qualifiers
source                  1..170
                        mol_type = protein
                        organism = synthetic construct
SEQUENCE: 207
MTENRDLHWM QLAMEMAQKA EALGEVPVGA VLVKDDKLIA CGWNQPIAAN DPCAHAEILC     60
LRQAGSQLEN YRLLDTTLYV TLEPCAMCAG AMVHARVGRL VYGAADPKTG AAGSVLDLVR    120
HPLFNHKLAV SAGVMEQECS EQLSAFFRRR QEQKTLKQA RKLNPPAAEN                170

SEQ ID NO: 208          moltype = AA   length = 163
FEATURE                 Location/Qualifiers
source                  1..163
                        mol_type = protein
                        organism = synthetic construct
SEQUENCE: 208
MKQQDEYWMR HALSLARRAW EQGEVPVGAV LVQNDRVIGE GWNRPIGQHD PTAHAEIMAL     60
RQGGKVLENY RLLETTLYVT LEPCVMCAGA MVHSRITRLV YGAHDLKSGA AGSLLDVLGH    120
PGMNHQVELA SGVLAEECAA MLSDFFRMRR EEKKALRQAQ RQS                      163

SEQ ID NO: 209          moltype = AA   length = 186
FEATURE                 Location/Qualifiers
source                  1..186
                        mol_type = protein
                        organism = synthetic construct
SEQUENCE: 209
MPACGIISVY NVAFFLLETR VTDRNDEYWM RHALQLARRA WNEGEVPVGA VLVLDGQVIG     60
EGWNRPIGHH DPTAHAEMMA LRQGGKVIEN YRLMDTTLYV TLEPCVMCAG AMVHGRVGRL    120
VYGARDAKTG AAGSLLDVLG HPGMNHRVRV DCGVLADECA AMLSEFFRQR RAEKKALRQR    180
QSTDGI                                                              186

SEQ ID NO: 210          moltype = AA   length = 173
FEATURE                 Location/Qualifiers
source                  1..173
                        mol_type = protein
                        organism = synthetic construct
SEQUENCE: 210
MNHTLDGHDT PDEYWMRHAL TLAQRAQEEG EVPVGAVLVL DNQVIGEGWN RPIGHHDPTA     60
HAEIMALRQG GNVLQNYRLI NATLYVTLEP CVMCAGAMVH SRIGRLVYGA NDEKTGAAGS    120
LVDILRHPGM NHQITITSGV LAAECAHTLS DFFRIRRAQH KARRAQEKAD GAA           173

SEQ ID NO: 211          moltype = AA   length = 165
FEATURE                 Location/Qualifiers
source                  1..165
                        mol_type = protein
                        organism = synthetic construct
SEQUENCE: 211
MNQSQDEYWM RHALRLARIA WEQGEVPVGA VLVQGDRVIG EGWNRPIGQH DPTAHAEIMA     60
LRQGGKVLEN YRLLDTTLYV TLEPCVMCAG AMVHSRITRL VYGASDEKTG AAGSLIDVLG    120
HPGMNHQVAL HAGVLAEECA AMLSDFFRMR REQKKALRQA QRGID                   165

SEQ ID NO: 212          moltype = AA   length = 181
```

```
FEATURE                 Location/Qualifiers
source                  1..181
                        mol_type = protein
                        organism = synthetic construct
SEQUENCE: 212
MPAAFFPLES TVSEMSDEYW MRYALQLAHR AREQGEVPVG AVLVQGSKVI GEGWNRPIGQ    60
HDPTAHAEMM ALRQGGKVLE NYRLLDTTLY VTLEPCIMCA GAIVHSRIGR LVFGARDEKT   120
GAAGSLLDIL GHPGMNHQVK VEHGLLAEEC AAMLSDFFRM RREQKKALRQ AQREAQQTPS   180
S                                                                  181

SEQ ID NO: 213          moltype = AA  length = 163
FEATURE                 Location/Qualifiers
source                  1..163
                        mol_type = protein
                        organism = synthetic construct
SEQUENCE: 213
MNEQDEYWMR RAMALAARAE QEGEVPVGAL VVYHGDCVGE GWNRSIGHHD ATAHAEIMAL    60
RQAGAHLGNY RLLECTLYVT LEPCMMCAGA MVHSRIQRLV YGASDAKTGA VDSVLQLLAT   120
PGLNHRVDWR AGVLADACSA QLSDFFRRRR AEKKAARKQA AGG                     163

SEQ ID NO: 214          moltype = AA  length = 207
FEATURE                 Location/Qualifiers
source                  1..207
                        mol_type = protein
                        organism = synthetic construct
SEQUENCE: 214
MSDQNSNRPT PNFDLANKQT QEKEAVQEPL TEIAMEDIAT KEDIMWMRHA LTLADKAESI    60
GEVPVGACVV LNGELIGEGF NTPITDNDPS AHAELRAVKE AAAAVQNYRL IDATLYVTLE   120
PCSMCAGMLV HARVKRVVFG AKDAKTGAAG SVMNLLQHPA LNHQLEVVSG VLADECANKL   180
SDFFRKRRKE IKAAKKAKRL LEGDASS                                      207

SEQ ID NO: 215          moltype = AA  length = 164
FEATURE                 Location/Qualifiers
source                  1..164
                        mol_type = protein
                        organism = synthetic construct
SEQUENCE: 215
MDTLADDEYW MRHALILAQR AWDEGEVPVG AVLVQGGKVI GEGWNRPIGQ HDPTAHAEMM    60
ALRQGGRVLQ NYRLLDTTLY ITLEPCIMCA GAMVHSRISR LVYGAADAKT GAAGSLVDIL   120
RHPGMNHQVA ITSGVLAEAC STLLSDFFRM RRQQKAARA AGNA                     164

SEQ ID NO: 216          moltype = AA  length = 168
FEATURE                 Location/Qualifiers
source                  1..168
                        mol_type = protein
                        organism = synthetic construct
SEQUENCE: 216
MNSVNDDEFW MQHALTLAQR AWDEGEVPVG AVLVLGNQVI GEGWNRSIGQ HDPTAHAEIM    60
ALRQGGMVVQ NYRLLNSTLY ITLEPCVMCA GAMVHSRIGR LVYGAADAKT GAAGSLVDIL   120
RHPGMNHQIE ITSGVLAEAC STQLSDFFRM RRKEQKARRA AAKRESLS                168

SEQ ID NO: 217          moltype = AA  length = 165
FEATURE                 Location/Qualifiers
source                  1..165
                        mol_type = protein
                        organism = synthetic construct
SEQUENCE: 217
MTDNNDEFWM RHALQLAQRA WEEGEVPVGA VLVHQGRVIG EGWNRPIGHH DPTAHAEMMA    60
IRQGGKVIEN YRLLDTTLYV TLEPCVMCAG AMVHSRIGRL VFGARDAKTG AAGSLLDVLG   120
HPGMNHQVKF EHGILAEECA ALLSDFFRQR RAEKKAQRQK NSGLV                   165

SEQ ID NO: 218          moltype = AA  length = 164
FEATURE                 Location/Qualifiers
source                  1..164
                        mol_type = protein
                        organism = synthetic construct
SEQUENCE: 218
MTQEQDEYWM RRALTLAQRA WDEGEVPVGA VLVHGDRVIG EGWNRPIGQH DPTAHAEIMA    60
LRQGGKVLEN YRLLDTTLYV TLEPCVMCAG AMVHSRIGRL VYGAHDVKTG AAGSLIDVLG   120
HPGMNHQVRL DHGVLEDACA ALLSDFFRMR RQQKALRQA QRES                     164

SEQ ID NO: 219          moltype = AA  length = 162
FEATURE                 Location/Qualifiers
source                  1..162
                        mol_type = protein
                        organism = synthetic construct
SEQUENCE: 219
MTDQQDQYWM RYALQLAQRA WQAGEVPVGA VLVHDDRIIG EGWNRPIGQH DPTAHAEIMA    60
LRQGGQALQN YRLLDATLYV TLEPCTMCAG AMVHSRIGRL VFGANDEKTG AAGSLLNVLG   120
```

```
HPGMNHQVQV SSGILAQECA ALLSDFFRMR REQKKARRSA PL                    162

SEQ ID NO: 220           moltype = AA  length = 207
FEATURE                  Location/Qualifiers
source                   1..207
                         mol_type = protein
                         organism = synthetic construct
SEQUENCE: 220
MKFKQAESEQ VQSKQAEIDV VSLSSVEKAP VSLDSPHFDQ SKVDKHWMRV AMAMAEKAEA  60
EGEVPVGAVL VKDGQQIAAG YNLSISQHDP CAHAEILCLR AAGGTVENYR LLDATLYVTF  120
EPCAMCAGAM VHSRIARVVF GVRNEKRGAA GTVLNLLQYP AFNHQVEVTS GVLAQDCADQ  180
LCRFYKRPRE VKNALKQAQK AQQERIS                                      207

SEQ ID NO: 221           moltype = AA  length = 208
FEATURE                  Location/Qualifiers
source                   1..208
                         mol_type = protein
                         organism = synthetic construct
SEQUENCE: 221
MEQTKLDPKT LHAKTHSSDE LGCDEVSGGE QTCPKQAALE QAQVDEHWMR VAMAMAEKAE  60
AEGEVPVGAV LVKDGQQIAT GYNLSISQHD PCAHAEILCL RAAGGTVENY RLLDATLYVT  120
FEPCAMCAGA MVHSRIARVV FGVRNEKRGA AGTVLNLLQY PVFNHQVEVT SGVLAQDCAD  180
QLCRFYKRPR EVKNALKQAQ KAQQERIS                                     208

SEQ ID NO: 222           moltype = AA  length = 165
FEATURE                  Location/Qualifiers
source                   1..165
                         mol_type = protein
                         organism = synthetic construct
SEQUENCE: 222
MNPQTDEYWM RHALRLARLA REQGEVPVGA VLVQGDTVIG EGWNRAIGQH DPTAHAEIMA  60
LRQGGKVLEN YRLLDTTLYV TFEPCVMCAG AMVHSRITRL VYGVKNEKRG AAGSLLNVIG  120
YPGMNHQIQI DSGVLAEECA AMLCDFYRMP REQKNALRQA QRDAG                  165

SEQ ID NO: 223           moltype = AA  length = 162
FEATURE                  Location/Qualifiers
source                   1..162
                         mol_type = protein
                         organism = synthetic construct
SEQUENCE: 223
MTDEDWMQYA IKLAAKAEEQ GEVPVGAVLV KDGVMLSEGW NQMISLNDPS AHAEMQAIRA  60
ASALVGNYRL PDCTLYVTFE PCSMCAGVMV HSRIKKVVFG VSNLKRGAAG SVLNLLQYHC  120
FNHQVEIVPG VLAQQCAAQL CGFYQRPRAV HNALKRIQPQ AN                     162

SEQ ID NO: 224           moltype = AA  length = 186
FEATURE                  Location/Qualifiers
source                   1..186
                         mol_type = protein
                         organism = synthetic construct
SEQUENCE: 224
MPACGIISVY NVAFFLLETR VTDRNDEYWM RHALQLARRA RNEGEVPVGA VLVLDGQVIG  60
EGWNRAIGHH DPTAHAEMMA LRQGGKVIEN YRLMDTTLYV TFEPCVMCAG AMVHGRVGRL  120
VYGVRNSKRG AAGSLLNVLG YPGMNHRVRV DCGVLADECA AMLCEFYRQP RAVKNALRQR  180
QSTDGI                                                             186

SEQ ID NO: 225           moltype = AA  length = 173
FEATURE                  Location/Qualifiers
source                   1..173
                         mol_type = protein
                         organism = synthetic construct
SEQUENCE: 225
MNHTLDGHDT PDEYWMRHAL TLAQRAQEEG EVPVGAVLVL DNQVIGEGWN RAIGHHDPTA  60
HAEIMALRQG GNVLQNYRLI NATLYVTFEP CVMCAGAMVH SRIGRLVYGV NNEKRGAAGS  120
LVNILRYPGM NHQITITSGV LAAECAHTLC DFYRIPRAQH NARRAQEKAD GAA         173

SEQ ID NO: 226           moltype = AA  length = 165
FEATURE                  Location/Qualifiers
source                   1..165
                         mol_type = protein
                         organism = synthetic construct
SEQUENCE: 226
MNQSQDEYWM RHALRLARIA REQGEVPVGA VLVQGDRVIG EGWNRAIGQH DPTAHAEIMA  60
LRQGGKVLEN YRLLDTTLYV TFEPCVMCAG AMVHSRITRL VYGVSNEKRG AAGSLINVLG  120
YPGMNHQVAL HAGVLAEECA AMLCDFYRMP REQKNALRQA QRGIN                  165

SEQ ID NO: 227           moltype = AA  length = 181
FEATURE                  Location/Qualifiers
source                   1..181
                         mol_type = protein
```

```
SEQUENCE: 227
MPAAFFPLES TVSEMSDEYW MRYALQLAHR AREQGEVPVG AVLVQGSKVI GEGWNRAIGQ    60
HDPTAHAEMM ALRQGGKVLE NYRLLDTTLY VTFEPCIMCA GAIVHSRIGR LVFGVRNEKR   120
GAAGSLLNIL GYPGMNHQVK VEHGLLAEEC AAMLCDFYRM PREQKKALRQ AQREAQQTPS   180
S                                                                  181

SEQ ID NO: 228           moltype = AA   length = 164
FEATURE                  Location/Qualifiers
source                   1..164
                         mol_type = protein
                         organism = synthetic construct
SEQUENCE: 228
MDTLADDEYW MRHALILAQR ARDEGEVPVG AVLVQGGKVI GEGWNRAIGQ HDPTAHAEMM    60
ALRQGGRVLQ NYRLLDTTLY ITFEPCIMCA GAMVHSRISR LVYGVANSKR GAAGSLVNIL   120
RYPGMNHQVA ITSGVLAEAC STLLCDFYRM PRQQQNAARA AGNA                    164

SEQ ID NO: 229           moltype = AA   length = 168
FEATURE                  Location/Qualifiers
source                   1..168
                         mol_type = protein
                         organism = synthetic construct
SEQUENCE: 229
MNSVNDDEFW MQHALTLAQR ARDEGEVPVG AVLVLGNQVI GEGWNRSIGQ HDPTAHAEIM    60
ALRQGGMVVQ NYRLLNSTLY ITFEPCVMCA GAMVHSRIGR LVYGVANSKR GAAGSLVNIL   120
RYPGMNHQIE ITSGVLAEAC STQLCDFYRM PRKVQNARRA AAKRESLS                168

SEQ ID NO: 230           moltype = AA   length = 165
FEATURE                  Location/Qualifiers
source                   1..165
                         mol_type = protein
                         organism = synthetic construct
SEQUENCE: 230
MTDNNDEFWM RHALQLAQRA REEGEVPVGA VLVLQGRVIG EGWNRAIGHH DPTAHAEMMA    60
IRQGGKVIEN YRLLDTTLYV TFEPCVMCAG AMVHSRIGRL VFGVRNSKRG AAGSLLNVLG   120
YPGMNHQVKF EHGILAEECA ALLCDFYRQP RAVKNAQRQK NSGLV                   165

SEQ ID NO: 231           moltype = AA   length = 164
FEATURE                  Location/Qualifiers
source                   1..164
                         mol_type = protein
                         organism = synthetic construct
SEQUENCE: 231
MTQEQDEYWM RRALTLAQRA RDEGEVPVGA VLVLGDRVIG EGWNRAIGQH DPTAHAEIMA    60
LRQGGKVLEN YRLLDTTLYV TFEPCVMCAG AMVHSRIGRL VYGVHNVKRG AAGSLINVLG   120
YPGMNHQVRL DHGVLEDACA ALLCDFYRMP RQQQNALRQA QRES                    164

SEQ ID NO: 232           moltype = AA   length = 162
FEATURE                  Location/Qualifiers
source                   1..162
                         mol_type = protein
                         organism = synthetic construct
SEQUENCE: 232
MTDQQDQYWM RYALQLAQRA RQAGEVPVGA VLVLDDRIIG EGWNRAIGQH DPTAHAEIMA    60
LRQGGQALQN YRLLDATLYV TFEPCTMCAG AMVHSRIGRL VFGVNNEKRG AAGSLLNVLG   120
YPGMNHQVQV SSGILAQECA ALLCDFYRMP REQKNARRSA PL                      162

SEQ ID NO: 233           moltype = AA   length = 163
FEATURE                  Location/Qualifiers
source                   1..163
                         mol_type = protein
                         organism = synthetic construct
SEQUENCE: 233
MKQQDEYWMR HALSLARRAR EQGEVPVGAV LVQNDRVIGE GWNRAIGQHD PTAHAEIMAL    60
RQGGKILENY RLLDTTLYVT FEPCVMCAGA MVHSRIARLV YGAHNSKSGA AGSLLDVLGH   120
PGMNHQVELH SGVLAEACAA MLCRFFRMPR RQKNALRQAQ RQG                     163

SEQ ID NO: 234           moltype = AA   length = 207
FEATURE                  Location/Qualifiers
source                   1..207
                         mol_type = protein
                         organism = synthetic construct
SEQUENCE: 234
MSDQNSNRPT PNFDLANKQT QEKEAVQEPL TEIAMEDIAT EEDIMWMRHA LTLADKAESI    60
GEVPVGACVV LNGELIGEGF NTAITDNDPS AHAELRAVKE AAAAVQNYRL IDATLYVTFE   120
PCSMCAGMLV HARVKRVVVG AKNAKTGAAG SVMNLLQHPA LNHQLEVVSG VLADECANKL   180
CRFFRKPRRV FNAAKKAKRL LEGDASN                                      207

SEQ ID NO: 235           moltype = AA   length = 212
```

```
FEATURE              Location/Qualifiers
source               1..212
                     mol_type = protein
                     organism = synthetic construct
SEQUENCE: 235
MEQIKLDPKT LHAKTNSSDE LGCDEVSADV LAGEQPCLEQ ASLEQARVDE HWMRVAMTMA     60
EKAEAAGEVP VGAVLVKDGQ QIAAGYNLSI SEHDPCAHAE IQCLRAAGQT IENYRLLDTT    120
LYVTFEPCAM CAGAMVHSRI ARVVVGAKNE KTGAAGTVLN LLQHPAFNHQ VEVTSGVLAQ    180
ECADQLCRFF KRPRRVKNAL KQAQKAQQGT LS                                  212

SEQ ID NO: 236       moltype = AA  length = 208
FEATURE              Location/Qualifiers
source               1..208
                     mol_type = protein
                     organism = synthetic construct
SEQUENCE: 236
MEQIKLDPKT LHAKTHSSDE LGCDDVSGGE QTCPKQADLE QAQVDEHWMR VAMAMAEKAE     60
AEGEVPVGAV LVKDGQQIAA GYNLSISQHD PCAHAEILCL RAAGQTVENY RLLDATLYVT    120
FEPCAMCAGA MVHSRIARVV VGARNEKTGA AGTVLNLLQH PVFNHQVEVT SGVLAQDCAD    180
QLCRFFKRPR RVKNALKQAQ KAQQERIS                                       208

SEQ ID NO: 237       moltype = AA  length = 165
FEATURE              Location/Qualifiers
source               1..165
                     mol_type = protein
                     organism = synthetic construct
SEQUENCE: 237
MNPQTDEYWM RHALRLARLA REQGEVPVGA VLVQGDTVIG EGWNRAIGQH DPTAHAEIMA     60
LRQGGKVLEN YRLLDTTLYV TFEPCVMCAG AMVHSRITRL VYGAKNEKTG AAGSLLDVIG    120
HPGMNHQIQI DSGVLAEECA AMLCRFFRMP RRQKNALRQA QRDAG                    165

SEQ ID NO: 238       moltype = AA  length = 162
FEATURE              Location/Qualifiers
source               1..162
                     mol_type = protein
                     organism = synthetic construct
SEQUENCE: 238
MTDEDWMQYA IKLAAKAEEQ GEVPVGAVLV KDGVMLSEGW NQMISLNDPS AHAEMQAIRA     60
ASALVGNYRL PDCTLYVTFE PCSMCAGVMV HSRIKKVVVG ASNLKTGAAG SVLNLLQHHC    120
FNHQVEIVPG VLAQQCAAQL CRFFQRPRRV HNALKRIQPQ AD                       162

SEQ ID NO: 239       moltype = AA  length = 170
FEATURE              Location/Qualifiers
source               1..170
                     mol_type = protein
                     organism = synthetic construct
SEQUENCE: 239
MTENRDLHWM QLAMEMAQKA EALGEVPVGA VLVKDDKLIA CGWNQAIAAN DPCAHAEILC     60
LRQAGSQLEN YRLLDTTLYV TFEPCAMCAG AMVHARVGRL VYGAANPKTG AAGSVLDLVR    120
HPLFNHKLAV SAGVMEQECS EQLCRFFRRP RRVQKTLNQA RKLNPPAAEN               170

SEQ ID NO: 240       moltype = AA  length = 163
FEATURE              Location/Qualifiers
source               1..163
                     mol_type = protein
                     organism = synthetic construct
SEQUENCE: 240
MKQQDEYWMR HALSLARRAR EQGEVPVGAV LVQNDRVIGE GWNRAIGQHD PTAHAEIMAL     60
RQGGKVLENY RLLETTLYVT FEPCVMCAGA MVHSRITRLY GAHNLKSGA AGSLLDVLGH    120
PGMNHQVELA SGVLAEECAA MLCRFFRMPR RVKNALRQAQ RQS                      163

SEQ ID NO: 241       moltype = AA  length = 163
FEATURE              Location/Qualifiers
source               1..163
                     mol_type = protein
                     organism = synthetic construct
SEQUENCE: 241
MNEQDEYWMR RAMALAARAE QEGEVPVGAL VVYHGDCVGE GWNRSIGHHD ATAHAEIMAL     60
RQAGAHLGNY RLLECTLYVT FEPCMMCAGA MVHSRIQRLV YGASNAKTGA VDSVLQLLAH    120
PGLNHRVDWR AGVLADACSA QLCRFFRRPR RVKNAARKQA AGG                      163

SEQ ID NO: 242       moltype = AA  length = 207
FEATURE              Location/Qualifiers
source               1..207
                     mol_type = protein
                     organism = synthetic construct
SEQUENCE: 242
MSDQNSNRPT PNFDLANKQT QEKEAVQEPL TEIAMEDIAT KEDIMWRHA LTLADKAESI     60
GEVPVGACVV LNGELIGEGF NTAITDNDPS AHAELRAVKE AAAAVQNYRL IDATLYVTFE    120
```

```
PCSMCAGMLV HARVKRVVVG AKNAKTGAAG SVMNLLQHPA LNHQLEVVSG VLADECANKL   180
CRFFRKPRRV FNAAKKAKRL LEGDASS                                      207

SEQ ID NO: 243         moltype = RNA   length = 20
FEATURE                Location/Qualifiers
source                 1..20
                       mol_type = other RNA
                       organism = synthetic construct
SEQUENCE: 243
ccccaccgtt gaagaaccag                                              20

SEQ ID NO: 244         moltype = RNA   length = 20
FEATURE                Location/Qualifiers
source                 1..20
                       mol_type = other RNA
                       organism = synthetic construct
SEQUENCE: 244
gagtccgagc agaagaagaa                                              20

SEQ ID NO: 245         moltype = RNA   length = 20
FEATURE                Location/Qualifiers
source                 1..20
                       mol_type = other RNA
                       organism = synthetic construct
SEQUENCE: 245
ctaattacag cgcggtgtgg                                              20

SEQ ID NO: 246         moltype = RNA   length = 20
FEATURE                Location/Qualifiers
source                 1..20
                       mol_type = other RNA
                       organism = synthetic construct
SEQUENCE: 246
caaaaggtga agaaagaagt                                              20

SEQ ID NO: 247         moltype = RNA   length = 20
FEATURE                Location/Qualifiers
source                 1..20
                       mol_type = other RNA
                       organism = synthetic construct
SEQUENCE: 247
tcaaaaggtg aagaaagaag                                              20

SEQ ID NO: 248         moltype = RNA   length = 20
FEATURE                Location/Qualifiers
source                 1..20
                       mol_type = other RNA
                       organism = synthetic construct
SEQUENCE: 248
tcacagatta tggcctgtat                                              20

SEQ ID NO: 249         moltype = RNA   length = 20
FEATURE                Location/Qualifiers
source                 1..20
                       mol_type = other RNA
                       organism = synthetic construct
SEQUENCE: 249
cccgcacctt ggcgcagcgg                                              20

SEQ ID NO: 250         moltype = RNA   length = 20
FEATURE                Location/Qualifiers
source                 1..20
                       mol_type = other RNA
                       organism = synthetic construct
SEQUENCE: 250
ggctggcagg ctccttgttc                                              20

SEQ ID NO: 251         moltype = RNA   length = 20
FEATURE                Location/Qualifiers
source                 1..20
                       mol_type = other RNA
                       organism = synthetic construct
SEQUENCE: 251
gcaaatcagc atgttcctca                                              20

SEQ ID NO: 252         moltype = RNA   length = 16
FEATURE                Location/Qualifiers
source                 1..16
                       mol_type = other RNA
```

```
                               organism = synthetic construct
SEQUENCE: 252
agtggaagaa ggagat                                                              16

SEQ ID NO: 253         moltype = RNA   length = 16
FEATURE                Location/Qualifiers
source                 1..16
                       mol_type = other RNA
                       organism = synthetic construct
SEQUENCE: 253
atcttcacca ggaagc                                                              16

SEQ ID NO: 254         moltype = RNA   length = 20
FEATURE                Location/Qualifiers
source                 1..20
                       mol_type = other RNA
                       organism = synthetic construct
SEQUENCE: 254
tgactcacac tcacccaaaa                                                          20

SEQ ID NO: 255         moltype = RNA   length = 20
FEATURE                Location/Qualifiers
source                 1..20
                       mol_type = other RNA
                       organism = synthetic construct
SEQUENCE: 255
ctggaactgt aagagaatta                                                          20

SEQ ID NO: 256         moltype = AA    length = 20
FEATURE                Location/Qualifiers
source                 1..20
                       mol_type = protein
                       organism = synthetic construct
SEQUENCE: 256
GGSGGSGGSG GSGGSGGSGG                                                          20

SEQ ID NO: 257         moltype = AA    length = 20
FEATURE                Location/Qualifiers
source                 1..20
                       mol_type = protein
                       organism = synthetic construct
SEQUENCE: 257
GSSGSETPGT SESATPESSG                                                          20

SEQ ID NO: 258         moltype = RNA   length = 20
FEATURE                Location/Qualifiers
source                 1..20
                       mol_type = other RNA
                       organism = synthetic construct
SEQUENCE: 258
gacaaaccag aagccgctcc                                                          20

SEQ ID NO: 259         moltype = RNA   length = 20
FEATURE                Location/Qualifiers
source                 1..20
                       mol_type = other RNA
                       organism = synthetic construct
SEQUENCE: 259
gttcacaccc atgacgaaca                                                          20

SEQ ID NO: 260         moltype = RNA   length = 22
FEATURE                Location/Qualifiers
source                 1..22
                       mol_type = other RNA
                       organism = synthetic construct
SEQUENCE: 260
atttacagcc tggcctttgg gg                                                       22

SEQ ID NO: 261         moltype = RNA   length = 22
FEATURE                Location/Qualifiers
source                 1..22
                       mol_type = other RNA
                       organism = synthetic construct
SEQUENCE: 261
ggtggaggag ggtgcatggg gt                                                       22

SEQ ID NO: 262         moltype =       length =
SEQUENCE: 262
000
```

```
SEQ ID NO: 263            moltype =    length =
SEQUENCE: 263
000

SEQ ID NO: 264            moltype = RNA   length = 20
FEATURE                   Location/Qualifiers
source                    1..20
                          mol_type = other RNA
                          organism = synthetic construct
SEQUENCE: 264
atcttattcg atcatgcgaa                                                       20

SEQ ID NO: 265            moltype = RNA   length = 20
FEATURE                   Location/Qualifiers
source                    1..20
                          mol_type = other RNA
                          organism = synthetic construct
SEQUENCE: 265
gcttaggtgg agcgcctatt                                                       20

SEQ ID NO: 266            moltype = RNA   length = 20
FEATURE                   Location/Qualifiers
source                    1..20
                          mol_type = other RNA
                          organism = synthetic construct
SEQUENCE: 266
ttcattaact gtggccggct                                                       20

SEQ ID NO: 267            moltype = RNA   length = 20
FEATURE                   Location/Qualifiers
source                    1..20
                          mol_type = other RNA
                          organism = synthetic construct
SEQUENCE: 267
gactaggcac aacagacaat                                                       20

SEQ ID NO: 268            moltype = AA   length = 184
FEATURE                   Location/Qualifiers
source                    1..184
                          mol_type = protein
                          organism = synthetic construct
SEQUENCE: 268
MYNAPRFSTG VDALGETELN HEYWMRHALN LAQRAREEGE VPVGAVLVYQ DKVIGEGWNR            60
AIGLHDPTAH AEIMALRQGG MVLQNYRLID ATLYVTFEPC VMCAGAMIHS RIGRVVFGVR           120
NSKRGAAGSL INVLNYPGMN HRVEVTEGVL AERCSSLLCD FYRVPRWQKN ALKRASQDPR           180
SSNA                                                                       184

SEQ ID NO: 269            moltype = AA   length = 184
FEATURE                   Location/Qualifiers
source                    1..184
                          mol_type = protein
                          organism = synthetic construct
SEQUENCE: 269
MYNAPRFSTG VDALSETELN HEYWMRHALN LAQRAREEGE VPVGAVLVYQ DKVIGEGWNR            60
AIGLHDPTAH AEIMALRQGG MVLQNYRLID ATLYVTFEPC VMCAGAMIHS RIGRVVFGVR           120
NSKRGAAGSL INVLNYPGMN HRVEVTEGVL AESCSSLLRD FYRWPRWQKN ALKRASQDPR           180
SSNA                                                                       184

SEQ ID NO: 270            moltype = AA   length = 164
FEATURE                   Location/Qualifiers
source                    1..164
                          mol_type = protein
                          organism = synthetic construct
SEQUENCE: 270
MSDNNDEYWM RHALMLARRA RDEGEVPVGA VLVLEGRVIG EGWNRAIGHH DPTAHAEIMA            60
LRQGGKVIEN YRLLDTTLYV TFEPCVMCAG AMVHSRIGRL VFGMRNYKRG AAGSLLNVLG           120
YPGMNHQVQI EEGILAAECA AMLCDFYRHP RAVKNALRQA GKLL                           164

SEQ ID NO: 271            moltype = AA   length = 1483
FEATURE                   Location/Qualifiers
source                    1..1483
                          mol_type = protein
                          organism = synthetic construct
SEQUENCE: 271
MKRTADGSEF ESPKKKRKVM YNAPRFSTGV DALSETELNH EYWMRHALNL AQRAREEGEV            60
PVGAVLVYQD KVIGEGWNRA IGLHDPTAHA EIMALRQGGM VLQNYRLIDA TLYVTFEPCV           120
MCAGAMIHSR IGRVVFGVRN SKRGAAGSLI NVLNYPGMNH RVEVTEGVLA ESCSSLLCDF           180
YREPREQKNA LKRASQDPRS SNASGGSSGG SSGSETPGTS ESATPESSGG SSGGSSKLEK           240
```

```
FTNCYSLSKT LRFKAIPVGK TQENIDNKRL LVEDEKRAED YKGVKKLLDR YYLSFINDVL   300
HSIKLKNLNN YISLFRKKTR TEKENKELEN LEINLRKEIA KAFKGNEGYK SLFKKDIIET   360
ILPEFLDDKD EIALVNSFNG FTTAFTGFFD NRENMFSEEA KSTSIAFRCI NENLTRYISN   420
MDIFEKVDAI FDKHEVQEIK EKILNSDYDV EDFFEGEFFN FVLTQEGIDV YNAIIGGFVT   480
ESGEKIKGLN EYINLYNQKT KQKLPKFKPL YKQVLSDRES LSFYGEGYTS DEEVLEVFRN   540
TLNKNSEIFS SIKKLEKLFK NFDEYSSAGI FVKNGPAIST ISKDIFGEWN VIRDKWNAEY   600
DDIHLKKKAV VTEKYEDDRR KSFKKIGSFS LEQLQEYADA DLSVVEKLKE IIIQKVDEIY   660
KVYGSSEKLF DADFVLEKSL KKNDAVVAIM KDLLDSVKSF ENYIKAFFGE GKETNRDESF   720
YGDFVLAYDI LLKVDHIYDA IRNYVTQKPY SKDKFKLYFQ NPQFMGGWDK DKETDYRATI   780
LRYGSKYYLA IMDKKYAKCL QKIDKDDVNG NYEKINYKLL PGPNKMLPKV FFSKKWMAYY   840
NPSEDIQKIY KNGTFKKGDM FNLNDCHKLI DFFKDSISRY PKWSNAYDFN FSETEKYKDI   900
AGFYREVEEQ GYKVSFESAS KKEVDKLVEE GKLYMFQIYN KDFSDKSHGT PNLHTMYFKL   960
LFDENNHGQI RLSGGAELFM RRASLKKEEL VVHPANSPIA NKNPDNPKKT TTLSYDVYKD  1020
KRFSEDQYEL HIPIAINKCP KNIFKINTEV RVLLKHDDNP YVIGIARGER NLLYIVVVDG  1080
KGNIVEQYSL NEIINNFNGI RIKTDYHSLL DKKEKERFEA RQNWTSIENI KELKAGYISQ  1140
VVHKICELVE KYDAVIALAD LNSGFKNSRV KVEKQVYQKF EKMLIDKLNY MVDKKSNPCA  1200
TGGALKGYQI TNKFESFKSM STQNGFIFYI PAWLTSKIDP STGFVNLLKT KYTSIADSKK  1260
FISSFDRIMY VPEEDLFEFA LDYKNFSRTD ADYIKKWKLY SYGNRIRIFR NPKKNNVFDW  1320
EEVCLTSAYK ELFNKYGINY QQGDIRALLC EQSDKAFYSS FMALMSLMLQ MRNSITGRTD  1380
VAFLISPVKN SDGIFYDSRN YEAQENAILP KNADANGAYN IARKVLWAIG QFKKAEDEKL  1440
DKVKIAISNK EWLEYAQTSV KHSGGSKRTA DGSEFEPKKK RKV                   1483

SEQ ID NO: 272          moltype = AA  length = 752
FEATURE                 Location/Qualifiers
source                  1..752
                        mol_type = protein
                        organism = synthetic construct
SEQUENCE: 272
MKRTADGSEF ESPKKKRKVM YNAPRFSTGV DALSETELNH EYWMRHALNL AQRAREEGEV    60
PVGAVLVYQD KVIGEGWNRA IGLHDPTAHA EIMALRQGGM VLQNYRLIDA TLYVTFEPCV   120
MCAGAMIHSR IGRVVFGVRN SKRGAAGSLI NVLNYPGMNH RVEVTEGVLA ESCSSLLCDF   180
YREPREQKNA LKRASQDPRS SNASGGSSGG SSGSETPGTS ESATPESSGG SSGGSMMAVV   240
YVISKSGKPL MPTTRCGHVR ILLKEGKARV VERKPFTIQL TYESAEETQP LVLGIAPGRT   300
NIGMSVVTES GESVFNAQIR TRNKDVPKLM KDRKQYRMAH RRLKRRCKRR RRAKAAGTAF   360
EEGEKQRLLP GCFKPITCKS IRNKEARFNN RKRPVGWLTP TANHLLVTHL NVVKKVQKIL   420
PVAKVVLELN RFSFMAMNNP KVQRWQYQRG PLYGKGSVEE AVSMQQDGHC LFCKHGIDHY   480
HHVVPRRKNG SETLENRVGL CEEHHRLVHT DKEWEANLAS KKSGMNKKYH ALSVLNQIIP   540
YLADQLADMF PGNFCVTSGQ DTYLFREEHG IPKDHYLDAY CIACSALTDA KKVSSPKGRP   600
YMVRQFRRHD RQACHKANLN RRYYMGGKLV ATNRHKAMDQ KTDSLEEYRA AHSAADVSKL   660
TVKHPSAQYK DMSRIMPGSI LVSGEGKLFT LRRSEGRNKG QVNYFVSTEG IKYWARKCQY   720
LRNNGGLQIY VSGGSKRTAD GSEFEPKKKR KV                                752

SEQ ID NO: 273          moltype = AA  length = 684
FEATURE                 Location/Qualifiers
source                  1..684
                        mol_type = protein
                        organism = synthetic construct
SEQUENCE: 273
MKRTADGSEF ESPKKKRKVM YNAPRFSTGV DALSETELNH EYWMRHALNL AQRAREEGEV    60
PVGAVLVYQD KVIGEGWNRA IGLHDPTAHA EIMALRQGGM VLQNYRLIDA TLYVTFEPCV   120
MCAGAMIHSR IGRVVFGVRN SKRGAAGSLI NVLNYPGMNH RVEVTEGVLA ESCSSLLCDF   180
YREPREQKNA LKRASQDPRS SNASGGSSGG SSGSETPGTS ESATPESSGG SSGGSMGSPK   240
KKRKVEFMVN KSYKFRLYPT KEQEQLLAKT FGCVRFVYNK MLEERIQIYE KFKDDKEALK   300
KQTFPTPAKY KKEFPWLKEV DSLALANAQL NLQKAFQNFF SGRAGFPKFK NRKAKQSYTT   360
NVVNGNIQLS DGYIKLPKLK WVKFKQHREI PAHHIIKACT IKKTKTGKYY VSILTEYEHQ   420
PVPKEIQTVV GLDFSMNGLF VDSEGKRANY PRFYRQALEK LAKEQRILSR RKKGSNRWHK   480
QRLKVAKLHE KIANQRKDFL HKKSYELAKQ YDCVVIENLN MKGMSQVLNF GKSVHDNGWG   540
MFTTFLQYKL EEQGKKLIKI DKWFPSSKTC SCCDQVKESL SLSERTFRCE CGFESDRAVN   600
AAINIKHEGM KRLAIAGSKR PAATKKAGQA KKKKTGYPYD VPDYAYPYDV PDYAYPYDVP   660
DYASGGSKRT ADGSEFEPKK KRKV                                         684
```

DEAMINASES AND VARIANTS THEREOF FOR USE IN BASE EDITING

CROSS-REFERENCE TO RELATED APPLICATIONS

This application is a continuation of and claims priority to U.S. application Ser. No. 18/835,660, filed on Aug. 2, 2024, which is National Phase application of and claims the benefit of priority under 35 U.S.C. § 371 to International Application No. PCT/CN2024/094938 filed May 23, 2024 which claims priority to PCT/CN2023/095959, filed May 24, 2023, entitled DEAMINASES AND VARIANTS THEREOF FOR USE IN BASE EDITING and PCT/CN2023/107820, filed Jul. 18, 2023, entitled DEAMINASES AND VARIANTS THEREOF FOR USE IN BASE EDITING, the contents of which are incorporated by reference in their entirety herein.

SEQUENCE LISTING

This application contains a Sequence Listing that has been submitted electronically as an XML file named "53333-0009002_SL_ST26.XML." The XML file, created on Aug. 22, 2024, is 203,748 bytes in size. The material in the XML file is hereby incorporated by reference in its entirety.

TECHNICAL FIELD

This disclosure relates to deaminases for use with, e.g., nucleic acid-guided nucleases for making modifications in target nucleic acid sequences.

BACKGROUND

Targeted editing of nucleic acid sequences, for example, the targeted cleavage or the targeted modification of genomic DNA, is an effective approach for the study of gene function and also has the potential to provide new therapies for human genetic diseases. Currently available base editors include cytidine base editors (e.g., BE4) that convert target C·G base pairs to T·A base pairs, and adenine base editors (e.g., ABE7.10) that convert A·T base pairs to G·C base pairs. There is a need in the art for improved base editors capable of inducing modifications within a target sequence with greater specificity and efficiency.

SUMMARY

In a first aspect, the disclosure features an adenosine deaminase comprising an amino acid sequence that is at least 80%, 85%, 90%, 95%, 96%, 97%, 98%, 99%, or 100% identical to any one of SEQ ID NOs: 74, 82, 241, 268-270, 36, 39-47, 49-52, 59, 71, 75-81, 84-87, 94, 116-140, and 220-240, 242. In some embodiments, the adenosine deaminase is capable of deaminating adenosine in DNA. In some embodiments, the adenosine deaminase is capable of deaminating cytosine in DNA.

In some embodiments, the adenosine deaminase comprises one or more alterations at positions S15X, L19X, N30X, A61X, G63X, M81X, V95X, V119X, S122X, S153X, S155X, C159X, E164X, E167X as numbered relative to SEQ ID NO: 74, or one or more corresponding alterations thereof, wherein X is any amino acid. In some embodiments, the adenosine deaminase comprises one or more alterations at positions S15G, L19A, N30R, A61C, G63Q, M81N, V119M, S122R, S153R, S155R, C159R, E164V, E164L, E164W, E167W as numbered relative to SEQ ID NO: 74.

In some embodiments, the adenosine deaminase comprises one or more alterations at positions V104X, E107X as numbered relative to SEQ ID NO: 82, or one or more corresponding alterations thereof, wherein X is any amino acid. In some embodiments, the adenosine deaminase comprises one or more alterations at positions V104M, E107Y, E107K as numbered relative to SEQ ID NO: 82.

In some embodiments, the adenosine deaminase comprises one or more alterations at positions G64X, L67X, N69X, Y70X, L73X, F81X, H93X, A119X, S139X, C143X as numbered relative to SEQ ID NO: 241, or one or more corresponding alterations thereof, wherein X is any amino acid. In some embodiments, the adenosine deaminase comprises one or more alterations at positions G64Y, L67Y, N69A, Y70A, Y70G, L73F, F81L, H93V, A119H, S139K, C143A as numbered relative to SEQ ID NO: 241.

In another aspect, the disclosure features a nucleobase editor comprising (i) a polynucleotide programmable DNA binding domain; and (ii) an adenosine deaminase, wherein the adenosine deaminase has an amino acid sequence that is at least 80%, 85%, 90%, 95%, 96%, 97%, 98%, or 99% identical to any one of SEQ ID NOs: 74, 82, 241, 268-270, 36, 39-47, 49-52, 59, 71, 75-81, 84-87, 94, 116-140, and 220-240, 242. In some embodiments, the nucleobase editor further includes one or more uracil glycosylase inhibitor (UGI) domains. In some embodiments, the nucleobase editor is an adenosine base editor (ABE). In some embodiments, the nucleobase editor is a cytidine base editor (CBE). In some embodiments, the polynucleotide programmable DNA binding domain comprises a domain selected from the group consisting of a Cas9 domain, Cas 12 domain, TnpB domain, IscB domain, meganuclease domain, zinc finger DNA binding domain, and transcription activator-like effector (TALE) DNA binding domain. In some embodiments, the polynucleotide programmable DNA binding domain comprises a Cas9 domain. In some embodiments, Cas9 domain is a *Staphylococcus aureus* Cas9 (SaCas9), *Streptococcus thermophilus* 1 Cas9 (St1Cas9), a *Streptococcus pyogenes* Cas9 (SpCas9), or variants thereof. In some embodiments, the polynucleotide programmable DNA binding domain is a nuclease inactive or nickase variant.

In some embodiments, the base editor comprises a nucleic acid-guided nuclease protein and an inlaid nucleotide base editor (NBE) domain. In some embodiments, the inlaid NBE domain is an adenosine base editor (ABE) domain. In some embodiments, the inlaid ABE domain is an inlaid adenosine deaminase protein domain. In some embodiments, the polynucleotide programmable DNA binding domain comprises a linker that flanks at least one inlaid domain protein.

In another aspect, the disclosure features a polynucleotide encoding an adenosine deaminase that is at least 80%, 85%, 90%, 95%, 96%, 97%, 98%, or 99% identical to any one of SEQ ID NOs: 74, 82, 241, 268-270, 36, 39-47, 49-52, 59, 71, 75-81, 84-87, 94, 116-140, and 220-240, 242.

In another aspect, the disclosure features an expression vector comprising a polynucleotide encoding an adenosine deaminase that is at least 80%, 85%, 90%, 95%, 96%, 97%, 98%, or 99% identical to any one of SEQ ID NOs: 74, 82, 241, 268-270, 36, 39-47, 49-52, 59, 71, 75-81, 84-87, 94, 116-140, and 220-240, 242. In some embodiments, the expression vector is a viral vector selected from the group consisting of adeno-associated virus (AAV), retroviral vector, adenoviral vector, lentiviral vector, Sendai virus vector, and herpesvirus vector.

In another aspect, the disclosure features a polynucleotide encoding a nucleobase editor comprising (i) a polynucleotide programmable DNA binding domain; and (ii) an adenosine deaminase, wherein the adenosine deaminase has an amino acid sequence that is at least 80%, 85%, 90%, 95%, 96%, 97%, 98%, or 99% identical to any one of SEQ ID NOs: 74, 82, 241, 268-270, 36, 39-47, 49-52, 59, 71, 75-81, 84-87, 94, 116-140, and 220-240, 242.

In another aspect, the disclosure features an expression vector comprising a polynucleotide encoding a nucleobase editor comprising (i) a polynucleotide programmable DNA binding domain; and (ii) an adenosine deaminase, wherein the adenosine deaminase has an amino acid sequence that is at least 80%, 85%, 90%, 95%, 96%, 97%, 98%, or 99% identical to any one of SEQ ID NOs: 74, 82, 241, 268-270, 36, 39-47, 49-52, 59, 71, 75-81, 84-87, 94, 116-140, and 220-240, 242. In some embodiments, the vector is a viral vector selected from the group consisting of adeno-associated virus (AAV), retroviral vector, adenoviral vector, lentiviral vector, Sendai virus vector, and herpesvirus vector.

In another aspect, the disclosure features a method for base editing comprising contacting a polynucleotide sequence with a nucleobase editor comprising (i) a polynucleotide programmable DNA binding domain; and (ii) an adenosine deaminase, wherein the adenosine deaminase has an amino acid sequence that is at least 80%, 85%, 90%, 95%, 96%, 97%, 98%, or 99% identical to any one of SEQ ID NOs: 74, 82, 241, 268-270, 36, 39-47, 49-52, 59, 71, 75-81, 84-87, 94, 116-140, and 220-240, 242, wherein the adenosine deaminase deaminates a nucleobase in the polynucleotide, thereby editing the polynucleotide sequence.

In another aspect, the disclosure provides a method of correcting a genetic defect in a subject, the method comprising administering to the subject a nucleobase editor comprising (i) a polynucleotide programmable DNA binding domain; and (ii) an adenosine deaminase, wherein the adenosine deaminase has an amino acid sequence that is at least 80%, 85%, 90%, 95%, 96%, 97%, 98%, or 99% identical to any one of SEQ ID NOs: 74, 82, 241, 268-270, 36, 39-47, 49-52, 59, 71, 75-81, 84-87, 94, 116-140, and 220-240, 242, to deaminate a target nucleobase in a target nucleotide sequence of the subject, thereby correcting the genetic defect.

In another aspect, the disclosure provides a method of correcting a genetic defect in a subject, the method comprising administering to the subject a polynucleotide encoding a nucleobase editor comprising (i) a polynucleotide programmable DNA binding domain; and (ii) an adenosine deaminase, wherein the adenosine deaminase has an amino acid sequence that is at least 80%, 85%, 90%, 95%, 96%, 97%, 98%, or 99% identical to any one of SEQ ID NOs: 74, 82, 241, 268-270, 36, 39-47, 49-52, 59, 71, 75-81, 84-87, 94, 116-140, and 220-240, 242, to deaminate a target nucleobase in a target nucleotide sequence of the subject, thereby correcting the genetic defect. In some embodiments the method includes delivering the nucleobase editor or the polynucleotide encoding the nucleobase editor, and one or more guide polynucleotides to a cell of the subject. In some embodiments, the subject is a mammal or a human. In some embodiments, the deamination of the target nucleobase replaces the target nucleobase with a wild type nucleobase.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used.

The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Adenosine Base Editors

Figure 1A:
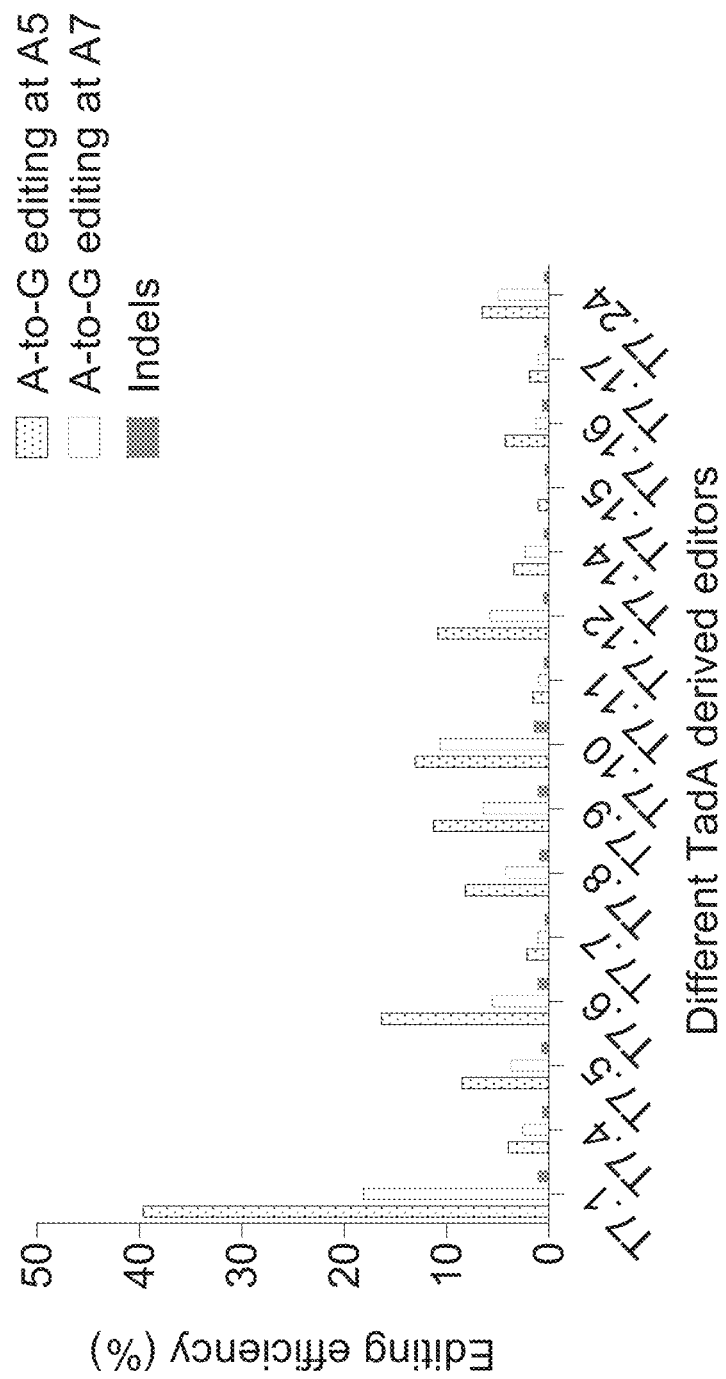
FIG. 1A is a plot of A-to-G editing efficiency and indel efficiency of adenine base editors with $1^{st}$ round engineered TadA variants at sgRNA0 target site measured by next-generation sequencing.

Disclosed herein are nucleobase editors, e.g., adenosine base editors, for editing, modifying or altering a target nucleotide sequence of a polynucleotide. Described herein are nucleobase editors comprising a programmable nucleotide binding domain, for example, a polynucleotide programmable nucleotide binding domain (e.g., Cas9) or zinc finger protein DNA binding domain or TALE DNA binding domain and at least one nucleobase editing domain, e.g., an adenosine deaminase. A polynucleotide programmable nucleotide binding domain (e.g., Cas9 or Cas12), when present in a cell and in conjunction with a bound guide polynucleotide (e.g., gRNA), can specifically bind to a target polynucleotide sequence (i.e., via complementary base pairing between bases of the bound guide nucleic acid and bases of the target polynucleotide sequence) and thereby localize the base editor to the target nucleic acid sequence desired to be edited.

In some embodiments, base editing activity is assessed by efficiency of editing. Base editing can be determined by any suitable means, for example, by Sanger sequencing or next generation sequencing. In some embodiments, base editing efficiency is measured by percentage of total sequencing reads with nucleobase conversion effected by the base editor, for example, percentage of total sequencing reads with target A-T base pair converted to a G-C base pair. In some embodiments, base editing efficiency is measured by percentage of total cells with nucleobase conversion effected by the base editor, when base editing is performed in a population of cells.

The term "base editor system" refers to the components required for editing a nucleobase of a target nucleotide sequence. In various embodiments, a base editor system comprises (1) a polynucleotide programmable nucleotide binding domain (e.g. Cas9); (2) a deaminase domain (e.g. an adenosine deaminase and/or cytidine deaminase; see PCT/US2019/044935, PCT/US2020/016288, each of which is incorporated herein by reference for its entirety) for deaminating said nucleobase; and (3) one or more guide polynucleotide (e.g., guide RNA). In some embodiments, a polynucleotide programmable nucleotide binding domain is a polynucleotide programmable DNA binding domain. In some embodiments, a base editor is an adenine or adenosine base editor (ABE).

In some embodiments, a base editor system can comprise more than one base editing component. For example, a base editor system can include more than one deaminase. In some embodiments, a base editor system can include one or more adenosine deaminases. In some embodiments, a single guide polynucleotide can be utilized to target different deaminases to a target nucleic acid sequence. In some embodiments, a pair of guide polynucleotides can be utilized to target different deaminases to a target nucleic acid sequence.

The deaminase domain and the polynucleotide programmable nucleotide binding component of a base editor system can be associated with each other covalently or noncovalently, or any combination of associations and interactions thereof. For example, in some embodiments, a deaminase domain can be targeted to a target nucleotide sequence by a polynucleotide programmable nucleotide binding domain.

In some embodiments, a polynucleotide programmable nucleotide binding domain can be fused or linked to a deaminase domain. In some embodiments, a polynucleotide programmable nucleotide binding domain can target a deaminase domain to a target nucleotide sequence by non-covalently interacting with or associating with the deaminase domain. For example, in some embodiments, the deaminase domain can comprise an additional heterologous portion or domain that is capable of interacting with, associating with, or capable of forming a complex with an additional heterologous portion or domain that is part of a polynucleotide programmable nucleotide binding domain.

In some embodiments, the additional heterologous portion can be capable of binding to, interacting with, associating with, or forming a complex with a polypeptide. In some embodiments, the additional heterologous portion can be capable of binding to, interacting with, associating with, or forming a complex with a polynucleotide. In some embodiments, the additional heterologous portion can be capable of binding to a guide polynucleotide. In some embodiments, the additional heterologous portion can be capable of binding to a polypeptide linker. In some embodiments, the additional heterologous portion can be capable of binding to a polynucleotide linker. The additional heterologous portion can be a protein domain. In some embodiments, the additional heterologous portion can be a K Homology (KH) domain, a MS2 coat protein domain, a PP7 coat protein domain, a SfMu Com coat protein domain, a steril alpha motif, a telomerase Ku binding motif and Ku protein, a telomerase Sm7 binding motif and Sm7 protein, or a RNA recognition motif.

A base editor system can further include a guide polynucleotide component. It should be appreciated that components of the base editor system can be associated with each other via covalent bonds, noncovalent interactions, or any combination of associations and interactions thereof. In some embodiments, a deaminase domain can be targeted to a target nucleotide sequence by a guide polynucleotide. For example, in some embodiments, the deaminase domain can comprise an additional heterologous portion or domain (e.g., polynucleotide binding domain such as an RNA or DNA binding protein) that is capable of interacting with, associating with, or capable of forming a complex with a portion or segment (e.g., a polynucleotide motif) of a guide polynucleotide. In some embodiments, the additional heterologous portion or domain (e.g., polynucleotide binding domain such as an RNA or DNA binding protein) can be fused or linked to the deaminase domain. In some embodiments, the additional heterologous portion can be capable of binding to, interacting with, associating with, or forming a complex with a polypeptide. In some embodiments, the additional heterologous portion can be capable of binding to, interacting with, associating with, or forming a complex with a polynucleotide. In some embodiments, the additional heterologous portion can be capable of binding to a guide polynucleotide. In some embodiments, the additional heterologous portion can be capable of binding to a polypeptide linker. In some embodiments, the additional heterologous portion can be capable of binding to a polynucleotide linker. The additional heterologous portion can be a protein domain. In some embodiments, the additional heterologous portion can be a K Homology (KH) domain, a MS2 coat protein domain, a PP7 coat protein domain, a SfMu Com coat protein domain, a sterile alpha motif, a telomerase Ku binding motif and Ku protein, a telomerase Sm7 binding motif and Sm7 protein, or a RNA recognition motif.

Guide Polynucleotides

In some embodiments, the guide polynucleotide is a guide RNA. An RNA/Cas complex can assist in "guiding" a Cas protein to a target DNA. Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA," or simply "gRNA") can be engineered so as to incorporate aspects of both the crRNA and tracrRNA into a single RNA species. See, e.g., Jinek M. et al., Science 337:816-821 (2012), the entire contents of which is hereby incorporated by reference. Cas9 recognizes a short motif in the CRISPR repeat sequences (the PAM or protospacer adjacent motif) to help distinguish self versus non-self.

Cas9 nuclease sequences and structures are well known to those of skill in the art (see e.g., "Complete genome sequence of an M1 strain of *Streptococcus pyogenes*." Ferretti, J. J. et al., Natl. Acad. Sci. U.S.A. 98:4658-4663 (2001); "CRISPR RNA maturation by trans-encoded small RNA and host factor RNase III." Deltcheva E. et al., Nature 471:602-607(2011); and "Programmable dual-RNA-guided DNA endonuclease in adaptive bacterial immunity." Jinek M. et al, Science 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences would be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain, that is, the Cas9 is a nickase. In some embodiments, the guide polynucleotide is at least one single guide RNA ("sgRNA" or "gNRA"). In some embodiments, the guide polynucleotide is at least one tracrRNA. In some embodiments, the guide polynucleotide does not require protospacer adjacent motif (PAM) sequence to guide the polynucleotide-programmable DNA-binding domain (e.g., Cas9 or Cpf1) to the target nucleotide sequence. The polynucleotide programmable nucleotide binding domain (e.g., a CRISPR-derived domain) of the base editors disclosed herein can recognize a target polynucleotide sequence by associating with a guide polynucleotide. A guide polynucleotide (e.g., gRNA) is typically single-stranded and can be programmed to site-specifically bind (i.e., via complementary base pairing) to a target sequence of a polynucleotide, thereby directing a base editor that is in conjunction with the guide nucleic acid to the target sequence. A guide polynucleotide can be DNA. A guide polynucleotide can be RNA. In some embodiments, the guide polynucleotide comprises natural nucleotides (e.g., adenosine). In some embodiments, the guide polynucleotide comprises non-natural (or unnatural) nucleotides (e.g., peptide nucleic acid or nucleotide analogs). In some embodiments, the targeting region of a guide nucleic acid sequence can be at least 15, 16, 17, 18, 19, 20, 21, 22, 23, 24, 25, 26, 27, 28, 29, or 30 nucleotides in length. A targeting region of a guide nucleic acid can be between 10-30 nucleotides in length, or between 15-25 nucleotides in length, or between 15-20 nucleotides in length.

Programmable Nucleotide Binding Domain

A programmable nucleotide binding domain of a base editor can itself comprise one or more domains. For example, a polynucleotide programmable nucleotide binding domain can comprise one or more nuclease domains. In some embodiments, the nuclease domain of a polynucleotide programmable nucleotide binding domain can comprise an endonuclease or an exonuclease. Herein the term "exonuclease" refers to a protein or polypeptide capable of digesting a nucleic acid (e.g., RNA or DNA) from free ends, and the term "endonuclease" refers to a protein or polypeptide capable of catalyzing (e.g., cleaving) internal regions in a nucleic acid (e.g., DNA or RNA). In some embodiments, an endonuclease can cleave a single strand of a double-stranded nucleic acid.

Any DNA destabilizing molecule can be used in the compositions described herein in any combination, including but not limited to a Cas9 or Cas12 nickase, a Cas9 or Cas12 protein (e.g., dCas) operably linked to a single guide RNA (sgRNA), any RNA programmable system, a zinc finger nuclease nickase (ZFN nickase), a TALEN nickase, and/or one or more nucleotides (e.g., one or more peptide nucleic acids (PNAs), locked nucleic acids (LNAs) and/or bridged nucleic acids (BNAs)). In certain embodiments, the base editing composition comprises more than one DNA destabilizing molecule, for example one or more proteins (e.g., nickases, etc.) and/or one or more nucleotides. In certain embodiments, the composition comprises a ZFN nickase and one or more additional proteins and/or nucleotide DNA destabilizing molecules (e.g., one or more nucleotides as described herein). In certain aspects, the base editing composition does not comprise a Cas9 protein, but may comprise other Cas protein (e.g., non-Cas9 RNA programmable systems). In certain embodiments, the DNA-destabilizing molecule comprises a zinc finger nuclease (ZFN) nickase.

In some embodiments, the nuclease is a zinc finger nuclease (ZFN) or TALE DNA binding domain-nuclease fusion (TALEN). ZFNs and TALENs comprise a DNA binding domain (zinc finger protein or TALE DNA binding domain) that has been engineered to bind to a target site in a gene of choice and cleavage domain or a cleavage half domain.

The at least one zinc finger protein (ZFP) DNA-binding domain of the base editing composition can be operably linked to one or more of the other components of the base editing composition, for example to one or more of the DNA destabilizing molecules (e.g., to Cas9 nickase, dCas9, etc.) and/or to the at least one adenine or cytosine deaminase. In certain embodiments, at least one ZFP DNA-binding domain is operably linked to the adenine or cytosine deaminase. In other embodiments, the base editing composition comprises first and second ZFP DNA-binding domains, wherein the first ZFP DNA-binding domain is operably linked to the Cas9 nickase. The ZFP DNA-binding domain can comprise 3, 4, 5, 6 or more fingers and may bind to a target site on either side (5' or 3') of the targeted base to be edited. In certain embodiments, the ZFP binds to a target site that is 1 to 100 (or any number therebetween) nucleotides on either side of the targeted base. In other embodiments, the ZFP binds to a target site that is 1 to 50 (or any number therebetween) nucleotides on either side of the targeted base.

In some embodiments, an endonuclease can cleave both strands of a double-stranded nucleic acid molecule. In some embodiments a polynucleotide programmable nucleotide binding domain can be a deoxyribonuclease. In some embodiments a polynucleotide programmable nucleotide binding domain can be a ribonuclease.

In some embodiments, a nuclease domain of a polynucleotide programmable nucleotide binding domain can cut zero, one, or two strands of a target polynucleotide. In some embodiments, the polynucleotide programmable nucleotide binding domain can comprise a nickase domain. Herein the term "nickase" refers to a polynucleotide programmable nucleotide binding domain comprising a nuclease domain that is capable of cleaving only one strand of the two strands in a duplexed nucleic acid molecule (e.g., DNA). In some embodiments, a nickase can be derived from a fully catalytically active (e.g., natural) form of a polynucleotide programmable nucleotide binding domain by introducing one or more mutations into the active polynucleotide programmable nucleotide binding domain. For example, where a polynucleotide programmable nucleotide binding domain comprises a nickase domain derived from Cas9, the Cas9-derived nickase domain can include a D10A mutation and a histidine at position 840. In such embodiments, the residue H840 retains catalytic activity and can thereby cleave a single strand of the nucleic acid duplex. In another example, a Cas9-derived nickase domain can comprise an H840A mutation, while the amino acid residue at position 10 remains a D. In some embodiments, a nickase can be derived from a fully catalytically active (e.g., natural) form of a polynucleotide programmable nucleotide binding domain by removing all or a portion of a nuclease domain that is not required for the nickase activity. For example, where a polynucleotide programmable nucleotide binding domain comprises a nickase domain derived from Cas9, the Cas9-derived nickase domain can comprise a deletion of all or a portion of the RuvC domain or the HNH domain.

A base editor comprising a polynucleotide programmable nucleotide binding domain comprising a nickase domain is thus able to generate a single-strand DNA break (nick) at a specific polynucleotide target sequence (e.g., determined by the complementary sequence of a bound guide nucleic acid). In some embodiments, the strand of a nucleic acid duplex target polynucleotide sequence that is cleaved by a base editor comprising a nickase domain (e.g., Cas9-derived nickase domain) is the strand that is not edited by the base editor (i.e., the strand that is cleaved by the base editor is opposite to a strand comprising a base to be edited). In other embodiments, a base editor comprising a nickase domain (e.g., Cas9-derived nickase domain) can cleave the strand of a DNA molecule which is being targeted for editing. In such embodiments, the non-targeted strand is not cleaved.

Also provided herein are base editors comprising a polynucleotide programmable nucleotide binding domain which is catalytically dead (i.e., incapable of cleaving a target polynucleotide sequence). Herein the terms "catalytically dead" and "nuclease dead" are used interchangeably to refer to a polynucleotide programmable nucleotide binding domain which has one or more mutations and/or deletions resulting in its inability to cleave a strand of a nucleic acid while retaining its ability, and specificity, to bind to a target polynucleotide. In some embodiments, a catalytically dead polynucleotide programmable nucleotide binding domain base editor can lack nuclease activity as a result of specific point mutations in one or more nuclease domains. For example, in the case of a base editor comprising a Cas9 domain, the Cas9 can comprise both a D10A mutation and an H840A mutation. Such mutations inactivate both nuclease domains, thereby resulting in the loss of nuclease activity. In other embodiments, a catalytically dead polynucleotide programmable nucleotide binding domain can comprise one or more deletions of all or a portion of a catalytic domain (e.g., RuvCl and/or HNH domains). In further embodiments, a catalytically dead polynucleotide programmable nucleotide binding domain comprises a point mutation (e.g., D10A or H840A) as well as a deletion of all or a portion of a nuclease domain.

Some aspects of the disclosure provide fusion proteins comprising domains that act as polynucleotide-programmable DNA binding proteins, which can be used to guide a protein, such as a base editor, to a specific nucleic acid (e.g., DNA or RNA) sequence. In particular embodiments, a fusion protein comprises a nucleic acid programmable DNA binding protein domain and one or more deaminase domains. Non-limiting examples of polynucleotide-programmable DNA binding proteins include, Cas9 (e.g., dCas9 and nCas9), Casl2a/Cpf1, Casl2b/C2cl, Casl2c/C2c3, Casl2d/CasY, Casl2e/CasX, Casl2g, Casl2h, and Casl2i. Non-limiting examples of Cas enzymes include Cas1, CaslB, Cas2, Cas3, Cas4, Cas5, Cas5d, Cas5t, Cas5h, Cas5a, Cas6, Cas7, Cas8, Cas8a, Cas8b, Cas8c, Cas9 (also known as Csnl or Csxl2), Cas10, Casl0d, Casl2a/Cpf1, Casl2b/C2cl, Casl2c/C2c3, Casl2d/CasY, Casl2e/CasX, Casl2g, Casl2h, Casl2i, Csy1, Csy2, Csy3, Csy4, Csel, Cse2, Cse3, Cse4, Cse5e, Cscl, Csc2, Csa5, Csnl, Csn2, Csml, Csm2, Csm3, Csm4, Csm5, Csm6, Cmr1, Cmr3, Cmr4, Cmr5, Cmr6, Csbl, Csb2, Csb3, Csx17, Csx14, Csx10, Csx16, CsaX, Csx3, Csx1, Csx1S, Csxl 1, Csfl, Csf2, CsO, Csf4, Csdl, Csd2, Cstl, Cst2, Cshl, Csh2, Csal, Csa2, Csa3, Csa4, Csa5, Type II Cas effector proteins, Type V Cas effector proteins, Type VI Cas effector proteins, CARF, DinG, homologues thereof, or modified or engineered versions thereof. Other nucleic acid programmable DNA binding proteins are also within the scope of this disclosure, although they may not be specifically listed in this disclosure. See, e.g., Makarova et al. "Classification and Nomenclature of CRISPR-Cas Systems: Where from Here?" CRISPR J. 2018 October; 1:325-336. doi: 10.1089/crispr.2018.0033; Yan et al., "Functionally diverse type V CRISPR-Cas systems" Science. 2019 Jan. 4; 363 (6422): 88-91. doi: 10.1 126/science.aav7271, the entire contents of each are hereby incorporated by reference.

In some embodiments, the disclosure provides a fusion protein comprising a type V CRISPR/Cas effector protein. Type V CRISPR/Cas effector proteins are a subtype of Class 2 CRISPR/Cas effector proteins. For examples of type V CRISPR/Cas systems and their effector proteins (e.g., Cas12 family proteins such as Cas12a), see, e.g., Shmakov et al., Nat Rev Microbial. 2017 March; 15 (3): 169-182: "Diversity and evolution of class 2 CRISPR-Cas systems." Examples include, but are not limited to: Cas12 family (Cas12a, Cas12b, Cas12c), C2c4, C2c8, C2c5, C2c10, and C2c9; as well as CasX (Cas12e) and CasY (Cas12d). Also see, e.g., Koonin et al., Curr Opin Microbial. 2017 June; 37:67-78: "Diversity, classification and evolution of CRISPR-Cas systems." In some embodiments, the CBEs disclosed herein comprise a type V CRISPR/Cas effector protein.

In some embodiments, the disclosure provides TALE base editors, which can comprise a TALE domain, a deaminase domain and/or cofactor protein (e.g. FokI endonuclease) domain that comprise fusion proteins having the general structure NH2-[TALE]-[deaminase domain]-COOH, NH2-[deaminase domain]-[TALE]-COOH, NH2-[TALE]-[deaminase domain]-[cofactor protein]-COOH, NH2-[cofactor protein]-[deaminase domain]-[TALE]-COOH, NH2-[cofactor protein]-[TALE]-[deaminase]-COOH or NH2-

[deaminase domain]-[TALE]-[cofactor protein]-COOH; wherein each instance of "]-[" comprises an optional linker, e.g. a peptide linker.

In some embodiments, the disclosed methods involve transducing (e.g. via transfection) cells with a plurality of complexes each comprising a fusion protein comprising a TAL effector domain and a deaminase domain and a cofactor protein, wherein each cofactor protein localizes the fusion protein to a distinct target sequence. Reference is made to Yang L. et al., Engineering and optimizing deaminase fusions for genome editing, Nature Comms., 2016. In particular embodiments, the methods disclosed herein involve TAL effector domains that bind target sites not by Watson-Crick hybridization, but by binding the major groove of the DNA double helix. In certain embodiments, the methods involve the transfection of nucleic acid constructs (e.g. plasmids) that each (or together) encode the components of a plurality of complexes of a TALE base editor comprising a TALE domain and a deaminase domain, and a cofactor protein. In certain embodiments, the disclosed fusion proteins comprise a cofactor protein domain—i.e. the domain is incorporated into the fusion protein construct. In other embodiments, the TALE base editor comprises a TALE domain and a deaminase domain, and the cofactor protein is introduced into the cell separately from the base editor.

In certain embodiments of the disclosed methods, the constructs that encode the TALE base editors are transfected into the cell separately from the constructs that encode the cofactor proteins. In certain embodiments, these components are encoded on a single construct and transfected together. In particular embodiments, these single constructs encoding the TALE base editor and cofactor proteins can be transfected into the cell iteratively, with each iteration associated with a subset of target sequences. In particular embodiments, these single constructs can be transfected into the cell over a period of days. In other embodiments, they can be transfected into the cell over a period of weeks.

A to G Editing

In some embodiments, a base editor described herein can comprise a deaminase domain which includes an adenosine deaminase. Such an adenosine deaminase domain of a base editor can facilitate the editing of an adenine (A) nucleobase to a guanine (G) nucleobase by deaminating the A to form inosine (I), which exhibits base pairing properties of G. Adenosine deaminase is capable of deaminating (i.e., removing an amine group) adenine of a deoxyadenosine residue in deoxyribonucleic acid (DNA).

In some embodiments, the nucleobase editors provided herein can be made by fusing together one or more protein domains, thereby generating a fusion protein. In certain embodiments, the fusion proteins provided herein comprise one or more features that improve the base editing activity (e.g., efficiency, selectivity, and specificity) of the fusion proteins. For example, the fusion proteins provided herein can comprise a Cas9 domain that has reduced nuclease activity. In some embodiments, the fusion proteins provided herein can have a Cas9 domain that does not have nuclease activity (dCas9), or a Cas9 domain that cuts one strand of a duplexed DNA molecule, referred to as a Cas9 nickase (nCas9). Without wishing to be bound by any particular theory, the presence of the catalytic residue (e.g., H840) maintains the activity of the Cas9 to cleave the non-edited (e.g., non-deaminated) strand containing a T opposite the targeted A. Mutation of the catalytic residue (e.g., D10 to A10) of Cas9 prevents cleavage of the edited strand containing the targeted A residue. Such Cas9 variants are able to generate a single-strand DNA break (nick) at a specific location based on the gRNA-defined target sequence, leading to repair of the non-edited strand, ultimately resulting in a T to C change on the non-edited strand. In some embodiments, an A-to-G base editor further comprises an inhibitor of inosine base excision repair, for example, a uracil glycosylase inhibitor (UGI) domain or a catalytically inactive inosine specific nuclease. Without wishing to be bound by any particular theory, the UGI domain or catalytically inactive inosine specific nuclease can inhibit or prevent base excision repair of a deaminated adenosine residue (e.g., inosine), which can improve the activity or efficiency of the base editor.

A base editor comprising an adenosine deaminase can act on any polynucleotide, including DNA, RNA and DNA-RNA hybrids. In certain embodiments, a base editor comprising an adenosine deaminase can deaminate a target A of a polynucleotide comprising RNA. For example, the base editor can comprise an adenosine deaminase domain capable of deaminating a target A of an RNA polynucleotide and/or a DNA-RNA hybrid polynucleotide. In an embodiment, an adenosine deaminase incorporated into a base editor comprises all or a portion of adenosine deaminase acting on RNA (ADAR, e.g., ADAR1 or ADAR2). In another embodiment, an adenosine deaminase incorporated into a base editor comprises all or a portion of adenosine deaminase acting on tRNA (ADAT). A base editor comprising an adenosine deaminase domain can also be capable of deaminating an A nucleobase of a DNA polynucleotide. In an embodiment an adenosine deaminase domain of a base editor comprises all or a portion of an ADAT comprising one or more mutations which permit the ADAT to deaminate a target A in DNA.

The adenosine deaminase can be derived from any suitable organism (e.g., *E. coli*). In some embodiments, the adenine deaminase is a naturally-occurring adenosine deaminase that includes one or more mutations corresponding to any of the mutations provided herein (e.g., mutations made in any one of SEQ NOs: 1, 4-12, 14-17, 24-31, and 200-219). The corresponding residue in any homologous protein can be identified by e.g., sequence alignment and determination of homologous residues. The mutations in any naturally-occurring adenosine deaminase that corresponds to any of the mutations described herein can be generated accordingly.

Adenosine Deaminases

Some aspects of the disclosure provide adenosine deaminases. In some embodiments, the adenosine deaminases provided herein are capable of deaminating adenine. In some embodiments, the adenosine deaminases provided herein are capable of deaminating adenine in a deoxyadenosine residue of DNA. As referred to herein, the term "adenosine deaminase" refers to a deaminase that can deaminate adenine in a deoxyadenosine residue of DNA, and in some cases, cytosine in a deoxycytidine residue of DNA. In some embodiments, the adenosine deaminases provided herein are capable of deaminating cytosine. In some embodiments, the adenosine deaminases provided herein are capable of deaminating cytosine in a deoxycytidine residue of DNA. The adenosine deaminase can be derived from any suitable organism (e.g., *E. coli*). In some embodiments, the adenine deaminase is a naturally-occurring adenosine deaminase that includes one or more mutations corresponding to any of the mutations provided herein. One of skill in the art will be able to identify the corresponding residue in any homologous protein and in the respective encoding nucleic acid by methods well known in the art, e.g., by sequence alignment and determination of homologous residues. Accordingly, one of skill in the art would be able to generate mutations in any naturally occurring adenosine deaminase that corresponds to any of the mutations described herein. In some embodiments, the adenosine deaminase is from a prokaryote. In some embodiments, the adenosine deaminase is from a bacterium. In some embodiments, the adenosine deaminase is from *Escherichia coli, Staphylococcus aureus, Salmonella typhi, Shewanella putrefaciens, Haemophilus influenzae, Caulobacter crescentus*, or *Bacillus subtilis*. In some embodiments, the adenosine deaminase is from *E. coli*.

In some embodiments, the adenosine deaminase comprises an amino acid sequence that is at least 60%, at least 65%, at least 70%, at least 75%, at least 80%, at least 85%, at least 90%, at least 95%, at least 96%, at least 97%, at least 98%, at least 99%, or 100% identical to any one of the amino acid sequences set forth in any one of SEQ ID NOs: 1, 4-12, 14-17, 24-31, 36, 39-47, 49-52, 59, 71, 74-82, 84-87, 94, 116-140, and 200-242 or to any of the adenosine deaminases provided herein. It should be appreciated that adenosine deaminases provided herein can include one or more mutations (e.g., any of the mutations provided herein). The disclosure provides any deaminase domains with a certain percent identify plus any of the mutations or combinations thereof described herein. In some embodiments, the adenosine deaminase comprises an amino acid sequence that has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50, or more mutations compared to any one of the amino acid sequences set forth in SEQ ID NOs: 1, 4-12, 14-17, 24-31, 200-219 or any of the adenosine deaminases provided herein. In some embodiments, the adenosine deaminase comprises an amino acid sequence that has at least 5, at least 10, at least 15, at least 20, at least 25, at least 30, at least 35, at least 40, at least 45, at least 50, at least 60, at least 70, at least 80, at least 90, at least 100, at least 110, at least 120, at least 130, at least 140, at least 150, at least 160, or at least 170 identical contiguous amino acid residues as compared to any one of the amino acid sequences set forth in SEQ ID NOs: 1, 4-12, 14-17, 24-31, 36, 39-47, 49-52, 59, 71, 74-82, 84-87, 94, 116-140, 200-242 or any of the adenosine deaminases provided herein.

In some embodiments, the deaminases provided herein are capable of deaminating adenine. In some embodiments, the adenosine deaminases provided herein are capable of deaminating adenine in a deoxyadenosine residue of DNA.

In some embodiments, the deaminases provided herein are capable of deaminating cytosine or 5-methylcytosine to uracil or thymine. In some embodiments, the deaminases provided herein are capable of deaminating cytosine in DNA.

In some embodiments, the adenosine deaminase comprises one or more amino acid substitutions selected from the group consisting of W45R, H58L, P70A, L106F, A128V, D130N, H145Y, S168C, R174P, E177V, I178F, and K179N as numbered relative to SEQ ID NO: 1. In an embodiment, the adenosine deaminase is an adenosine deaminase enzyme having an amino acid sequence of SEQ ID NO: 36.

In some embodiments, the adenosine deaminase comprises one or more amino acid substitutions selected from the group consisting of W36R, P61A, R64L, L97F, A119V, D121N, H136Y, S159C, D160Y, R165P, and K170N as numbered relative to SEQ ID NO: 4. In an embodiment, the adenosine deaminase is an adenosine deaminase enzyme having an amino acid sequence of SEQ ID NO: 39.

In some embodiments, the adenosine deaminase comprises one or more amino acid substitutions selected from the group consisting of W23R, P48A, R51L, L84F, A106V, D108N, H123Y, S146C, D147Y, R152P, E155V, and K157N as numbered relative to SEQ ID NO: 5. In an embodiment, the adenosine deaminase is an adenosine deaminase enzyme having an amino acid sequence of SEQ ID NO: 40.

In some embodiments, the adenosine deaminase comprises one or more amino acid substitutions selected from the group consisting of W23R, P48A, R51L, L84F, A106V, D108N, H123Y, S146C, R152P, E155V, and K157N as numbered relative to SEQ ID NO: 6. In an embodiment, the adenosine deaminase is an adenosine deaminase enzyme having an amino acid sequence of SEQ ID NO: 41.

In some embodiments, the adenosine deaminase comprises one or more amino acid substitutions selected from the group consisting of W22R, P47A, R50L, L83F, A105V, D107N, H122Y, S145C, D146Y, R151P and K156N as numbered relative to SEQ ID NO: 7. In an embodiment, the adenosine deaminase is an adenosine deaminase enzyme having an amino acid sequence of SEQ ID NO: 42.

In some embodiments, the adenosine deaminase comprises one or more amino acid substitutions selected from the group consisting of W23R, L84F, A106V, D108N, H123Y, S146C, D147Y, R152P, E155V, and K157N as numbered relative to SEQ ID NO: 8. In an embodiment, the adenosine deaminase is an adenosine deaminase enzyme having an amino acid sequence of SEQ ID NO: 43.

In some embodiments, the adenosine deaminase comprises one or more amino acid substitutions selected from the group consisting of W21R, P46A, R49L, L82F, A104V, D106N, H121Y, S144C, D145Y, R150P, and K155N as numbered relative to SEQ ID NO: 9. In an embodiment, the adenosine deaminase is an adenosine deaminase enzyme having an amino acid sequence of SEQ ID NO: 44.

In some embodiments, the adenosine deaminase comprises one or more amino acid substitutions selected from the group consisting of W21R, H34L, P46A, L82F, A104V, D106N, H121Y, S144C, D145Y, R150P, E153V, and K155N as numbered relative to SEQ ID NO: 10. In an embodiment, the adenosine deaminase is an adenosine deaminase enzyme having an amino acid sequence of SEQ ID NO: 45.

In some embodiments, the adenosine deaminase comprises one or more amino acid substitutions selected from the group consisting of W21R, P46A, L82F, A104V, D106N, H121Y, S144C, D145Y, R150P, E153V, and K155N as numbered relative to SEQ ID NO: 11. In an embodiment, the adenosine deaminase is an adenosine deaminase enzyme having an amino acid sequence of SEQ ID NO: 46.

In some embodiments, the adenosine deaminase comprises one or more amino acid substitutions selected from the group consisting of W21R, H34L, P46A, L82F, A104V, D106N, H121Y, S144C, D145Y, R150P, E153V, and K155N as numbered relative to SEQ ID NO: 12. In an embodiment, the adenosine deaminase is an adenosine deaminase enzyme having an amino acid sequence of SEQ ID NO: 47.

In some embodiments, the adenosine deaminase comprises one or more amino acid substitutions selected from the group consisting of W28R, P53A, L89F, A111V, D113N, H128Y, S151C, D152Y, R157P, and K162N as numbered relative to SEQ ID NO: 14. In an embodiment, the adenosine deaminase is an adenosine deaminase enzyme having an amino acid sequence of SEQ ID NO: 49.

In some embodiments, the adenosine deaminase comprises one or more amino acid substitutions selected from the group consisting of W21R, P46A, L82F, A104V, D106N, H121Y, S144C, D145Y, R150P and K155N as numbered relative to SEQ ID NO: 15. In an embodiment, the adenosine deaminase is an adenosine deaminase enzyme having an amino acid sequence of SEQ ID NO: 50.

In some embodiments, the adenosine deaminase comprises one or more amino acid substitutions selected from the group consisting of W21R, P46A, L82F, A104V, D106N, H121Y, S144C, D145Y, R150P and K155N as numbered relative to SEQ ID NO: 16. In an embodiment, the adenosine deaminase is an adenosine deaminase enzyme having an amino acid sequence of SEQ ID NO: 51.

In some embodiments, the adenosine deaminase comprises one or more amino acid substitutions selected from the group consisting of W21R, P46A, L82F, A104V, D106N, H121Y, S144C, D145Y, R150P and K155N as numbered relative to SEQ ID NO: 17. In an embodiment, the adenosine deaminase is an adenosine deaminase enzyme having an amino acid sequence of SEQ ID NO: 52.

In some embodiments, the adenosine deaminase comprises one or more amino acid substitutions selected from the group consisting of L125F, A147V, D149N, H164Y, S187C, R193P, E196V, and K198N as numbered relative to SEQ ID NO: 24. In an embodiment, the adenosine deaminase is an adenosine deaminase enzyme having an amino acid sequence of SEQ ID NO: 59.

In some embodiments, the adenosine deaminase comprises one or more amino acid substitutions selected from the group consisting of W45R, H58L, P70A, L106F, A128V, D130N, A131S, T133R, D141N, H144N, H145Y, S168C, F171Y, R174P, E177V, I178F, K179N, T188I, and D189N as numbered relative to SEQ ID NO: 1. In an embodiment, the adenosine deaminase is an adenosine deaminase enzyme having an amino acid sequence of SEQ ID NO: 71.

In some embodiments, the adenosine deaminase comprises one or more amino acid substitutions selected from the group consisting of W36R, P61A, R64L, L97F, A119V, D121N, A122S, T124R, D132N, H135N, H136Y, S159C, F162Y, R165P, K170N, and D183N as numbered relative to SEQ ID NO: 4. In an embodiment, the adenosine deaminase is an adenosine deaminase enzyme having an amino acid sequence of SEQ ID NO: 74.

In some embodiments, the adenosine deaminase comprises one or more amino acid substitutions selected from the group consisting of W23R, P48A, R51L, L84F, A106V, D108N, A109S, T111R, H123Y, S146C, F149Y, R152P, E155V, K157N, and D166N as numbered relative to SEQ ID NO: 5. In an embodiment, the adenosine deaminase is an adenosine deaminase enzyme having an amino acid sequence of SEQ ID NO: 75.

In some embodiments, the adenosine deaminase comprises one or more amino acid substitutions selected from the group consisting of W23R, P48A, R51L, L84F, A106V, D108N, A109S, T111R, H123Y, S146C, F149Y, R152P, E155V, K157N, and D166N as numbered relative to SEQ ID NO: 6. In an embodiment, the adenosine deaminase is an adenosine deaminase enzyme having an amino acid sequence of SEQ ID NO: 76.

In some embodiments, the adenosine deaminase comprises one or more amino acid substitutions selected from the group consisting of W22R, P47A, R50L, L83F, A105V, D107N, A108S, T110R, D118N, H122Y, S145C, F148Y, R151P and K156N as numbered relative to SEQ ID NO: 7. In an embodiment, the adenosine deaminase is an adenosine deaminase enzyme having an amino acid sequence of SEQ ID NO: 77.

In some embodiments, the adenosine deaminase comprises one or more amino acid substitutions selected from the group consisting of W23R, L84F, A106V, D108N, A109S, T111R, D119N, H123Y, S146C, F149Y, R152P, E155V, and K157N as numbered relative to SEQ ID NO: 8. In an embodiment, the adenosine deaminase is an adenosine deaminase enzyme having an amino acid sequence of SEQ ID NO: 78.

In some embodiments, the adenosine deaminase comprises one or more amino acid substitutions selected from the group consisting of W21R, P46A, R49L, L82F, A104V, D106N, A107S, T109R, D117N, H121Y, S144C, F147Y, R150P, K155N, and D165N as numbered relative to SEQ ID NO: 9. In an embodiment, the adenosine deaminase is an adenosine deaminase enzyme having an amino acid sequence of SEQ ID NO: 79.

In some embodiments, the adenosine deaminase comprises one or more amino acid substitutions selected from the group consisting of W21R, H34L, P46A, L82F, A104V, D106N, A107S, T109R, D117N, H121Y, S144C, F147Y, R150P, E153V, and K155N as numbered relative to SEQ ID NO: 10. In an embodiment, the adenosine deaminase is an adenosine deaminase enzyme having an amino acid sequence of SEQ ID NO: 80.

In some embodiments, the adenosine deaminase comprises one or more amino acid substitutions selected from the group consisting of W21R, P46A, L82F, A104V, D106N, T109R, D117N, H121Y, S144C, F147Y, R150P, E153V, K155N, and D165N as numbered relative to SEQ ID NO: 11. In an embodiment, the adenosine deaminase is an adenosine deaminase enzyme having an amino acid sequence of SEQ ID NO: 81.

In some embodiments, the adenosine deaminase comprises one or more amino acid substitutions selected from the group consisting of W21R, H34L, P46A, L82F, A104V, D106N, T109R, D117N, H121Y, S144C, F147Y, R150P, E153V, and K155N as numbered relative to SEQ ID NO: 12. In an embodiment, the adenosine deaminase is an adenosine deaminase enzyme having an amino acid sequence of SEQ ID NO: 82.

In some embodiments, the adenosine deaminase comprises one or more amino acid substitutions selected from the group consisting of W28R, P53A, L89F, A111V, D113N, T116R, D124N, H128Y, S151C, F154Y, R157P, and K162N as numbered relative to SEQ ID NO: 14. In an embodiment, the adenosine deaminase is an adenosine deaminase enzyme having an amino acid sequence of SEQ ID NO: 84.

In some embodiments, the adenosine deaminase comprises one or more amino acid substitutions selected from the group consisting of W21R, P46A, L82F, A104V, D106N, T109R, D117N, H121Y, S144C, F147Y, R150P, K155N, and T163I as numbered relative to SEQ ID NO: 15. In an embodiment, the adenosine deaminase is an adenosine deaminase enzyme having an amino acid sequence of SEQ ID NO: 85.

In some embodiments, the adenosine deaminase comprises one or more amino acid substitutions selected from the group consisting of W21R, P46A, L82F, A104V, D106N, T109R, D117N, H121Y, S144C, F147Y, R150P and K155N as numbered relative to SEQ ID NO: 16. In an embodiment, the adenosine deaminase is an adenosine deaminase enzyme having an amino acid sequence of SEQ ID NO: 86.

In some embodiments, the adenosine deaminase comprises one or more amino acid substitutions selected from the group consisting of W21R, P46A, L82F, A104V, D106N, T109R, D117N, H121Y, S144C, F147Y, R150P and K155N as numbered relative to SEQ ID NO: 17. In an embodiment, the adenosine deaminase is an adenosine deaminase enzyme having an amino acid sequence of SEQ ID NO: 87.

In some embodiments, the adenosine deaminase comprises one or more amino acid substitutions selected from the group consisting of L125F, A147V, D149N, T152R, H164Y, S187C, F190Y, R193P, E196V, K198N, and T210I as numbered relative to SEQ ID NO: 24. In an embodiment, the adenosine deaminase is an adenosine deaminase enzyme having an amino acid sequence of SEQ ID NO: 94.

In some embodiments, the adenosine deaminase comprises one or more amino acid substitutions selected from the group consisting of W23R, P48A, L84F, A106V, D108N, T111R, D119N, H123Y, S146C, F149Y, R152P, K157N, and D169N as numbered relative to SEQ ID NO: 25. In an embodiment, the adenosine deaminase is an adenosine deaminase enzyme having an amino acid sequence of SEQ ID NO: 116.

In some embodiments, the adenosine deaminase comprises one or more amino acid substitutions selected from the group consisting of W23R, P48A, L84F, A106V, D108N, T111R, D119N, H123Y, S146C, F149Y, R152P, K157N, and D169N as numbered relative to SEQ ID NO: 26. In an embodiment, the adenosine deaminase is an adenosine deaminase enzyme having an amino acid sequence of SEQ ID NO: 117.

In some embodiments, the adenosine deaminase comprises one or more amino acid substitutions selected from the group consisting of W22R, P47A, L83F, A105V, D107N, T110R, D118N, H122Y, S145C, F148Y, R151P, E154V, and K156N as numbered relative to SEQ ID NO: 27. In an embodiment, the adenosine deaminase is an adenosine deaminase enzyme having an amino acid sequence of SEQ ID NO: 118.

In some embodiments, the adenosine deaminase comprises one or more amino acid substitutions selected from the group consisting of W21R, P46A, L82F, A104V, D106N, T109R, D117N, H121Y, S144C, F147Y, R150P, and K155N as numbered relative to SEQ ID NO: 28. In an embodiment, the adenosine deaminase is an adenosine deaminase enzyme having an amino acid sequence of SEQ ID NO: 119.

In some embodiments, the adenosine deaminase comprises one or more amino acid substitutions selected from the group consisting of W21R, P46A, L82F, A104V, D106N, A107S, T109R, D117N, H121Y, S144C, F147Y, R150P, E153V, and K155N as numbered relative to SEQ ID NO: 29. In an embodiment, the adenosine deaminase is an adenosine deaminase enzyme having an amino acid sequence of SEQ ID NO: 120.

In some embodiments, the adenosine deaminase comprises one or more amino acid substitutions selected from the group consisting of W21R, H34L, P46A, L82F, A104V, D106N, T109R, D117N, H121Y, S144C, F147Y, R150P, E153V, and K155N as numbered relative to SEQ ID NO: 30. In an embodiment, the adenosine deaminase is an adenosine deaminase enzyme having an amino acid sequence of SEQ ID NO: 121.

In some embodiments, the adenosine deaminase comprises one or more amino acid substitutions selected from the group consisting of W21R, P46A, L82F, A104V, D106N, A107S, T109R, D117N, H121Y, S144C, F147Y, R150P, and K155N as numbered relative to SEQ ID NO: 31. In an embodiment, the adenosine deaminase is an adenosine deaminase enzyme having an amino acid sequence of SEQ ID NO: 122.

In some embodiments, the adenosine deaminase comprises one or more amino acid substitutions selected from the group consisting of W45R, H58L, P70A, L106F, A128V, D130Q, A131S, T133R, D141N, H144N, H145Y, S168C, F171Y, R174P, E177V, I178F, K179N, T188I, and D189N as numbered relative to SEQ ID NO: 1. In an embodiment, the adenosine deaminase is an adenosine deaminase enzyme having an amino acid sequence of SEQ ID NO: 123.

In some embodiments, the adenosine deaminase comprises one or more amino acid substitutions selected from the group consisting of W36R, P61A, R64L, L97F, A119V, D121Q, A122S, T124R, D132N, H135N, H136Y, S159C, F162Y, R165P, K170N, and D183N as numbered relative to SEQ ID NO: 4. In an embodiment, the adenosine deaminase is an adenosine deaminase enzyme having an amino acid sequence of SEQ ID NO: 124.

In some embodiments, the adenosine deaminase comprises one or more amino acid substitutions selected from the group consisting of W45R, E49A, V50A, H58L, P70A, M83I, L106F, H118N, A128V, D130N, A131S, T133R, D141N, H144N, H145Y, S168C, F171Y, R174P, E177V, I178F, K179N, T188I, and D189N as numbered relative to SEQ ID NO: 1. In an embodiment, the adenosine deaminase is an adenosine deaminase enzyme having an amino acid sequence of SEQ ID NO: 125.

In some embodiments, the adenosine deaminase comprises one or more amino acid substitutions selected from the group consisting of W45R, R48G, E49A, V50G, H58L, P70A, L98F, L106F, H118N, A128V, D130N, A131S, T133R, D141N, H144N, H145Y, S168C, F171Y, R174P, E177V, I178F, K179N, A180S, T188I, and D189N as numbered relative to SEQ ID NO: 1. In an embodiment, the adenosine deaminase is an adenosine deaminase enzyme having an amino acid sequence of SEQ ID NO: 126.

In some embodiments, the adenosine deaminase comprises one or more amino acid substitutions selected from the group consisting of W36R, E40A, V41A, P61A, R64L, M74I, L97F, H109N, A119V, D121N, A122S, T124R, D132N, H135N, H136Y, S159C, F162Y, R165P, K170N, and D183N as numbered relative to SEQ ID NO: 4. In an embodiment, the adenosine deaminase is an adenosine deaminase enzyme having an amino acid sequence of SEQ ID NO: 127.

In some embodiments, the adenosine deaminase comprises one or more amino acid substitutions selected from the group consisting of W36R, E40A, V41G, P61A, R64L, I89F, L97F, H109N, A119V, D121N, A122S, T124R, D132N, H135N, H136Y, S159C, F162Y, R165P, K170N, A171S, and D183N as numbered relative to SEQ ID NO: 4. In an embodiment, the adenosine deaminase is an adenosine deaminase enzyme having an amino acid sequence of SEQ ID NO: 128.

In some embodiments, the adenosine deaminase comprises one or more amino acid substitutions selected from the group consisting of W23R, E27A, V28A, P48A, R51L, M61I, L84F, H96N, A106V, D108N, A109S, T111R, H123Y, S146C, F149Y, R152P, E155V, K157N, and D166N as numbered relative to SEQ ID NO: 5. In an embodiment, the adenosine deaminase is an adenosine deaminase enzyme having an amino acid sequence of SEQ ID NO: 129.

In some embodiments, the adenosine deaminase comprises one or more amino acid substitutions selected from the group consisting of W23R, E27A, V28G, P48A, R51L, L76F, L84F, H96N, A106V, D108N, A109S, T111R, H123Y, S146C, F149Y, R152P, E155V, K157N, A158S, and D166N as numbered relative to SEQ ID NO: 5. In an embodiment, the adenosine deaminase is an adenosine deaminase enzyme having an amino acid sequence of SEQ ID NO: 130.

In some embodiments, the adenosine deaminase comprises one or more amino acid substitutions selected from the group consisting of W23R, E27A, V28A, M61I, L84F, H96N, A106V, D108N, A109S, T111R, D119N, H123Y, S146C, F149Y, R152P, E155V, and K157N as numbered relative to SEQ ID NO: 8. In an embodiment, the adenosine deaminase is an adenosine deaminase enzyme having an amino acid sequence of SEQ ID NO: 131.

In some embodiments, the adenosine deaminase comprises one or more amino acid substitutions selected from the group consisting of W23R, E27A, V28G, L76F, L84F, H96N, A106V, D108N, A109S, T111R, D119N, H123Y, S146C, F149Y, R152P, E155V, K157N and A158S as numbered relative to SEQ ID NO: 8. In an embodiment, the adenosine deaminase is an adenosine deaminase enzyme having an amino acid sequence of SEQ ID NO: 132.

In some embodiments, the adenosine deaminase comprises one or more amino acid substitutions selected from the group consisting of W21R, E25A, V26A, P46A, R49L, M59I, L82F, H94N, A104V, D106N, A107S, T109R, D117N, H121Y, S144C, F147Y, R150P, K155N, and D165N as numbered relative to SEQ ID NO: 9. In an embodiment, the adenosine deaminase is an adenosine deaminase enzyme having an amino acid sequence of SEQ ID NO: 133.

In some embodiments, the adenosine deaminase comprises one or more amino acid substitutions selected from the group consisting of W21R, E25A, V26G, P46A, R49L, L74F, L82F, H94N, A104V, D106N, A107S, T109R, D117N, H121Y, S144C, F147Y, R150P, K155N, A156S, and D165N as numbered relative to SEQ ID NO: 9. In an embodiment, the adenosine deaminase is an adenosine deaminase enzyme having an amino acid sequence of SEQ ID NO: 134.

In some embodiments, the adenosine deaminase comprises one or more amino acid substitutions selected from the group consisting of W21R, E25A, V26A, H34L, P46A, M59I, L82F, H94N, A104V, D106N, A107S, T109R, D117N, H121Y, S144C, F147Y, R150P, E153V, and K155N as numbered relative to SEQ ID NO: 10. In an embodiment, the adenosine deaminase is an adenosine deaminase enzyme having an amino acid sequence of SEQ ID NO: 135.

In some embodiments, the adenosine deaminase comprises one or more amino acid substitutions selected from the group consisting of W21R, E25A, V26G, H34L, P46A, L74F, L82F, H94N, A104V, D106N, A107S, T109R, D117N, H121Y, S144C, F147Y, R150P, E153V, K155N, and A156S as numbered relative to SEQ ID NO: 10. In an embodiment, the adenosine deaminase is an adenosine deaminase enzyme having an amino acid sequence of SEQ ID NO: 136.

In some embodiments, the adenosine deaminase comprises one or more amino acid substitutions selected from the group consisting of W21R, E25A, V26A, H34L, P46A, M59I, L82F, H94N, A104V, D106N, T109R, D117N, H121Y, S144C, F147Y, R150P, E153V, and K155N as numbered relative to SEQ ID NO: 12. In an embodiment, the adenosine deaminase is an adenosine deaminase enzyme having an amino acid sequence of SEQ ID NO: 137.

In some embodiments, the adenosine deaminase comprises one or more amino acid substitutions selected from the group consisting of W21R, E25A, V26G, H34L, P46A, L74F, L82F, H94N, A104V, D106N, T109R, D117N, H121Y, S144C, F147Y, R150P, E153V, K155N, and A156S as numbered relative to SEQ ID NO: 12. In an embodiment, the adenosine deaminase is an adenosine deaminase enzyme having an amino acid sequence of SEQ ID NO: 138.

In some embodiments, the adenosine deaminase comprises one or more amino acid substitutions selected from the group consisting of E68A, V69A, L125F, H137N, A147V, D149N, T152R, H164Y, S187C, F190Y, R193P, E196V, K198N, and T210I as numbered relative to SEQ ID NO: 24. In an embodiment, the adenosine deaminase is an adenosine deaminase enzyme having an amino acid sequence of SEQ ID NO: 139.

In some embodiments, the adenosine deaminase comprises one or more amino acid substitutions selected from the group consisting of E68A, V69G, L117F, L125F, H137N, A147V, D149N, T152R, H164Y, S187C, F190Y, R193P, E196V, K198N, A199S, and T210I as numbered relative to SEQ ID NO: 24. In an embodiment, the adenosine deaminase is an adenosine deaminase enzyme having an amino acid sequence of SEQ ID NO: 140.

In some embodiments, the adenosine deaminase comprises one or more amino acid substitutions selected from the group consisting of L120F, A142V, D144N, T147R, H159Y, S182C, F185Y, R188P, E191V, and K193N as numbered relative to SEQ ID NO: 202. In an embodiment, the adenosine deaminase is an adenosine deaminase enzyme having an amino acid sequence of SEQ ID NO: 220.

In some embodiments, the adenosine deaminase comprises one or more amino acid substitutions selected from the group consisting of L121F, A143V, D145N, T148R, H160Y, S183C, F186Y, R189P, E192V, and K194N as numbered relative to SEQ ID NO: 203. In an embodiment, the adenosine deaminase is an adenosine deaminase enzyme having an amino acid sequence of SEQ ID NO: 221.

In some embodiments, the adenosine deaminase comprises one or more amino acid substitutions selected from the group consisting of W21R, P46A, L82F, A104V, D106N, T109R, D117N, H121Y, S144C, F147Y, R150P, and K155N as numbered relative to SEQ ID NO: 205. In an embodiment, the adenosine deaminase is an adenosine deaminase enzyme having an amino acid sequence of SEQ ID NO: 222.

In some embodiments, the adenosine deaminase comprises one or more amino acid substitutions selected from the group consisting of L79F, A101V, D103N, T106R, H118Y, S141C, F144Y, R147P, E150V, K152N, and D162N as numbered relative to SEQ ID NO: 206. In an embodiment, the adenosine deaminase is an adenosine deaminase enzyme having an amino acid sequence of SEQ ID NO: 223.

In some embodiments, the adenosine deaminase comprises one or more amino acid substitutions selected from the group consisting of W41R, P66A, L102F, A124V, D126N, A127S, T129R, D137N, H141Y, S164C, F167Y, R170P, E173V, and K175N as numbered relative to SEQ ID NO: 209. In an embodiment, the adenosine deaminase is an adenosine deaminase enzyme having an amino acid sequence of SEQ ID NO: 224.

In some embodiments, the adenosine deaminase comprises one or more amino acid substitutions selected from the group consisting of P52A, L88F, A110V, D112N, T115R, D123N, H127Y, S150C, F153Y, R156P, and K161N as numbered relative to SEQ ID NO: 210. In an embodiment, the adenosine deaminase is an adenosine deaminase enzyme having an amino acid sequence of SEQ ID NO: 225.

In some embodiments, the adenosine deaminase comprises one or more amino acid substitutions selected from the group consisting of W21R, P46A, L82F, A104V, D106N, T109R, D117N, H121Y, S144C, F147Y, R150P, K155N and D165N as numbered relative to SEQ ID NO: 211. In an embodiment, the adenosine deaminase is an adenosine deaminase enzyme having an amino acid sequence of SEQ ID NO: 226.

In some embodiments, the adenosine deaminase comprises one or more amino acid substitutions selected from the group consisting of P57A, L93F, A115V, D117N, T120R, D128N, H132Y, S155C, F158Y, and R161P as numbered relative to SEQ ID NO: 212. In an embodiment, the adenosine deaminase is an adenosine deaminase enzyme having an amino acid sequence of SEQ ID NO: 227.

In some embodiments, the adenosine deaminase comprises one or more amino acid substitutions selected from the group consisting of W22R, P47A, L83F, A105V, D107N, A108S, T110R, D118N, H122Y, S145C, F148Y, R151P, and K156N as numbered relative to SEQ ID NO: 215. In an embodiment, the adenosine deaminase is an adenosine deaminase enzyme having an amino acid sequence of SEQ ID NO: 228.

In some embodiments, the adenosine deaminase comprises one or more amino acid substitutions selected from the group consisting of W22R, L83F, A105V, D107N, A108S, T110R, D118N, H122Y, S145C, F148Y, R151P, E154V and K156N as numbered relative to SEQ ID NO: 216. In an embodiment, the adenosine deaminase is an adenosine deaminase enzyme having an amino acid sequence of SEQ ID NO: 229.

In some embodiments, the adenosine deaminase comprises one or more amino acid substitutions selected from the group consisting of W21R, H34L, P46A, L82F, A104V, D106N, A107S, T109R, D117N, H121Y, S144C, F147Y, R150P, E153V, and K155N as numbered relative to SEQ ID NO: 217. In an embodiment, the adenosine deaminase is an adenosine deaminase enzyme having an amino acid sequence of SEQ ID NO: 230.

In some embodiments, the adenosine deaminase comprises one or more amino acid substitutions selected from the group consisting of W21R, P46A, L82F, A104V, D106N, A107S, T109R, D117N, H121Y, S144C, F147Y, R150P, and K155N as numbered relative to SEQ ID NO: 218. In an embodiment, the adenosine deaminase is an adenosine deaminase enzyme having an amino acid sequence of SEQ ID NO: 231.

In some embodiments, the adenosine deaminase comprises one or more amino acid substitutions selected from the group consisting of W21R, H34L, P46A, L82F, A104V, D106N, T109R, H121Y, S144C, F147Y, R150P, and K155N as numbered relative to SEQ ID NO: 219. In an embodiment, the adenosine deaminase is an adenosine deaminase enzyme having an amino acid sequence of SEQ ID NO: 232.

In some embodiments, the adenosine deaminase comprises one or more amino acid substitutions selected from the group consisting of W20R, P45A, L81F, D105N, S143C, D144R, R149P, E151R, and K154N as numbered relative to SEQ ID NO: 200. In an embodiment, the adenosine deaminase is an adenosine deaminase enzyme having an amino acid sequence of SEQ ID NO: 233.

In some embodiments, the adenosine deaminase comprises one or more amino acid substitutions selected from the group consisting of P83A, L119F, F139V, D143N, S181C, D182R, R187P, K189R, E190V, 1191F, and K192N as numbered relative to SEQ ID NO: 201. In an embodiment, the adenosine deaminase is an adenosine deaminase enzyme having an amino acid sequence of SEQ ID NO: 234.

In some embodiments, the adenosine deaminase comprises one or more amino acid substitutions selected from the group consisting of L125F, F145V, D149N, S187C, R193P, E195R, E196V, and K198N as numbered relative to SEQ ID NO: 24. In an embodiment, the adenosine deaminase is an adenosine deaminase enzyme having an amino acid sequence of SEQ ID NO: 235.

In some embodiments, the adenosine deaminase comprises one or more amino acid substitutions selected from the group consisting of L121F, F141V, D145N, S183C, R189P, E191R, E192V, and K194N as numbered relative to SEQ ID NO: 204. In an embodiment, the adenosine deaminase is an adenosine deaminase enzyme having an amino acid sequence of SEQ ID NO: 236.

In some embodiments, the adenosine deaminase comprises one or more amino acid substitutions selected from the group consisting of W21R, P46A, L82F, D106N, S144C, D145R, R150P, E152R, and K155N as numbered relative to SEQ ID NO: 205. In an embodiment, the adenosine deaminase is an adenosine deaminase enzyme having an amino acid sequence of SEQ ID NO: 237.

In some embodiments, the adenosine deaminase comprises one or more amino acid substitutions selected from the group consisting of L79F, F99V, D103N, S141C, G142R, R147P, A149R, E150V, and K152N as numbered relative to SEQ ID NO: 206. In an embodiment, the adenosine deaminase is an adenosine deaminase enzyme having an amino acid sequence of SEQ ID NO: 238.

In some embodiments, the adenosine deaminase comprises one or more amino acid substitutions selected from the group consisting of P46A, L82F, D106N, S144C, A145R, R150P, Q152R, E153V, and K158N as numbered relative to SEQ ID NO: 207. In an embodiment, the adenosine deaminase is an adenosine deaminase enzyme having an amino acid sequence of SEQ ID NO: 239.

In some embodiments, the adenosine deaminase comprises one or more amino acid substitutions selected from the group consisting of W20R, P45A, L81F, D105N, S143C, D144R, R149P, E151R, E152V, and K154N as numbered relative to SEQ ID NO: 208. In an embodiment, the adenosine deaminase is an adenosine deaminase enzyme having an amino acid sequence of SEQ ID NO: 240.

In some embodiments, the adenosine deaminase comprises one or more amino acid substitutions selected from the group consisting of L81F, D105N, T120H, S143C, D144R, R149P, A151R, E152V, and K154N as numbered relative to SEQ ID NO: 213. In an embodiment, the adenosine deaminase is an adenosine deaminase enzyme having an amino acid sequence of SEQ ID NO: 241.

In some embodiments, the adenosine deaminase comprises one or more amino acid substitutions selected from the group consisting of P83A, L119F, F139V, D143N, S181C, D182R, R187P, K189R, E190V, 1191F, and K192N as numbered relative to SEQ ID NO: 214. In an embodiment, the adenosine deaminase is an adenosine deaminase enzyme having an amino acid sequence of SEQ ID NO: 242.

It should be appreciated that any of the mutations provided herein (e.g., relative to the amino acid sequence of SEQ ID NOs: 1, 4-12, 14-17, 24-31, 200-219) can be introduced into other adenosine deaminases, such as *S. aureus* TadA (saTadA), or other adenosine deaminases (e.g., bacterial adenosine deaminases). It would be apparent to the skilled artisan how to identify amino acid residues from other adenosine deaminases that are homologous to the mutated residues in SEQ ID NOs: 1, 4-12, 14-17, 24-31, 200-219. Thus, any of the mutations identified in SEQ ID NOs: 1, 4-12, 14-17, 24-31, 200-219 to produce SEQ ID NOs: 36, 39-47, 49-52, 59 and SEQ ID NOs: 71, 74-82, 84-87, 94, 116-140, and 220-242 can be made in other adenosine deaminases. It should also be appreciated that any of the mutations provided herein can be made individually or in any combination in another adenosine deaminase.

TABLE 1

Amino Acid Sequences of Deaminases

| Name | SEQ ID NO | Amino acid sequence |
|---|---|---|
| Traw.1 | 1 | MPVQLAPGRVYNAPAFITGVTPLSDIQLSHEYWMRHALTLAK<br>RAWDAREVPVGAVLVHNNRAIGEGWNRPIGHHDPTAHAEIMA<br>LRQGGLVLENYRLLDATLYVTLEPCVMCAGAMVHSRIARVVE<br>GARDAKTGAAGSLMDVLHHPGMNHRVEVTEGVLGEECAALLS<br>EFFRMRRREIKALKRASAQTDEGQSAAAGPGER |
| Traw.4 | 4 | MYNAPRFSTGVDALSETELNHEYWMRHALNLAQRAWEEGEVP<br>VGAVLVYQDKVIGEGWNRPIGRHDPTAHAEIMALRQGGMVLQ<br>NYRLIDATLYVTLEPCVMCAGAMIHSRIGRVVFGARDAKTGA<br>AGSLIDVLHHPGMNHRVEVTEGVLAESCSSLLSDFFRERREQ<br>KKALKRASQDPRSSDA |
| Traw.5 | 5 | MSDTEFTHEYWMQHALTLAQRAWDEGEVPVGAVLVQDNRVIG<br>EGWNRPIGRHDPTAHAEIMALRQGGMVLQNYRLLNTTLYVTL<br>EPCIMCAGAMVHSRIGTLVFGARDAKTGAVGSLMNVPAHPGM<br>NHHMQVIEGVLAPSCSALLSDFFRVRRLEKKAQKEASRKD |
| Traw.6 | 6 | MSETEFSHEYWMRHALTLAQRAWDEGEVPVGAVLVQDNRVIG<br>EGWNRPIGRHDPTAHAEIMALRQGGMVLQNYRLLNTTLYVTL<br>EPCIMCAGAMVHSRIGTLVFGARDAKTGAVGSLMNIPAHPQM<br>NHHMQIIEGVLAPTCSALLSEFFRVRRLEKKAQKEALRKD |
| Traw.7 | 7 | MSDNHDHEYWMQHALTLARRAWDEGEVPVGAVLVRNGELIGE<br>GWNRPIGRHDPTAHAEIMALRQGGVVLQNYRLLDATLYVTLE<br>PCVMCAGAMVHSRIGRLVEGARDAKTGAAGSLMDVLAHPGMN<br>HRVEVTEGVLAPACSTLLSDEFRERRLQQKALKEASRKPE |
| Traw.8 | 8 | MTTPALTHEYWMNYALTLARRAWDEGEVPVGAVLVYDNRVIG<br>EGWNRSIGKHDPTAHAEIMALRQGGMVQQNYRLLDTTLYVTL<br>EPCVMCAGAMIHSRIGTLVFGARDAKTGAVGSQMDILNHPGM<br>NHQVQIIEGVLAPQCSALLSDFFRMRRKEKKALKIASRDPHP<br>AAPQR |
| Traw.9 | 9 | MDNHDHEYWMQHALTLAQRAWEEGEVPVGAVLVLNGQAIGEG<br>WNRPIGRHDPTAHAEMMALRQGGAVLQNYRLLNATLYVTLEP<br>CVMCAGAMVHSRIARLVEGARDAKTGAAGSLLDVLAHPGMNH<br>RVAVTEGVLAPACSALLSDFFRQRRQQKALKDANRKRD |
| Traw.10 | 10 | MSDNNDEFWMRHALTLARRAWQEGEVPVGAVLVHEGRVIGEG<br>WNRPIGHHDPTAHAEIMALRQGGKVIENYRLLDTTLYVTLEP<br>CVMCAGAMVHGRVGRLVFGARDAKTGAAGSLIDVLSHPGMNH<br>QVQVDEGVLAEECAAMLSDFFRQRRAEKKALRQQQQQGTSSA<br>E |
| Traw.11 | 11 | MTDYNDELWMRHALTLARRAWDEGEVPVGAVLVQDNRVIGEG<br>WNRPIGHHDPTAHAEMMALRQGGKVLENYRLLDTTLYVTLEP<br>CVMCAGAIVHSRIGRLVFGARDGKTGAAGSLIDILGHPGMNH<br>QVIVSEGILAETCAGMLSDFFRQRREEKKALRKTRETPDR |
| Traw.12 | 12 | MSDNNDEYWMRHALMLARRAWDEGEVPVGAVLVHEGRVIGEG<br>WNRPIGHHDPTAHAEIMALRQGGKVIENYRLLDTTLYVTLEP<br>CVMCAGAMVHSRIGRLVFGARDEKTGAAGSLLDVLGHPGMNH<br>QVQIEEGILAAECAAMLSDFFRHRRAEKKALRQAGKLL |
| Traw.14 | 14 | MLPGVVCVTQEQDEYWMRRALTLAQRAWEQGEVPVGAVLVQG<br>DRVIGEGWNRPIGQHDPTAHAEIMALRQGGKVLENYRLLNTT<br>LYVTLEPCIMCAGAMVHSRIGRLVYGAHDVKTGAAGSLIDIL<br>GHPGMNHQVALHQGVLEEECAAMLSDFFRMRRQQQKALRQAQ<br>RES |
| Traw.15 | 15 | MNPQTDEYWMRYALELAKRAWEQGEVPVGAVLVQGDKVIGEG<br>WNRPIGQHDPTAHAEIMALRQGGKVLENYRLLDTTLYVTLEP<br>CVMCAGAMVHGRITRLVYGAKDDKTGAAGSLLDVIGHPGMNH<br>QIQIDCGVLAEECAGMLSDFFRMRREQKKALRQAQRTG |
| Traw.16 | 16 | MNQQRDEYWMRHALGLARLAWEQGEVPVGAVLVQDERVIGEG<br>WNRPIGQHDPTAHAEMMALRQGGKVLENYRLLNTTLYVTLEP<br>CVMCAGAMVHSRITRLVYGAHDVKTGAAGSLLDVLGHPGMNH<br>QIELHSGVLAEECAAMLSDFFRMRREQKKALRQAQRQS |
| Traw.17 | 17 | MNQQHDEYWMRHALGLARLAWEQGEVPVGAVLVQADRVIGEG<br>WNRPIGQHDPTAHAEMMALRQGGKVLENYRLLNTTLYVTLEP<br>CVMCAGAMVHSRITRLVYGAHDVKTGAAGSLLDVLGHPGMNH<br>QVELHSGVLADECAAMLSDEFQMRREQKKALRQAQRQG |

TABLE 1-continued

Amino Acid Sequences of Deaminases

| Name | SEQ ID NO | Amino acid sequence |
|---|---|---|
| Traw.24 | 24 | MEQIKLDPKTLHAKTNSSDELGCDEVSADVLAGEQPCLEQAS LEQARVDEHWMRVAMTMAEKAEAAGEVPVGAVLVKDGQQIAA GYNLSISEHDPCAHAEIQCLRAAGQTIENYRLLDTTLYVTLE PCAMCAGAMVHSRIARVVFGAKDEKTGAAGTVLNLLQHPAFN HQVEVTSGVLAQECADQLSRFFKRRREEKKALKQAQKAQQGT LS |
| Traw.101 | 25 | MTESETDHIRWMRHALSLAQRAWDEGEVPVGAVLVYQGQVIG EGWNRPIGHHDPTAHAEMMALRQGGIVLQNYRLLDTTLYVTL EPCVMCAGAMVHSRIGQLIYGASDVKTGAAGSLMDVLGHPGM NHKVSVAGGVLAQECAGLLSDFFRMRRQVHKANKQAARQPSE DQ |
| Traw.102 | 26 | MTGSETDHIRWMRHALTLAQRAWDEGEVPVGAVLVYQGQVIG EGWNRPIGHHDPTAHAEMMALRQGGIVLQNYRLLDTTLYVTL EPCVMCAGAMVHSRIGQLIYGASDVKTGAAGSLMDVLGHPGM NHKVSVAGGVLAQECAGLLSDFFRMRRQVHKANKQAARQQSE DQ |
| Traw.108 | 27 | MSDTLIDEKWMRHALTLARRAWEEGEVPVGAVLVQGDTVIGE GWNRPIGHHDPTAHAEIMALRQGGKVLENYRLLDTTLYVTLE PCVMCAGAMVHGRVGRLVFGARDEKTGAAGSLLDILGHAGMN HQVRVDQGVLAAECAAMLSDFFRHRRAEKKALRDRLRAERLK GE |
| Traw.109 | 28 | MTDYNDEFWMRHALTLAQRAWDEGEVPVGAVLVQGNRVIGEG WNRPIGHHDPTAHAEIMALRQGGKVLENYRLIDTTLYVTLEP CVMCAGAIVHSRIGRLVFGARDEKTGAAGSLLDVLGHPGMNH QVKMTEGILAQQCAGMLSDFFRMRREQKKALRKSVKQ |
| Traw.110 | 29 | MTDHNDEYWMRHALRLARRAWDEGEVPVGAVLVDNQVIGEG WNRPIGHHDPTAHAEMMALRQGGKMIENYRLLDTTLYVTLEP CVMCAGAMIHSRIGRLVYGARDAKTGAAGSLLDVLGHPGMNH QVPAECGLLNDECAAMLSDFFRQRRAEKKMLRQQQNPGRV |
| Traw.111 | 30 | MSDNNDEYWMRHALMLARRAWDEGEVPVGAVLVHEGRAIGEG WNRPIGHHDPTAHAEIMALRQGGKVIENYRLLNTTLYVTLEP CVMCAGAMVHSRIGRLVFGARDGKTGAAGSLLDVLGHPGMNH QVQIEEGILATECAAMLSDFFRHRRAEKKAQRQAGKLL |
| Traw.113 | 31 | MTQEQDEYWMRRALTLAQRAWEQGEVPVGAVLVQGDRVIGEG WNRPIGQHDPTAHAEIMALRQGGKVLENYRLLNTTLYVTLEP CIMCAGAMVHSRIGRLVYGAHDAKTGAAGSLIDILGHPGMNH QVALHQGVLEEECAAMLSDFFRMRRQQQKALRQAQRES |
| T7.1 | 36 | MPVQLAPGRVYNAPAFITGVTPLSDIQLSHEYWMRHALTLAK RARDAREVPVGAVLVLNNRAIGEGWNRAIGHHDPTAHAEIMA LRQGGLVLENYRLLDATLYVTFEPCVMCAGAMVHSRIARVVF GVRNAKTGAAGSLMDVLHYPGMNHREVTEGVLGEECAALLC EFFRMPRRVENALKRASAQTDEGQSAAAGPGER |
| T7.4 | 39 | MYNAPRFSTGVDALSETELNHEYWMRHALNLAQRAREEGEVP VGAVLVYQDKVIGEGWNRAIGLHDPTAHAEIMALRQGGMVLQ NYRLIDATLYVTFEPCVMCAGAMIHSRIGRVVFGVRNAKTGA AGSLIDVLHYPGMNHREVTEGVLAESCSSLLCYFFREPREQ KNALKRASQDPRSSDA |
| T7.5 | 40 | MSDTEFTHEYWMQHALTLAQRARDEGEVPVGAVLVQDNRVIG EGWNRAIGLHDPTAHAEIMALRQGGMVLQNYRLLNTTLYVTF EPCIMCAGAMVHSRIGTLVFGVRNAKTGAVGSLMNVPAYPGM NHHMQVIEGVLAPSCSALLCYFFVPRLVKNAQKEASRKD |
| T7.6 | 41 | MSETEFSHEYWMRHALTLAQRARDEGEVPVGAVLVQDNRVIG EGWNRAIGLHDPTAHAEIMALRQGGMVLQNYRLLNTTLYVTF EPCIMCAGAMVHSRIGTLVFGVRNAKTGAVGSLMNIPAYPQM NHHMQIIEGVLAPTCSALLCEFFRVPRLVKNAQKEALRKD |
| T7.7 | 42 | MSDNHDHEYWMQHALTLARRARDEGEVPVGAVLVRNGELIGE GWNRAIGLHDPTAHAEIMALRQGGVVLQNYRLLDATLYVTFE PCVMCAGAMVHSRIGRLVFGVRNAKTGAAGSLMDVLAYPGMN HRVEVTEGVLAPACSTLLCYFFREPRLQQNALKEASRKPE |
| T7.8 | 43 | MTTPALTHEYWMNYALTLARRARDEGEVPVGAVLVYDNRVIG EGWNRSIGKHDPTAHAEIMALRQGGMVQQNYRLLDTTLYVTF EPCVMCAGAMIHSRIGTLVFGVRNAKTGAVGSQMDILNYPGM |

TABLE 1-continued

Amino Acid Sequences of Deaminases

| Name | SEQ ID NO | Amino acid sequence |
|---|---|---|
| | | NHQVQIIEGVLAPQCSALLCYFFRMPRKVKNALKIASRDPHP AAPQR |
| T7.9 | 44 | MDNHDHEYWMQHALTLAQRAREEGEVPVGAVLVLNGQAIGEG WNRAIGLHDPTAHAEMMALRQGGAVLQNYRLLNATLYVTFEP CVMCAGAMVHSRIARLVFGVRNAKTGAAGSLLDVLAYPGMNH RVAVTEGVLAPACSALLCYFFRQPRQQNALKDANRKRD |
| T7.10 | 45 | MSDNNDEFWMRHALTLARRARQEGEVPVGAVLVLEGRVIGEG WNRAIGHHDPTAHAEIMALRQGGKVIENYRLLDTTLYVTFEP CVMCAGAMVHGRVGRLVFGVRNAKTGAAGSLIDVLSYPGMNH QVQVDEGVLAEECAAMLCYFFRQPRAVKNALRQQQQQGTSSA |
| T7.11 | 46 | MTDYNDELWMRHALTLARRARDEGEVPVGAVLVQDNRVIGEG WNRAIGHHDPTAHAEMMALRQGGKVLENYRLLDTTLYVTFEP CVMCAGAIVHSRIGRLVFGVRNGKTGAAGSLIDILGYPGMNH QVIVSEGILAETCAGMLCYFFRQPREVKNALRKTRETPDR |
| T7.12 | 47 | MSDNNDEYWMRHALMLARRARDEGEVPVGAVLVLEGRVIGEG WNRAIGHHDPTAHAEIMALRQGGKVIENYRLLDTTLYVTFEP CVMCAGAMVHSRIGRLVFGVRNEKTGAAGSLLDVLGYPGMNH QVQIEEGILAAECAAMLCYFFRHPRAVKNALRQAGKLL |
| T7.14 | 49 | MLPGVVCVTQEQDEYWMRRALTLAQRAREQGEVPVGAVLVQG DRVIGEGWNRAIGQHDPTAHAEIMALRQGGKVLENYRLLNTT LYVTFEPCIMCAGAMVHSRIGRLVYGVHNVKTGAAGSLIDIL GYPGMNHQVALHQGVLEEECAAMLCYFFRMPRQQQNALRQAQ RES |
| T7.15 | 50 | MNPQTDEYWMRYALELAKRAREQGEVPVGAVLVQGDKVIGEG WNRAIGQHDPTAHAEIMALRQGGKVLENYRLLDTTLYVTFEP CVMCAGAMVHGRITRLVYGVKNDKTGAAGSLLDVIGYPGMNH QIQIDCGVLAEECAGMLCYFFRMPREQKNALRQAQRTG |
| T7.16 | 51 | MNQQRDEYWMRHALGLARLAREQGEVPVGAVLVQDERVIGEG WNRAIGQHDPTAHAEMMALRQGGKVLENYRLLNTTLYVTFEP CVMCAGAMVHSRITRLVYGVHNVKTGAAGSLLDVLGYPGMNH QIELHSGVLAEECAAMLCYFFRMPREQKNALRQAQRQS |
| T7.17 | 52 | MNQQHDEYWMRHALGLARLAREQGEVPVGAVLVQADRVIGEG WNRAIGQHDPTAHAEMMALRQGGKVLENYRLLNTTLYVTFEP CVMCAGAMVHSRITRLVYGVHNVKTGAAGSLLDVLGYPGMNH QVELHSGVLADECAAMLCYFFQMPREQKNALRQAQRQG |
| T7.24 | 59 | MEQIKLDPKTLHAKTNSSDELGCDEVSADVLAGEQPCLEQAS LEQARVDEHWMRVAMTMAEKAEAAGEVPVGAVLVKDGQQIAA GYNLSISEHDPCAHAEIQCLRAAGQTIENYRLLDTTLYVTFE PCAMCAGAMVHSRIARVVFGVKNEKTGAAGTVLNLLQYPAFN HQVEVTSGVLAQECADQLCRFFKRPREVKNALKQAQKAQQGT LS |
| T8.1 | 71 | MPVQLAPGRVYNAPAFITGVTPLSDIQLSHEYWMRHALTLAK RARDAREVPVGAVLVLNNRAIGEGWNRAIGHHDPTAHAEIMA LRQGGLVLENYRLLDATLYVTFEPCVMCAGAMVHSRIARVVF GVRNSKRGAAGSLMNVLNYPGMNHRVEVTEGVLGEECAALLC EFYRMPRRVFNALKRASAQINEGQSAAAGPGER |
| T8.4 | 74 | MYNAPRFSTGVDALSETELNHEYWMRHALNLAQRAREEGEVP VGAVLVYQDKVIGEGWNRAIGLHDPTAHAEIMALRQGGMVLQ NYRLIDATLYVTFEPCVMCAGAMIHSRIGVVFGVRNSKRGA AGSLINVLNYPGMNHRVEVTEGVLAESCSSLLCDFYREPREQ KNALKRASQDPRSSNA |
| T8.5 | 75 | MSDTEFTHEYWMQHALTLAQRARDEGEVPVGAVLVQDNRVIG EGWNRAIGLHDPTAHAEIMALRQGGMVLQNYRLLNTTLYVTF EPCIMCAGAMVHSRIGTLVFGVRNSKRGAVGSLMNVPAYPGM NHHMQVIEGVLAPSCSALLCDFYRVPRLVKNAQKEASRKN |
| T8.6 | 76 | MSETEFSHEYWMRHALTLAQRARDEGEVPVGAVLVQDNRVIG EGWNRAIGLHDPTAHAEIMALRQGGMVLQNYRLLNTTLYVTF EPCIMCAGAMVHSRIGTLVFGVRNSKRGAVGSLMNIPAYPQM NHHMQIIEGVLAPTCSALLCEFYRVPRLVKNAQKEALRKN |
| T8.7 | 77 | MSDNHDHEYWMQHALTLARRARDEGEVPVGAVLVRNGELIGE GWNRAIGLHDPTAHAEIMALRQGGVVLQNYRLLDATLYVTFE |

TABLE 1-continued

Amino Acid Sequences of Deaminases

| Name | SEQ ID NO | Amino acid sequence |
|------|-----------|---------------------|
| | | PCVMCAGAMVHSRIGRLVFGVRNSKRGAAGSLMNVLAYPGMN HRVEVTEGVLAPACSTLLCDFYREPRLQQNALKEASRKPE |
| T8.8 | 78 | MTTPALTHEYWMNYALTLARRARDEGEVPVGAVLVYDNRVIG EGWNRSIGKHDPTAHAEIMALRQGGMVQQNYRLLDTTLYVTF EPCVMCAGAMIHSRIGTLVFGVRNSKRGAVGSQMNILNYPGM NHQVQIIEGVLAPQCSALLCDFYRMPRKVKNALKIASRDPHP AAPQR |
| T8.9 | 79 | MDNHDHEYWMQHALTLAQRAREEGEVPVGAVLVLNGQAIGEG WNRAIGLHDPTAHAEMMALRQGGAVLQNYRLLNATLYVTFEP CVMCAGAMVHSRIARLVFGVRNSKRGAAGSLLNVLAYPGMNH RVAVTEGVLAPACSALLCDFYRQPRQQQNALKDANRKRN |
| T8.10 | 80 | MSDNNDEFWMRHALTLARRARQEGEVPVGAVLVLEGRVIGEG WNRAIGHHDPTAHAEIMALRQGGKVIENYRLLDTTLYVTFEP CVMCAGAMVHGRVGRLVFGVRNSKRGAAGSLINVLSYPGMNH QVQVDEGVLAEECAAMLCDFYRQPRAVKNALRQQQQQGTSSA E |
| T8.11 | 81 | MTDYNDELWMRHALTLARRARDEGEVPVGAVLVQDNRVIGEG WNRAIGHHDPTAHAEMMALRQGGKVLENYRLLDTTLYVTFEP CVMCAGAIVHSRIGRLVFGVRNGKRGAAGSLINILGYPGMNH QVIVSEGILAETCAGMLCDFYRQPREVKNALRKTRETPNR |
| T8.12 | 82 | MSDNNDEYWMRHALMLARRARDEGEVPVGAVLVLEGRVIGEG WNRAIGHHDPTAHAEIMALRQGGKVIENYRLLDTTLYVTFEP CVMCAGAMVHSRIGRLVFGVRNEKRGAAGSLLNVLGYPGMNH QVQIEEGILAAECAAMLCDFYRHPRAVKNALRQAGKLL |
| T8.14 | 84 | MLPGVVCVTQEQDEYWMRRALTLAQRAREQGEVPVGAVLVQG DRVIGEGWNRAIGQHDPTAHAEIMALRQGGKVLENYRLLNTT LYVTFEPCIMCAGAMVHSRIGRLVYGVHNVKRGAAGSLINIL GYPGMNHQVALHQGVLEEECAAMLCDFYRMPRQQQNALRQAQ RES |
| T8.15 | 85 | MNPQTDEYWMRYALELAKRAREQGEVPVGAVLVQGDKVIGEG WNRAIGQHDPTAHAEIMALRQGGKVLENYRLLDTTLYVTFEP CVMCAGAMVHGRITRLVYGVKNDKRGAAGSLLNVIGYPGMNH QIQIDCGVLAEECAGMLCDFYRMPREQKNALRQAQRIG |
| T8.16 | 86 | MNQQRDEYWMRHALGLARLAREQGEVPVGAVLVQDERVIGEG WNRAIGQHDPTAHAEMMALRQGGKVLENYRLLNTTLYVTFEP CVMCAGAMVHSRITRLVYGVHNVKRGAAGSLLNVLGYPGMNH QIELHSGVLAEECAAMLCDFYRMPREQKNALRQAQRQS |
| T8.17 | 87 | MNQQHDEYWMRHALGLARLAREQGEVPVGAVLVQADRVIGEG WNRAIGQHDPTAHAEMMALRQGGKVLENYRLLNTTLYVTFEP CVMCAGAMVHSRITRLVYGVHNVKRGAAGSLLNVLGYPGMNH QVELHSGVLADECAAMLCDFYQMPREQKNALRQAQRQG |
| T8.24 | 94 | MEQIKLDPKTLHAKTNSSDELGCDEVSADVLAGEQPCLEQAS LEQARVDEHWMRVAMTMAEKAEAAGEVPVGAVLVKDGQQIAA GYNLSISEHDPCAHAEIQCLRAAGQTIENYRLLDTTLYVTFE PCAMCAGAMVHSRIARVVFGVKNEKRGAAGTVLNLLQYPAFN HQVEVTSGVLAQECADQLCRFYKRPREVKNALKQAQKAQQGI LS |
| T8.101 | 116 | MTESETDHIRWMRHALSLAQRARDEGEVPVGAVLVYQGQVIG EGWNRAIGHHDPTAHAEMMALRQGGIVLQNYRLLDTTLYVTF EPCVMCAGAMVHSRIGQLIYGVSNVKRGAAGSLMNVLGYPGM NHKVSVAGGVLAQECAGLLCDFYRMPRQVHNANKQAARQPSE NQ |
| T8.102 | 117 | MTGSETDHIRWMRHALTLAQRARDEGEVPVGAVLVYQGQVIG EGWNRAIGHHDPTAHAEMMALRQGGIVLQNYRLLDTTLYVTF EPCVMCAGAMVHSRIGQLIYGVSNVKRGAAGSLMNVLGYPGM NHKVSVAGGVLAQECAGLLCDFYRMPRQVHNANKQAARQQSE NQ |
| T8.108 | 118 | MSDTLIDEKWMRHALTLARRAREEGEVPVGAVLVQGDTVIGE GWNRAIGHHDPTAHAEIMALRQGGKVLENYRLLDTTLYVTFE PCVMCAGAMVHGRVGRLVFGVRNEKRGAAGSLLNILGYAGMN HQVRVDQGVLAAECAAMLCDFYRHPRAVKNALRDRLRAERLK GE |

TABLE 1-continued

Amino Acid Sequences of Deaminases

| Name | SEQ ID NO | Amino acid sequence |
|---|---|---|
| T8.109 | 119 | MTDYNDEFWMRHALTLAQRARDEGEVPVGAVLVQGNRVIGEG<br>WNRAIGHHDPTAHAEIMALRQGGKVLENYRLIDTTLYVTFEP<br>CVMCAGAIVHSRIGRLVFGVRNEKRGAAGSLLNVLGYPGMNH<br>QVKMTEGILAQQCAGMLCDFYRMPREQKNALRKSVKQ |
| T8.110 | 120 | MTDHNDEYWMRHALRLARRARDEGEVPVGAVLVLDNQVIGEG<br>WNRAIGHHDPTAHAEMMALRQGGKMIENYRLLDTTLYVTFEP<br>CVMCAGAMIHSRIGRLVYGVRNSKRGAAGSLLNVLGYPGMNH<br>QVPAECGLLNDECAAMLCDFYRQPRAVKNMLRQQQNPGRV |
| T8.111 | 121 | MSDNNDEYWMRHALMLARRARDEGEVPVGAVLVLEGRAIGEG<br>WNRAIGHHDPTAHAEIMALRQGGKVIENYRLLNTTLYVTFEP<br>CVMCAGAMVHSRIGRLVFGVRNGKRGAAGSLLNVLGYPGMNH<br>QVQIEEGILATECAAMLCDFYRHPRAVKNAQRQAGKLL |
| T8.113 | 122 | MTQEQDEYWMRRALTLAQRAREQGEVPVGAVLVQGDRVIGEG<br>WNRAIGQHDPTAHAEIMALRQGGKVLENYRLLNTTLYVTFEP<br>CIMCAGAMVHSRIGRLVYGVHNSKRGAAGSLINILGYPGMNH<br>QVALHQGVLEEECAAMLCDFYRMPRQQNALRQAQRES |
| T8.1-Q | 123 | MPVQLAPGRVYNAPAFITGVTPLSDIQLSHEYWMRHALTLAK<br>RARDAREVPVGAVLVLNNRAIGEGWNRAIGHHDPTAHAEIMA<br>LRQGGLVLENYRLLDATLYVTFEPCVMCAGAMVHSRIARVVF<br>GVRQSKRGAAGSLMNVLNYPGMNHRVEVTEGVLGEECAALLC<br>EFYRMPRRVFNALKRASAQINEGQSAAAGPGER |
| T8.4-Q | 124 | MYNAPRESTGVDALSETELNHEYWMRHALNLAQRAREEGEVP<br>VGAVLVYQDKVIGEGWNRAIGLHDPTAHAEIMALRQGGMVLQ<br>NYRLIDATLYVTFEPCVMCAGAMIHSRIGRVVFGVRQSKRGA<br>AGSLINVLNYPGMNHRVEVTEGVLAESCSSLLCDFYREPREQ<br>KNALKRASQDPRSSNA |
| T8.1-com1 | 125 | MPVQLAPGRVYNAPAFITGVTPLSDIQLSHEYWMRHALTLAK<br>RARDARAAPVGAVLVLNNRAIGEGWNRAIGHHDPTAHAEIIA<br>LRQGGLVLENYRLLDATLYVTFEPCVMCAGAMVNSRIARVVF<br>GVRNSKRGAAGSLMNVLNYPGMNHRVEVTEGVLGEECAALLC<br>EFYRMPRRVFNALKRASAQINEGQSAAAGPGER |
| T8.1-com2 | 126 | MPVQLAPGRVYNAPAFITGVTPLSDIQLSHEYWMRHALTLAK<br>RARDAGAGPVGAVLVLNNRAIGEGWNRAIGHHDPTAHAEIMA<br>LRQGGLVLENYRLFDATLYVTFEPCVMCAGAMVNSRIARVVF<br>GVRNSKRGAAGSLMNVLNYPGMNHRVEVTEGVLGEECAALLC<br>EFYRMPRRVENSLKRASAQINEGQSAAAGPGER |
| T8.4-com1 | 127 | MYNAPRFSTGVDALSETELNHEYWMRHALNLAQRAREEGAAP<br>VGAVLVYQDKVIGEGWNRAIGLHDPTAHAEIIALRQGGMVLQ<br>NYRLIDATLYVTFEPCVMCAGAMINSRIGRVVFGVRNSKRGA<br>AGSLINVLNYPGMNHRVEVTEGVLAESCSSLLCDFYREPREQ<br>KNALKRASQDPRSSNA |
| T8.4-com2 | 128 | MYNAPRFSTGVDALSETELNHEYWMRHALNLAQRAREEGAGP<br>VGAVLVYQDKVIGEGWNRAIGLHDPTAHAEIMALRQGGMVLQ<br>NYRLFDATLYVTFEPCVMCAGAMINSRIGRVVFGVRNSKRGA<br>AGSLINVLNYPGMNHRVEVTEGVLAESCSSLLCDFYREPREQ<br>KNSLKRASQDPRSSNA |
| T8.5-com1 | 129 | MSDTEFTHEYWMQHALTLAQRARDEGAAPVGAVLVQDNRVIG<br>EGWNRAIGLHDPTAHAEIIALRQGGMVLQNYRLLNTTLYVTF<br>EPCIMCAGAMVNSRIGTLVFGVRNSKRGAVGSLMNVPAYPGM<br>NHHMQVIEGVLAPSCSALLCDFYRVPRLVKNAQKEASRKN |
| T8.5-com2 | 130 | MSDTEFTHEYWMQHALTLAQRARDEGAGPVGAVLVQDNRVIG<br>EGWNRAIGLHDPTAHAEIMALRQGGMVLQNYRLENTTLYVTF<br>EPCIMCAGAMVNSRIGTLVFGVRNSKRGAVGSLMNVPAYPGM<br>NHHMQVIEGVLAPSCSALLCDFYRVPRLVKNSQKEASRKN |
| T8.8-com1 | 131 | MTTPALTHEYWMNYALTLARRARDEGAAPVGAVLVYDNRVIG<br>EGWNRSIGKHDPTAHAEIIALRQGGMVQQNYRLLDTTLYVTF<br>EPCVMCAGAMINSRIGTLVFGVRNSKRGAVGSQMNILNYPGM<br>NHQVQIIEGVLAPQCSALLCDFYRMPRKVKNALKIASRDPHP<br>AAPQR |
| T8.8-com2 | 132 | MTTPALTHEYWMNYALTLARRARDEGAGPVGAVLVYDNRVIG<br>EGWNRSIGKHDPTAHAEIMALRQGGMVQQNYRLFDTTLYVTF |

TABLE 1-continued

Amino Acid Sequences of Deaminases

| Name | SEQ ID NO | Amino acid sequence |
|---|---|---|
| | | EPCVMCAGAMINSRIGTLVFGVRNSKRGAVGSQMNILNYPGM<br>NHQVQIIEGVLAPQCSALLCDFYRMPRKVKNSLKIASRDPHP<br>AAPQR |
| T8.9-com1 | 133 | MDNHDHEYWMQHALTLAQRAREEGAAPVGAVLVLNGQAIGEG<br>WNRAIGLHDPTAHAEMIALRQGGAVLQNYRLLNATLYVTFEP<br>CVMCAGAMVNSRIARLVFGVRNSKRGAAGSLLNVLAYPGMNH<br>RVAVTEGVLAPACSALLCDFYRQPRQQQNALKDANRKRN |
| T8.9-com2 | 134 | MDNHDHEYWMQHALTLAQRAREEGAGPVGAVLVLNGQAIGEG<br>WNRAIGLHDPTAHAEMMALRQGGAVLQNYRLENATLYVTFEP<br>CVMCAGAMVNSRIARLVFGVRNSKRGAAGSLLNVLAYPGMNH<br>RVAVTEGVLAPACSALLCDFYRQPRQQQNSLKDANRKRN |
| T8.10-com1 | 135 | MSDNNDEFWMRHALTLARRARQEGAAPVGAVLVLEGRVIGEG<br>WNRAIGHHDPTAHAEIIALRQGGKVIENYRLLDTTLYVTFEP<br>CVMCAGAMVNGRVGRLVFGVRNSKRGAAGSLINVLSYPGMNH<br>QVQVDEGVLAEECAAMLCDFYRQPRAVKNALRQQQQQGTSSA<br>E |
| T8.10-com2 | 136 | MSDNNDEFWMRHALTLARRARQEGAGPVGAVLVLEGRVIGEG<br>WNRAIGHHDPTAHAEIMALRQGGKVIENYRLEDTTLYVTFEP<br>CVMCAGAMVNGRVGRLVFGVRNSKRGAAGSLINVLSYPGMNH<br>QVQVDEGVLAEECAAMLCDFYRQPRAVKNSLRQQQQQGTSSA<br>E |
| T8.12-com1 | 137 | MSDNNDEYWMRHALMLARRARDEGAAPVGAVLVLEGRVIGEG<br>WNRAIGHHDPTAHAEIIALRQGGKVIENYRLLDTTLYVTFEP<br>CVMCAGAMVNSRIGRLVFGVRNEKRGAAGSLLNVLGYPGMNH<br>QVQIEEGILAAECAAMLCDFYRHPRAVKNALRQAGKLL |
| T8.12-com2 | 138 | MSDNNDEYWMRHALMLARRARDEGAGPVGAVLVLEGRVIGEG<br>WNRAIGHHDPTAHAEIMALRQGGKVIENYRLFDTTLYVTFEP<br>CVMCAGAMVNSRIGRLVFGVRNEKRGAAGSLLNVLGYPGMNH<br>QVQIEEGILAAECAAMLCDFYRHPRAVKNSLRQAGKLL |
| T8.24-com1 | 139 | MEQIKLDPKTLHAKTNSSDELGCDEVSADVLAGEQPCLEQAS<br>LEQARVDEHWMRVAMTMAEKAEAAGAAPVGAVLVKDGQQIAA<br>GYNLSISEHDPCAHAEIQCLRAAGQTIENYRLLDTTLYVTFE<br>PCAMCAGAMVNSRIARVVFGVKNEKRGAAGTVLNLLQYPAFN<br>HQVEVTSGVLAQECADQLCRFYKRPREVKNALKQAQKAQQGI<br>LS |
| T8.24-com2 | 140 | MEQIKLDPKTLHAKTNSSDELGCDEVSADVLAGEQPCLEQAS<br>LEQARVDEHWMRVAMTMAEKAEAAGAGPVGAVLVKDGQQIAA<br>GYNLSISEHDPCAHAEIQCLRAAGQTIENYRLFDTTLYVTFE<br>PCAMCAGAMVNSRIARVVFGVKNEKRGAAGTVLNLLQYPAFN<br>HQVEVTSGVLAQECADQLCRFYKRPREVKNSLKQAQKAQQGI<br>LS |
| Traw.13 | 200 | MKQQDEYWMRHALSLARRAWEQGEVPVGAVLVQNDRVIGEGW<br>NRPIGQHDPTAHAEIMALRQGGKILENYRLLDTTLYVTLEPC<br>VMCAGAMVHSRIARLVYGAHDSKSGAAGSLLDVLGHPGMNHQ<br>VELHSGVLAEACAAMLSDFFRMRREQKKALRQAQRQG |
| Traw.23 | 201 | MSDQNSNRPTPNEDLANKQTQEKEAVQEPLTEIAMEDIATEE<br>DIMWMRHALTLADKAESIGEVPVGACVVLNGELIGEGENTPI<br>TDNDPSAHAELRAVKEAAAAVQNYRLIDATLYVTLEPCSMCA<br>GMLVHARVKRVVFGAKDAKTGAAGSVMNLLQHPALNHQLEVV<br>SGVLADECANKLSDFFRKRRKEIKAAKKAKRLLEGDASN |
| Traw.26 | 202 | MKFKQAESEQVQSKQAEIDVVSLSSVEKAPVSLDSPHFDQSK<br>VDKHWMRVAMAMAEKAEAEGEVPVGAVLVKDGQQIAAGYNLS<br>ISQHDPCAHAEILCLRAAGQTVENYRLLDATLYVTLEPCAMC<br>AGAMVHSRIARVVFGARDEKTGAAGTVLNLLQHPAFNHQVEV<br>TSGVLAQDCADQLSRFFKRRREEKKALKQAQKAQQERIS |
| Traw.28 | 203 | MEQTKLDPKTLHAKTHSSDELGCDEVSGGEQTCPKQAALEQA<br>QVDEHWMRVAMAMAEKAEAEGEVPVGAVLVKDGQQIATGYNL<br>SISQHDPCAHAEILCLRAAGQTVENYRLLDATLYVTLEPCAM<br>CAGAMVHSRIARVVFGARDEKTGAAGTVLNLLQHPVENHQVE<br>VTSGVLAQDCADQLSRFFKRRREEKKALKQAQKAQQERIS |
| Traw.30 | 204 | MEQIKLDPKTLHAKTHSSDELGCDDVSGGEQTCPKQADLEQA<br>QVDEHWMRVAMAMAEKAEAEGEVPVGAVLVKDGQQIAAGYNL |

TABLE 1-continued

Amino Acid Sequences of Deaminases

| Name | SEQ ID NO | Amino acid sequence |
|------|-----------|---------------------|
| | | SISQHDPCAHAEILCLRAAGQTVENYRLLDATLYVTLEPCAM<br>CAGAMVHSRIARVVFGARDEKTGAAGTVLNLLQHPVENHQVE<br>VTSGVLAQDCADQLSRFFKRRREEKKALKQAQKAQQERIS |
| Traw.37 | 205 | MNPQTDEYWMRHALRLARLAWEQGEVPVGAVLVQGDTVIGEG<br>WNRPIGQHDPTAHAEIMALRQGGKVLENYRLLDTTLYVTLEP<br>CVMCAGAMVHSRITRLVYGAKDEKTGAAGSLLDVIGHPGMNH<br>QIQIDSGVLAEEECAAMLSDFFRMRREQKKALRQAQRDAG |
| Traw.52 | 206 | MTDEDWMQYAIKLAAKAEEQGEVPVGAVLVKDGVMLSEGWNQ<br>MISLNDPSAHAEMQAIRAASALVGNYRLPDCTLYVTLEPCSM<br>CAGVMVHSRIKKVVFGASDLKTGAAGSVLNLLQHHCFNHQVE<br>IVPGVLAQQCAAQLSGFFQRRRAEHKALKRIQPQAD |
| Traw.54 | 207 | MTENRDLHWMQLAMEMAQKAEALGEVPVGAVLVKDDKLIACG<br>WNQPIAANDPCAHAEILCLRQAGSQLENYRLLDTTLYVTLEP<br>CAMCAGAMVHARVGRLVYGAADPKTGAAGSVLDLVRHPLENH<br>KLAVSAGVMEQECSEQLSAFFRRRRQEQKTLKQARKLNPPAA<br>EN |
| Traw.57 | 208 | MKQQDEYWMRHALSLARRAWEQGEVPVGAVLVQNDRVIGEGW<br>NRPIGQHDPTAHAEIMALRQGGKVLENYRLLETTLYVTLEPC<br>VMCAGAMVHSRITRLVYGAHDLKSGAAGSLLDVLGHPGMNHQ<br>VELASGVLAEEECAAMLSDFFRMRREEKKALRQAQRQS |
| Traw.60 | 209 | MPACGIISVYNVAFFLLETRVTDRNDEYWMRHALQLARRAWN<br>EGEVPVGAVLVLDGQVIGEGWNRPIGHHDPTAHAEMMALRQG<br>GKVIENYRLMDTTLYVTLEPCVMCAGAMVHGRVGRLVYGARD<br>AKTGAAGSLLDVLGHPGMNHRVRVDCGVLADECAAMLSEFER<br>QRRAEKKALRQRQSTDGI |
| Traw.61 | 210 | MNHTLDGHDTPDEYWMRHALTLAQRAQEEGEVPVGAVLVLDN<br>QVIGEGWNRPIGHHDPTAHAEIMALRQGGNVLQNYRLINATL<br>YVTLEPCVMCAGAMVHSRIGRLVYGANDEKTGAAGSLVDILR<br>HPGMNHQITITSGVLAAECAHTLSDFFRIRRAQHKARRAQEK<br>ADGAA |
| Traw.62 | 211 | MNQSQDEYWMRHALRLARIAWEQGEVPVGAVLVQGDRVIGEG<br>WNRPIGQHDPTAHAEIMALRQGGKVLENYRLLDTTLYVTLEP<br>CVMCAGAMVHSRITRLVYGASDEKTGAAGSLIDVLGHPGMNH<br>QVALHAGVLAEEECAAMLSDFFRMRREQKKALRQAQRGID |
| Traw.65 | 212 | MPAAFFPLESTVSEMSDEYWMRYALQLAHRAREQGEVPVGAV<br>LVQGSKVIGEGWNRPIGQHDPTAHAEMMALRQGGKVLENYRL<br>LDTTLYVTLEPCIMCAGAIVHSRIGRLVFGARDEKTGAAGSL<br>LDILGHPGMNHQVKVEHGLLAEEECAAMLSDFFRMRREQKKAL<br>RQAQREAQQTPSS |
| Traw.74 | 213 | MNEQDEYWMRRAMALAARAEQEGEVPVGALVVYHGDCVGEGW<br>NRSIGHHDATAHAEIMALRQAGAHLGNYRLLECTLYVTLEPC<br>MMCAGAMVHSRIQRLVYGASDAKTGAVDSVLQLLATPGLNHR<br>VDWRAGVLADACSAQLSDFFRRRRAEKKAARKQAAGG |
| Traw.84 | 214 | MSDQNSNRPTPNEDLANKQTQEKEAVQEPLTEIAMEDIATKE<br>DIMWMRHALTLADKAESIGEVPVGACVVLNGELIGEGENTPI<br>TDNDPSAHAELRAVKEAAAAVQNYRLIDATLYVTLEPCSMCA<br>GMLVHARVKRVVFGAKDAKTGAAGSVMNLLQHPALNHQLEVV<br>SGVLADECANKLSDFFRKRRKEIKAAKKAKRLLEGDASS |
| Traw.103 | 215 | MDTLADDEYWMRHALILAQRRAWDEGEVPVGAVLVQGGKVIGE<br>GWNRPIGQHDPTAHAEMMALRQGGRVLQNYRLLDTTLYITLE<br>PCIMCAGAMVHSRISRLVYGAADAKTGAAGSLVDILRHPGMN<br>HQVAITSGVLAEECSTLLSDFFRMRRQQQKAARAAGNA |
| Traw.105 | 216 | MNSVNDDEFWMQHALTLAQRAWDEGEVPVGAVLVLGNQVIGE<br>GWNRSIGQHDPTAHAEIMALRQGGMVVQNYRLLNSTLYITLE<br>PCVMCAGAMVHSRIGRLVYGAADAKTGAAGSLVDILRHPGMN<br>HQIEITSGVLAEECSTQLSDFFRMRRKEQKARRAAAKRESLS |
| Traw.112 | 217 | MTDNNDEFWMRHALQLAQRAWEEGEVPVGAVLVHQGRVIGEG<br>WNRPIGHHDPTAHAEMMAIRQGGKVIENYRLLDTTLYVTLEP<br>CVMCAGAMVHSRIGRLVFGARDAKTGAAGSLLDVLGHPGMNH<br>QVKFEHGILAEECAALLSDFFRQRRAEKKAQRQKNSGLV |

TABLE 1-continued

Amino Acid Sequences of Deaminases

| Name | SEQ ID NO | Amino acid sequence |
|---|---|---|
| Traw.114 | 218 | MTQEQDEYWMRRALTLAQRAWDEGEVPVGAVLVHGDRVIGEG<br>WNRPIGQHDPTAHAEIMALRQGGKVLENYRLLDTTLYVTLEP<br>CVMCAGAMVHSRIGRLVYGAHDVKTGAAGSLIDVLGHPGMNH<br>QVRLDHGVLEDACAALLSDFFRMRRQQQKALRQAQRES |
| Traw.107 | 219 | MTDQQDQYWMRYALQLAQRAWQAGEVPVGAVLVHDDRIIGEG<br>WNRPIGQHDPTAHAEIMALRQGGQALQNYRLLDATLYVTLEP<br>CTMCAGAMVHSRIGRLVFGANDEKTGAAGSLLNVLGHPGMNH<br>QVQVSSGILAQECAALLSDFFRMRREQKKARRSAPL |
| T8.26 | 220 | MKFKQAESEQVQSKQAEIDVVSLSSVEKAPVSLDSPHFDQSK<br>VDKHWMRVAMAMAEKAEAEGEVPVGAVLVKDGQQIAAGYNLS<br>ISQHDPCAHAEILCLRAAGQTVENYRLLDATLYVTFEPCAMC<br>AGAMVHSRIARVVFGVRNEKRGAAGTVLNLLQYPAFNHQVEV<br>TSGVLAQDCADQLCRFYKRPREVKNALKQAQKAQQERIS |
| T8.28 | 221 | MEQTKLDPKTLHAKTHSSDELGCDEVSGGEQTCPKQAALEQA<br>QVDEHWMRVAMAMAEKAEAEGEVPVGAVLVKDGQQIATGYNL<br>SISQHDPCAHAEILCLRAAGQTVENYRLLDATLYVTFEPCAM<br>CAGAMVHSRIARVVFGVRNEKRGAAGTVLNLLQYPVENHQVE<br>VTSGVLAQDCADQLCRFYKRPREVKNALKQAQKAQQERIS |
| T8.37 | 222 | MNPQTDEYWMRHALRLARLAREQGEVPVGAVLVQGDTVIGEG<br>WNRAIGQHDPTAHAEIMALRQGGKVLENYRLLDTTLYVTFEP<br>CVMCAGAMVHSRITRLVYGVKNEKRGAAGSLLNVIGYPGMNH<br>QIQIDSGVLAEECAAMLCDFYRMPREQKNALRQAQRDAG |
| T8.52 | 223 | MTDEDWMQYAIKLAAKAEEQGEVPVGAVLVKDGVMLSEGWNQ<br>MISLNDPSAHAEMQAIRAASALVGNYRLPDCTLYVTFEPCSM<br>CAGVMVHSRIKKVVFGVSNLKRGAAGSVLNLLQYHCENHQVE<br>IVPGVLAQQCAAQLCGFYQRPRAVHNALKRIQPQAN |
| T8.60 | 224 | MPACGIISVYNVAFFLLETRVTDRNDEYWMRHALQLARRARN<br>EGEVPVGAVLVLDGQVIGEGWNRAIGHHDPTAHAEMMALRQG<br>GKVIENYRLMDTTLYVTFEPCVMCAGAMVHGRVGRLVYGVRN<br>SKRGAAGSLLNVLGYPGMNHRVRVDCGVLADECAAMLCEFYR<br>QPRAVKNALRQRQSTDGI |
| T8.61 | 225 | MNHTLDGHDTPDEYWMRHALTLAQRAQEEGEVPVGAVLVLDN<br>QVIGEGWNRAIGHHDPTAHAEIMALRQGGNVLQNYRLINATL<br>YVTFEPCVMCAGAMVHSRIGRLVYGVNNEKRGAAGSLVNILR<br>YPGMNHQITITSGVLAAECAHTLCDFYRIPRAQHNARRAQEK<br>ADGAA |
| T8.62 | 226 | MNQSQDEYWMRHALRLARIAREQGEVPVGAVLVQGDRVIGEG<br>WNRAIGQHDPTAHAEIMALRQGGKVLENYRLLDTTLYVTFEP<br>CVMCAGAMVHSRITRLVYGVSNEKRGAAGSLINVLGYPGMNH<br>QVALHAGVLAEECAAMLCDFYRMPREQKNALRQAQRGIN |
| T8.65 | 227 | MPAAFFPLESTVSEMSDEYWMRYALQLAHRAREQGEVPVGAV<br>LVQGSKVIGEGWNRAIGQHDPTAHAEMMALRQGGKVLENYRL<br>LDTTLYVTFEPCIMCAGAIVHSRIGRLVFGVRNEKRGAAGSL<br>LNILGYPGMNHQVKVEHGLLAEECAAMLCDFYRMPREQKKAL<br>RQAQREAQQTPSS |
| T8.103 | 228 | MDTLADDEYWMRHALILAQRARDEGEVPVGAVLVQGGKVIGE<br>GWNRAIGQHDPTAHAEMMALRQGGRVLQNYRLLDTTLYITFE<br>PCIMCAGAMVHSRISRLVYGVANSKRGAAGSLVNILRYPGMN<br>HQVAITSGVLAEACSTLLCDFYRMPRQQQNAARAAGNA |
| T8.105 | 229 | MNSVNDDEFWMQHALTLAQRARDEGEVPVGAVLVLGNQVIGE<br>GWNRSIGQHDPTAHAEIMALRQGGMVVQNYRLLNSTLYITFE<br>PCVMCAGAMVHSRIGRLVYGVANSKRGAAGSLVNILRYPGMN<br>HQIEITSGVLAEACSTQLCDFYRMPRKVQNARRAAAKRESLS |
| T8.112 | 230 | MTDNNDEFWMRHALQLAQRAREEGEVPVGAVLVLQGRVIGEG<br>WNRAIGHHDPTAHAEMMAIRQGGKVIENYRLLDTTLYVTFEP<br>CVMCAGAMVHSRIGRLVFGVRNSKRGAAGSLLNVLGYPGMNH<br>QVKFEHGILAEECAALLCDFYRQPRAVKNAQRQKNSGLV |
| T8.114 | 231 | MTQEQDEYWMRRALTLAQRARDEGEVPVGAVLVLGDRVIGEG<br>WNRAIGQHDPTAHAEIMALRQGGKVLENYRLLDTTLYVTFEP<br>CVMCAGAMVHSRIGRLVYGHNVKRGAAGSLINVLGYPGMNH<br>QVRLDHGVLEDACAALLCDFYRMPRQQQNALRQAQRES |

TABLE 1-continued

Amino Acid Sequences of Deaminases

| Name | SEQ ID NO | Amino acid sequence |
|---|---|---|
| T8.107 | 232 | MTDQQDQYWMRYALQLAQRARQAGEVPVGAVLVLDDRIIGEG<br>WNRAIGQHDPTAHAEIMALRQGGQALQNYRLLDATLYVTFEP<br>CTMCAGAMVHSRIGRLVFGVNNEKRGAAGSLLNVLGYPGMNH<br>QVQVSSGILAQECAALLCDFYRMPREQKNARRSAPL |
| T88.13 | 233 | MKQQDEYWMRHALSLARRAREQGEVPVGAVLVQNDRVIGEGW<br>NRAIGQHDPTAHAEIMALRQGGKILENYRLLDTTLYVTFEPC<br>VMCAGAMVHSRIARLVYGAHNSKSGAAGSLLDVLGHPGMNHQ<br>VELHSGVLAEACAAMLCRFFRMPRRQKNALRQAQRQG |
| T88.23 | 234 | MSDQNSNRPTPNFDLANKQTQEKEAVQEPLTEIAMEDIATEE<br>DIMWMRHALTLADKAESIGEVPVGACVVLNGELIGEGENTAI<br>TDNDPSAHAELRAVKEAAAAVQNYRLIDATLYVTFEPCSMCA<br>GMLVHARVKRVVVGAKNAKTGAAGSVMNLLQHPALNHQLEVV<br>SGVLADECANKLCRFFRKPRRVFNAAKKAKRLLEGDASN |
| T88.24 | 235 | MEQIKLDPKTLHAKTNSSDELGCDEVSADVLAGEQPCLEQAS<br>LEQARVDEHWMRVAMTMAEKAEAAGEVPVGAVLVKDGQQIAA<br>GYNLSISEHDPCAHAEIQCLRAAGQTIENYRLLDTTLYVTFE<br>PCAMCAGAMVHSRIARVVVGAKNEKTGAAGTVLNLLQHPAFN<br>HQVEVTSGVLAQECADQLCRFFKRPRRVKNALKQAQKAQQGT<br>LS |
| T88.30 | 236 | MEQIKLDPKTLHAKTHSSDELGCDDVSGGEQTCPKQADLEQA<br>QVDEHWMRVAMAMAEKAEAEGEVPVGAVLVKDGQQIAAGYNL<br>SISQHDPCAHAEILCLRAAGQTVENYRLLDATLYVTFEPCAM<br>CAGAMVHSRIARVVVGARNEKTGAAGTVLNLLQHPVENHQVE<br>VTSGVLAQDCADQLCRFFKRPRRVKNALKQAQKAQQERIS |
| T88.37 | 237 | MNPQTDEYWMRHALRLARLAREQGEVPVGAVLVQGDTVIGEG<br>WNRAIGQHDPTAHAEIMALRQGGKVLENYRLLDTTLYVTFEP<br>CVMCAGAMVHSRITRLVYGAKNEKTGAAGSLLDVIGHPGMNH<br>QIQIDSGVLAEECAAMLCRFFRMPRRQKNALRQAQRDAG |
| T88.52 | 238 | MTDEDWMQYAIKLAAKAEEQGEVPVGAVLVKDGVMLSEGWNQ<br>MISLNDPSAHAEMQAIRAASALVGNYRLPDCTLYVTFEPCSM<br>CAGVMVHSRIKKVVVGASNLKTGAAGSVLNLLQHHCENHQVE<br>IVPGVLAQQCAAQLCRFFQRPRRVHNALKRIQPQAD |
| T88.54 | 239 | MTENRDLHWMQLAMEMAQKAEALGEVPVGAVLVKDDKLIACG<br>WNQAIAANDPCAHAEILCLRQAGSQLENYRLLDTTLYVTFEP<br>CAMCAGAMVHARVGRLVYGAANPKTGAAGSVLDLVRHPLENH<br>KLAVSAGVMEQECSEQLCRFFRRPRRVQKTLNQARKLNPPAA<br>EN |
| T88.57 | 240 | MKQQDEYWMRHALSLARRAREQGEVPVGAVLVQNDRVIGEGW<br>NRAIGQHDPTAHAEIMALRQGGKVLENYRLLETTLYVTFEPC<br>VMCAGAMVHSRITRLVYGAHNLKSGAAGSLLDVLGHPGMNHQ<br>VELASGVLAEECAAMLCRFFRMPRRVKNALRQAQRQS |
| T88.74 | 241 | MNEQDEYWMRRAMALAARAEQEGEVPVGALVVYHGDCVGEGW<br>NRSIGHHDATAHAEIMALRQAGAHLGNYRLLECTLYVTFEPC<br>MMCAGAMVHSRIQRLVYGASNAKTGAVDSVLQLLAHPGLNHR<br>VDWRAGVLADACSAQLCRFFRRPRRVKNAARKQAAGG |
| T88.84 | 242 | MSDQNSNRPTPNEDLANKQTQEKEAVQEPLTEIAMEDIATKE<br>DIMWMRHALTLADKAESIGEVPVGACVVLNGELIGEGENTAI<br>TDNDPSAHAELRAVKEAAAAVQNYRLIDATLYVTFEPCSMCA<br>GMLVHARVKRVVVGAKNAKTGAAGSVMNLLQHPALNHQLEVV<br>SGVLADECANKLCRFFRKPRRVFNAAKKAKRLLEGDASS |
| T8.4-S15G-<br>S153R-<br>E164V-<br>E167W | 268 | MYNAPRFSTGVDALGETELNHEYWMRHALNLAQRAREEGE<br>VPVGAVLVYQDKVIGEGWNRAIGLHDPTAHAEIMALRQGGM<br>VLQNYRLIDATLYVTFEPCVMCAGAMIHSRIGRVVFGVRNSK<br>RGAAGSLINVLNYPGMNHRVEVTEGVLAERCSSLLCDFYRVP<br>RWQKNALKRASQDRSSNA |
| T8.4-<br>C159R-<br>E164W-<br>E167W | 269 | MYNAPRFSTGVDALSETELNHEYWMRHALNLAQRAREEGEV<br>PVGAVLVYQDKVIGEGWNRAIGLHDPTAHAEIMALRQGGMV<br>LQNYRLIDATLYVTFEPCVMCAGAMIHSRIGRVVFGVRNSKR<br>GAAGSLINVLNYPGMNHRVEVTEGVLAESCSSLLRDFYRWPR<br>WQKNALKRASQDPRSSNA |

TABLE 1-continued

Amino Acid Sequences of Deaminases

| Name | SEQ ID NO | Amino acid sequence |
|---|---|---|
| T8.12-V104M-E107Y | 270 | MSDNNDEYWMRHALMLARRARDEGEVPVGAVLVLEGRVIGEG WNRAIGHHDPTAHAEIMALRQGGKVIENYRLLDTTLYVTFEP CVMCAGAMVHSRIGRLVFGMRNYKRGAAGSLLNVLGYPGMNH QVQIEEGILAAECAAMLCDFYRHPRAVKNALRQAGKLL |
| T8.4-LbCpf1 | 271 | MKRTADGSEFESPKKKRKVMYNAPRFSTGVDALSETELNHE YWMRHALNLAQRAREEGEVPVGAVLVYQDKVIGEGWNRAI GLHDPTAHAEIMALRQGGMVLQNYRLIDATLYVTFEPCVMC AGAMIHSRIGRVVFGVRNSKRGAAGSLINVLNYPGMNHRVE VTEGVLAESCSSLLCDFYREPREQKNALKRASQDPRSSNAS GGSSGGSSGSETPGTSESATPESSGGSSGGSSKLEKFTNC YSLSKTLRFKAIPVGKTQENIDNKRLLVEDEKRAEDYKGVKKL LDRYYLSFINDVLHSIKLKNLNNYISLFRKKTRTEKENKELENL EINLRKEIAKAFKGNEGYKSLFKKDIIETILPEFLDDKDEIALVN SFNGFTTAFTGFFDNRENMFSEEAKSTSIAFRCINENLTRYIS NMDIFEKVDAIFDKHEVQEIKEKILNSDYDVEDFFEGEFFNFV LTQEGIDVYNAIIGGFVTESGEKIKGLNEYINLYNQKTKQKLPK FKPLYKQVLSDRESLSFYGEGYTSDEEVLEVFRNTLNKNSEI FSSIKKLEKLFKNFDEYSSAGIFVKNGPAISTISKDIFGEWNVI RDKWNAEYDDIHLKKKAVVTEKYEDDRRKSFKKIGSFSLEQL QEYADADLSVVEKLKEIIIQKVDEIYKVYGSSEKLFDADFVLEK SLKKNDAVVAIMKDLLDSVKSFENYIKAFFGEGKETNRDESF YGDFVLAYDILLKVDHIYDAIRNYVTQKPYSKDKFKLYFQNPQ FMGGWDKDKETDYRATILRYGSKYYLAIMDKKYAKCLQKIDK DDVNGNYEKINYKLLPGPNKMLPKVFFSKKWMAYYNPSEDI QKIYKNGTFKKGDMFNLNDCHKLIDFFKDSISRYPKWSNAYD FNFSETEKYKDIAGFYREVEEQGYKVSFESASKKEVDKLVEE GKLYMFQIYNKDFSDKSHGTPNLHTMYFKLLFDENNHGQIRL SGGAELFMRRASLKKEELVVHPANSPIANKNPDNPKKTTTLS YDVYKDKRFSEDQYELHIPIAINKCPKNIFKINTEVRVLLKHDD NPYVIGIARGERNLLYIVVVDGKGNIVEQYSLNEIINNFNGIRIK TDYHSLLDKKEKERFEARQNWTSIENIKELKAGYISQVVHKIC ELVEKYDAVIALADLNSGFKNSRVKVEKQVYQKFEKMLIDKL NYMVDKKSNPCATGGALKGYQITNKFESFKSMSTQNGFIFYI PAWLTSKIDPSTGFVNLLKTKYTSIADSKKFISSFDRIMYVPEE DLFEFALDYKNFSRTDADYIKKWKLYSYGNRIRIFRNPKKNN VFDWEEVCLTSAYKELFNKYGINYQQGDIRALLCEQSDKAFY SSFMALMSLMLQMRNSITGRTDVAFLISPVKNSDGIFYDSRN YEAQENAILPKNADANGAYNIARKVLWAIGQFKKAEDEKLDK VKIAISNKEWLEYAQTSVKHSGGSKRTADGSEFEPKKKRKV |
| T8.4-IscB-D61A | 272 | MKRTADGSEFESPKKKRKVMYNAPRFSTGVDALSETELNHE YWMRHALNLAQRAREEGEVPVGAVLVYQDKVIGEGWNRAI GLHDPTAHAEIMALRQGGMVLQNYRLIDATLYVTFEPCVMC AGAMIHSRIGRVVFGVRNSKRGAAGSLINVLNYPGMNHRVE VTEGVLAESCSSLLCDFYREPREQKNALKRASQDPRSSNAS GGSSGGSSGSETPGTSESATPESSGGSSGGSMMAVVYVIS KSGKPLMPTTRCGHVRILLKEGKARVVERKPFTIQLTYESAE ETQPLVLGIAPGRTNIGMSVVTESGESVFNAQIRTRNKDVPK LMKDRKQYRMAHRRLKRRCKRRRRAKAAGTAFEEGEKQRL LPGCFKPITCKSIRNKEARFNNRKRPVGWLTPTANHLLVTHL NVVKKVQKILPVAKVVLELNRFSFMAMNNPKVQRWQYQRG PLYGKGSVEEAVSMQQDGHCLFCKHGIDHYHHVVPRRKNG SETLENRVGLCEEHHRLVHTDKEWEANLASKKSGMNKKYH ALSVLNQIIPYLADQLADMFPGNFCVTSGQDTYLFREEHGIPK DHYLDAYCIACSALTDAKKVSSPKGRPYMVRQFRRHDRQAC HKANLNRRYYMGGKLVATNRHKAMDQKTDSLEEYRAAHSA ADVSKLTVKHPSAQYKDMSRIMPGSILVSGEGKLFTLRRSEG RNKGQVNYFVSTEGIKYWARKCQYLRNNGGLQIYVSGGSK RTADGSEFEPKKKRKV |
| T8.4_TnpB-D363A | 273 | MKRTADGSEFESPKKKRKVMYNAPRFSTGVDALSETELNHE YWMRHALNLAQRAREEGEVPVGAVLVYQDKVIGEGWNRAI GLHDPTAHAEIMALRQGGMVLQNYRLIDATLYVTFEPCVMC AGAMIHSRIGRVVFGVRNSKRGAAGSLINVLNYPGMNHRVE VTEGVLAESCSSLLCDFYREPREQKNALKRASQDPRSSNAS GGSSGGSSGSETPGTSESATPESSGGSSGGSMGSPKKKRK VEFMVNKSYKFRLYPTKEQEQLLAKTFGCVRFVYNKMLEERI QIYEKFKDDKEALKKQTFPTPAKYKKEFPWLKEVDSLALANA QLNLQKAFQNFFSGRAGFPKFKNRKAKQSYTTNVVNGNIQL SDGYIKLPKLKWVKFKQHREIPAHHIIKACTIKKTKTGKYYVSI LTEYEHQPVPKEIQTVVGLDFSMNGLFVDSEGKRANYPRFY RQALEKLAKEQRILSRRKKGSNRWHKQRLKVAKLHEKIANQ RKDFLHKKSYELAKQYDCVVIENLNMKGMSQVLNFGKSVHD |

TABLE 1-continued

Amino Acid Sequences of Deaminases

| Name | SEQ ID NO | Amino acid sequence |
|---|---|---|
| | | NGWGMFTTFLQYKLEEQGKKLIKIDKWFPSSKTCSCCDQVK ESLSLSERTFRCECGFESDRAVNAAINIKHEGMKRLAIAGSK RPAATKKAGQAKKKKTGYPYDVPDYAYPYDVPDYAYPYDVP DYASGGSKRTADGSEFEPKKKRKV |

Polynucleotide Sequence of ABE8e Expression Vector:

(SEQ ID NO: 106)

TCTAGAGGGCCCGTTTAAACCCGCTGATCAGCCTCGACTGTGCCTTCTAGTTGCCAGCC

ATCTGTTGTTTGCCCCTCCCCCGTGCCTTCCTTGACCCTGGAAGGTGCCACTCCCACTG

TCCTTTCCTAATAAAATGAGGAAATTGCATCGCATTGTCTGAGTAGGTGTCATTCTATT

CTGGGGGGTGGGGTGGGGCAGGACAGCAAGGGGGAGGATTGGGAAGACAATAGCAGGCA

TGCTGGGGATGCGGTGGGCTCTATGGTTTGTTACTTTATAGAAGAAATTTTGAGTTTTT

GTTTTTTTTAATAAATAAATAAACATAAATAAATTGTTTGTTGAATTTATTATTAGTA

TGTAAGTGTAAATATAATAAAACTTAATATCTATTCAAATTAATAAATAAACCTCGATA

TACAGACCGATAAAACACATGCGTCAATTTTACGCATGATTATCTTTAACGTACGTCAC

AATATGATTATCTTTCTAGGGTTAACTTCTACTGGGCGGTTTTATGGACAGCAAGCGAA

CCGGAATTGCCAGCTGGGGCGCCCTCTGGTAAGGTTGGGAAGCCCTGCAAAGTAAACTG

GATGGCTTTCTCGCCGCCAAGGATCTGATGGCGCAGGGGATCAAGCTCTGATCAAGAGA

CAGGATGAGGATCGTTTCGCATGATTAACAAGATGGATTGCACGCAGGTTCTCCGGCC

GCTTGGGTGGAGAGGCTATTCGGCTATGACTGGGCACAACAGACAATCGGCTGCTCTGA

TGCCGCCGTGTTCCGGCTGTCAGCGCAGGGGCGCCCGGTTCTTTTTGTCAAGACCGACC

TGTCCGGTGCCCTGAATGAACTGCAAGACGAGGCAGCGCGGCTATCGTGGCTGGCCACG

ACGGGCGTTCCTTGCGCAGCTGTGCTCGACGTTGTCACTGAAGCGGGAAGGGACTGGCT

GCTATTGGGCGAAGTGCCGGGGCAGGATCTCCTGTCATCTCACCTTGCTCCTGCCGAGA

AAGTATCCATCATGGCTGATGCAATGCGGCGGCTGCATACGCTTGATCCGGCTACCTGC

CCATTCGACCACCAAGCGAAACATCGCATCGAGCGAGCACGTACTCGGATGGAAGCCGG

TCTTGTCGATCAGGATGATCTGGACGAAGAGCATCAGGGGCTCGCGCCAGCCGAACTGT

TCGCCAGGCTCAAGGCGAGCATGCCCGACGGCGAGGATCTCGTCGTGACCCATGGCGAT

GCCTGCTTGCCGAATATCATGGTGGAAAATGGCCGCTTTTCTGGATTCATCGACTGTGG

CCGGCTGGGTGTGGCGGACCGCTATCAGGACATAGCGTTGGCTACCCGTGATATTGCTG

AAGAGCTTGGCGGCGAATGGGCTGACCGCTTCCTCGTGCTTTACGGTATCGCCGCTCCC

GATTCGCAGCGCATCGCCTTCTATCGCCTTCTTGACGAGTTCTTCTGAATTATTAACGC

TTACAATTTCCTGATGCGGTATTTTCTCCTTACGCATCTGTGCGGTATTTCACACCGCA

TACAGGTGGCACTTTTCGGGGAAATGTGCGCGGAACCCCTATTTGTTTATTTTTCTAAA

TACATTCAAATATGTATCCGCTCATGAGACAATAACCCTGATAAATGCTTCAATAATAG

CACGTGCTAAAACTTCATTTTTAATTTAAAAGGATCTAGGTGAAGATCCTTTTTGATAA

TCTCATGACCAAAATCCCTTAACGTGAGTTTTCGTTCCACTGAGCGTCAGACCCCGTAG

AAAAGATCAAAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCTACCAACTCT

-continued
```
TTTTCCGAAGGTAACTGGCTTCAGCAGAGCGCAGATACCAAATACTGTCCTTCTAGTGT
AGCCGTAGTTAGGCCACCACTTCAAGAACTCTGTAGCACCGCCTACATACCTCGCTCTG
CTAATCCTGTTACCAGTGGCTGCTGCCAGTGGCGATAAGTCGTGTCTTACCGGGTTGGA
CTCAAGACGATAGTTACCGGATAAGGCGCAGCGGTCGGGCTGAACGGGGGGTTCGTGCA
CACAGCCCAGCTTGGAGCGAACGACCTACACCGAACTGAGATACCTACAGCGTGAGCTA
TGAGAAAGCGCCACGCTTCCCGAAGGGAGAAAGGCGGACAGGTATCCGGTAAGCGGCAG
GGTCGGAACAGGAGAGCGCACGAGGGAGCTTCCAGGGGGAAACGCCTGGTATCTTTATA
GTCCTGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGGCTTTTG
CTGGCCTTTTGCTCACATGTTCTTGCTGCTTCGCGATGTACGGGCCAGATATATTAACC
CTAGAAAGATAGTCTGCGTAAAATTGACGCATGCATTCTTGAAATATTGCTCTCTCTTT
CTAAATAGCGCGAATCCGTCGCTGTGCATTTAGGACATCTCAGTCGCCGCTTGGAGCTC
CCGTGAGGCGTGCTTGTCAATGCGGTAAGTGTCACTGATTTTGAACTATAACGACCGCG
TGAGTCAAAATGACGCATGATTATCTTTTACGTGACTTTTAAGATTTAACTCATACGAT
AATTATATTGTTATTTCATGTTCTACTTACGTGATAACTTATTATATATATATTTTCTT
GTTATATGCAGATATACGCGTTGACATTGATTATTGACTAGTTATTAATAGTAATCAAT
TACGGGGTCATTAGTTCATAGCCCATATATGGAGTTCCGCGTTACATAACTTACGGTAA
ATGGCCCGCCTGGCTGACCGCCCAACGACCCCCGCCCATTGACGTCAATAATGACGTAT
GTTCCCATAGTAACGCCAATAGGGACTTTCCATTGACGTCAATGGGTGGAGTATTTACG
GTAAACTGCCCACTTGGCAGTACATCAAGTGTATCATATGCCAAGTACGCCCCCTATTG
ACGTCAATGACGGTAAATGGCCCGCCTGGCATTATGCCCAGTACATGACCTTATGGGAC
TTTCCTACTTGGCAGTACATCTACGTATTAGTCATCGCTATTACCATGGTGATGCGGTT
TTGGCAGTACATCAATGGGCGTGGATAGCGGTTTGACTCACGGGGATTTCCAAGTCTCC
ACCCCATTGACGTCAATGGGAGTTTGTTTTGGCACCAAAATCAACGGGACTTTCCAAAA
TGTCGTAACAACTCCGCCCCATTGACGCAAATGGGCGGTAGGCGTGTACGGTGGGAGGT
CTATATAAGCAGAGCTGGTTTAGTGAACCGTCAGATCCGCTAGAGATCCGCGGCCGCTA
ATACGACTCACTATAGGGAGAGCCGCCACCATGAAACGGACAGCCGACGGAAGCGAGTT
CGAGTCACCAAAGAAGAAGCGGAAAGTCTCTGAGGTGGAGTTTTCCCACGAGTACTGGA
TGAGACATGCCCTGACCCTGGCCAAGAGGGCACGGGATGAGAGGGAGGTGCCTGTGGGA
GCCGTGCTGGTGCTGAACAATAGAGTGATCGGCGAGGGCTGGAACAGAGCCATCGGCCT
GCACGACCCAACAGCCCATGCCGAAATTATGGCCCTGAGACAGGGCGGCCTGGTCATGC
AGAACTACAGACTGATTGACGCCACCCTGTACGTGACATTCGAGCCTTGCGTGATGTGC
GCCGGCGCCATGATCCACTCTAGGATCGGCCGCGTGGTGTTTGGCGTGAGGAACTCAAA
AAGAGGCGCCGCAGGCTCCCTGATGAACGTGCTGAACTACCCCGGCATGAATCACCGCG
TCGAAATTACCGAGGGAATCCTGGCAGATGAATGTGCCGCCCTGCTGTGCGATTTCTAT
CGGATGCCTAGACAGGTGTTCAATGCTCAGAAGAAGGCCCAGAGCTCCATCAACTCCGG
AGGATCTAGCGGAGGCTCCTCTGGCTCTGAGACACCTGGCACAAGCGAGAGCGCAACAC
CTGAAAGCAGCGGGGGCAGCAGCGGGGGGTCAGACAAGAAGTACAGCATCGGCCTGGCC
ATCGGCACCAACTCTGTGGGCTGGGCCGTGATCACCGACGAGTACAAGGTGCCCAGCAA
GAAATTCAAGGTGCTGGGCAACACCGACCGGCACAGCATCAAGAAGAACCTGATCGGAG
CCCTGCTGTTCGACAGCGGCGAAACAGCCGAGGCCACCCGGCTGAAGAGAACCGCCAGA
```

-continued

```
AGAAGATACACCAGACGGAAGAACCGGATCTGCTATCTGCAAGAGATCTTCAGCAACGA

GATGGCCAAGGTGGACGACAGCTTCTTCCACAGACTGGAAGAGTCCTTCCTGGTGGAAG

AGGATAAGAAGCACGAGCGGCACCCCATCTTCGGCAACATCGTGGACGAGGTGGCCTAC

CACGAGAAGTACCCCACCATCTACCACCTGAGAAAGAAACTGGTGGACAGCACCGACAA

GGCCGACCTGCGGCTGATCTATCTGGCCCTGGCCCACATGATCAAGTTCCGGGGCCACT

TCCTGATCGAGGGCGACCTGAACCCCGACAACAGCGACGTGGACAAGCTGTTCATCCAG

CTGGTGCAGACCTACAACCAGCTGTTCGAGGAAAACCCCATCAACGCCAGCGGCGTGGA

CGCCAAGGCCATCCTGTCTGCCAGACTGAGCAAGAGCAGACGGCTGGAAAATCTGATCG

CCCAGCTGCCCGGCGAGAAGAAGAATGGCCTGTTCGGAAACCTGATTGCCCTGAGCCTG

GGCCTGACCCCCAACTTCAAGAGCAACTTCGACCTGGCCGAGGATGCCAAACTGCAGCT

GAGCAAGGACACCTACGACGACGACCTGGACAACCTGCTGGCCCAGATCGGCGACCAGT

ACGCCGACCTGTTTCTGGCCGCCAAGAACCTGTCCGACGCCATCCTGCTGAGCGACATC

CTGAGAGTGAACACCGAGATCACCAAGGCCCCCCTGAGCGCCTCTATGATCAAGAGATA

CGACGAGCACCACCAGGACCTGACCCTGCTGAAAGCTCTCGTGCGGCAGCAGCTGCCTG

AGAAGTACAAAGAGATTTTCTTCGACCAGAGCAAGAACGGCTACGCCGGCTACATTGAC

GGCGGAGCCAGCCAGGAAGAGTTCTACAAGTTCATCAAGCCCATCCTGGAAAAGATGGA

CGGCACCGAGGAACTGCTCGTGAAGCTGAACAGAGAGGACCTGCTGCGGAAGCAGCGGA

CCTTCGACAACGGCAGCATCCCCCACCAGATCCACCTGGGAGAGCTGCACGCCATTCTG

CGGCGGCAGGAAGATTTTTACCCATTCCTGAAGGACAACCGGGAAAAGATCGAGAAGAT

CCTGACCTTCCGCATCCCCTACTACGTGGGCCCTCTGGCCAGGGGAAACAGCAGATTCG

CCTGGATGACCAGAAAGAGCGAGGAAACCATCACCCCCTGGAACTTCGAGGAAGTGGTG

GACAAGGGCGCTTCCGCCCAGAGCTTCATCGAGCGGATGACCAACTTCGATAAGAACCT

GCCCAACGAGAAGGTGCTGCCCAAGCACAGCCTGCTGTACGAGTACTTCACCGTGTATA

ACGAGCTGACCAAAGTGAAATACGTGACCGAGGGAATGAGAAAGCCCGCCTTCCTGAGC

GGCGAGCAGAAAAAGGCCATCGTGGACCTGCTGTTCAAGACCAACCGGAAAGTGACCGT

GAAGCAGCTGAAAGAGGACTACTTCAAGAAAATCGAGTGCTTCGACTCCGTGGAAATCT

CCGGCGTGGAAGATCGGTTCAACGCCTCCCTGGGCACATACCACGATCTGCTGAAAATT

ATCAAGGACAAGGACTTCCTGGACAATGAGGAAAACGAGGACATTCTGGAAGATATCGT

GCTGACCCTGACACTGTTTGAGGACAGAGAGATGATCGAGGAACGGCTGAAAACCTATG

CCCACCTGTTCGACGACAAAGTGATGAAGCAGCTGAAGCGGCGGAGATACACCGGCTGG

GGCAGGCTGAGCCGGAAGCTGATCAACGGCATCCGGGACAAGCAGTCCGGCAAGACAAT

CCTGGATTTCCTGAAGTCCGACGGCTTCGCCAACAGAAACTTCATGCAGCTGATCCACG

ACGACAGCCTGACCTTTAAAGAGGACATCCAGAAAGCCCAGGTGTCCGGCCAGGGCGAT

AGCCTGCACGAGCACATTGCCAATCTGGCCGGCAGCCCCGCCATTAAGAAGGGCATCCT

GCAGACAGTGAAGGTGGTGGACGAGCTCGTGAAAGTGATGGGCCGGCACAAGCCCGAGA

ACATCGTGATCGAAATGGCCAGAGAGAACCAGACCACCCAGAAGGGACAGAAGAACAGC

CGCGAGAGAATGAAGCGGATCGAAGAGGGCATCAAAGAGCTGGGCAGCCAGATCCTGAA

AGAACACCCCGTGGAAAACACCCAGCTGCAGAACGAGAAGCTGTACCTGTACTACCTGC

AGAATGGGCGGGATATGTACGTGGACCAGGAACTGGACATCAACCGGCTGTCCGACTAC

GATGTGGACCATATCGTGCCTCAGAGCTTTCTGAAGGACGACTCCATCGACAACAAGGT
```

-continued

```
GCTGACCAGAAGCGACAAGAACCGGGGCAAGAGCGACAACGTGCCCTCCGAAGAGGTCG

TGAAGAAGATGAAGAACTACTGGCGGCAGCTGCTGAACGCCAAGCTGATTACCCAGAGA

AAGTTCGACAATCTGACCAAGGCCGAGAGAGGCGGCCTGAGCGAACTGGATAAGGCCGG

CTTCATCAAGAGACAGCTGGTGGAAACCCGGCAGATCACAAAGCACGTGGCACAGATCC

TGGACTCCCGGATGAACACTAAGTACGACGAGAATGACAAGCTGATCCGGGAAGTGAAA

GTGATCACCCTGAAGTCCAAGCTGGTGTCCGATTTCCGGAAGGATTTCCAGTTTTACAA

AGTGCGCGAGATCAACAACTACCACCACGCCCACGACGCCTACCTGAACGCCGTCGTGG

GAACCGCCCTGATCAAAAAGTACCCTAAGCTGGAAAGCGAGTTCGTGTACGGCGACTAC

AAGGTGTACGACGTGCGGAAGATGATCGCCAAGAGCGAGCAGGAAATCGGCAAGGCTAC

CGCCAAGTACTTCTTCTACAGCAACATCATGAACTTTTTCAAGACCGAGATTACCCTGG

CCAACGGCGAGATCCGGAAGCGGCCTCTGATCGAGACAAACGGCGAAACCGGGGAGATC

GTGTGGGATAAGGGCCGGGATTTTGCCACCGTGCGGAAAGTGCTGAGCATGCCCCAAGT

GAATATCGTGAAAAAGACCGAGGTGCAGACAGGCGGCTTCAGCAAAGAGTCTATCCTGC

CCAAGAGGAACAGCGATAAGCTGATCGCCAGAAAGAAGGACTGGGACCCTAAGAAGTAC

GGCGGCTTCGACAGCCCCACCGTGGCCTATTCTGTGCTGGTGGTGGCCAAAGTGGAAAA

GGGCAAGTCCAAGAAACTGAAGAGTGTGAAAGAGCTGCTGGGGATCACCATCATGGAAA

GAAGCAGCTTCGAGAAGAATCCCATCGACTTTCTGGAAGCCAAGGGCTACAAAGAAGTG

AAAAAGGACCTGATCATCAAGCTGCCTAAGTACTCCCTGTTCGAGCTGGAAAACGGCCG

GAAGAGAATGCTGGCCTCTGCCGGCGAACTGCAGAAGGGAAACGAACTGGCCCTGCCCT

CCAAATATGTGAACTTCCTGTACCTGGCCAGCCACTATGAGAAGCTGAAGGGCTCCCCC

GAGGATAATGAGCAGAAACAGCTGTTTGTGGAACAGCACAAGCACTACCTGGACGAGAT

CATCGAGCAGATCAGCGAGTTCTCCAAGAGAGTGATCCTGGCCGACGCTAATCTGGACA

AAGTGCTGTCCGCCTACAACAAGCACCGGGATAAGCCCATCAGAGAGCAGGCCGAGAAT

ATCATCCACCTGTTTACCCTGACCAATCTGGGAGCCCCTGCCGCCTTCAAGTACTTTGA

CACCACCATCGACCGGAAGAGGTACACCAGCACCAAAGAGGTGCTGGACGCCACCCTGA

TCCACCAGAGCATCACCGGCCTGTACGAGACACGGATCGACCTGTCTCAGCTGGGAGGT

GACTCTGGCGGCTCAAAAAGAACCGCCGACGGCAGCGAATTCGAGCCCAAGAAGAAGAG

GAAAGTCGGAAGCGGAGCTACTAACTTCAGCCTGCTGAAGCAGGCTGGAGACGTGGAGG

AGAACCCTGGACCTATGAGCGAGCTGATCAAGGAGAACATGCACATGAAGCTGTACATG

GAGGGCACCGTGAACAACCACCACTTCAAGTGCACATCCGAGGGCGAAGGCAAGCCCTA

CGAGGGCACCCAGACCATGAAGATCAAGGTGGTCGAGGGCGGCCCTCTCCCCTTCGCCT

TCGACATCCTGGCTACCAGCTTCATGTACGGCAGCAAAGCCTTCATCAACCACACCCAG

GGCATCCCCGACTTCTTTAAGCAGTCCTTCCCTGAGGGCTTCACATGGGAGAGAATCAC

CACATACGAAGACGGGGGCGTGCTGACCGCTACCCAGGACACCAGCTTCCAGAACGGCT

GCATCATCTACAACGTCAAGATCAACGGGGTGAACTTCCCATCCAACGGCCCTGTGATG

CAGAAGAAAACACGCGGCTGGGAGGCCAACACCGAGATGCTGTACCCCGCTGACGGCGG

CCTGAGAGGCCACAGCCAGATGGCCCTGAAGCTCGTGGGCGGGGCTACCTGCACTGCT

CCTTCAAGACCACATACAGATCCAAGAAACCCGCTAAGAACCTCAAGATGCCCGGCTTC

CACTTCGTGGACCACAGACTGGAAAGAATCAAGGAGGCCGACAAAGAGACCTACGTCGA

GCAGCACGAGATGGCTGTGGCCAAGTACTGCGACCTCCCTAGCAAACTGGGGCACAGAT

CTGGTGGTTCTCCCAAGAAGAAGAGGAAAGTCTAA
```

Polynucleotide Sequence of BE4max Expression Vector:

(SEQ ID NO: 142)
TCTAGAGGGCCCGTTTAAACCCGCTGATCAGCCTCGACTGTGCCTTCTAGTTGCCAGCC

ATCTGTTGTTTGCCCCTCCCCCGTGCCTTCCTTGACCCTGGAAGGTGCCACTCCCACTG

TCCTTTCCTAATAAAATGAGGAAATTGCATCGCATTGTCTGAGTAGGTGTCATTCTATT

CTGGGGGGTGGGGTGGGGCAGGACAGCAAGGGGGAGGATTGGGAAGACAATAGCAGGCA

TGCTGGGGATGCGGTGGGCTCTATGGTTTGTTACTTTATAGAAGAAATTTTGAGTTTTT

GTTTTTTTTAATAAATAAATAAACATAAATAAATTGTTTGTTGAATTTATTATTAGTA

TGTAAGTGTAAATATAATAAAACTTAATATCTATTCAAATTAATAAATAAACCTCGATA

TACAGACCGATAAAACACATGCGTCAATTTTACGCATGATTATCTTTAACGTACGTCAC

AATATGATTATCTTTCTAGGGTTAACTTCTACTGGGCGGTTTTATGGACAGCAAGCGAA

CCGGAATTGCCAGCTGGGGCGCCCTCTGGTAAGGTTGGGAAGCCCTGCAAAGTAAACTG

GATGGCTTTCTCGCCGCCAAGGATCTGATGGCGCAGGGGATCAAGCTCTGATCAAGAGA

CAGGATGAGGATCGTTTCGCATGATTGAACAAGATGGATTGCACGCAGGTTCTCCGGCC

GCTTGGGTGGAGAGGCTATTCGGCTATGACTGGGCACAACAGACAATCGGCTGCTCTGA

TGCCGCCGTGTTCCGGCTGTCAGCGCAGGGGCGCCCGGTTCTTTTTGTCAAGACCGACC

TGTCCGGTGCCCTGAATGAACTGCAAGACGAGGCAGCGCGGCTATCGTGGCTGGCCACG

ACGGGCGTTCCTTGCGCAGCTGTGCTCGACGTTGTCACTGAAGCGGGAAGGGACTGGCT

GCTATTGGGCGAAGTGCCGGGGCAGGATCTCCTGTCATCTCACCTTGCTCCTGCCGAGA

AAGTATCCATCATGGCTGATGCAATGCGGCGGCTGCATACGCTTGATCCGGCTACCTGC

CCATTCGACCACCAAGCGAAACATCGCATCGAGCGAGCACGTACTCGGATGGAAGCCGG

TCTTGTCGATCAGGATGATCTGGACGAAGAGCATCAGGGGCTCGCGCCAGCCGAACTGT

TCGCCAGGCTCAAGGCGAGCATGCCCGACGGCGAGGATCTCGTCGTGACCCATGGCGAT

GCCTGCTTGCCGAATATCATGGTGGAAAATGGCCGCTTTTCTGGATTCATCGACTGTGG

CCGGCTGGGTGTGGCGGACCGCTATCAGGACATAGCGTTGGCTACCCGTGATATTGCTG

AAGAGCTTGGCGGCGAATGGGCTGACCGCTTCCTCGTGCTTTACGGTATCGCCGCTCCC

GATTCGCAGCGCATCGCCTTCTATCGCCTTCTTGACGAGTTCTTCTGAATTATTAACGC

TTACAATTTCCTGATGCGGTATTTTCTCCTTACGCATCTGTGCGGTATTTCACACCGCA

TACAGGTGGCACTTTTCGGGGAAATGTGCGCGGAACCCCTATTTGTTTATTTTTCTAAA

TACATTCAAATATGTATCCGCTCATGAGACAATAACCCTGATAAATGCTTCAATAATAG

CACGTGCTAAAACTTCATTTTTAATTTAAAAGGATCTAGGTGAAGATCCTTTTTGATAA

TCTCATGACCAAAATCCCTTAACGTGAGTTTTCGTTCCACTGAGCGTCAGACCCCGTAG

AAAAGATCAAAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCTACCAACTCT

TTTTCCGAAGGTAACTGGCTTCAGCAGAGCGCAGATACCAAATACTGTCCTTCTAGTGT

AGCCGTAGTTAGGCCACCACTTCAAGAACTCTGTAGCACCGCCTACATACCTCGCTCTG

CTAATCCTGTTACCAGTGGCTGCTGCCAGTGGCGATAAGTCGTGTCTTACCGGGTTGGA

CTCAAGACGATAGTTACCGGATAAGGCGCAGCGGTCGGGCTGAACGGGGGGTTCGTGCA

CACAGCCCAGCTTGGAGCGAACGACCTACACCGAACTGAGATACCTACAGCGTGAGCTA

TGAGAAAGCGCCACGCTTCCCGAAGGGAGAAAGGCGGACAGGTATCCGGTAAGCGGCAG

GGTCGGAACAGGAGAGCGCACGAGGGAGCTTCCAGGGGGAAACGCCTGGTATCTTTATA

-continued
```
GTCCTGTCGGGTTTCGCCACCTCTGACTTGAGCGTCGATTTTGTGATGCTCGTCAGGG

GGGCGGAGCCTATGGAAAAACGCCAGCAACGCGGCCTTTTTACGGTTCCTGGGCTTTTG

CTGGCCTTTTGCTCACATGTTCTTGCTGCTTCGCGATGTACGGGCCAGATATATTAACC

CTAGAAAGATAGTCTGCGTAAAATTGACGCATGCATTCTTGAAATATTGCTCTCTCTTT

CTAAATAGCGCGAATCCGTCGCTGTGCATTTAGGACATCTCAGTCGCCGCTTGGAGCTC

CCGTGAGGCGTGCTTGTCAATGCGGTAAGTGTCACTGATTTTGAACTATAACGACCGCG

TGAGTCAAAATGACGCATGATTATCTTTTACGTGACTTTTAAGATTTAACTCATACGAT

AATTATATTGTTATTTCATGTTCTACTTACGTGATAACTTATTATATATATATTTTCTT

GTTATATGCAGATATACGCGTTGACATTGATTATTGACTAGTTATTAATAGTAATCAAT

TACGGGGTCATTAGTTCATAGCCCATATATGGAGTTCCGCGTTACATAACTTACGGTAA

ATGGCCCGCCTGGCTGACCGCCCAACGACCCCCGCCCATTGACGTCAATAATGACGTAT

GTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTG

ACGTCAATGACGGTAAATGGCCCGCCTGGCATTATGCCCAGTACATGACCTTATGGGAC

TTTCCTACTTGGCAGTACATCTACGTATTAGTCATCGCTATTACCATGGTGATGCGGTT

TTGGCAGTACATCAATGGGCGTGGATAGCGGTTTGACTCACGGGGATTTCCAAGTCTCC

ACCCCATTGACGTCAATGGGAGTTTGTTTTGGCACCAAAATCAACGGGACTTTCCAAAA

TGTCGTAACAACTCCGCCCCATTGACGCAAATGGGCGGTAGGCGTGTACGGTGGGAGGT

CTATATAAGCAGAGCTGGTTTAGTGAACCGTCAGATCCGCTAGAGATCCGCGGCCGCTA

ATACGACTCACTATAGGGAGAGCCGCCACCATGAAACGGACAGCCGACGGAAGCGAGTT

CGAGTCACCAAAGAAGAAGCGGAAAGTCTCCTCAGAGACTGGGCCTGTCGCCGTCGATC

CAACCCTGCGCCGCCGGATTGAACCTCACGAGTTTGAAGTGTTCTTTGACCCCCGGGAG

CTGAGAAAGGAGACATGCCTGCTGTACGAGATCAACTGGGGAGGCAGGCACTCCATCTG

GAGGCACACCTCTCAGAACACAAATAAGCACGTGGAGGTGAACTTCATCGAGAAGTTTA

CCACAGAGCGGTACTTCTGCCCCAATACCAGATGTAGCATCACATGGTTTCTGAGCTGG

TCCCCTTGCGGAGAGTGTAGCAGGGCCATCACCGAGTTCCTGTCCAGATATCCACACGT

GACACTGTTTATCTACATCGCCAGGCTGTATCACCACGCAGACCCAAGGAATAGGCAGG

GCCTGCGCGATCTGATCAGCTCCGGCGTGACCATCCAGATCATGACAGAGCAGGAGTCC

GGCTACTGCTGGCGGAACTTCGTGAATTATTCTCCTAGCAACGAGGCCCACTGGCCTAG

GTACCCACACCTGTGGGTGCGCCTGTACGTGCTGGAGCTGTATTGCATCATCCTGGGCC

TGCCCCCTTGTCTGAATATCCTGCGGAGAAAGCAGCCCCAGCTGACCTTCTTTACAATC

GCCCTGCAGTCTTGTCACTATCAGAGGCTGCCACCCCACATCCTGTGGGCCACAGGCCT

GAAGTCTGGAGGATCTAGCGGAGGATCCTCTGGCAGCGAGACACCAGGAACAAGCGAGT

CAGCAACACCAGAGAGCAGTGGCGGCAGCAGCGGCGGCAGCGACAAGAAGTACAGCATC

GGCCTGGCCATCGGCACCAACTCTGTGGGCTGGGCCGTGATCACCGACGAGTACAAGGT

GCCCAGCAAGAAATTCAAGGTGCTGGGCAACACCGACCGGCACAGCATCAAGAAGAACC

TGATCGGAGCCCTGCTGTTCGACAGCGGCGAAACAGCCGAGGCCACCCGGCTGAAGAGA

ACCGCCAGAAGAAGATACACCAGACGGAAGAACCGGATCTGCTATCTGCAAGAGATCTT

CAGCAACGAGATGGCCAAGGTGGACGACAGCTTCTTCCACAGACTGGAAGAGTCCTTCC

TGGTGGAAGAGGATAAGAAGCACGAGCGGCACCCCATCTTCGGCAACATCGTGGACGAG

GTGGCCTACCACGAGAAGTACCCCACCATCTACCACCTGAGAAAGAAACTGGTGGACAG
```

-continued

```
CACCGACAAGGCCGACCTGCGGCTGATCTATCTGGCCCTGGCCCACATGATCAAGTTCC
GGGGCCACTTCCTGATCGAGGGCGACCTGAACCCCGACAACAGCGACGTGGACAAGCTG
TTCATCCAGCTGGTGCAGACCTACAACCAGCTGTTCGAGGAAAACCCCATCAACGCCAG
CGGCGTGGACGCCAAGGCCATCCTGTCTGCCAGACTGAGCAAGAGCAGACGGCTGGAAA
ATCTGATCGCCCAGCTGCCCGGCGAGAAGAAGAATGGCCTGTTCGGAAACCTGATTGCC
CTGAGCCTGGGCCTGACCCCCAACTTCAAGAGCAACTTCGACCTGGCCGAGGATGCCAA
ACTGCAGCTGAGCAAGGACACCTACGACGACGACCTGGACAACCTGCTGGCCCAGATCG
GCGACCAGTACGCCGACCTGTTTCTGGCCGCCAAGAACCTGTCCGACGCCATCCTGCTG
AGCGACATCCTGAGAGTGAACACCGAGATCACCAAGGCCCCCCTGAGCGCCTCTATGAT
CAAGAGATACGACGAGCACCACCAGGACCTGACCCTGCTGAAAGCTCTCGTGCGGCAGC
AGCTGCCTGAGAAGTACAAAGAGATTTTCTTCGACCAGAGCAAGAACGGCTACGCCGGC
TACATTGACGGCGGAGCCAGCCAGGAAGAGTTCTACAAGTTCATCAAGCCCATCCTGGA
AAAGATGGACGGCACCGAGGAACTGCTCGTGAAGCTGAACAGAGAGGACCTGCTGCGGA
AGCAGCGGACCTTCGACAACGGCAGCATCCCCCACCAGATCCACCTGGGAGAGCTGCAC
GCCATTCTGCGGCGGCAGGAAGATTTTTACCCATTCCTGAAGGACAACCGGGAAAAGAT
CGAGAAGATCCTGACCTTCCGCATCCCCTACTACGTGGGCCCTCTGGCCAGGGGAAACA
GCAGATTCGCCTGGATGACCAGAAAGAGCGAGGAAACCATCACCCCCTGGAACTTCGAG
GAAGTGGTGGACAAGGGCGCTTCCGCCCAGAGCTTCATCGAGCGGATGACCAACTTCGA
TAAGAACCTGCCCAACGAGAAGGTGCTGCCCAAGCACAGCCTGCTGTACGAGTACTTCA
CCGTGTATAACGAGCTGACCAAAGTGAAATACGTGACCGAGGGAATGAGAAAGCCCGCC
TTCCTGAGCGGCGAGCAGAAAAAGGCCATCGTGGACCTGCTGTTCAAGACCAACCGGAA
AGTGACCGTGAAGCAGCTGAAAGAGGACTACTTCAAGAAAATCGAGTGCTTCGACTCCG
TGGAAATCTCCGGCGTGGAAGATCGGTTCAACGCCTCCCTGGGCACATACCACGATCTG
CTGAAAATTATCAAGGACAAGGACTTCCTGGACAATGAGGAAAACGAGGACATTCTGGA
AGATATCGTGCTGACCCTGACACTGTTTGAGGACAGAGAGATGATCGAGGAACGGCTGA
AAACCTATGCCCACCTGTTCGACGACAAAGTGATGAAGCAGCTGAAGCGGCGGAGATAC
ACCGGCTGGGGCAGGCTGAGCCGGAAGCTGATCAACGGCATCCGGGACAAGCAGTCCGG
CAAGACAATCCTGGATTTCCTGAAGTCCGACGGCTTCGCCAACAGAAACTTCATGCAGC
TGATCCACGACGACAGCCTGACCTTTAAAGAGGACATCCAGAAAGCCCAGGTGTCCGGC
CAGGGCGATAGCCTGCACGAGCACATTGCCAATCTGGCCGGCAGCCCCGCCATTAAGAA
GGGCATCCTGCAGACAGTGAAGGTGGTGGACGAGCTCGTGAAAGTGATGGGCCGGCACA
AGCCCGAGAACATCGTGATCGAAATGGCCAGAGAGAACCAGACCACCCAGAAGGGACAG
AAGAACAGCCGCGAGAGAATGAAGCGGATCGAAGAGGGCATCAAAGAGCTGGGCAGCCA
GATCCTGAAAGAACACCCCGTGGAAAACACCCAGCTGCAGAACGAGAAGCTGTACCTGT
ACTACCTGCAGAATGGGCGGGATATGTACGTGGACCAGGAACTGGACATCAACCGGCTG
TCCGACTACGATGTGGACCATATCGTGCCTCAGAGCTTTCTGAAGGACGACTCCATCGA
CAACAAGGTGCTGACCAGAAGCGACAAGAACCGGGGCAAGAGCGACAACGTGCCCTCCG
AAGAGGTCGTGAAGAAGATGAAGAACTACTGGCGGCAGCTGCTGAACGCCAAGCTGATT
ACCCAGAGAAAGTTCGACAATCTGACCAAGGCCGAGAGAGGCGGCCTGAGCGAACTGGA
TAAGGCCGGCTTCATCAAGAGACAGCTGGTGGAAACCCGGCAGATCACAAAGCACGTGG
```

-continued

```
CACAGATCCTGGACTCCCGGATGAACACTAAGTACGACGAGAATGACAAGCTGATCCGG

GAAGTGAAAGTGATCACCCTGAAGTCCAAGCTGGTGTCCGATTTCCGGAAGGATTTCCA

GTTTTACAAAGTGCGCGAGATCAACAACTACCACCACGCCCACGACGCCTACCTGAACG

CCGTCGTGGGAACCGCCCTGATCAAAAAGTACCCTAAGCTGGAAAGCGAGTTCGTGTAC

GGCGACTACAAGGTGTACGACGTGCGGAAGATGATCGCCAAGAGCGAGCAGGAAATCGG

CAAGGCTACCGCCAAGTACTTCTTCTACAGCAACATCATGAACTTTTTCAAGACCGAGA

TTACCCTGGCCAACGGCGAGATCCGGAAGCGGCCTCTGATCGAGACAAACGGCGAAACC

GGGGAGATCGTGTGGGATAAGGGCCGGGATTTTGCCACCGTGCGGAAAGTGCTGAGCAT

GCCCCAAGTGAATATCGTGAAAAAGACCGAGGTGCAGACAGGCGGCTTCAGCAAAGAGT

CTATCCTGCCCAAGAGGAACAGCGATAAGCTGATCGCCAGAAAGAAGGACTGGGACCCT

AAGAAGTACGGCGGCTTCGACAGCCCCACCGTGGCCTATTCTGTGCTGGTGGTGGCCAA

AGTGGAAAAGGGCAAGTCCAAGAAACTGAAGAGTGTGAAAGAGCTGCTGGGGATCACCA

TCATGGAAAGAAGCAGCTTCGAGAAGAATCCCATCGACTTTCTGGAAGCCAAGGGCTAC

AAAGAAGTGAAAAAGGACCTGATCATCAAGCTGCCTAAGTACTCCCTGTTCGAGCTGGA

AAACGGCCGGAAGAGAATGCTGGCCTCTGCCGGCGAACTGCAGAAGGGAAACGAACTGG

CCCTGCCCTCCAAATATGTGAACTTCCTGTACCTGGCCAGCCACTATGAGAAGCTGAAG

GGCTCCCCCGAGGATAATGAGCAGAAACAGCTGTTTGTGGAACAGCACAAGCACTACCT

GGACGAGATCATCGAGCAGATCAGCGAGTTCTCCAAGAGAGTGATCCTGGCCGACGCTA

ATCTGGACAAAGTGCTGTCCGCCTACAACAAGCACCGGGATAAGCCCATCAGAGAGCAG

GCCGAGAATATCATCCACCTGTTTACCCTGACCAATCTGGGAGCCCCTGCCGCCTTCAA

GTACTTTGACACCACCATCGACCGGAAGAGGTACACCAGCACCAAAGAGGTGCTGGACG

CCACCCTGATCCACCAGAGCATCACCGGCCTGTACGAGACACGGATCGACCTGTCTCAG

CTGGGAGGTGACAGCGGCGGGAGCGGCGGGAGCGGGGGGAGCACTAATCTGAGCGACAT

CATTGAGAAGGAGACTGGGAAACAGCTGGTCATTCAGGAGTCCATCCTGATGCTGCCTG

AGGAGGTGGAGGAAGTGATCGGCAACAAGCCAGAGTCTGACATCCTGGTGCACACCGCC

TACGACGAGTCCACAGATGAGAATGTGATGCTGCTGACCTCTGACGCCCCCGAGTATAA

GCCTTGGGCCCTGGTCATCCAGGATTCTAACGGCGAGAATAAGATCAAGATGCTGAGCG

GAGGATCCGGAGGATCTGGAGGCAGCACCAACCTGTCTGACATCATCGAGAAGGAGACA

GGCAAGCAGCTGGTCATCCAGGAGAGCATCCTGATGCTGCCCGAAGAAGTCGAAGAAGT

GATCGGAAACAAGCCTGAGAGCGATATCCTGGTCCATACCGCCTACGACGAGAGTACCG

ACGAAAATGTGATGCTGCTGACATCCGACGCCCCAGAGTATAAGCCCTGGGCTCTGGTC

ATCCAGGATTCCAACGGAGAGAACAAAATCAAATGCTGTCTGGCGGCTCAAAAAGAAC

CGCCGACGGCAGCGAATTCGAGCCCAAGAAGAAGAGGAAAGTCGGAAGCGGAGCTACTA

ACTTCAGCCTGCTGAAGCAGGCTGGAGACGTGGAGGAGAACCCTGGACCTATGAGCGAG

CTGATCAAGGAGAACATGCACATGAAGCTGTACATGGAGGGCACCGTGAACAACCACCA

CTTCAAGTGCACATCCGAGGGCGAAGGCAAGCCCTACGAGGGCACCCAGACCATGAAGA

TCAAGGTGGTCGAGGGCGGCCCTCTCCCCTTCGCCTTCGACATCCTGGCTACCAGCTTC

ATGTACGGCAGCAAAGCCTTCATCAACCACACCCAGGGCATCCCCGACTTCTTTAAGCA

GTCCTTCCCTGAGGGCTTCACATGGGAGAGAATCACCACATACGAAGACGGGGGCGTGC

TGACCGCTACCCAGGACACCAGCTTCCAGAACGGCTGCATCATCTACAACGTCAAGATC

AACGGGGTGAACTTCCCATCCAACGGCCCTGTGATGCAGAAGAAAACACGCGGCTGGGA
```

```
GGCCAACACCGAGATGCTGTACCCCGCTGACGGCGGCCTGAGAGGCCACAGCCAGATGG

CCCTGAAGCTCGTGGGCGGGGGCTACCTGCACTGCTCCTTCAAGACCACATACAGATCC

AAGAAACCCGCTAAGAACCTCAAGATGCCCGGCTTCCACTTCGTGGACCACAGACTGGA

AAGAATCAAGGAGGCCGACAAAGAGACCTACGTCGAGCAGCACGAGATGGCTGTGGCCA

AGTACTGCGACCTCCCTAGCAAACTGGGGCACAGATCTGGTGGTTCTCCCAAGAAGAAG

AGGAAAGTCTAA
```

Split System

In some embodiments, the ABE disclosed herein comprises a "split" system, where either the Cas protein, the adenosine deaminase, or both, is split into two constituent parts and can be reconstituted to form a functional protein to execute base editing. A "split Cas9 protein," "split Cas9," or "split adenosine deaminase" refers to a Cas9 or adenosine deaminase protein that is provided as an N-terminal fragment and a C-terminal fragment encoded by two separate nucleotide sequences. The polypeptides corresponding to the N-terminal portion and the C-terminal portion of the Cas9 protein or adenosine deaminase can be spliced to form a "reconstituted" Cas9 protein or adenosine deaminase. In some embodiments, the Cas9 protein or adenosine deaminase is divided into two fragments within a disordered region of the protein, e.g., as described in Nishimasu et al., Cell, Volume 156, Issue 5, pp. 935-949, 2014, or as described in Jiang et al. (2016) Science 351:867-871. PDB file: 5F9R, each of which is incorporated herein by reference.

Inlaid System

In some embodiments, the ABE system disclosed herein comprises an inlaid system, where the adenosine deaminase is inserted into the Cas9 as exemplified in Example 10. In some embodiments, the disclosure provides a fusion protein comprising a nucleic acid-guided nuclease protein (e.g., a Cas9 or any nuclease disclosed herein) and an inlaid nucleotide deaminase protein domain. In some embodiments, the inlaid nucleotide deaminase protein domain is an inlaid adenosine deaminase protein domain. In some embodiments, the inlaid adenosine deaminase has an amino acid sequence that is at least 80%, 85%, 90%, 95%, 96%, 97%, 98%, or 99% identical to any one of SEQ ID NO: 74, 82, 241, 268-270, 36, 39-47, 49-52, 59, 71, 75-81, 84-87, 94, 116-140, and 220-240, 242.

EXAMPLES

The compositions and methods disclosed herein are further described in the following examples, which do not limit the scope of the compositions and methods described in the claims.

Example 1: Designing Adenine Deaminase Variants and Measuring Editing Efficiency by NGS 15 TadA deaminases were selected for targeted mutagenesis to produce adenine deaminase variants with DNA as a substrate. Structure-guided and sequence-guided mutations were introduced into those 15 TadA deaminases and the polynucleotide sequence encoding ecTadA8e in the ABE8e expression vector was replaced with polynucleotide sequences encoding each of the 15 engineered TadA variants to generate a series of 15 ABEs: T7.1, T7.4, T7.5, T7.6, T7.7, T7.8, T7.9, T7.10, T7.11, T7.12, T7.14, T7.15, T7.16, T7.17, and T7.24 (Table 1). Editing activities of the 15 ABEs were measured in HEK293T-GFP cell lines as described in further detail below.

HEK293T-GFP cells ($1.5 \times 10^4$) were seeded in a 96-well plate (Corning) 20-24 h before transfection. For on-target editing experiments, cells were transfected with 80 ng of the expression vector encoding the ABE, 40 ng spCas9 gRNA0 (GTT TAG AGT GAG CCA TGT AG (SEQ ID NO: 110)) expression plasmid, and 3.6 μL FuGENE HD Transfection Reagent (E2312) according to the manufacturer's protocols. After 48 hours, genomic DNA of the cells was extracted and analyzed by NGS for editing efficiency. Results for the 15 ABEs are shown in FIG. 1A.

Figure 1B:
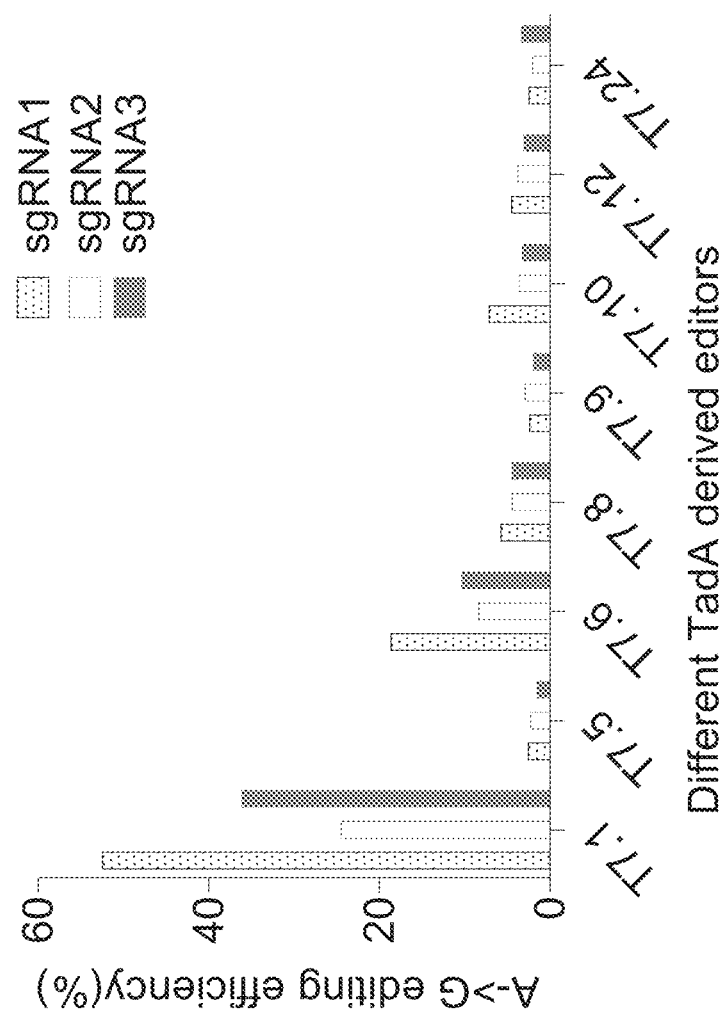
FIG. 1B is a plot of A-to-G editing efficiency of adenine base editors with $1^{st}$ round engineered TadA variants at 3 different sgRNA target sites measured by next-generation sequencing.

Next, editing efficiency of a subset of 8 of the 15 ABEs (T7.1, T7.5, T7.6, T7.8, T7.9, T7.10, T7.12, T7.24) was measured using additional sgRNAs (sgRNAs 1-3 shown in Table 2). 88 ng of the expression vector encoding each of the 15 ABEs, 24 ng sgRNA1, 24 ng sgRNA2 and 24 ng sgRNA3 expression plasmids were co-transfected into HEK293T cells. After 48 hours, genomic DNA of those cells was extracted and analyzed by NGS for editing efficiency. Results for the 8 ABEs are shown in FIG. 1B and Table 3. A-to-G editing efficiency is calculated as the percentage of reads with A to G mutations in total reads.

These results demonstrate that ABEs comprising TadA variants disclosed herein have low to moderate DNA adenine deamination activities, showing the possibility of evolving new ABEs from TadA orthologs.

TABLE 2

| spCas9 sgRNA sequences | | |
|---|---|---|
| sgRNA name | Sequence | Target gene |
| sgRNA1 | CACACACACTTAGAATCTGT (SEQ ID NO: 107) | intergenic |
| sgRNA2 | GCAGAGAGTCGCCGTCTCCA (SEQ ID NO: 108) | intergenic |
| sgRNA3 | CCCGCACCTTGGCGCAGCGG (SEQ ID NO: 109) | PCSK9 |

TABLE 2-continued spCas9 sgRNA sequences

| sgRNA name | Sequence | Target gene |
|---|---|---|
| sgRNA4 | CCCCACCGTTGAAGAACCAG (SEQ ID NO: 243) | CEACAM16 |
| sgRNA5 | GAGTCCGAGCAGAAGAAGAA (SEQ ID NO: 244) | EMX1 |

TABLE 3

A to G editing efficiency of 8 ABEs

| Base editor | sgRNA1 | sgRNA2 | sgRNA3 |
|---|---|---|---|
| T7.1 | 52.48 | 24.53 | 36.2 |
| T7.5 | 2.62 | 2.3 | 1.61 |
| T7.6 | 18.71 | 8.41 | 10.39 |
| T7.8 | 5.82 | 4.53 | 4.46 |
| T7.9 | 2.45 | 2.99 | 1.99 |
| T7.10 | 7.2 | 3.7 | 3.3 |
| T7.12 | 4.58 | 3.81 | 3.11 |
| T7.24 | 2.51 | 2.11 | 3.41 |

Figure 2A:
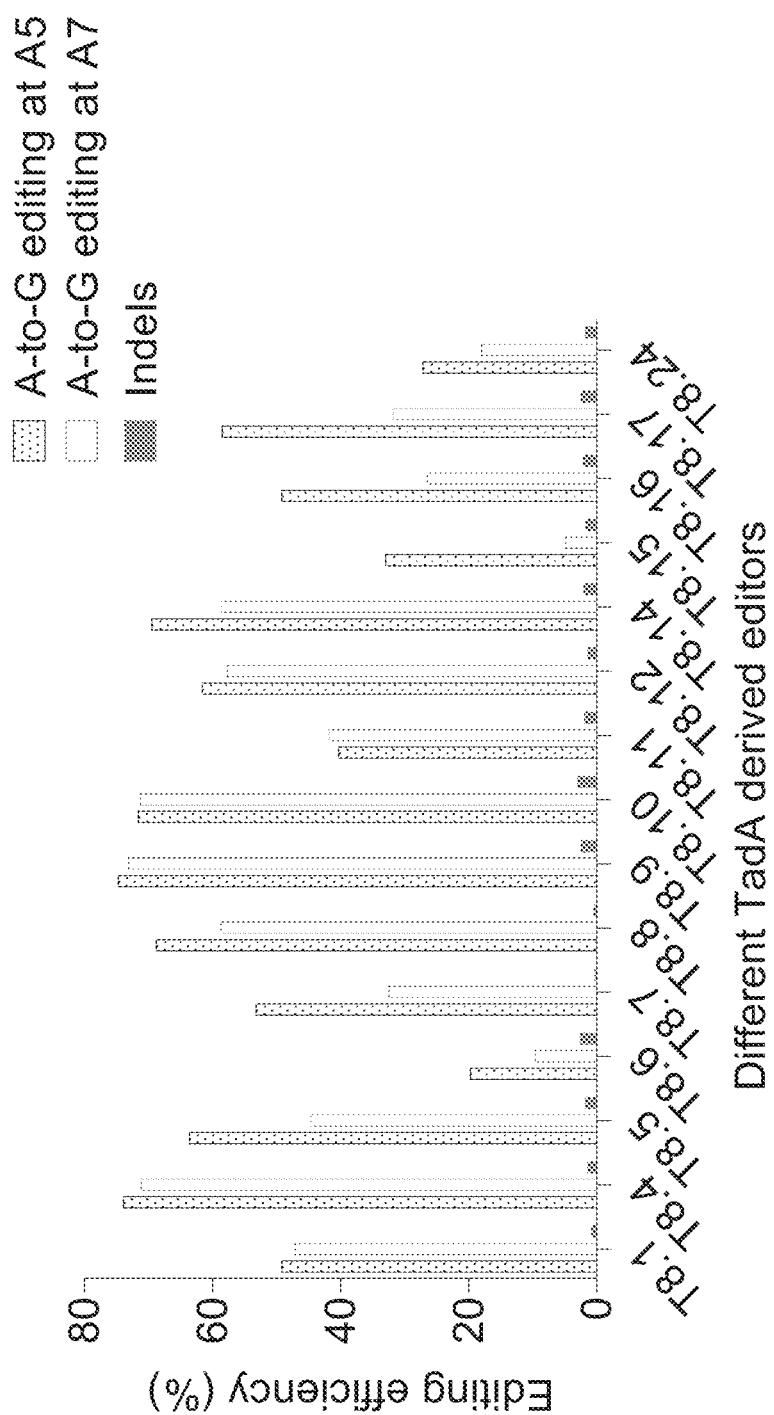
FIG. 2A is a plot of A-to-G editing efficiency and indel efficiency of adenine base editors with 2nd round engineered TadA variants at sgRNA0 target site measured by next-generation sequencing.

Example 2: Further Targeted Engineering of TadA Orthologs Generate DNA Deaminases with High Activity The 15 ABEs described in Example 1 and Table 1 were further engineered with additional functional mutations with the goal of further improving DNA deamination activity. These 15 additional ABE variants were designated T8.1, T8.4, T8.5, T8.6, T8.7, T8.8, T8.9, T8.10, T8.11, T8.12, T8.14, T8.15, T8.16, T8.17, T8.24. The additional 15 ABE variants were tested in HEK293T-GFP cells with sgRNA0 (GTT TAG AGT GAG CCA TGT AG (SEQ ID NO: 110)) according to the protocol described in Example 1. Several of these additional 15 ABE variants exhibited moderate to high A-to-G editing efficiency with top variants exhibited around 75% A-to-G editing efficiency (FIG. 2A).

Figure 2B:
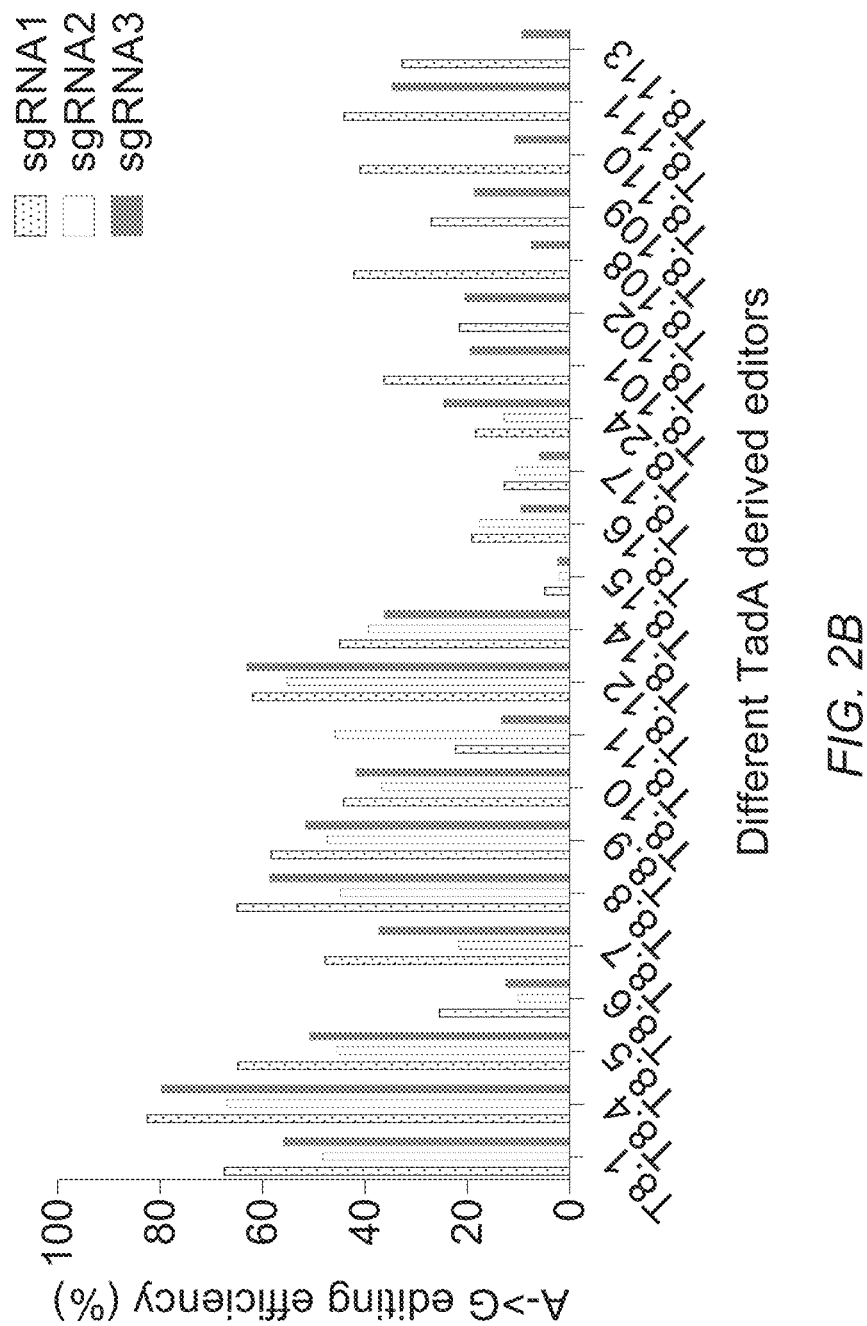
FIG. 2B is a plot of A-to-G editing efficiency of adenine base editors with 2nd round engineered TadA variants at 3 different sgRNA target sites measured by next-generation sequencing.

The additional ABE variants were further characterized using additional sgRNAs (sgRNAs 1-3 shown in Table 2) according to the protocol described in Example 1. ABE variants T8.1, T8.4, T8.5, T8.8, T8.9, T8.10, T8.12, and T8.14 exhibited robust editing across all sites (FIG. 2B and Table 4). A-to-G editing efficiency is calculated as the percentage of reads comprising an A-to-G mutations, out of the total number of reads.

Figure 3A:
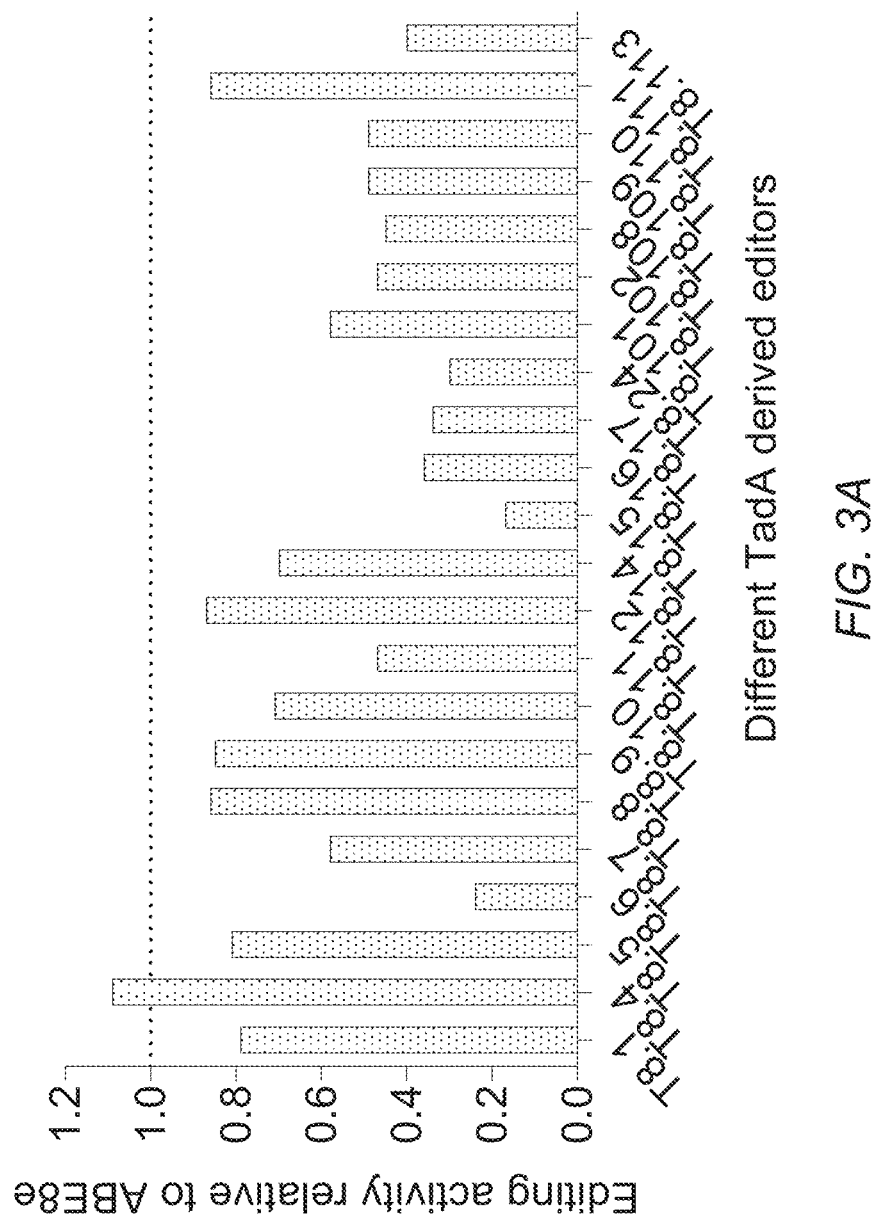
FIG. 3A is a plot of average value of A-to-G editing efficiency relative to ABE8e across 3 or 2 sites for new adenine base editors measured by next-generation sequencing.

A subset of the ABE variants were further engineered to generate ABE variants T8.101, T8.102, T8.108, T8.109, T8.110, T8.111, T8.113, T8.26, T8.28, T8.37, T8.52, T8.60, T8.61, T8.62, T8.65, T88.13, T88.23, T88.24, T88.30, T88.37, T88.52, T88.54, T88.57, T88.74, T88.84, T8.103, T8.105, T8.112, T8.114 and T8.107. Several of these additional ABE variants exhibited robust editing activities across different sites (FIG. 2B and Table 4). These additional ABE variants were compared with the ABE8e base editor, with several of the engineered ABE variants disclosed herein exhibiting comparable editing efficiency. ABE T8.4 exhibited higher editing efficiency than ABE8e (FIG. 3A and Table 5).

TABLE 4

A to G editing efficiency of further engineered ABEs

| Base editor | sgRNA1 | sgRNA2 | sgRNA3 | sgRNA0 |
|---|---|---|---|---|
| T8.1 | 67.56 | 48.19 | 55.91 | 49.20 |
| T8.4 | 82.59 | 67.07 | 79.79 | 73.99 |
| T8.5 | 64.89 | 45.63 | 50.77 | 63.68 |
| T8.6 | 25.54 | 10.12 | 12.54 | 19.80 |
| T8.7 | 47.87 | 21.69 | 37.3 | 53.28 |
| T8.8 | 65.07 | 44.81 | 58.65 | 68.86 |
| T8.9 | 58.41 | 47.41 | 51.67 | 74.77 |
| T8.10 | 44.22 | 36.71 | 41.82 | 71.66 |
| T8.11 | 22.45 | 45.83 | 13.39 | 41.80 |
| T8.12 | 62.01 | 55.2 | 63.11 | 61.69 |
| T8.14 | 45.01 | 39.3 | 36.24 | 69.52 |
| T8.15 | 4.97 | 2.1 | 2.36 | 33.03 |
| T8.16 | 19.21 | 17.65 | 9.64 | 49.25 |
| T8.17 | 12.92 | 10.65 | 5.95 | 58.53 |
| T8.24 | 18.43 | 12.92 | 24.71 | 27.21 |
| T8.101 | 36.33 | | 19.56 | |
| T8.102 | 21.61 | | 20.49 | |
| T8.108 | 42.22 | | 7.55 | |
| T8.109 | 27.1 | | 18.71 | |
| T8.110 | 41.07 | | 10.78 | |
| T8.111 | 44.16 | | 34.75 | |
| T8.113 | 32.83 | | 9.38 | |
| T8.26 | 13.39 | 4.33 | 10.49 | 10.11 |
| T8.28 | 14.91 | 6.14 | 14.64 | 14.61 |
| T8.37 | 10.51 | | 3.95 | 15.16 |
| T8.52 | 10.47 | | 13.83 | 18.76 |
| T8.60 | 5.08 | | 4.40 | 26.38 |
| T8.61 | 9.95 | | 7.43 | 29.43 |
| T8.62 | 0.86 | | 1.70 | 19.78 |
| T8.65 | 4.09 | | 3.34 | 19.84 |
| T88.13 | 27.87 | | 6.09 | 16.56 |
| T88.23 | 19.80 | | 7.77 | 15.30 |
| T88.24 | 7.29 | | | |
| T88.30 | 1.38 | | | |
| T88.37 | 8.91 | | 7.14 | 8.17 |
| T88.52 | 14.63 | | 6.93 | 14.93 |
| T88.54 | 16.81 | | 4.99 | 13.55 |
| T88.57 | 12.39 | | 2.43 | 10.45 |
| T88.74 | 4.26 | | | |
| T88.84 | 17.42 | | 0.06 | 18.46 |
| T8.103 | 23.73 | | 6.04 | |
| T8.105 | 14.86 | | 5.78 | |
| T8.112 | 30.59 | | 16.68 | |
| T8.114 | 30.45 | | 11.69 | |
| T8.107 | 29.57 | | 16.51 | |

TABLE 5

A-to-G editing efficiency of ABE variants relative to ABE8e

| Base editor | A-to-G editing ratio normalized by ABE8e activity in same experiment | | | | Average ratio |
|---|---|---|---|---|---|
| | sgRNA0 | sgRNA1 | sgRNA2 | sgRNA3 | |
| T8.1 | 0.81 | 0.82 | 0.76 | 0.75 | 0.79 |
| T8.4 | 1.21 | 1.01 | 1.06 | 1.08 | 1.09 |
| T8.5 | 1.04 | 0.79 | 0.72 | 0.69 | 0.81 |
| T8.6 | 0.32 | 0.31 | 0.16 | 0.17 | 0.24 |
| T8.7 | 0.87 | 0.58 | 0.34 | 0.50 | 0.58 |

TABLE 5-continued

A-to-G editing efficiency of ABE variants relative to ABE8e

| Base editor | A-to-G editing ratio normalized by ABE8e activity in same experiment | | | | Average ratio |
|---|---|---|---|---|---|
| | sgRNA0 | sgRNA1 | sgRNA2 | sgRNA3 | |
| T8.8 | 1.13 | 0.79 | 0.71 | 0.79 | 0.86 |
| T8.9 | 1.22 | 0.71 | 0.75 | 0.70 | 0.85 |
| T8.10 | 1.17 | 0.54 | 0.58 | 0.56 | 0.71 |
| T8.11 | 0.68 | 0.27 | 0.73 | 0.18 | 0.47 |
| T8.12 | 1.01 | 0.76 | 0.87 | 0.85 | 0.87 |
| T8.14 | 1.14 | 0.55 | 0.62 | 0.49 | 0.70 |
| T8.15 | 0.54 | 0.06 | 0.03 | 0.03 | 0.17 |
| T8.16 | 0.81 | 0.23 | 0.28 | 0.13 | 0.36 |
| T8.17 | 0.96 | 0.16 | 0.17 | 0.08 | 0.34 |
| T8.24 | 0.45 | 0.22 | 0.20 | 0.33 | 0.30 |
| T8.101 | | 0.59 | | 0.60 | 0.59 |
| T8.102 | | 0.35 | | 0.22 | 0.28 |
| T8.108 | | 0.68 | | 0.55 | 0.61 |
| T8.109 | | 0.44 | | 0.31 | 0.38 |
| T8.110 | | 0.66 | | 1.01 | 0.84 |
| T8.111 | | 0.71 | | 0.27 | 0.49 |
| T8.113 | | 0.53 | | 0.13 | 0.33 |
| T7.1 | 0.65 | 0.64 | 0.39 | 0.49 | 0.54 |
| T7.5 | 0.14 | 0.03 | 0.04 | 0.02 | 0.06 |
| T7.6 | 0.27 | 0.23 | 0.13 | 0.14 | 0.19 |
| T7.8 | 0.13 | 0.07 | 0.07 | 0.06 | 0.08 |
| T7.9 | 0.19 | 0.03 | 0.05 | 0.03 | 0.07 |
| T7.10 | 0.21 | 0.09 | 0.06 | 0.04 | 0.10 |
| T7.12 | 0.18 | 0.06 | 0.06 | 0.04 | 0.08 |
| T7.24 | 0.11 | 0.03 | 0.03 | 0.05 | 0.05 |
| T8.26 | 0.17 | 0.16 | 0.07 | 0.14 | 0.13 |
| T8.28 | 0.24 | 0.18 | 0.10 | 0.20 | 0.18 |
| T8.37 | 0.24 | 0.17 | | 0.08 | 0.16 |
| T8.52 | 0.30 | 0.29 | | 0.29 | 0.29 |
| T8.60 | 0.42 | 0.14 | | 0.09 | 0.22 |
| T8.61 | 0.46 | 0.27 | | 0.16 | 0.30 |
| T8.62 | 0.31 | 0.02 | | 0.04 | 0.12 |
| T8.65 | 0.31 | 0.11 | | 0.07 | 0.17 |
| T8.103 | | 0.38 | | 0.18 | 0.28 |
| T8.105 | | 0.24 | | 0.17 | 0.20 |
| T8.112 | | 0.49 | | 0.49 | 0.49 |
| T8.114 | | 0.49 | | 0.34 | 0.42 |
| T8.107 | | 0.48 | | 0.48 | 0.48 |
| T88.13 | 0.26 | 0.45 | | 0.13 | 0.28 |
| T88.23 | 0.24 | 0.32 | | 0.16 | 0.24 |
| T88.24 | | 0.12 | | | 0.12 |
| T88.30 | | 0.02 | | | 0.02 |
| T88.37 | 0.13 | 0.14 | | 0.15 | 0.14 |
| T88.52 | 0.24 | 0.24 | | 0.15 | 0.21 |
| T88.54 | 0.21 | 0.27 | | 0.11 | 0.20 |
| T88.57 | 0.16 | 0.20 | | 0.05 | 0.14 |
| T88.74 | | 0.07 | | | 0.07 |
| T88.84 | 0.29 | 0.28 | | 0.00 | 0.19 |

Example 3: Characterization of Off-Target Activity and Editing Window of ABEs Comprising TadA Variants To evaluate unguided single-stranded DNA deamination (unguided DNA off-target) mediated by the ABEs comprising TadA variants, R-loop assays were performed. The R-loop assay is a high-throughput method for assessing sgRNA-independent off-target effects of base editors that leverages the orthogonal R-loops generated by SaCas9 nickase to mimic actively transcribed genomic loci that are more susceptible to deaminases. The SaCas9 nickase is fused with two copies of uracil glycosylase inhibitor (UGI), which serves to amplify the potential for off-target effects which are then detected by the assay. As performed in this example, sgRNA3 provided in Table 2 was used to direct on-target editing and two saCas9 gRNAs provided in Table 6 were used to mimic off-target editing.

TABLE 6 saCas9 gRNAs used in off-target experiments

| SgRNA name | Sequence | Target gene |
|---|---|---|
| saRNA3 | GTGTCAGGTAATGTGCTAAACA (SEQ ID NO: 113) | SSH2 |
| saRNA5 | TCTGCTTCTCCAGCCCTGGC (SEQ ID NO: 115) | LINC01509 |

For R-loop experiments, 48 ng of the expression vector encoding each of the base editors, 32 ng SpCas9 guide RNA plasmid (sgRNA3 provided in Table 2), 48 ng nSaCas9-2× UGI plasmid and 32 ng SaCas9 guide RNA plasmid were co-transfected into HEK293T cells in a 96-well plate. After two days, NGS analysis was used to detect off-target deamination at the two nSaCas9 loci.

Figure 3B:
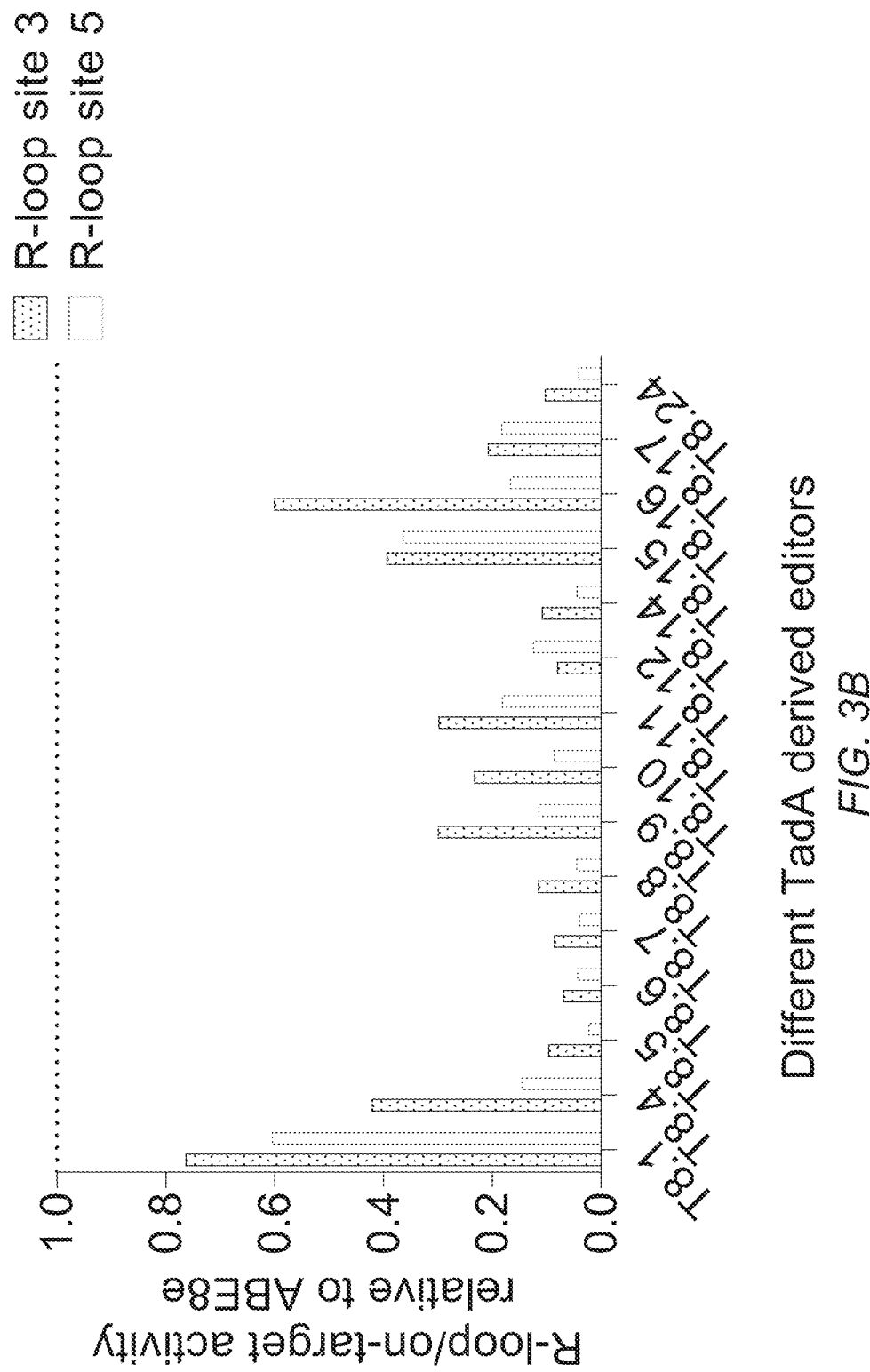
FIG. 3B is a plot of R-loop/on-target activity relative to ABE8e at two R-loop sites for new adenine base editors measured by next-generation sequencing.

Results of the orthogonal R-loop assay are shown in FIG. 3B and Table 7. All variants tested showed lower R-loop activity comparable to ABE8e, and several variants show also higher editing efficiency at on-target site.

Figure 3C:
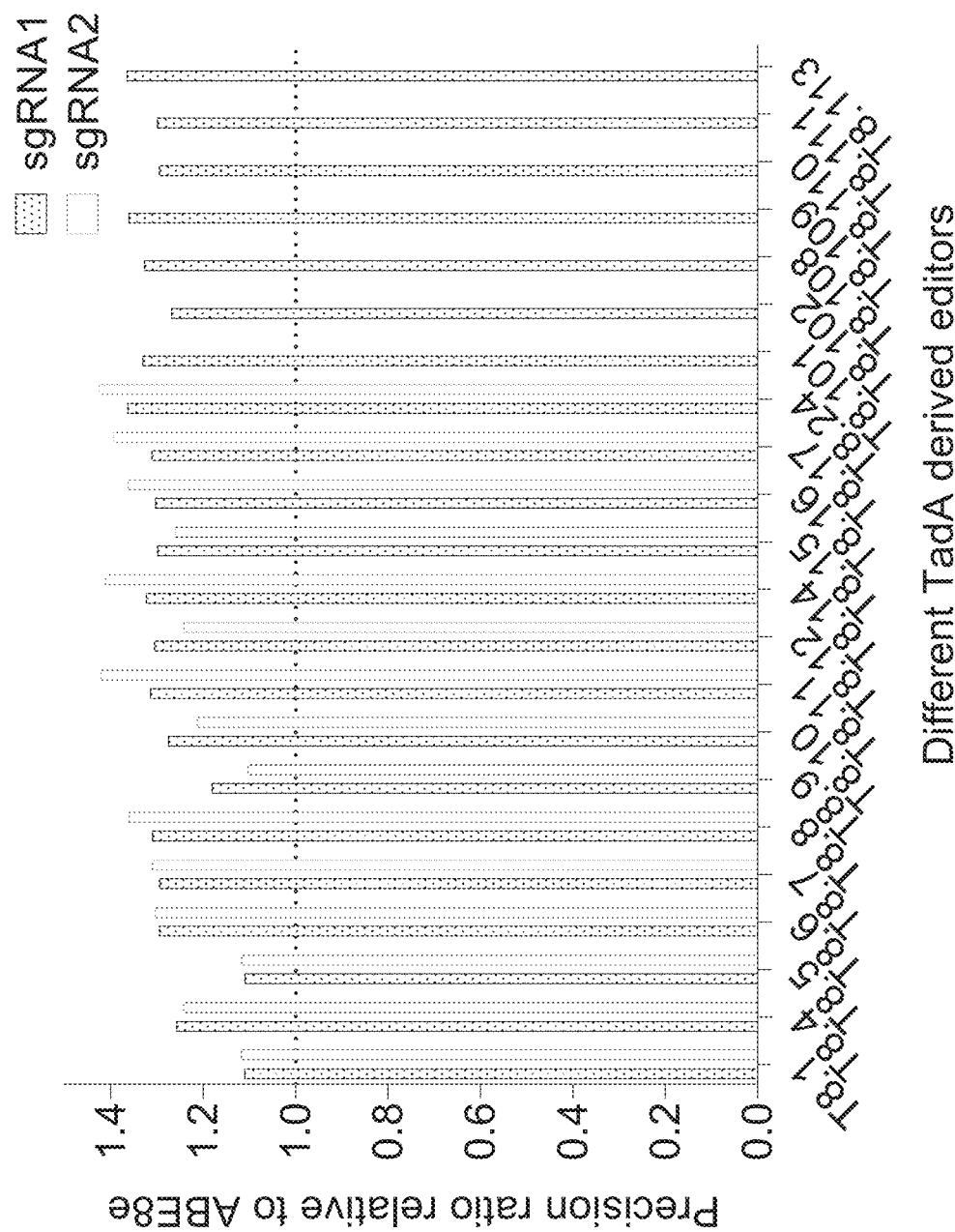
FIG. 3C is a plot of calculated precision ratio relative to ABE8e at 2 or 1 target sites for new adenine base editors measured by next-generation sequencing.

In order to determine the precision of the editing window of the ABEs disclosed herein, the precision ratio for each ABE was estimated. The precision ratio is calculated by dividing the sum of editing at each editable nucleotide within the classical 4-8 basepair window by the sum of editing at each editable nucleotide within the whole protospacer region (5' position of protospacer numbered 1). Editors with lower precision are expected to induce more editing events outside of the classical window and are therefore estimated to have a lower precision ratio. Results of precision ratio of the ABEs disclosed herein are shown in FIG. 3C and Table 8. Most variants showed higher precision ratio than ABE8e, indicating they could induce less bystander editing.

Figure 3D:
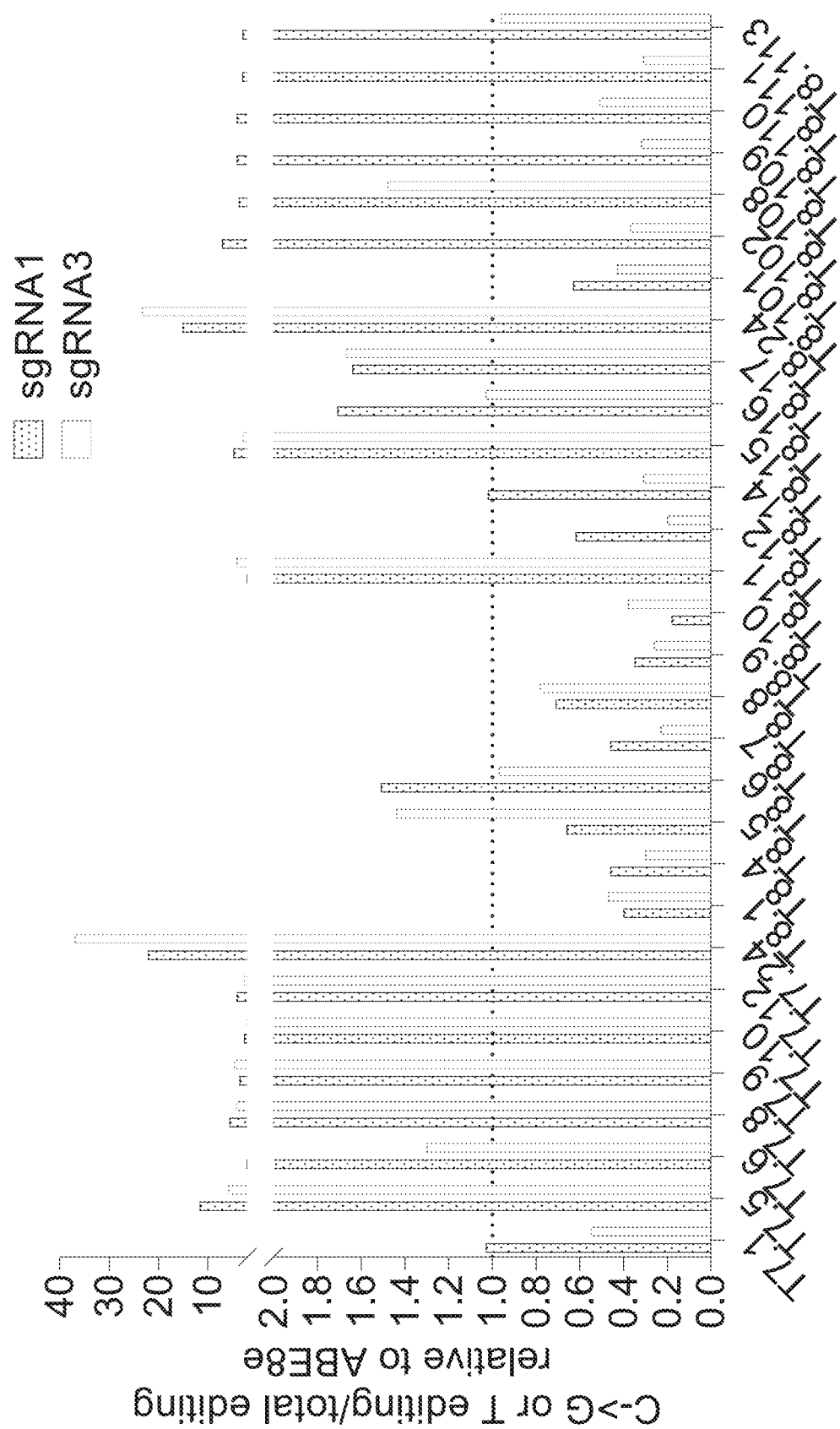
FIG. 3D is a plot of C-to-G or T editing divided by total editing (impurity ratio) relative to ABE8e at 2 target sites for new adenine base editors measured by next-generation sequencing.
Figure 3E:
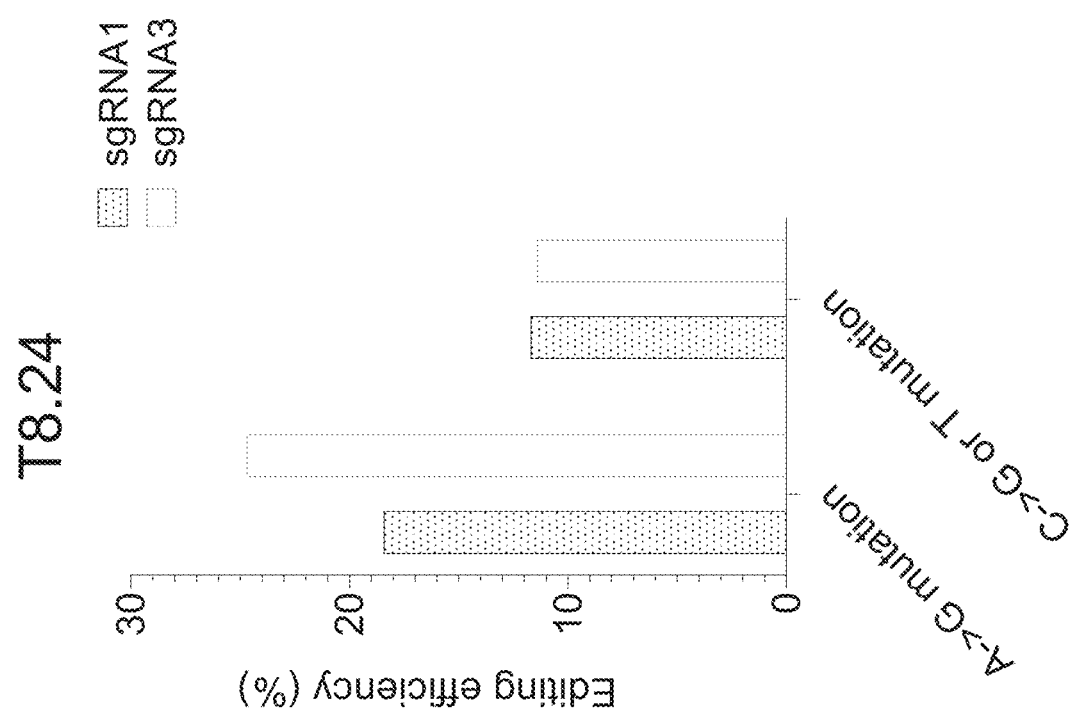
FIG. 3E is a plot of A-to-G editing efficiency and C-to-G or T editing efficiency at 2 target sites for new adenine base editor T8.24 measured by next-generation sequencing.

In some cases, ABEs can induce C-to-T or G editing, which decreases the editing purity of ABEs as an undesired outcome for therapeutic applications. The impurity ratio for the ABEs disclosed herein was estimated by calculating C-to-T or G editing efficiency/total editing efficiency relative to ABE8e. Results are shown in FIG. 3D and Table 9. ABEs T8.1, 4, 7, 8, 9, 10, 12 exhibited higher editing purity compared ABE8e. ABE variant T8.24, T88.74, T8.26, T8.28, T88.24, T88.30 showed greater than 10-fold higher impurity ratio compared to ABE8e, indicating it can be applied for both ABE and CBE (CABE) applications. Further characterization showed that ABE T8.24 could achieve robust A-to-G and C-to-T editing at the same time at different genomic loci (FIG. 3E and Table 10). Among them, ABE variant T88.74 showed robust C-to-T or G editing with low A-to-G editing across three tested sites, which could be potentially used as a CBE deaminase with high editing purity.

TABLE 7

R-loop assays for new ABE variants relative to ABE8e

| Base editor | ON target editing efficiency | R-loop site 3 editing efficiency/on-target editing efficiency relative to ABE8e | R-loop site 5 editing efficiency/on-target editing efficiency relative to ABE8e |
|---|---|---|---|
| T8.1 | 43.265 | 0.764 | 0.604 |
| T8.4 | 58.209 | 0.421 | 0.147 |
| T8.5 | 30.923 | 0.097 | 0.023 |
| T8.6 | 17.068 | 0.070 | 0.043 |
| T8.7 | 23.776 | 0.087 | 0.040 |
| T8.8 | 28.752 | 0.117 | 0.046 |
| T8.9 | 33.504 | 0.300 | 0.115 |
| T8.10 | 41.943 | 0.233 | 0.087 |
| T8.11 | 7.582 | 0.299 | 0.182 |
| T8.12 | 36.214 | 0.081 | 0.126 |
| T8.14 | 25.042 | 0.109 | 0.045 |
| T8.15 | 2.096 | 0.394 | 0.365 |
| T8.16 | 6.975 | 0.601 | 0.168 |
| T8.17 | 4.682 | 0.208 | 0.184 |
| T8.24 | 15.456 | 0.104 | 0.043 |
| ABE8e | 40.226 | 1.000 | 1.000 |
| T7.1 | 16.034 | 0.099 | 0.090 |
| T7.6 | 25.690 | 0.150 | 0.317 |

TABLE 8

Editing precision of new ABE variants relative to ABE8e

| Base editor | sgRNA1 | sgRNA2 |
|---|---|---|
| T8.1 | 1.111 | 1.118 |
| T8.4 | 1.258 | 1.244 |
| T8.5 | 1.110 | 1.117 |
| T8.6 | 1.295 | 1.304 |
| T8.7 | 1.295 | 1.310 |
| T8.8 | 1.311 | 1.361 |
| T8.9 | 1.181 | 1.104 |
| T8.10 | 1.276 | 1.213 |
| T8.11 | 1.315 | 1.422 |
| T8.12 | 1.306 | 1.243 |
| T8.14 | 1.324 | 1.412 |
| T8.15 | 1.299 | 1.261 |
| T8.16 | 1.304 | 1.363 |
| T8.17 | 1.312 | 1.395 |
| T8.24 | 1.364 | 1.427 |
| T8.101 | 1.331 | |
| T8.102 | 1.269 | |
| T8.108 | 1.328 | |
| T8.109 | 1.362 | |
| T8.110 | 1.296 | |
| T8.111 | 1.300 | |
| T8.113 | 1.366 | |
| T7.1 | 1.296 | 1.326 |
| T7.5 | 1.307 | 1.417 |
| T7.6 | 1.291 | 1.299 |
| T7.8 | 1.336 | 1.406 |
| T7.9 | 1.271 | 1.392 |
| T7.10 | 1.315 | 1.404 |
| T7.12 | 1.330 | 1.401 |
| T7.24 | 1.337 | 1.439 |
| T8.1-Q | 1.422 | |
| T8.4-Q | 1.440 | |
| T8.26 | 1.35 | 1.32 |
| T8.28 | 1.35 | 1.39 |
| T8.37 | 1.21 | |
| T8.52 | 1.01 | |
| T8.60 | 0.74 | |
| T8.61 | 0.78 | |
| T8.62 | 0.46 | |
| T8.65 | 0.90 | |
| T8.103 | 1.29 | |
| T8.105 | 1.36 | |
| T8.112 | 1.32 | |
| T8.114 | 1.36 | |
| T8.107 | 1.40 | |
| T88.13 | 1.23 | |
| T88.23 | 1.21 | |
| T88.24 | 1.22 | |
| T88.30 | 1.19 | |
| T88.37 | 1.22 | |
| T88.52 | 1.21 | |
| T88.54 | 1.20 | |
| T88.57 | 1.22 | |
| T88.74 | 1.17 | |
| T88.84 | 1.21 | |
| ABE8e | 1.000 | 1.000 |

TABLE 9

C-to-G or T editing/total editing (impurity ratio) relative to ABE8e

| Base editor | sgRNA1 | sgRNA3 |
|---|---|---|
| T7.1 | 1.03 | 0.55 |
| T7.5 | 11.64 | 5.77 |
| T7.6 | 2.10 | 1.30 |
| T7.8 | 5.56 | 4.31 |
| T7.9 | 3.55 | 4.69 |
| T7.10 | 2.64 | 2.11 |
| T7.12 | 4.07 | 2.66 |
| T7.24 | 22.09 | 36.91 |
| T8.1 | 0.40 | 0.47 |
| T8.4 | 0.46 | 0.30 |
| T8.5 | 0.66 | 1.44 |
| T8.6 | 1.51 | 0.97 |
| T8.7 | 0.46 | 0.23 |
| T8.8 | 0.71 | 0.78 |
| T8.9 | 0.35 | 0.26 |
| T8.10 | 0.18 | 0.38 |
| T8.11 | 2.07 | 4.10 |
| T8.12 | 0.62 | 0.20 |
| T8.14 | 1.02 | 0.31 |

TABLE 9-continued

C-to-G or T editing/total editing (impurity ratio) relative to ABE8e

| Base editor | sgRNA1 | sgRNA3 |
|---|---|---|
| T8.15 | 4.79 | 3.00 |
| T8.16 | 1.71 | 1.03 |
| T8.17 | 1.64 | 1.67 |
| T8.24 | 15.03 | 23.26 |
| T8.101 | 0.63 | 0.43 |
| T8.102 | 7.10 | 0.37 |
| T8.108 | 3.63 | 1.48 |
| T8.109 | 4.08 | 0.32 |
| T8.110 | 4.09 | 0.51 |
| T8.111 | 2.99 | 0.31 |
| T8.113 | 2.95 | 0.96 |
| T8.26 | 18.09 | 16.22 |
| T8.28 | 13.73 | 10.62 |
| T8.37 | 5.22 | 1.66 |
| T8.52 | 0.44 | 0.40 |
| T8.60 | 1.50 | 1.48 |
| T8.61 | 0.68 | 0.65 |
| T8.62 | 3.18 | 1.83 |
| T8.65 | 1.25 | 1.26 |
| T8.103 | 7.01 | 1.80 |
| T8.105 | 9.05 | 2.51 |
| T8.112 | 3.75 | 0.60 |
| T8.114 | 3.55 | 0.52 |
| T8.107 | 5.20 | 0.65 |
| T88.13 | 1.68 | 0.87 |
| T88.23 | 1.14 | 0.72 |
| T88.24 | 21.87 | |
| T88.30 | 24.23 | |
| T88.37 | 0.99 | |
| T88.52 | 3.29 | 0.78 |
| T88.54 | 1.66 | 1.44 |
| T88.57 | 1.67 | 2.11 |
| T88.74 | 33.31 | |
| T88.84 | 1.73 | 26.55 |

TABLE 10

A-to-G and C-to-T/G editing of selected ABE variants

| Base editor | sgRNA4 A-to-G mutation | C-to-G/T mutation | sgRNA1 A-to-G mutation | C-to-G/T mutation | sgRNA5 A-to-G mutation | C-to-G/T mutation |
|---|---|---|---|---|---|---|
| T8.24 | 3.46 | 12.89 | 18.43 | 11.71 | 3.42 | 35.15 |
| T8.26 | 2.05 | 3.49 | 4.56 | 4.13 | 0.83 | 16.23 |
| T8.28 | 3.13 | 4.72 | 6.01 | 3.32 | 1.45 | 18.92 |
| T88.24 | 1.37 | 23.15 | 2.32 | 3.02 | 0.74 | 34.05 |
| T88.30 | 0.47 | 6.81 | 0.88 | 1.47 | 0.20 | 20.68 |
| T88.74 | 2.32 | 18.25 | 1.73 | 10.70 | 0.49 | 36.64 |

Example 4: Further Engineering of ABEs to Enhance Precision

Figure 4:
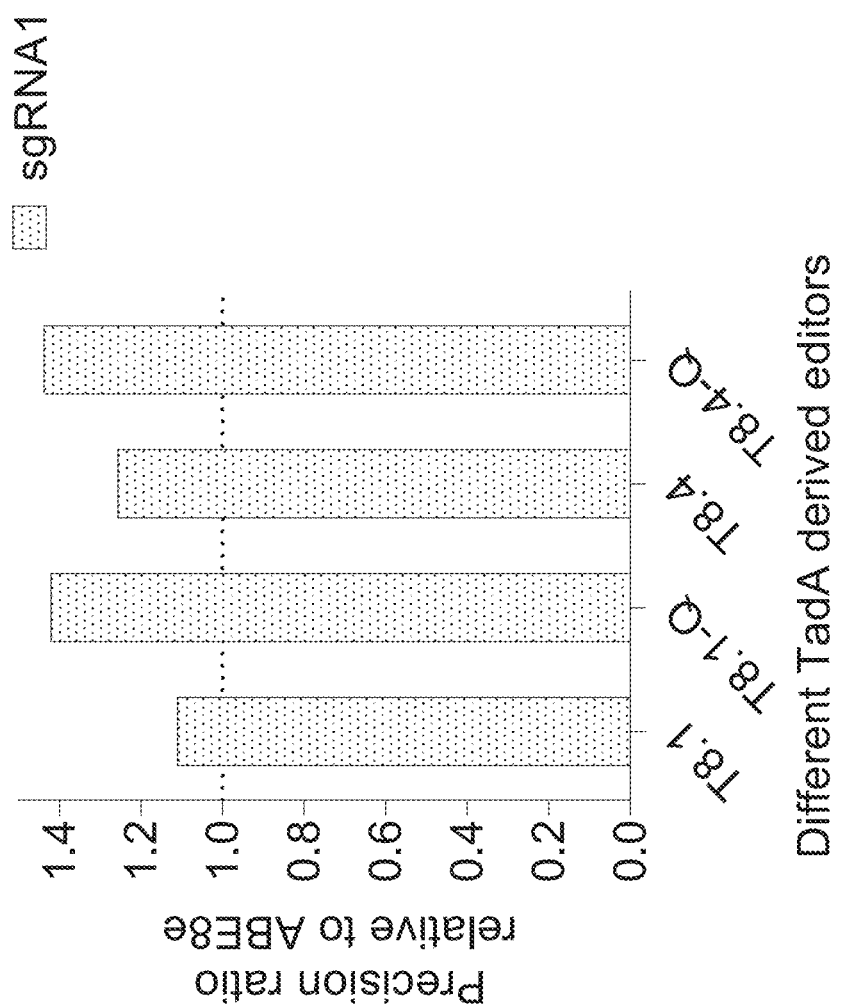
FIG. 4 is a plot of calculated precision ratio relative to ABE8e of T8.1, T8.4, T8.1-Q and T8.4-Q measured by next-generation sequencing.

To further improve editing precision, ABEs T8.1 and T8.4 were further engineered, with the resulting ABE variants designated T8.1-Q and T8.4-Q, respectively. The precision ratio for T8.1-Q and T8.4-Q was estimated as described above. Results are shown in FIG. 4 and Table 8. T8.1-Q and T8.4-Q showed improved precision relative to T8.1 and T8.4 and relative to ABE8e.

Example 5: Further Engineering of TadA Variants to Yield CBE Activity

TadA variants were further engineered in order to explore whether TadA variants could mediate high C-to-T editing in the human genome.

Figure 5:
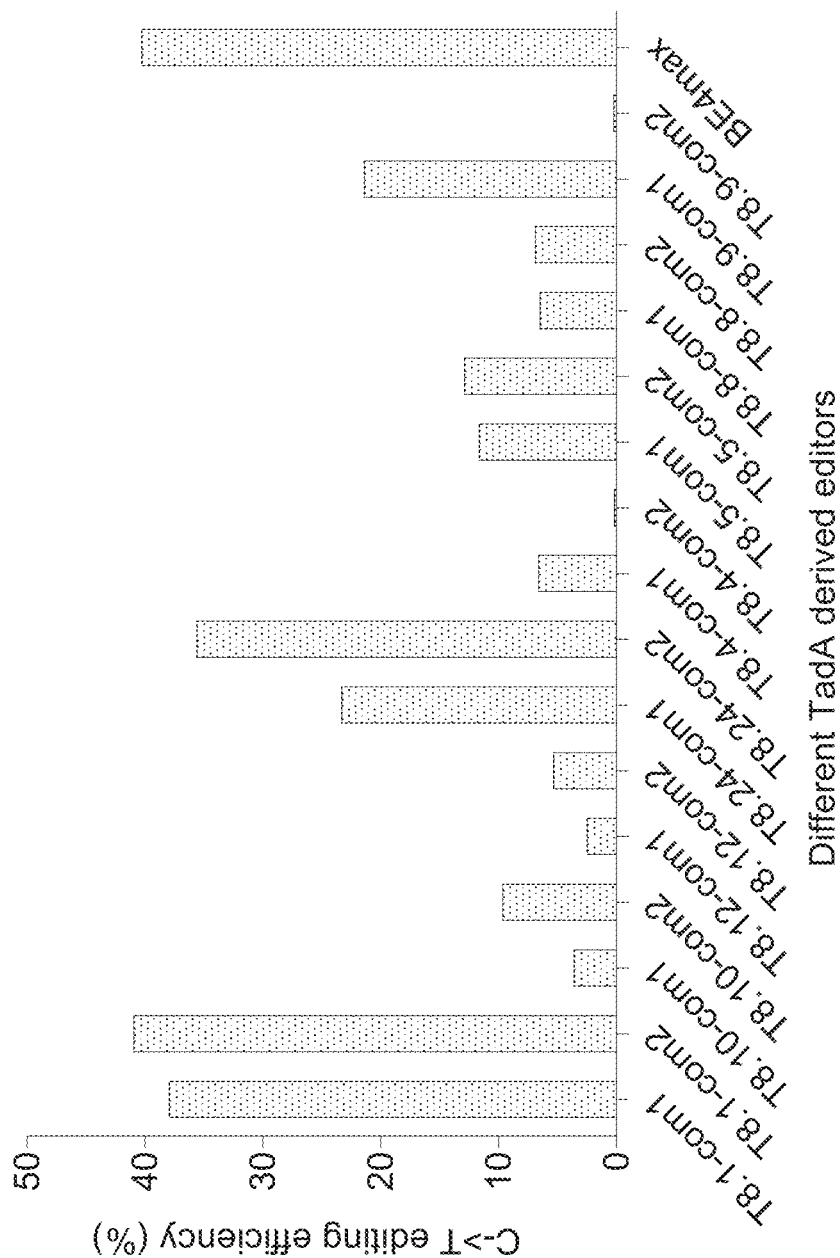
FIG. 5 is a plot of C-to-T editing efficiency of engineered TadA derived CBEs and BE4max measured by next-generation sequencing.

TadA variants with either high A-to-G editing activity or high C-to-G/T editing activity were further engineered to enhance their cytidine deaminase activity. The polynucleotide sequence encoding rAPOBEC1 in BE4max expression vector was replaced with the polynucleotide sequences encoding different TadA variants to generate new CBE variants. Their CBE activities were tested using sgRNA4 (GAG TCC GAG CAG AAG AAG AA (SEQ ID NO: 141)) using the methods described above. Results are shown in FIG. 5 and Table 11. Functional CBEs were obtained with engineered TadA variants and several of the TadA-derived CBEs achieved comparable editing efficiency as BE4max. In general, TadA-derived CBEs induced much less unguided DNA off-target editing and RNA off-target editing compared to rAPOBEC1. The size of most TadA variants are also smaller compared to rAPOBEC1 used by BE4max. Those attributes can be advantageous for use of the TadA variants disclosed herein in CBEs that are safer and smaller alternatives to BE4max.

TABLE 11

C-to-T editing efficiency of TadA-derived CBEs

| Base editor | C-to-T editing efficiency |
|---|---|
| T8.1-com1 | 37.96 |
| T8.1-com2 | 40.97 |
| T8.10-com1 | 3.63 |
| T8.10-com2 | 9.68 |
| T8.12-com1 | 2.51 |
| T8.12-com2 | 5.38 |
| T8.24-com1 | 23.32 |
| T8.24-com2 | 35.63 |
| T8.4-com1 | 6.63 |
| T8.4-com2 | 0.22 |

TABLE 11-continued

C-to-T editing efficiency of TadA-derived CBEs

| Base editor | C-to-T editing efficiency |
|---|---|
| T8.5-com1 | 11.68 |
| T8.5-com2 | 12.92 |
| T8.8-com1 | 6.50 |
| T8.8-com2 | 6.91 |
| T8.9-com1 | 21.41 |
| T8.9-com2 | 0.25 |
| BE4max | 40.30 |

Example 6: Evaluating ABE Activity Encoded by mRNA Administered to Huh7 Cells In order to evaluate base editing activity for ABEs administered as mRNA, mRNA was produced for selected ABE editors and was combined with selected potent sgRNAs (described in Table 12) for activity characterization in Huh7 cells. Huh7 cells were cultured in DMEM media supplemented with 10% fetal bovine serum. Cells were plated at a density of 8000 cells/well in 96-well plates 24 hours prior to transfection. For each sample, 100 ng base editor mRNA and 100 ng end-modified synthesized sgRNA were transfected with Lipofectamine MessengerMAX (ThermoFisher, Cat. LMRNA003) following the manufacturer's protocol. After 72 hours, genomic DNA was harvested from the Huh7 cells and editing efficiency was analyzed by amplicon-seq using NGS. Editing efficiency for each combination of base editor and sgRNA was calculated and is shown in Table 13. All selected base editor variants showed successful editing when administered to cells as mRNA in combination with sgRNAs. T8.1, T8.4, T8.10, T8.12 and T8.111 showed higher average on-target activities relative to the well-known ABE variant ABE8.8 at selected loci.

TABLE 12 sgRNA used for on-target activity characterization in Huh7 cells (RNA components)

| gRNA | Spacer sequence | SEQ ID NO |
|---|---|---|
| gRNA_h1 | CTAATTACAGCGCGGTGTGG | 245 |
| gRNA_h2 | CAAAAGGTGAAGAAAGAAGT | 246 |
| gRNA_h3 | TCAAAAGGTGAAGAAAGAAG | 247 |
| gRNA_h4 | TCACAGATTATGGCCTGTAT | 248 |
| gRNA_PCSK9 | CCCGCACCTTGGCGCAGCGG | 249 |

TABLE 13

A-to-G Editing Efficiency (%) of ABEs Administered as mRNA in Huh7 Cells

| Base editor | gRNA_h1 | gRNA_h2 | gRNA_h3 | gRNA_h4 | gRNA_PCSK9 | Mean |
|---|---|---|---|---|---|---|
| T7.1 | 51.49 | 24.89 | 18.04 | 16.73 | 55.65 | 33.36 |
| T8.1 | 73.80 | 75.34 | 70.88 | 74.71 | 92.33 | 77.41 |
| T8.4 | 82.46 | 81.10 | 78.17 | 75.19 | 92.18 | 81.82 |
| T8.5 | 87.64 | 43.99 | 58.28 | 26.52 | 77.81 | 58.85 |
| T8.8 | 84.21 | 77.22 | 69.23 | 50.15 | 87.79 | 73.72 |
| T8.10 | 85.73 | 77.61 | 78.95 | 71.34 | 85.46 | 79.82 |
| T8.12 | 87.58 | 76.32 | 77.67 | 61.19 | 89.80 | 78.51 |
| T8.111 | 86.44 | 83.34 | 85.08 | 64.72 | 90.51 | 82.02 |
| T8.112 | 82.35 | 64.23 | 77.12 | 46.11 | 77.04 | 69.37 |
| T8.113 | 79.18 | 14.41 | 27.64 | 17.52 | 64.99 | 40.75 |
| ABE8.8 | 71.46 | 71.10 | 62.15 | 69.96 | 88.60 | 72.65 |

Example 7: Evaluating ABE Activity Encoded by mRNA Administered to Primary Human Hepatocytes (PHH)

Editing activity of selected ABEs administered as mRNA and in combination with selected sgRNAs was further evaluated in primary human hepatocytes (PHH). PHHs were cultured per the manufacturer's protocol. Cells were thawed and resuspended in hepatocyte thawing medium with supplements followed by centrifugation at 100 g for 10 minutes for concentration. The supernatant was discarded and the pelleted cells were resuspended in hepatocyte plating medium plus supplement. Cells were counted and plated on Bio-coat collagen I coated 48-well plates (ThermoFisher, Cat. 877272) at a density of 132,000 cells/well. Plated cells were allowed to settle and adhere for 4-6 hours in a tissue culture incubator at 37° C. and 5% $CO_2$ atmosphere. Each well was transfected with 250 ng base editor mRNA and 250 ng end-modified sgRNA using RNAiMax according to manufacturer's protocol. After 24 hours, the culture medium was changed for fresh medium. 72 hours after transfection, genomic DNA were extracted from cells and editing efficiency was analyzed by amplicon-seq using NGS. The editing efficiencies achieved in PHH for each combination of base editor and sgRNA are shown in Table 14. All selected variants showed successful editing in PHH when delivered as mRNA in combination with sgRNAs.

TABLE 14

A-to-G Editing Efficiency (%) of ABEs Administered as mRNA in PHHs

| Based editor | gRNA_h1 | gRNA_h2 | gRNA_h3 | gRNA_h4 | gRNA_PCSK9 |
|---|---|---|---|---|---|
| T8.4 | 44.14 | 40.94 | 42.36 | 23.21 | 72.49 |
| T8.12 | 30.99 | 22.89 | 31.93 | 14.44 | 58.82 |
| T8.111 | 39.71 | 41.16 | 37.05 | 18.84 | 64.91 |

Example 8: Evaluating ABE Activity in Humanized Mice Model

The editing efficacy of selected base editors was further evaluated using a humanized PCSK9 mouse model with mouse Pcsk9 gene replaced by human PCSK9 gene. A guide RNA (gRNA_PCSK9, detailed in Table 12, SEQ ID NO: 249) was designed specifically to disrupt the human PCSK9 gene and employed in the experiment. The mRNA and modified gRNA (Finn et al., 2018) were combined and encapsulated into lipid nanoparticles (LNPs), following the methodology outlined in patent application WO/2023/185697A2. These formulated LNPs were then administered to humanized mice through tail vein injections at varying doses (0.3/0.6/1/3 mg/kg).

After a 1 or 2-week period, mouse liver and blood samples were collected for analysis. DNA editing in the liver and PCSK9 protein levels in the blood were evaluated. These results demonstrated a higher DNA editing efficiency and PCSK9 protein knock-down efficacy in mice dosed with T8.4 relative to those dosed with ABE8.8 across all dosage ranges. In-laid design of T8.4 also achieved up to 40% editing in liver at 1 mg/kg (mpk) when delivered by LNP. Another two leads T8.1 ABE and T8.111 ABE achieved >50% editing at 3 mpk (shown in Table 15).

TABLE 15

DNA Editing Efficiency (%) and PCSK9 Protein Reduction Achieved by ABEs in a Humanized PCSK9 Mouse Model

| Editor | Dose (mpk) | DNA Editing Efficiency (%) | PCSK9 Protein Reduction (%) |
| --- | --- | --- | --- |
| T8.4 ABE | 1 | 59.18 | 97.15 |
| ABE8.8 | 1 | 46.46 | 90.38 |
| T8.4 ABE-Inlaid | 1 | 40.36 | 65.17 |
| T8.4 ABE | 0.6 | 51.14 | 88.26 |
| ABE8.8 | 0.6 | 36.08 | 72.18 |
| T8.4 ABE-Inlaid | 0.6 | 21.48 | 65.73 |
| T8.4 ABE | 0.3 | 25.08 | 43.81 |
| T8.4 ABE | 0.3 | 22.03 | 68.58 |
| T8.4 ABE | 0.3 | 24.64 | 48.74 |
| ABE8.8 | 0.3 | 13.78 | −7.69 |
| ABE8.8 | 0.3 | 8.03 | 15.44 |
| ABE8.8 | 0.3 | 8.34 | 19.34 |
| T8.4 ABE-Inlaid | 0.3 | 6.37 | 11.00 |
| T8.4 ABE | 3 | 70.51 | 98.46 |
| ABE8.8 | 3 | 69.56 | 97.82 |
| T8.1 ABE | 3 | 50.81 | 80.18 |
| T8.111 ABE | 3 | 63.26 | 93.56 |

Example 9: Deaminase T8.4 Shows Activity Combined with Other Programmable DNA Binding Proteins To evaluate the potential of T8.4 deaminase (SEQ ID NO: 74) in combination with other programmable DNA binding domains, dead LbCpf1, ISAam1-D363A (TnpB) and enIscB-D61A (IscB) were each fused with the T8.4 deaminase sequence at their N terminus. Following transfection with T8.4-fused base editor (80 ng) and gRNA (40 ng) expression plasmids (gRNA sequence in Table 16), as per the provided instructions mentioned above, genomic DNA was collected from these cells after a 72-hour incubation period for NGS analysis to determine DNA editing efficiencies. The results are shown in Table 17.

TABLE 16

| gRNA | Spacer sequence | SEQ ID NO | Target gene |
| --- | --- | --- | --- |
| gRNA_t1 | GGCTGGCAGGCTCCTTGTTC | 250 | PGK1 |
| gRNA_t2 | GCAAATCAGCATGTTCCTCA | 251 | AGBL1 |
| gRNA_i1 | AGTGGAAGAAGGAGAT | 252 | ALDH1A3 |
| gRNA_i2 | ATCTTCACCAGGAAGC | 253 | PCSK9 |
| gRNA_c1 | TGACTCACACTCACCCAAAA | 254 | HSD17B13 |
| gRNA_c1 | CTGGAACTGTAAGAGAATTA | 255 | HSD17B13 |

TABLE 17

A-to-G Editing Efficiency of T8.4 in Combination with Different Programmable DNA Binding Proteins

| Base editor | gRNA | Editing efficiency (%) |
| --- | --- | --- |
| T8.4_TnpB-D363A | gRNA_t1 | 8.11 |
| | gRNA_t2 | 6.13 |
| T8.4-IscB-D61A | gRNA_i1 | 14.69 |
| | gRNA_i2 | 10.63 |
| T8.4-LbCpf1 | gRNA_c1 | 12.12 |
| | gRNA_c1 | 5.95 |

Example 10: Evaluating Editing Activity and Specificity of T8.4 Inlaid Variants

To test whether inlaid variants of the deaminases disclosed herein can improve the specificity of the T8.4 deaminase in the context of base-editing, wherein the deaminase is inlaid into a location within a nuclease protein, the deaminase variant T8.4 was inserted into nCas9 at different sites (detailed in Table 18) by a 20 amino acid linker (Linker1: GGSGGSGGSGGSGGSGGSGG (SEQ ID NO: 256); Linker2: GSSGSETPGTSESATPESSG (SEQ ID NO: 257)) or a GGS/GSS linker. On-target and R-loop assays for those inlaid variants were conducted in the same manner as described in Example 2 and 3. The sgRNAs for on and off-target analysis are listed in Table 19 and Table 20. The results of these experiments are shown in Table 21 and Table 22. In particular, Inliad-1, Inlaid-2, Inlaid-6, Inlaid-7, Inlaid-9 and Inlaid-10 showed comparable editing efficiency when compared with the original T8.4, while the off-target editing was lower.

TABLE 18

Design of T8.4 Inlaid Variants

| Base editor | Architecture |
| --- | --- |
| Inlaid-1 | Use Linker1-T8.4-Linker2 to replace 1048-1063 of Cas9 |
| Inlaid-2 | insert Linker1-T8.4-linker2 between R535 and K536 |
| Inlaid-3 | insert Linker1-T8.4-linker2 between Q768 and T769 |
| Inlaid-4 | insert Linker1-T8.4-linker2 between S909 and E910 |

TABLE 18-continued

Design of T8.4 Inlaid Variants

| Base editor | Architecture |
|---|---|
| Inlaid-5 | insert Linker1-T8.4-linker2 between P1249 and E1250 |
| Inlaid-6 | insert Linker1-T8.4-linker2 between I1029 and G1030 |
| Inlaid-7 | insert Linker1-T8.4-linker2 between E1068 and T1069 |
| Inlaid-8 | insert Linker1-T8.4-linker2 between I1022 and A1023 |
| Inlaid-9 | insert GGS-T8.4-GSS between P1249 and E1250 |
| Inlaid-10 | insert Linker1-T8.4 between P1249 and E1250 |

TABLE 19 spCas9 sgRNA sequences

| sgRNA | Sequence | Target gene |
|---|---|---|
| sgRNA4 | GACAAACCAGAAGCCGCTCC (SEQ ID NO: 258) | CTNNB1 |
| sgRNA5 | GTTCACACCCATGACGAACA (SEQ ID NO: 259) | GAPDH |
| sgRNA3 | CCCGCACCTTGGCGCAGCGG (SEQ ID NO: 109) | PCSK9 |

TABLE 20 saCas9 gRNAs used in off-target experiments

| sgRNA name | Sequence | Target gene |
|---|---|---|
| Sa-gRNA2 | ATTTACAGCCTGGCCTTTGGGG (SEQ ID NO: 260) | GAPDH |
| Sa-gRNA4 | GGTGGAGGAGGGTGCATGGGGT (SEQ ID NO: 261) | intergenic |
| Sa-gRNA5 | TCTGCTTCTCCAGCCCTGGC (SEQ ID NO: 115) | LINC01509 |

TABLE 21

A-to-G Editing Efficiency of T8.4 and its Inlaid Variants

| Base editor | sgRNA4 | sgRNA5 | sgRNA3 | mean |
|---|---|---|---|---|
| T8.4 | 57.37 | 50.22 | 37.26 | 48.29 |
| Inlaid-1 | 56.48 | 46.40 | 35.57 | 46.15 |
| Inlaid-2 | 49.91 | 30.63 | 39.60 | 40.05 |
| Inlaid-3 | 41.68 | 8.00 | 8.79 | 19.49 |
| Inlaid-4 | 41.04 | 19.18 | 17.08 | 25.77 |
| Inlaid-5 | 48.72 | 29.08 | 34.52 | 37.44 |
| Inlaid-6 | 57.19 | 39.19 | 37.43 | 44.60 |
| Inlaid-7 | 56.63 | 49.43 | 34.99 | 47.02 |
| Inlaid-8 | 52.04 | 35.23 | 29.06 | 38.77 |
| Inlaid-9 | 60.84 | 40.44 | 39.57 | 46.95 |
| Inlaid-10 | 53.01 | 37.86 | 33.02 | 41.30 |

TABLE 22

Ratio of R-loop Editing to On-target Editing for Engineered inlaid Variants Relative to T8.4

| Base editor | Sa2 R-loop editing/on-target editing efficiency relative to T8.4 | Sa4 R-loop editing/on-target editing efficiency relative to T8.4 | Sa5 R-loop editing/on-target editing efficiency relative to T8.4 | Mean |
|---|---|---|---|---|
| T8.4 | 1.00 | 1.00 | 1.00 | 1.00 |
| Inlaid-1 | 0.10 | 0.15 | 0.25 | 0.17 |
| Inlaid-2 | 0.46 | 1.02 | 0.60 | 0.69 |
| Inlaid-3 | 0.31 | 0.72 | 0.84 | 0.62 |
| Inlaid-4 | 0.17 | 0.77 | 0.30 | 0.42 |
| Inlaid-5 | 0.23 | 0.22 | 0.31 | 0.26 |
| Inlaid-6 | 0.20 | 0.42 | 0.46 | 0.36 |
| Inlaid-7 | 0.25 | 0.77 | 0.67 | 0.56 |
| Inlaid-8 | 0.22 | 0.26 | 0.62 | 0.37 |
| Inlaid-9 | 0.17 | 0.39 | 0.29 | 0.28 |
| Inlaid-10 | 0.20 | 0.73 | 0.46 | 0.46 |

Example 12: Improve T8.4 Deaminase Activity Through Directed Evolution

To augment the activity of T8.4, mutations were intentionally introduced into its sequence and subjected to directed evolution. Two distinct methods were employed to generate the mutational library: an NNK library encompassing 40 residues of T8.4, and an error-prone PCR library using T8.4 as the template and with a mutation frequency ranging from 1 to 3 mutations per sequence. The experimental system utilized three plasmids: a selection plasmid that expressed mutated Kanamycin resistance gene ($Kan^R$_Q4*W15*D208N), featuring three inactivation mutations, a sgRNA expression plasmid that expressed three sgRNAs targeting the mutated sites (Kan-sgRNA 1-3 in Table 23); and an editor plasmid that expressed the T8.4- dCas9 library. Library members capable of effecting A·T to G·C edits at all three sites simultaneously would restore Kanamycin resistance, thereby enabling survival upon challenge with Kanamycin.

Figure 8:
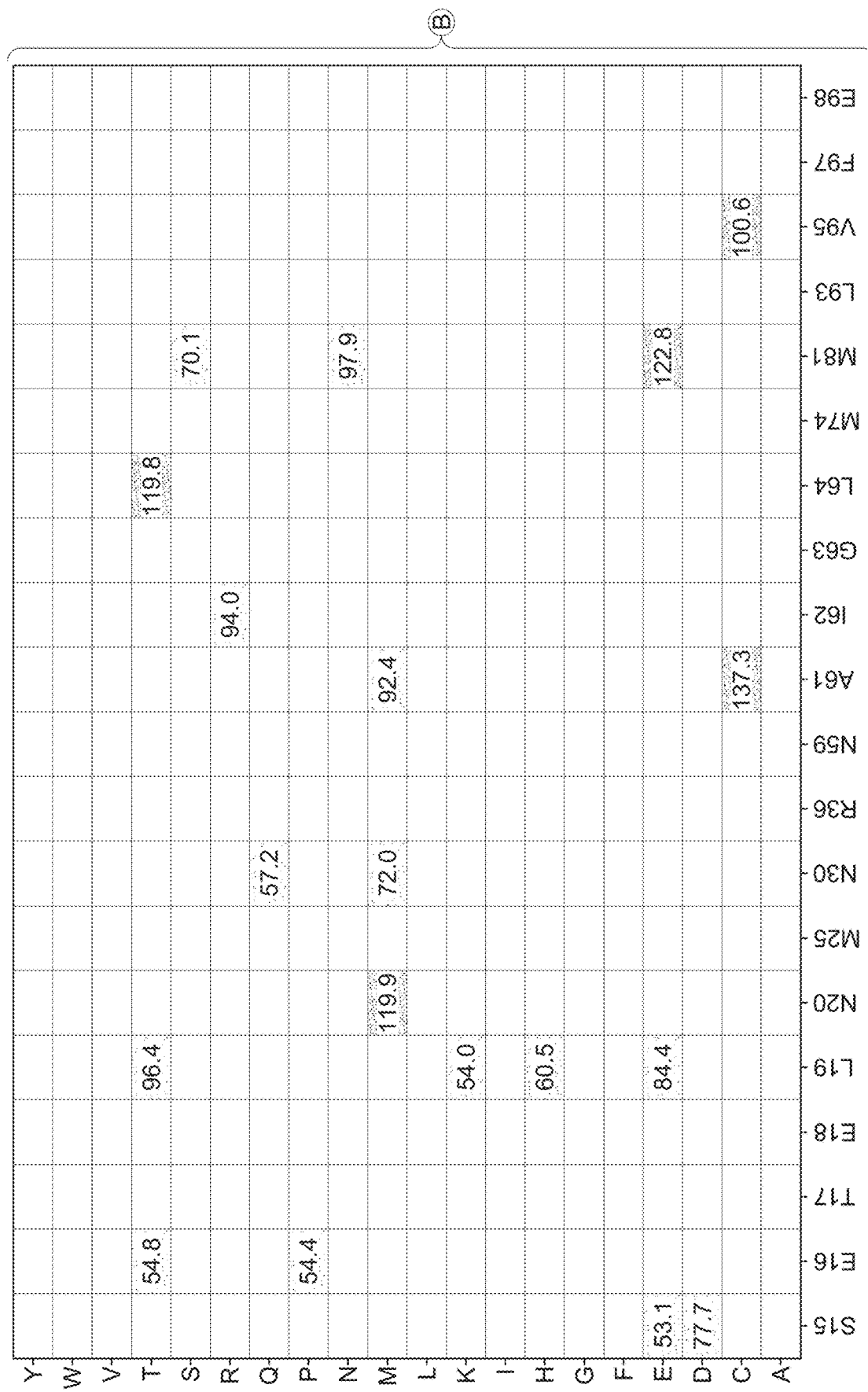
FIG. 8 is a plot showing the fold change in percentage of mutations before and after selection.
Figure 8:
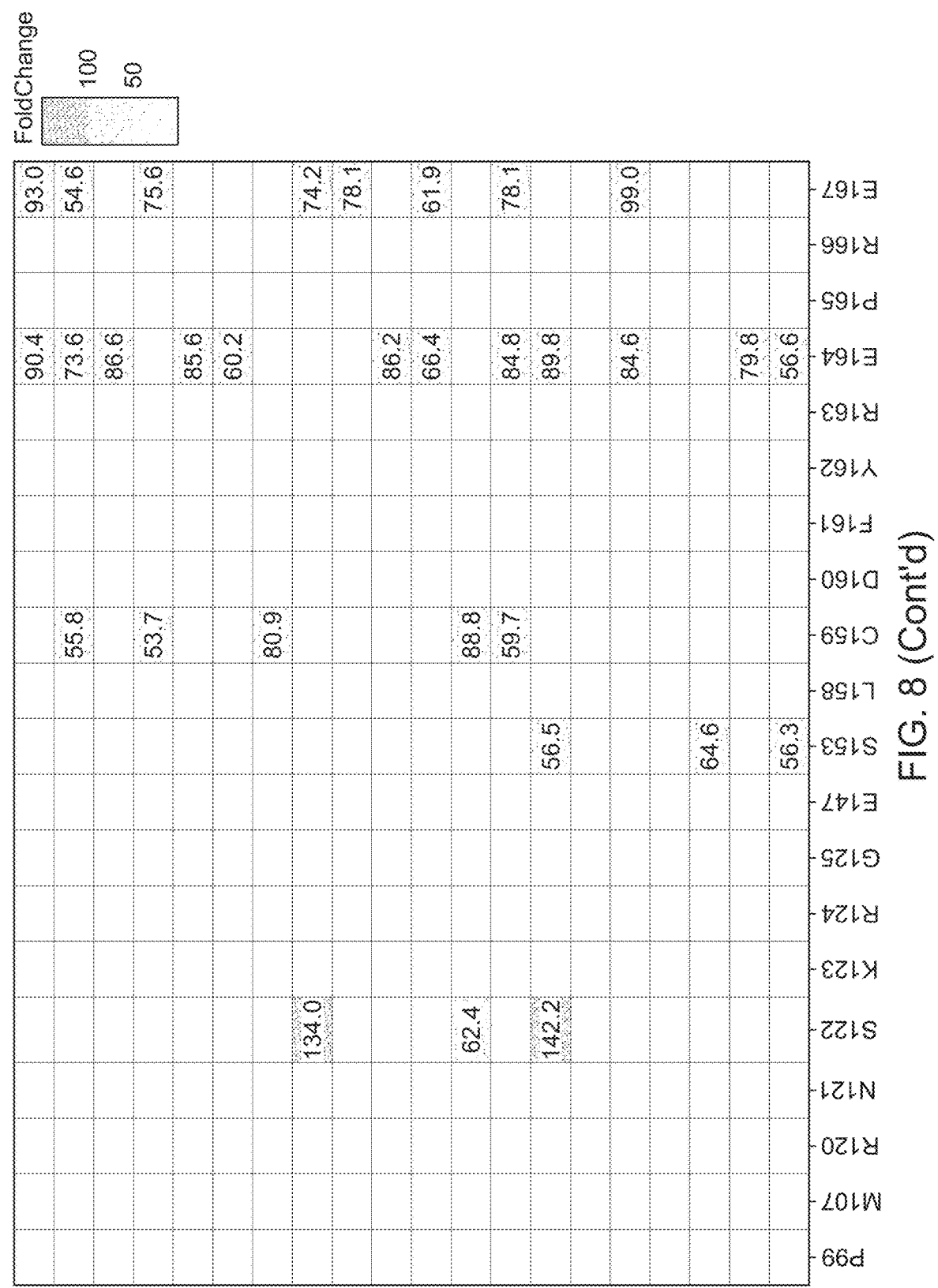

In conducting the experiment, E. coli strain DH10B, co-transformed with the selection plasmid and sgRNA expression plasmid, was rendered electrocompetent. Subsequently, 100-200 ng of the Editor plasmid was electroporated into DH10B cells. The bacteria were then recovered in 10 mL of LB medium before inoculation into 20 mL of LB medium supplemented with three antibiotics for plasmid maintenance (50 μg/mL Chloramphenicol, 150 μg/mL Spectinomycin and 100 μg/mL Ampicillin). Additionally, 1% Arabinose was introduced to induce the expression of T8.4-dCas9 library. The bacteria were cultured for an additional 16 hours before being plated onto bioassay dishes containing 1.5% agar-2×YT, the plasmid maintenance antibiotic, and various concentrations of Kanamycin (ranging from 64 to 256 μg/mL). Parallel experiments were conducted on two separate plates. Following incubation at 37° C. overnight, 120 surviving colonies from one plate were individually amplified by PCR and subsequently subjected to Sanger sequencing. Surviving colonies from the other plate were pooled together and subjected to plasmid extraction, defined as post-selection sample. Bacteria without selection were also isolated as a pre-selection control. The T8.4 library genes were then amplified from these extracted plasmids and subsequently subjected to Next-generation sequencing for analysis.

in post-selection samples by that in the pre-selection controls, The top 50 values are displayed in FIG. 8.

A second round of evolution was conducted using the combinatorial library of emerged mutations with KanR-Q4*W15*W24*D208N, applying higher selection pressure. The combinatorial library was generated through DNA shuffling. The directed evolution was conducted as described previously. The T8.4 library genes of colonies from pre-selection library and the post-selection library were sequenced via Sanger sequencing. By comparing the mutation ratios before and after selection, enrichment of S15G, S153R, E164V, E164L, and E167W was observed (Shown in Table 24).

TABLE 24

| | Mutation counts before and after selection | | | | | |
|---|---|---|---|---|---|---|
| Position | 15 | 20 | 153 | 159 | 164 | 167 |
| Residue | S/G | N/RKS | S/R | C/R | E/GV*WLKRM | E/W |
| Count of pre-selection | 11/19 | 9/4/9/8 | 20/10 | 14/16 | 2/1/6/1/5/4/2/4/5 | 15/15 |
| Count of post-selection | 13/28 | 12/7/8/14 | 4/37 | 41/0 | 0/1/12/2/2/19/1/1/3 | 13/28 |

Example 13: Validation of Beneficial Mutations in E. coli

To validate the editing efficiency of enriched mutations in the two rounds of directed evolution, the single or combinational mutations was cloned back to the Editor plasmid. 50 ng Editor plasmid was transformed into 20 μL of chemically competent TOP10 cells together with 50 ng Target plasmid (selection plasmid $KanR\_Q4*W15*D208N$ in Example 12) and 50 ng corresponding sgRNA expression plasmid (Kan-sgRNA 1-3 in Table 23). Bacteria were recovered in 1 mL of LB medium at 37° C. with shaking for 1 h. Then another 1 mL of LB medium containing selection plasmid maintenance antibiotic (ampicillin, spectinomycin and chloramphenicol) and 1% arabinose was added. Bacteria were grown

TABLE 23

Target sites of Kanamycin resistance gene

| Target site | Inactivating mutation | Position of target A/C in protospacer | Corresponding sgRNA |
|---|---|---|---|
| ATCTTATTCGATCATGCGAA (SEQ ID NO: 264) | Q4* | 6 | Kan-sgRNA1 |
| GCTTAGGTGGAGCGCCTATT (SEQ ID NO: 265) | W15* | 5 | Kan-sgRNA2 |
| TTCATTAACTGTGGCCGGCT (SEQ ID NO: 266) | D208N | 7 | Kan-sgRNA3 |
| GACTAGGCACAACAGACAAT (SEQ ID NO: 267) | W24* | 5 | Kan-sgRNA4 |

Figure 6:
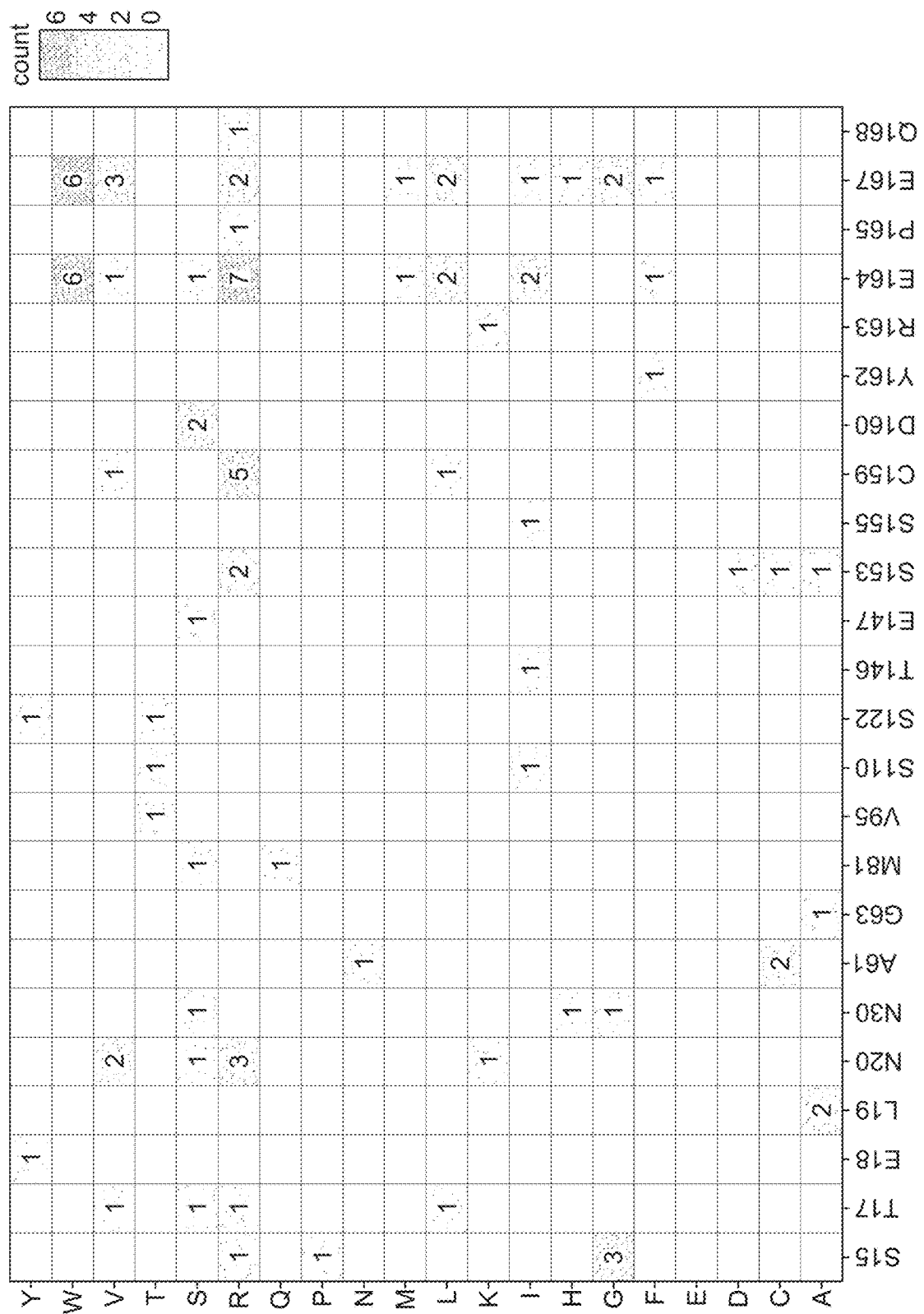
FIG. 6 is a plot of mutation counts identified in survival colonies by Sanger sequencing.

The Sanger results of surviving colonies are shown in FIG. 6. E164, E167, C159, N20, S153, S15 are mutation hotspots.

Figure 7:
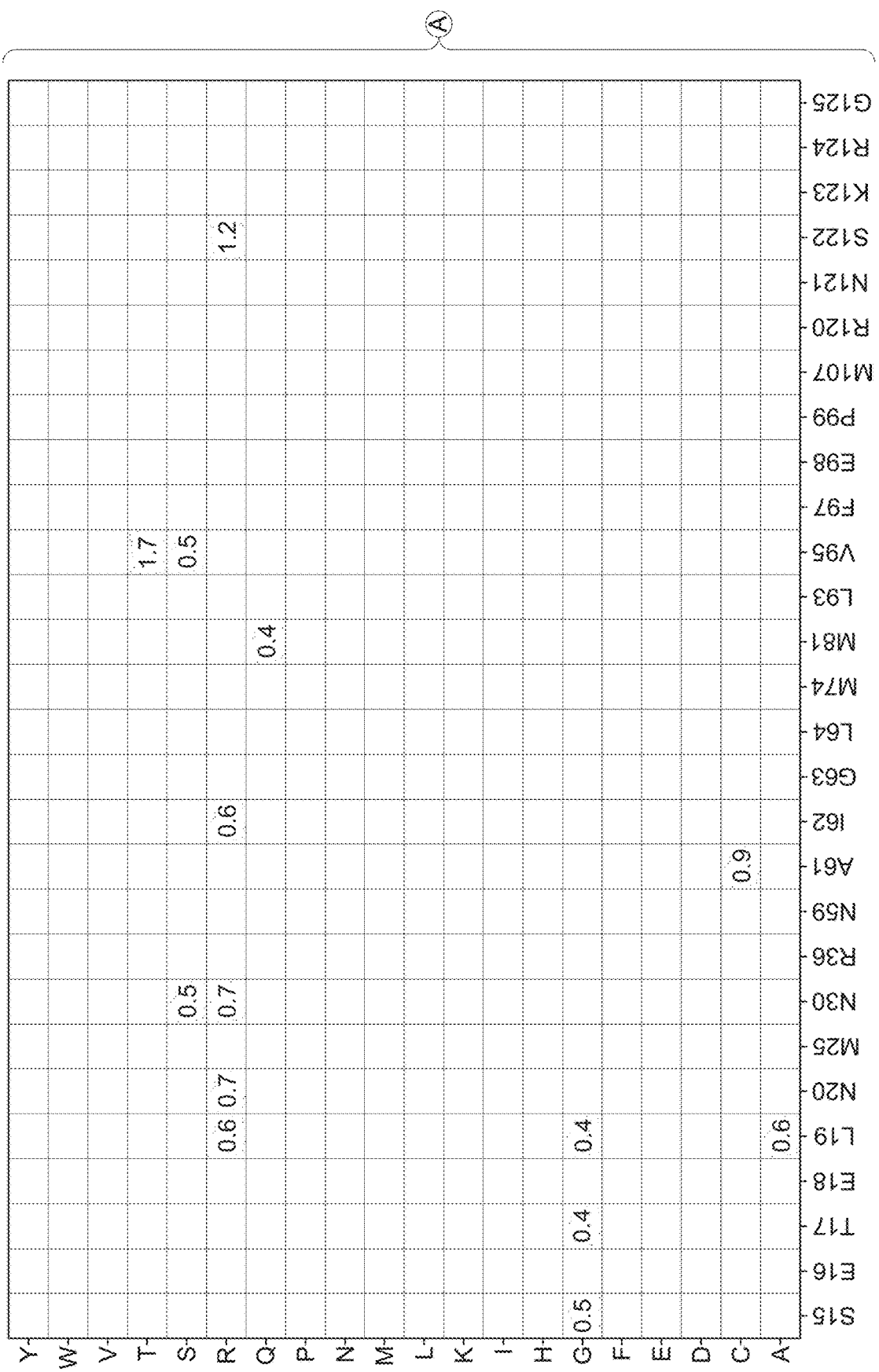
FIG. 7 is a plot of percentage of mutations identified in survival colonies by next-generation sequencing.
Figure 7:
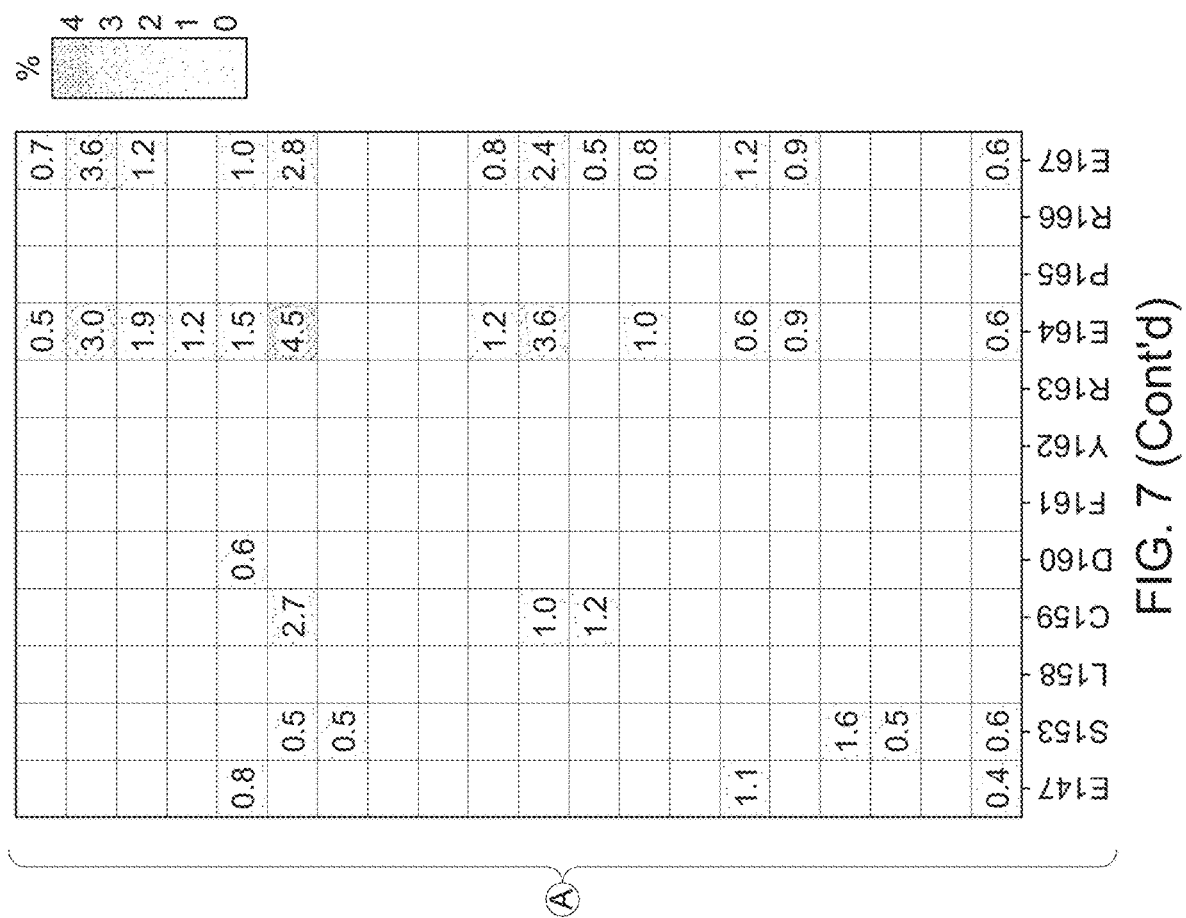

For the NGS analysis, the percentage of mutations present in post-selection samples was calculated for each position by dividing the number of reads containing mutations by the total number of reads. The top 50 values are displayed in FIG. 7. Additionally, the fold change of enrichment was calculated by dividing the percentage of survived mutations at 37° C. with shaking for another 16 h. The resulting bacterial culture was subjected to plasmid extraction. The 3 sgRNA targeting sites were then amplified from these extracted plasmids and subsequently subjected to Next-generation sequencing. As shown in Table 25, all of the tested variants showed higher editing efficiency when compared with the original T8.4. And the combination of some mutations exhibited more significant and pronounced effects on editing efficiency.

TABLE 25

A-to-G Editing Efficiency of T8.4 and its Variants in E.coli

| Base editor | Kan-sgRNA1 | Kan-sgRNA2 | Kan-sgRNA3 | Mean |
|---|---|---|---|---|
| T8.4 | 11.65 | 13.32 | 20.10 | 15.02 |
| T8.4-S155R | 52.00 | 60.00 | 47.22 | 53.07 |
| T8.4-C159R | 49.38 | 41.05 | 45.23 | 45.22 |
| T8.4-D12H | 18.42 | 23.68 | 14.29 | 18.80 |
| T8.4-N20H | 20.00 | 16.67 | 17.86 | 18.17 |
| T8.4-H21D | 34.90 | 28.66 | 29.07 | 30.88 |
| T8.4-E167R | 37.31 | 39.53 | 40.57 | 39.14 |
| T8.4-E164R-E167W | 41.25 | 40.32 | 72.21 | 51.26 |
| T8.4-E164W-E167W | 41.53 | 38.52 | 67.40 | 49.15 |
| T8.4-E164W-E167W-C159R | 53.03 | 60.32 | 77.74 | 63.70 |
| T8.4-S155R-E167R | 41.03 | 51.02 | 52.41 | 48.15 |
| T8.4-S155R-H21D-E167R | 53.87 | 65.41 | 64.58 | 61.29 |
| T8.4-S153R-E164V-E167W | 57.13 | 72.85 | 89.60 | 73.19 |
| T8.4-S153R-E164L-E167W | 49.10 | 58.68 | 83.24 | 63.68 |
| T8.4-S15G-S153R-E164V-E167W | 57.43 | 72.18 | 88.66 | 72.76 |
| T8.4-S15G-S153R-E164L-E167W | 55.43 | 61.99 | 84.90 | 67.44 |
| T8.4-N20S-S153R-E164L-E167W | 53.88 | 57.41 | 83.35 | 64.88 |

Example 14: Validation of Beneficial Mutations in Mammalian Cells (mRNA+sgRNA Library) sgRNA Library To systematically evaluate the editing performance of T8.4 variants in mammalian cells, we prepared a library wherein more than 10,000 target sites were individually paired with their cognate sgRNAs. The paired sgRNA-target library was cloned into Tol2 transposon plasmid. To establish a stable expression of the library, HEK293T cells were seeded into two 6-well plates at a density of $1\times10^6$ cells per well. For each well, 50 ng of the library plasmid and 250 ng of the Tol2 transposase enzyme plasmid were transfected using FuGENE HD Transfection Reagent (E2312) according to the manufacturer's protocols. Two days after transfection, cells were harvested and puromycin was added to select for cells containing the library. After 2-3 weeks of selection, cell lines with stable Tol2-mediated genomic integration were generated. To evaluate the editing performance, the mRNA of the variants was produced. HEK293T library cells ($1\times10^5$) were seeded in a 24-well plate (Corning) 20-24 h before transfection. 400 ng T8.4 variant mRNA was transfected into cells using Lipofectamine MessengerMAX (ThermoFisher, Cat. LMRNA003) following the manufacturer's protocol. After 72 hours, genomic DNA of the cells was extracted and analyzed by NGS for editing efficiency. The sgRNA detected in all samples were defined as valid sgRNAs. The A-to-G editing efficiency of these paired target sites was analyzed.

To quantify the potency of the variants, the mean editing efficiency value of the strong T8.4 editing window (positions edited to equal to or more than 40% of the peak editing rate, 3-8 for T8.4) was calculated. As shown in Table 26, the mean editing efficiency of many engineered variants was higher than original T8.4.

TABLE 26

A-to-G Editing Efficiency of T8.4 and its Variants in library cells

| Base editor | Average editing efficiency within strong editing window (3-8) |
|---|---|
| T8.4 | 49.50 |
| T8.4-E164L | 52.71 |
| T8.4-E164R | 57.01 |
| T8.4-E164W | 57.04 |
| T8.4-E167W | 57.31 |
| T8.4-C159R | 54.52 |
| T8.4-S155R | 52.76 |
| T8.4-E167R | 53.08 |
| T8.4-E164R-E167W | 58.81 |
| T8.4-E164W-E167W | 57.65 |
| T8.4-E164W-E167W-C159R | 62.76 |
| T8.4-S153R-E164V-E167W | 55.88 |
| T8.4-S153R-E164L-E167W | 59.37 |
| T8.4-S15G-S153R-E164V-E167W | 61.26 |
| T8.4-S15G-S153R-E164L-E167W | 58.90 |
| T8.4-N20S-S153R-E164L-E167W | 58.60 |

Figure 9:
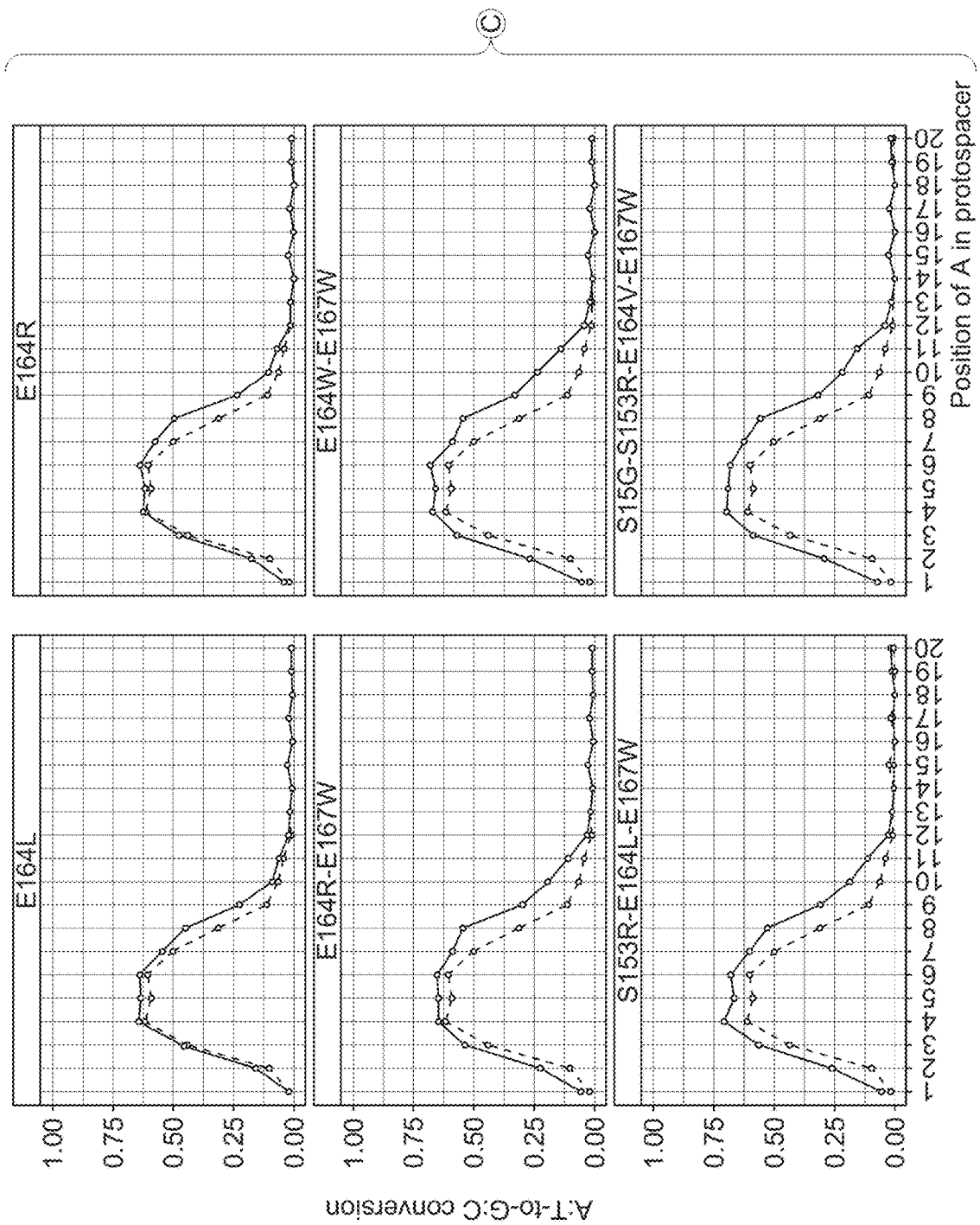
FIG. 9 is a plot of A to G editing efficiency of T8.4 variants in library cells.
Figure 9:
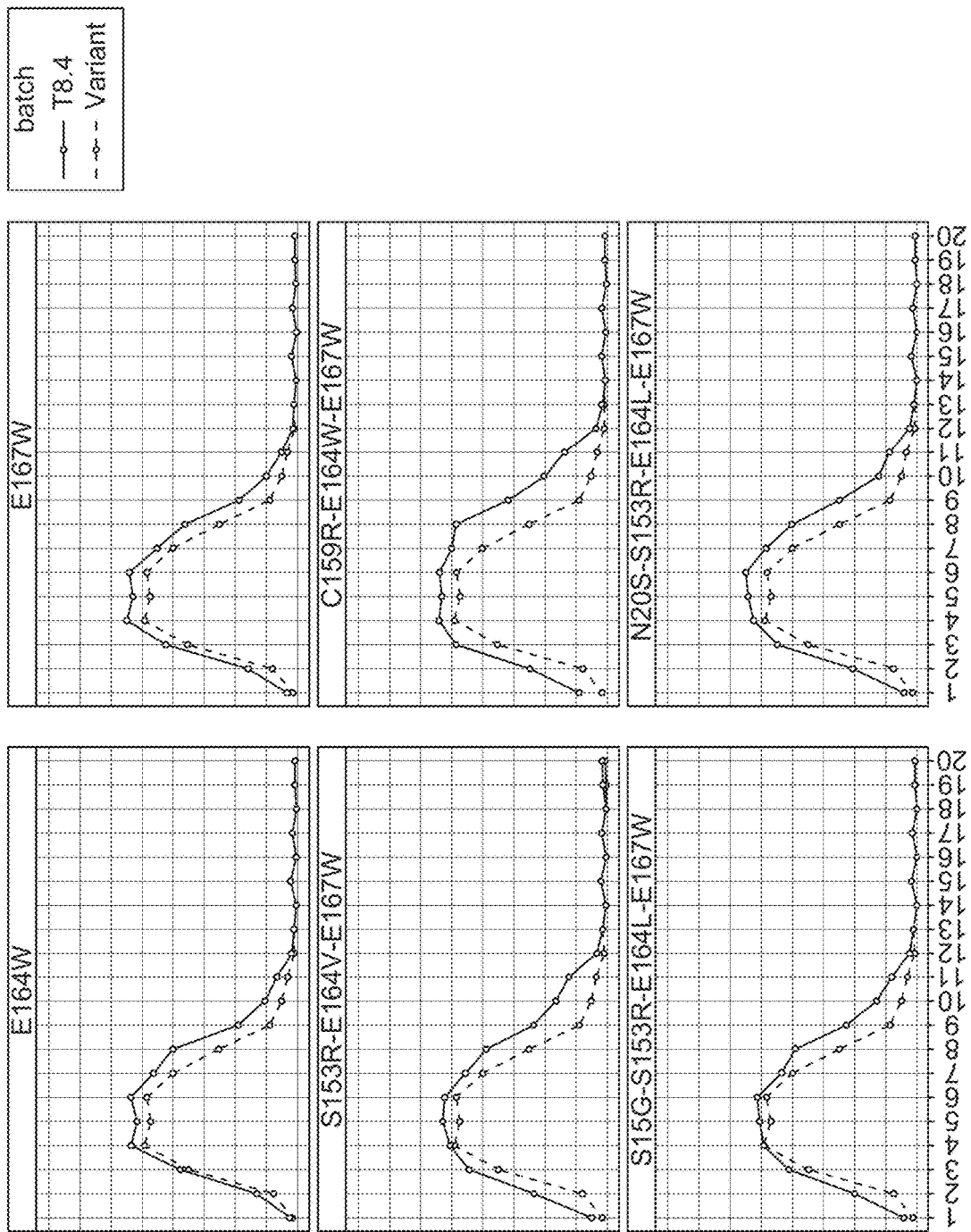

The overall editing results for some ABEs are shown in FIG. 9. When compared with T8.4, some variants showed similar editing window but higher efficiency. Some variants showed broader window and higher potency.

Example 15: Improve T8.12 Deaminase Activity Through Directed Evolution

To augment the activity of T8.12, a site-saturation mutagenesis library was synthesized and cloned into the editor plasmid backbone. The directed evolution was performed in a similar way as in Example 12. The percentage of mutations in post-selection samples are displayed in Table 27. Three mutations: E107Y, E107K and V104M-E107Y were validated in bacteria as in Example 13. As shown in Table 28 below, all of the three variants showed higher editing efficiency when compared with T8.12.

TABLE 27

Percentage of mutations identified in survival colonies

| Mutation | Percentage |
|---|---|
| E107Y | 21.23 |
| E107K | 19.59 |
| 147Q | 10.60 |
| E57Y | 6.63 |
| V104L | 4.16 |
| R105G | 3.72 |
| E57Y | 3.65 |
| V86D | 3.30 |
| A137V; Q159W | 3.04 |
| R18A | 3.00 |
| V104M; E107Y | 2.76 |
| E57K | 2.28 |
| G113Y | 2.24 |
| V101R | 2.22 |
| G29M | 1.98 |
| A60Q | 1.58 |
| H149L | 1.51 |
| A60D | 1.42 |
| V67P | 1.38 |
| V33S | 1.24 |
| N117V | 1.20 |
| A54P | 1.19 |
| V104M | 1.14 |

TABLE 28

A-to-G Editing Efficiency of T8.12 and its Variants in E. coli

| Base editor | KAN-sgRNA1 | KAN-sgRNA2 | KAN-sgRNA3 | Mean |
|---|---|---|---|---|
| T8.12 | 13.02 | 8.29 | 12.18 | 11.16 |
| T8.12-E107K | 10.78 | 10.23 | 24.46 | 15.16 |
| T8.12-E107Y | 29.68 | 32.34 | 29.38 | 30.47 |
| T8.12-V104M-E107Y | 31.16 | 35.99 | 25.03 | 30.73 |

To validate the efficacy of T8.12 variants in mammalian cells, the variants were transcribed in vitro into mRNA and co-transfected into Huh7 cells with synthetic sgRNA at an equivalent mass. Huh7 cells ($8\times10^3$ cells per well) were plated in a 96-well plate 20-24 hours before transfection. Transfection was carried out with varying doses of mRNA and sgRNA3 as described in Table 29 using lipofectamine MessengerMax Reagent (LMRNA015), following the manufacturer's protocols. After 72 hours, cells were harvested, genomic DNA was extracted, and the editing efficiency was analyzed by NGS. T8.12 variants demonstrated higher on-target editing efficiency compared to unmodified T8.12 (Table 29).

TABLE 29

C-to-T Editing Efficiency of sgRNA3 with T8.12 Variants

| mRNA dose(ng) mRNA:sgRNA = 1:1 | T8.12 | T8.12-E107Y | T8.12-V104M-E107Y |
|---|---|---|---|
| 20 | 87.32 | 87.44 | 88.01 |
| 6.67 | 71.46 | 77.87 | 85.00 |
| 2.22 | 41.35 | 57.72 | 66.89 |
| 0.74 | 17.94 | 27.18 | 36.40 |
| 0.25 | 7.73 | 10.50 | 16.26 |
| 0.08 | 2.98 | 3.30 | 5.73 |

Example 16: Directed Evolution of T88.74 to Improve its C to T Editing Activity

To improve the activity of T88.74 (SEQ ID NO: 241), a site-saturation mutagenesis library of T88.74 was generated as described above, and this library was subjected to directed evolution. The experimental system utilized three plasmids: a selection plasmid that expressed mutated Chloramphenicol resistant gene ($Cam^R$-L158P, H193R), featuring two inactivation mutations, an sgRNA expression plasmid that expressed two sgRNAs targeting the mutated sites; and an editor plasmid that expressed the T88.74-dCas9-2×UGI library. Library members capable of introducing C·G to T·A edits at all two sites simultaneously would restore Chloramphenicol resistance, thereby enabling survival upon challenge with Chloramphenicol.

In conducting the experiment, E. coli strain DH10B, co-transformed with the selection plasmid and sgRNA expression plasmid, was made electrocompetent. Subsequently, 100-200 ng of the editor plasmid library was electroporated into DH10B cells. The bacteria were then recovered in 10 mL of LB medium before inoculation into 20 mL of LB medium supplemented with three antibiotics for plasmid maintenance (kanamycin 30 µg/mL, ampicillin 100 µg/mL, spectinomycin 150 µg/mL). Additionally, 1% Arabinose was introduced to induce the expression of T88.74-dCas9-2×UGI library.

Figure 10:
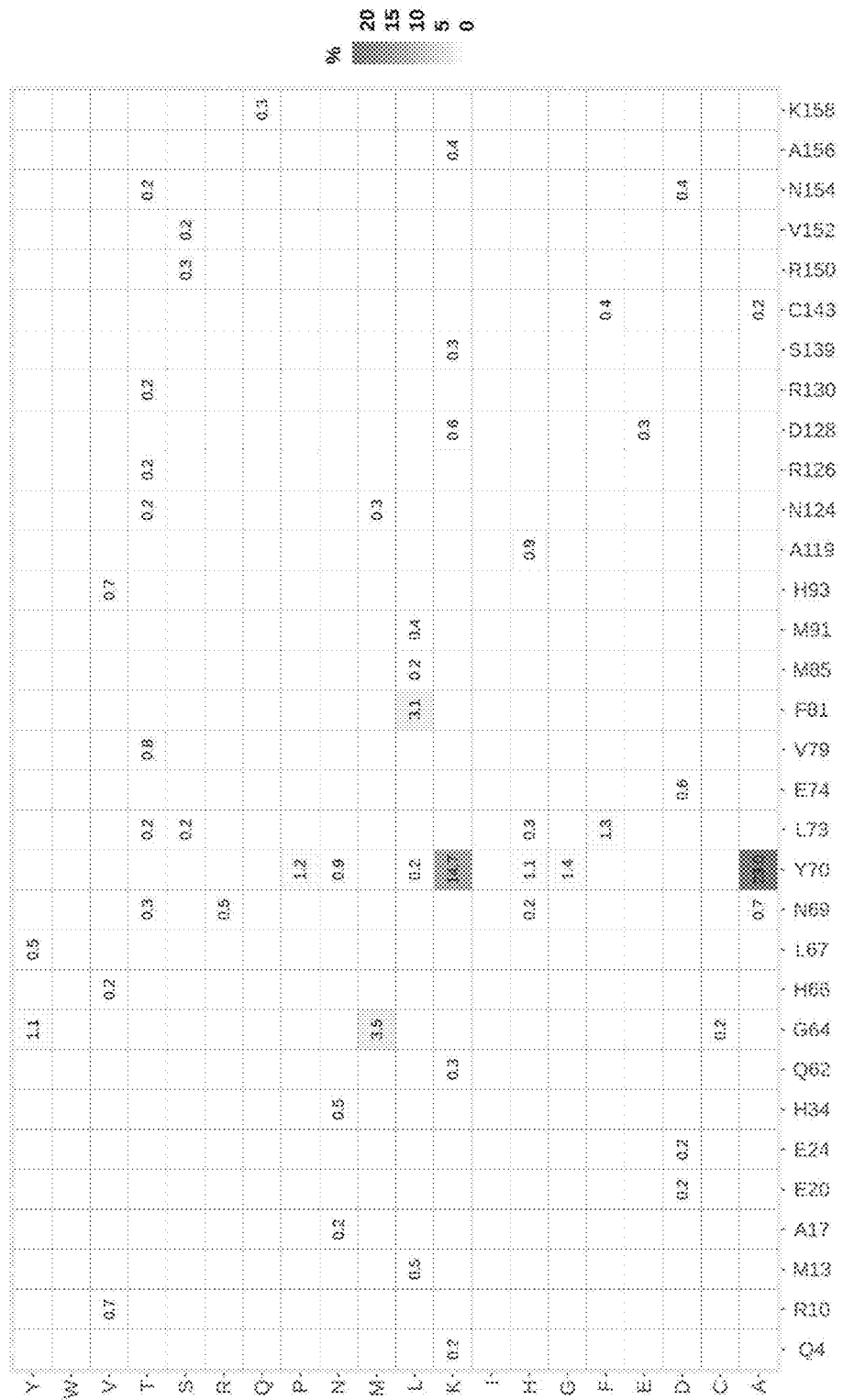
FIG. 10 is a plot of percentage of mutations identified in survival colonies by next-generation sequencing.
Figure 11:
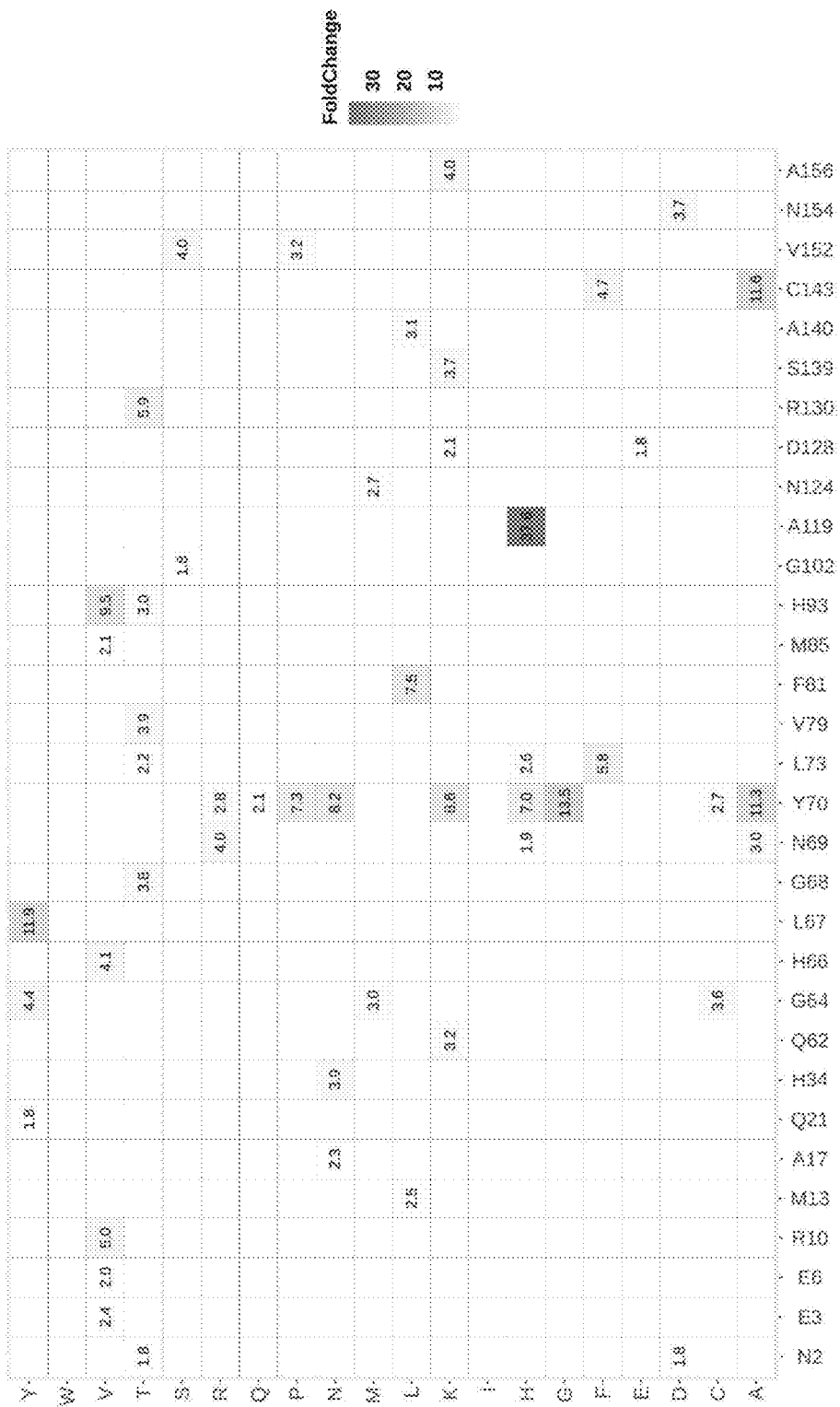
FIG. 11 is a plot showing the fold change in percentage of mutations before and after selection.

The bacteria were cultured for an additional 16 hours before being plated onto bioassay dishes containing 1.5% agar-2×YT, the plasmid maintenance antibiotic, and various concentrations of Chloramphenicol (16-64 µg/mL). Parallel experiments were conducted on two separate plates. Following incubation at 37° C. overnight, 48 surviving colonies from one plate were individually amplified by PCR and subsequently subjected to Sanger sequencing. At the same time, surviving colonies from the other plate were pooled together and subjected to plasmid extraction. The T88.74 gene library from those surviving colonies were then amplified from these extracted plasmids and subsequently subjected to Next-generation sequencing for comprehensive analysis. The percentage of mutations and the fold change of enrichment was calculated in a similar way in Example 12. The top 50 values are shown in FIG. 10 and FIG. 11.

Figure 12:
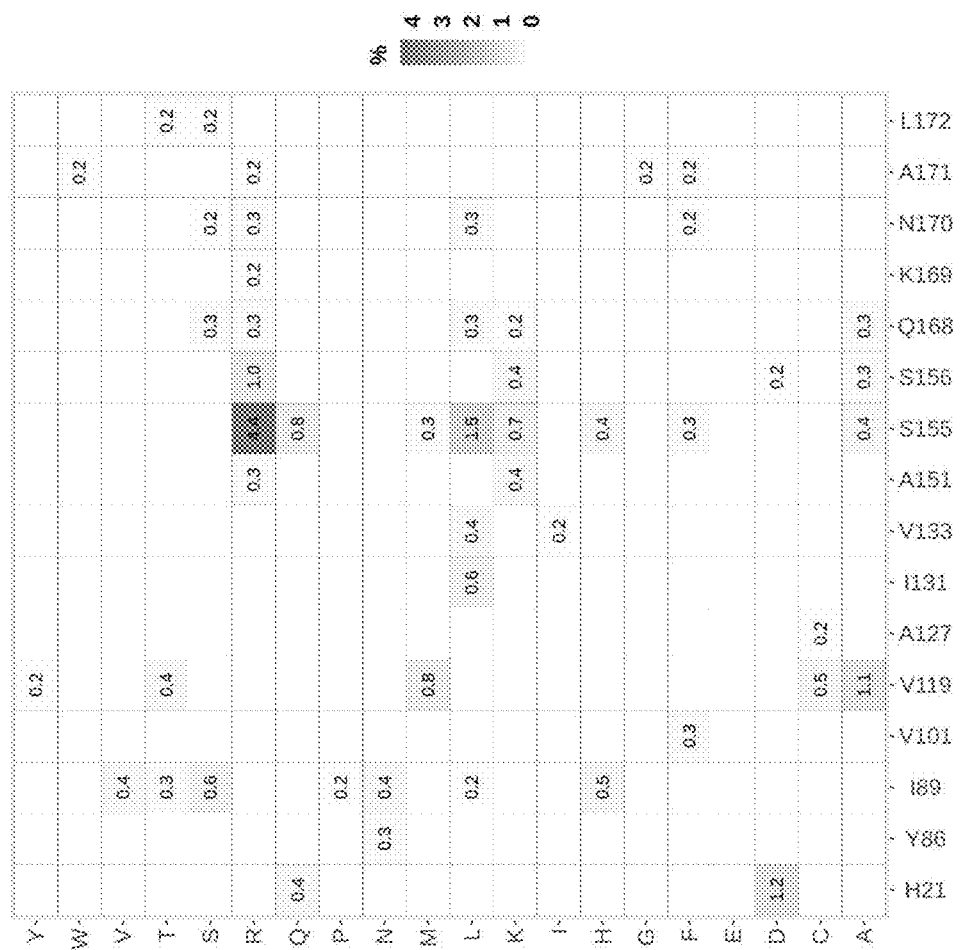
FIG. 12 is a plot of percentage of mutations identified in survival colonies after directed evolution of an NNK mutation library of the T8.4 variant as screened by next-generation sequencing.
Figure 13:
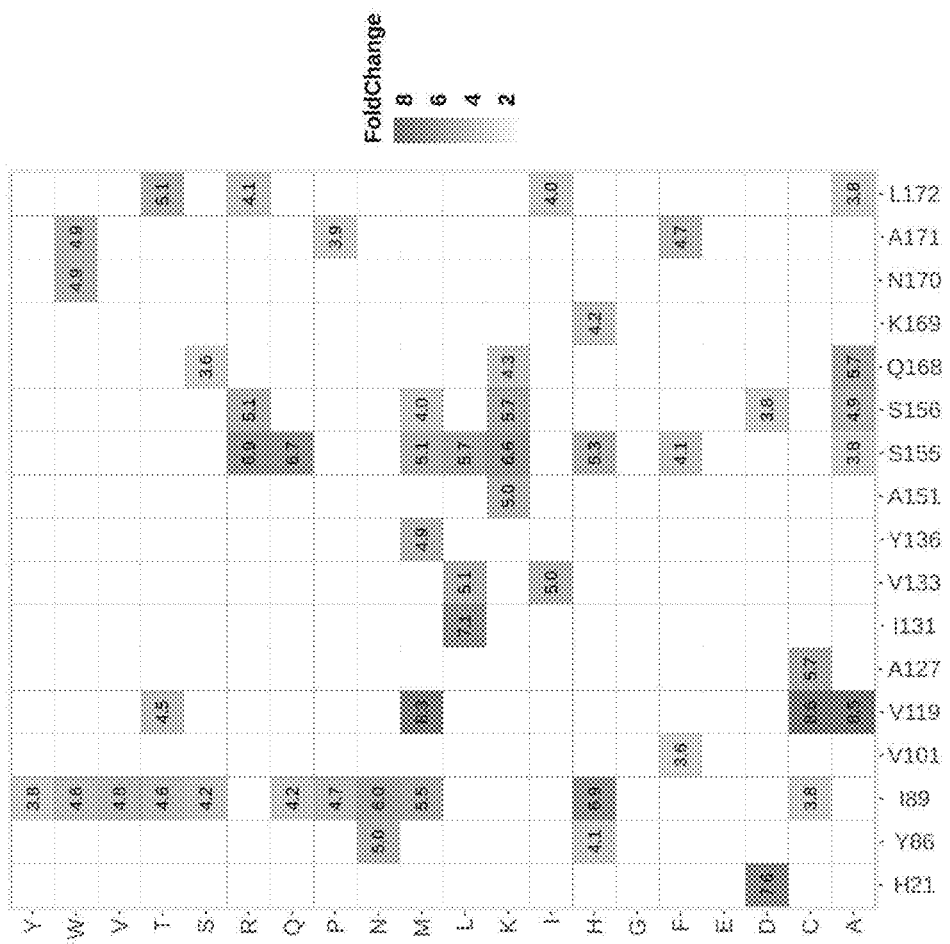
FIG. 13 is a plot showing the fold change in percentage of mutations before and after selection for an NNK mutation library of the T8.4 variant as screened by next-generation sequencing.

Example 17: Directed Evolution of T8.4 to Further Improve its a to G Editing Activity To further improve the activity of T8.4, the original T8.4 NNK library was expanded to contain another 60 NNK mutations across the sequence and subjected to directed evolution. Similar experimental systems were employed to enrich beneficial mutations (detailed KanR mutations). The NGS analysis results of enriched mutants were shown in FIG. 12 and FIG. 13.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An adenosine deaminase comprising an amino acid sequence having at least 92% sequence identity to SEQ ID NO:74.

2. The adenosine deaminase of claim 1, wherein the amino acid sequence has at least 95% sequence identity to SEQ ID NO:74.

3. The adenosine deaminase of claim 1, wherein the amino acid sequence has at least 99% sequence identity to SEQ ID NO:74.

4. The adenosine deaminase of claim 1, wherein the amino acid sequence has the sequence shown in SEQ ID NO:74.

5. The adenosine deaminase of claim 1, wherein the adenosine deaminase comprises one or more alterations at positions S15X, L19X, N30X, A61X, G63X, M81N, V95X, V119X, S122X, S153X, S155X, C159X, E164X, E167X as numbered relative to SEQ ID NO: 74, wherein X is any amino acid.

6. The adenosine deaminase of claim 5, wherein the adenosine deaminase comprises one or more alterations at positions S15G, L19A, N30R, A61C, G63Q, M81N, V95T, V119M, S122R, S153R, S155R, C159R, E164V, E164L, E164W, E167W as numbered relative to SEQ ID NO: 74.

7. The adenosine deaminase of claim 1, wherein the adenosine deaminase is capable of deaminating adenosine in DNA.

8. The adenosine deaminase of claim 1, wherein the adenosine deaminase is capable of deaminating cytidine in DNA.

9. The adenosine deaminase of claim 1, wherein the adenosine deaminase comprises one or more amino acid substitutions selected from the group consisting of W36R, R64L, L97F, A119V, D121N, A122S, T124R, D132N, H135N, H136Y, S159C, F162Y, R165P, K170N, and D183N as numbered relative to SEQ ID NO: 4.

10. The adenosine deaminase of claim 9, wherein the adenosine deaminase is an adenosine deaminase enzyme having an amino acid sequence of SEQ ID NO: 74.

11. An adenosine deaminase comprising an amino acid sequence having at least 85% sequence identity to SEQ ID NO:74 and having an Asn at position 121, wherein the adenosine deaminase exhibits DNA deaminase activity.

12. The adenosine deaminase of claim 11, wherein the amino acid sequence has at least 90% sequence identity to SEQ ID NO:74.

13. The adenosine deaminase of claim 11, wherein the amino acid sequence has at least 95% sequence identity to SEQ ID NO:74.

14. The adenosine deaminase of claim 11, wherein the amino acid sequence has at least 99% sequence identity to SEQ ID NO:74.

15. The adenosine deaminase of claim 11, wherein the amino acid sequence has the sequence shown in SEQ ID NO:74.

16. An adenosine deaminase comprising an amino acid sequence having at least 85% sequence identity to SEQ ID NO: 74 and having a Val at position 119, wherein the adenosine deaminase exhibits DNA deaminase activity.

* * * * *